United States Patent
Bursavich et al.

(10) Patent No.: US 7,947,712 B2
(45) Date of Patent: May 24, 2011

(54) 8-HYDROXYQUINOLINE COMPOUNDS AND METHODS THEREOF

(75) Inventors: Matthew G. Bursavich, Tuckahoe, NY (US); Sabrina Lombardi, Wilton, CT (US); Adam M. Gilbert, Congers, NY (US); Leif Mark Laakso, Chester, NY (US); Gulnaz Khafizova, West Nyack, NY (US); David Brian How, Nyack, NY (US); Joshua James Sabatini, White Plains, NY (US); Phaik-Eng Sum, Pomona, NY (US); Jeremy Clemens, New City, NY (US)

(73) Assignee: Wyeth LLC, Madison, NJ (US)

( * ) Notice: Subject to any disclaimer, the term of this patent is extended or adjusted under 35 U.S.C. 154(b) by 780 days.

(21) Appl. No.: 11/895,222

(22) Filed: Aug. 23, 2007

(65) Prior Publication Data

US 2008/0269213 A1  Oct. 30, 2008

Related U.S. Application Data

(60) Provisional application No. 60/839,568, filed on Aug. 23, 2006.

(51) Int. Cl.
*C07D 215/04* (2006.01)
*A61K 31/04* (2006.01)

(52) U.S. Cl. .................. 514/312; 546/159; 546/167

(58) Field of Classification Search .............. 546/159, 546/167; 514/312
See application file for complete search history.

(56) References Cited

U.S. PATENT DOCUMENTS

| | | | |
|---|---|---|---|
| 6,818,722 B2 | 11/2004 | Kym et al. | |
| 6,863,895 B2 * | 3/2005 | Bertozzi et al. | 424/248.1 |
| 7,619,091 B2 * | 11/2009 | Barnham et al. | 546/167 |
| 7,741,354 B2 * | 6/2010 | Thormann et al. | 514/381 |
| 2002/0086067 A1 * | 7/2002 | Choi et al. | 424/729 |
| 2004/0096499 A1 * | 5/2004 | Vaya et al. | 424/468 |

FOREIGN PATENT DOCUMENTS

WO   WO2004007461   *   1/2004

OTHER PUBLICATIONS

Bakken, CA 134:25113, abstract only of J Med Chem, vol. 43(23), pp. 45344541, 2000.*
Taylor, CA 108:34675, abstract only of Archivos de invenstigacion Medica, 18(2), pp. 119-126, 1987.*
Berkson, Int j Cancer, vol. 115, pp. 701-710, 2005.*
Varga, CA 117:277, abstract only of Molecular Immunology, vol. 28(6_, 641-654, 1991.*
Scheibel, CA 97:138147, abstract only of Mol Pharm, vol. 22(1), pp. 140-144, 1982.*
Tang, Int. J. Biochem. Cell. Biol 33:33-44 (2001).
Abbaszade et al., J. Biol. Chem 274:23443-23-450 (1999).
Colige et al., Proc. Natl. Acad. Sci. USA 94:2374-2379 (1997).
Vazquez et al., J. Biol. Chem. 274:23349-23357 (1999).
Kuno et al., J. Biol. Chem. 272:556-562 (1997).
Jerry March, Advanced Organic Chemistry: Reactions, Mechanisms and Structures, Fourth Edition, John Wiley & Sons, pp. 69-74 (1992).
Mohrle, H. et al. Chem. Ber. 1974, 107, 2675.
Pirrone, F. Gazz. Chim Ital. 1936, 66, 518.
Pirrone, F. Gazz. Chim Ital. 1937, 67, 529.
Shen, Liang et al. Tetrahedron Letters 2004, 45, 3961.
Bradshaw, Jerald S. et al. Supremolecular Chemistry 2001, 13, 499.
Berkson, R.G., International Journal of Cancer, 2005, vol. 115, No. 5 pp. 701-710.

* cited by examiner

*Primary Examiner* — D Seaman
(74) *Attorney, Agent, or Firm* — Ram W. Sabnis

(57) ABSTRACT

The present invention relates to 8-Hydroxyquinoline Compounds; compositions comprising an 8-Hydroxyquinoline Compound; and methods for treating or preventing a metalloproteinase-related disorder, such as, an arthritic disorder, osteoarthritis, malignant neoplasm, rheumatoid arthritis, asthma, chronic obstructive pulmonary disease, atherosclerosis, age-related macular degeneration, myocardial infarction, a corneal ulceration, an ocular surface disease, hepatitis, an aortic aneurysm, tendonitis, a central nervous system disorder, abnormal wound healing, angiogenesis, restenosis, cirrhosis, multiple sclerosis, glomerulonephritis, graft versus host disease, diabetes, an inflammatory bowel disease, shock, invertebral disc degeneration, stroke, osteopenia or a periodontal disease or comprising administering an effective dose of an 8-Hydroxyquinoline Compound to a mammal in need thereof.

52 Claims, No Drawings

US 7,947,712 B2

8-HYDROXYQUINOLINE COMPOUNDS AND METHODS THEREOF

This application claims the benefit under 35 U.S.C. 119(e) of U.S. Provisional Application No. 60/839,568, filed Aug. 23, 2006. The entire disclosure of that application is relied upon and incorporated herein by reference.

1. FIELD OF THE INVENTION

The present invention relates to 8-Hydroxyquinoline Compounds, as defined below; compositions comprising an 8-Hydroxyquinoline Compound; and methods for treating or preventing a metalloproteinase-related disorder comprising administering to a mammal in need thereof an effective dose of an 8-Hydroxyquinoline Compound.

2. BACKGROUND OF THE INVENTION

Metalloproteinases, including matrix metalloproteinases and aggrecanases, are known to have a role in the breakdown of connective tissue. Matrix metalloproteinases ("MMPs") constitute a superfamily of proteolytic enzymes that are genetically related and capable of degrading almost all the constituents of extracellular matrix and basement membrane that restrict cell movement. Aggrecanases are members of the ADAMTS (A disintegrin and metalloproteinase with thrombospondin motifs) family of proteins. Aggrecanase-1 and aggrecanase-2 have been designated ADAMTS-4 and ADAMTS-5, respectively (Tang, *Int. J. Biochem. Cell. Biol.* 33:33-44 (2001)).

The ADAMTS family is involved in cleaving aggrecan, a cartilage component also known as the large aggregating chondroitin sulphate proteoglycan (Abbaszade et al., *J. Biol. Chem.* 274:23443-23450 (1999)), procollagen processing (Colige et al., *Proc. Natl. Acad. Sci.* USA 94:2374-2379 (1997)), angiogenesis and tumor invasion (Vazquez et al., *J. Biol. Chem.* 274:23349-23357 (1999)), inflammation (Kuno et al., *J. Biol. Chem.* 272:556-562 (1997)). MMPs have been shown to cleave aggrecan as well.

The loss of aggrecan has been implicated in the degradation of articular cartilage in arthritic diseases, for example osteoarthritis is a debilitating disease which affects at least 30 million Americans. Degradation of articular cartilage and the resulting chronic pain can severely reduce quality of life. An early and important characteristic of the osteoarthritic process is loss of aggrecan from the extracellular matrix, resulting in deficiencies in the biomechanical characteristics of the cartilage. Likewise, MMPs and aggrecanases are known to play a role in many disorders in which extracellular protein degradation or destruction occurs, such as malignant neoplasm, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

Accordingly, there is a need for metalloproteinase inhibitors, such as inhibitors of MMPs and aggrecanases. The present invention addresses this need.

Throughout this application, various publications are referenced. The disclosures of these publications in their entireties are hereby incorporated by reference into this application.

3. SUMMARY OF THE INVENTION

The present invention relates to 8-Hydroxyquinoline Compounds; compositions comprising an 8-Hydroxyquinoline Compound; and methods for treating or preventing a metalloproteinase-related disorder, such as, an arthritic disorder, osteoarthritis, malignant neoplasm, rheumatoid arthritis, asthma, chronic obstructive pulmonary disease, atherosclerosis, age-related macular degeneration, myocardial infarction, a corneal ulceration, an ocular surface disease, hepatitis, an aortic aneurysm, tendonitis, a central nervous system disorder, abnormal wound healing, angiogenesis, restenosis, cirrhosis, multiple sclerosis, glomerulonephritis, graft versus host disease, diabetes, an inflammatory bowel disease, shock, invertebral disc degeneration, stroke, osteopenia or a periodontal disease or comprising administering an effective dose of an 8-Hydroxyquinoline Compound to a mammal in need thereof.

The invention provides compounds of the Formula (I):

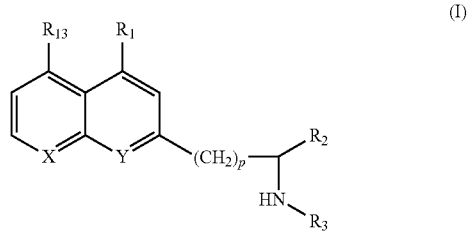

and pharmaceutically acceptable salts or hydrates thereof, wherein
X is —N— and Y is —COR$_4$, or Y is —N— and X is —COR$_4$;
p is 0 or 1;
R$_1$ and R$_{13}$ are each independently hydrogen, halogen, —OR$_7$, —CN, —C$_1$-C$_6$-alkyl, —C$_2$-C$_6$-alkenyl, —C$_2$-C$_6$-alkynyl, —NO$_2$, —NR$_5$R$_6$, —SO$_2$NR$_5$R$_6$, —COR$_7$, —COOR$_7$, —C$_5$-C$_7$-cycloalkyl or —C$_5$-C$_7$-aryl, wherein (a) one or more of the carbon atoms in the alkyl, alkenyl, alkynyl, cycloalkyl or aryl group is each independently optionally replaced with a nitrogen, sulfur or oxygen atom, and (b) the alkyl, alkenyl, alkynyl, cycloalkyl or aryl is optionally substituted with a halogen or a —C$_1$-C$_3$-alkyl, provided that when X is —N— then R$_{13}$ is hydrogen and when Y is —N— then R$_1$ is hydrogen;
R$_2$ is hydrogen, —C$_1$-C$_6$-alkyl, —C$_2$-C$_6$-alkenyl, —C$_2$-C$_6$-alkynyl, —C$_5$-C$_7$-aryl, —C$_5$-C$_{10}$-arylalkyl, —C$_5$-C$_{10}$-arylalkenyl, —C$_7$-C$_{12}$-bicyclic hydrocarbon wherein at least one cyclic group is aromatic, C$_9$-C$_{15}$-tricyclic hydrocarbon wherein at least one cyclic group is aromatic or —COR$_7$, wherein (a) at least one of the carbon atoms in the alkyl, alkenyl, alkynyl, aryl, arylalkyl, arylalkenyl, bicyclic hydrocarbon or tricyclic hydrocarbon group is each independently optionally replaced with a nitrogen, sulfur or oxygen atom, and (b) the alkyl, alkenyl, alkynyl, aryl or arylalkyl, arylalkenyl, bicyclic hydrocarbon or tricyclic hydrocarbon group is optionally substituted with at least one hydroxyl, halogen, oxygen, —C$_1$-C$_6$-alkyl, —C$_2$-C$_6$-alkenyl, —C$_2$-C$_6$-alkynyl, —C$_5$-C$_7$-cycloalkyl, —C$_1$-C$_3$-alkyl-C$_5$-C$_7$-cycloalkyl, —C$_5$-C$_7$-aryl, —C$_5$-C$_{10}$-arylalkyl, —C$_5$-C$_{10}$-arylalkenyl, —C$_5$-C$_{10}$-arylalkynyl, —NO$_2$, —CH$_2$NR$_5$R$_6$, —NR$_5$R$_6$, —NR$_5$SO$_2$R$_6$, —SO$_2$NR$_5$R$_6$, —SO$_2$R$_7$, —COR$_7$, —C$_1$-C$_3$-alkyl-COR$_7$, —COOR$_7$ or —CONR$_5$R$_6$, wherein (1) one or more of the carbon atoms in the alkyl, alkenyl, alkynyl, cycloalkyl, aryl, arylalkyl, arylalkenyl or arylalkynyl group is each independently optionally replaced with a nitrogen, sulfur or oxygen atom, and (2) the alkyl, alkenyl, alkynyl, cycloalkyl, aryl arylalkyl, arylalkenyl or arylalkynyl group is optionally substituted with a halogen, a —$C_1$-$C_3$-alkyl or a —$C_5$-$C_7$-aryl;

$R_3$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_7$-cycloalkyl, —$R_8$—$C_5$-$C_7$-cycloalkyl, —$C_5$-$C_{10}$-arylalkyl, —$C_7$-$C_{12}$-bicyclic hydrocarbon or —$R_{12}$—$C_7$-$C_{12}$-bicyclic hydrocarbon wherein at least one cyclic group is aromatic, —$SO_2NR_5R_6$, —$COR_7$, —$COOR_7$, —$CONR_5R_6$, —$COR_8$—B—$R_9$, or —$R_8$—B—$R_9$, wherein (a) one or more of the carbon atoms in the alkyl, alkenyl, alkynyl, cycloalkyl, aryl, arylalkyl or bicyclic hydrocarbon group is each independently optionally replaced with a nitrogen, sulfur or oxygen atom, and (b) the alkyl, alkenyl, alkynyl, cycloalkyl, aryl, arylalkyl or bicyclic hydrocarbon group is optionally substituted with at least one, (e.g., one to three) halogen or a —$C_1$-$C_4$-alkyl that is optionally branched, —$C_2$-$C_3$-alkynyl, —$C_5$-$C_7$-aryl, —$NR_5R_6$, —C≡N, or —$COR_7$;

$R_4$ is hydrogen, —$C_1$-$C_6$-alkyl, —$C_2$-$C_6$-alkenyl, —$C_2$-$C_6$-alkynyl, —$SO_2NR_5R_6$, —$SO_2R_7$, —$COR_7$, —$COOR_7$ or —$CONR_5R_6$, wherein (a) one or more of the carbon atoms in the alkyl, alkenyl, or alkynyl group is each independently optionally replaced with a nitrogen, sulfur or oxygen atom, and (b) the alkyl, alkenyl or alkynyl group is optionally substituted with a halogen or a —$C_1$-$C_3$-alkyl;

$R_5$ and $R_6$ are each independently hydrogen, —$C_1$-$C_6$-alkyl, —$C_2$-$C_6$-alkenyl, —$C_2$-$C_6$-alkynyl, —$COR_7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, an oxygen or a —$C_1$-$C_3$-alkyl;

$R_7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with at least one halogen, a —$C_1$-$C_3$-alkyl, —$C_5$-$C_7$-aryl, or —$NR_5R_6$, —$OR_5$;

$R_8$ is —$C_1$-$C_6$-alkyl, —$C_2$-$C_6$-alkenyl, or —$C_2$-$C_6$-alkynyl, wherein (a) one or more of the carbon atoms in the alkyl, alkenyl or alkynyl, group is each independently optionally replaced with a nitrogen, sulfur or oxygen atom, and (b) the alkyl, alkenyl or alkynyl group is optionally substituted with a halogen or a —$C_1$-$C_3$-alkyl;

$R_9$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_{10}$-arylalkyl or —$C_7$-$C_{12}$-bicyclic hydrocarbon wherein at least one cyclic group is aromatic, wherein (a) one or more of the carbon atoms in the alkyl, alkenyl, alkynyl, aryl, arylalkyl or bicyclic hydrocarbon group is each independently optionally replaced with a nitrogen, sulfur or oxygen atom, and (b) the alkyl, alkenyl, alkynyl, aryl, arylalkyl or bicyclic hydrocarbon group is optionally substituted with at least one halogen, a —$C_1$-$C_4$-alkyl that is optionally branched, a —$C_5$-$C_7$-aryl, B—$C_5$-$C_7$-aryl, —$NR_5R_6$, or —$COR_7$, and wherein one to three carbon atoms are each independently optionally replaced with an oxygen or nitrogen atom;

$R_{12}$ is —$CH_2$— or —$CH_2CH_2$—;

B is a bond, —O—, —$NR_7$— or —S—.

A compound of Formula (I) or a pharmaceutically acceptable salt thereof, (hereinafter being an "8-Hydroxyquinoline Compound") is useful for treating or preventing an arthritic disorder, osteoarthritis, malignant neoplasm, rheumatoid arthritis, asthma, chronic obstructive pulmonary disease, atherosclerosis, age-related macular degeneration, a myocardial infarction, a corneal ulceration, an ocular surface disease, hepatitis, an aortic aneurysm, tendonitis, a central nervous system disorder, a wound that has healed abnormally, angiogenesis, restenosis, cirrhosis, multiple sclerosis, glomerulonephritis, graft versus host disease, diabetes, an inflammatory bowel disease, shock, invertebral disc degeneration, stroke, osteopenia, a periodontal disease or a metalloproteinase-related disorder (hereinafter, each individually or collectively, being a "Condition").

The invention also provides compositions comprising an 8-Hydroxyquinoline Compound and a physiologically acceptable carrier or vehicle. The compositions are useful for treating or preventing a Condition.

The invention further provides methods for treating or preventing a Condition comprising administering an effective dose of an 8-Hydroxyquinoline Compound to a mammal in need thereof.

The details of the invention are set forth in the accompanying description below. Other features, objects, and advantages of the invention will be apparent from the description and from the claims. All patents, patent applications and publications cited in this specification are incorporated herein by reference for all purposes.

4. DETAILED DESCRIPTION OF THE INVENTION

4.1 Definitions and Abbreviations

The term "$C_1$-$C_6$-alkyl" as used herein refers to a linear or branched, saturated hydrocarbon having from 1 to 6 carbon atoms. Representative $C_1$-$C_6$-alkyl groups include, but are not limited to, methyl, ethyl, propyl, isopropyl, butyl, sec-butyl, tert-butyl, pentyl, isopentyl, neopentyl, hexyl, isohexyl, and neohexyl. In one embodiment, the $C_1$-$C_6$-alkyl group is substituted with one or more (e.g., one to three) of the following groups: halogen, —$N_3$, —$NO_2$, —CN, —OR', —SR', —$SO_2R'$, —$SO_2N(R')_2$, —$N(R')_2$, —COR', —$CO_2R'$, —$NR'CO_2R'$, —NR'COR', —NR'CONR', or —$CON(R')_2$, wherein each R' is independently selected to be hydrogen or unsubstituted —$C_1$-$C_6$-alkyl.

The term "$C_2$-$C_6$-alkenyl" as used herein refers to a linear or branched hydrocarbon having from 2 to 6 carbon atoms and having at least one carbon-carbon double bond. In one embodiment, the $C_2$-$C_6$-alkenyl has one or two double bonds. The $C_2$-$C_6$-alkenyl moiety may exist in the E or Z configuration and the compounds of the present invention include both configurations. Representative $C_2$-$C_6$-alkenyl groups include, but are not limited to, ethylenyl, propylenyl, 1-butylenyl, 2-butylenyl, isobutylenyl, sec-butylenyl, 1-pentenyl, 2-pentenyl, isopentenyl, 1-hexenyl, 2-hexenyl, 3-hexenyl, and isohexenyl. In one embodiment, the $C_2$-$C_6$-alkenyl group is substituted with one or more (e.g., one to three) of the following groups: halogen, —$N_3$, —$NO_2$, —CN, —OR', —SR', —$SO_2R'$, —$SO_2N(R')_2$, —$N(R')_2$, —COR', —$CO_2R'$, —$NR'CO_2R'$, —NR'COR', —NR'CONR', or —$CON(R')_2$, wherein each R' is independently hydrogen or unsubstituted $C_1$-$C_6$-alkyl.

The term "$C_1$-$C_6$-heteroalkyl" refers to a linear or branched, saturated hydrocarbon having from 1 to 6 carbon atoms, which also includes one or more heteroatom each independently selected from sulfur, nitrogen and oxygen.

The term "$C_5$-$C_7$-cycloalkyl" as used herein refers to a non-aromatic hydrocarbon ring. Representative $C_5$-$C_7$-cycloalkyl groups include, but are not limited to, cyclopentyl, cyclohexyl, and cycloheptyl. In one embodiment, the $C_5$-$C_7$-cycloalkyl group is independently substituted with one or more of the following groups: halogen, —$N_3$, —$NO_2$, —CN, —OR', —SR', —$SO_2$R', —$SO_2$N(R')$_2$, —N(R')$_2$, —COR', —$CO_2$R', —NR'$CO_2$R', —NR'COR', —NR'CONR', or —CON(R')$_2$, wherein each R' is independently hydrogen or unsubstituted $C_1$-$C_6$-alkyl. When so specified, a $C_5$-$C_7$-cycloalkyl can have one to three ring carbon atoms each independently optionally replaced with a nitrogen, sulfur or oxygen atom (i.e., a "$C_5$-$C_7$ heterocycloalkyl").

The term "$C_2$-$C_6$-alkynyl" as used herein refers to a linear or branched hydrocarbon having from 2 to 6 carbon atoms and having at least one carbon-carbon triple bond. Representative $C_2$-$C_6$-alkynyl groups include, but are not limited to, acetylenyl, propynyl, 1-butynyl, isobutynyl, sec-butynyl, 1-pentynyl, 2-pentynyl, isopentynyl, 1-hexynyl, 2-hexynyl, 3-hexynyl, and isohexynyl. In one embodiment, the $C_2$-$C_6$-alkynyl group is substituted with one or more of the following groups: halogen, —$N_3$, —$NO_2$, —CN, —OR', —SR', —$SO_2$R', —$SO_2$N(R')$_2$, —N(R')$_2$, —COR', —$CO_2$R', —NR'$CO_2$R', —NR'COR', —NR'CONR', or —CON(R')$_2$, wherein each R' is independently hydrogen or unsubstituted $C_1$-$C_6$-alkyl.

The terms "$C_5$-$C_{10}$-arylalkyl," "$C_5$-$C_{10}$-arylalkenyl," or "$C_5$-$C_{10}$-arylalkynyl" as used herein refer to an alkyl, alkenyl, or alkynyl, respectively, substituted with an aryl group, as those terms are defined herein. Illustrative examples include benzyl, phenethyl, styryl, cinnamyl and the like.

The term "administer", "administering", or "administration", as used herein refers to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "aryl" as used herein refers to an aromatic species containing 1 to 3 aromatic rings, either fused or linked. In one embodiment, the aryl group is independently substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted $C_1$-$C_6$-alkyl; and wherein each V is independently a bond or $C_1$-$C_6$-alkyl. The term "aryl" as used herein, may therefore be understood to refer to substituted aryl, heteroaryl, or substituted heteroaryl groups. A "$C_5$-$C_7$ aryl," for example, has from 5 to 7 carbon atoms, wherein one to three carbon atoms of the aryl are each independently optionally replaced with a nitrogen, sulfur or oxygen atom (i.e., a "$C_5$-$C_7$ heteroaryl" group").

The term "conditions effective to" as used herein refers to synthetic reaction conditions which will be apparent to those skilled in the art.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "carrier", as used herein, encompasses carriers, excipients, and diluents.

The term "prodrug", as used herein means a compound which is convertible in vivo by metabolic means (e.g. by hydrolysis) to a compound of Formula (I).

The term "halogen" as used herein refers to fluorine, chlorine, bromine, and iodine.

The term "isolated and purified" as used herein refers to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "pharmaceutically acceptable salt" as used herein refers to a salt of an acid and a basic nitrogen atom of a compound of an 8-Hydroxyquinoline Compound. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of an 8-Hydroxyquinoline Compound and a hydrate of a pharmaceutically acceptable salt of an 8-Hydroxyquinoline Compound.

The term "phenyl" as used herein refers to a substituted or unsubstituted phenyl group. In one embodiment, the phenyl group is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted $C_1$-$C_6$-alkyl; and wherein each V is independently a bond or $C_1$-$C_6$-alkyl.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The term "treating", with regard to an animal, refers to improving at least one symptom of the animal's disease or disorder. Treating can be curing the disease or condition or improving it.

The following abbreviations are used herein and have the indicated definitions: ACN or MeCN is acetonitrile; DIEA is diisopropyl ethylamine; DMF is dimethylformamide; DMSO is dimethylsulfoxide; HPLC is high-performance liquid chromatography; LC/MS is liquid chromatography/mass spectrometry; NMP is N-methyl-2-pyrrolidone; THF is tetrahydrofuran; and t-BuOK is potassium tert-butoxide.

4.2 8-Hydroxyquinoline Compounds

As stated above, the present invention encompasses 8-Hydroxyquinoline Compounds of Formula (I):

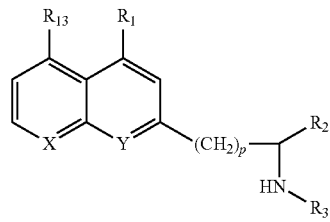

(I)

and pharmaceutically acceptable salts or hydrates thereof, wherein

X is —N— and Y is —$COR_4$, or Y is —N— and X is —$COR_4$;

p is 0 or 1;

$R_1$ and $R_{13}$ are each independently hydrogen, halogen, —$OR_7$, —CN, —$C_1$-$C_6$-alkyl, —$C_2$-$C_6$-alkenyl, —$C_2$-$C_6$-alkynyl, —$NO_2$, —$NR_5R_6$, —$SO_2NR_5R_6$, —$COR_7$, —$COOR_7$, —$C_5$-$C_7$-cycloalkyl or —$C_5$-$C_7$-aryl, wherein (a) one or more of the carbon atoms in the alkyl, alkenyl, alkynyl, cycloalkyl or aryl group is each independently optionally replaced with a nitrogen, sulfur or oxygen atom, and (b) the alkyl, alkenyl, alkynyl, cycloalkyl or aryl is optionally substituted with a halogen or a —$C_1$-$C_3$-alkyl, provided that when X is —N— then $R_{13}$ is hydrogen and when Y is —N— then $R_1$ is hydrogen;

$R_2$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_{10}$-arylalkyl, —$C_5$-$C_{10}$-arylalkenyl, —$C_7$-$C_{12}$-bicyclic hydrocarbon wherein at least one cyclic group is aromatic, $C_9$-$C_{15}$-tricyclic hydrocarbon wherein at least one cyclic group is aromatic or —$COR_7$, wherein (a) at least one of the carbon atoms in the alkyl, alkenyl, alkynyl, aryl, arylalkyl, arylalkenyl, bicyclic hydrocarbon or tricyclic hydrocarbon group is each independently optionally replaced with a nitrogen, sulfur or oxygen atom, and (b) the alkyl, alkenyl, alkynyl, aryl or arylalkyl, arylalkenyl, bicyclic hydrocarbon or tricyclic hydrocarbon group is optionally substituted with at least one hydroxyl, halogen, oxygen, —$C_1$-$C_6$-alkyl, —$C_2$-$C_6$-alkenyl, —$C_2$-$C_6$-alkynyl, —$C_5$-$C_7$-cycloalkyl, —$C_1$-$C_3$-alkyl-$C_5$-$C_7$-cycloalkyl, —$C_5$-$C_7$-aryl, —$C_5$-$C_{10}$-arylalkyl, —$C_5$-$C_{10}$-arylalkenyl, —$C_5$-$C_{10}$-arylalkynyl, —$NO_2$, —$CH_2NR_5R_6$, —$NR_5R_6$, —$NR_5SO_2R_6$, —$SO_2NR_5R_6$, —$SO_2R_7$, —$COR_7$, —$C_1$-$C_3$-alkyl-$COR_7$, —$COOR_7$ or —$CONR_5R_6$, wherein (1) one or more of the carbon atoms in the alkyl, alkenyl, alkynyl, cycloalkyl, aryl, arylalkyl, arylalkenyl or arylalkynyl group is each independently optionally replaced with a nitrogen, sulfur or oxygen atom, and (2) the alkyl, alkenyl, alkynyl, cycloalkyl, aryl arylalkyl, arylalkenyl or arylalkynyl group is optionally substituted with a halogen, a —$C_1$-$C_3$-alkyl or a —$C_5$-$C_7$-aryl;

$R_3$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_7$-cycloalkyl, —$R_8$—$C_5$-$C_7$-cycloalkyl, —$C_5$-$C_{10}$-arylalkyl, —$C_7$-$C_{12}$-bicyclic hydrocarbon or —$R_{12}$—$C_7$-$C_{12}$-bicyclic hydrocarbon wherein at least one cyclic group is aromatic, —$SO_2NR_5R_6$, —$COR_7$, —$COOR_7$, —$CONR_5R_6$, —$COR_8$—B—$R_9$, or —$R_8$—B—$R_9$, wherein (a) one or more of the carbon atoms in the alkyl, alkenyl, alkynyl, cycloalkyl, aryl, arylalkyl or bicyclic hydrocarbon group is each independently optionally replaced with a nitrogen, sulfur or oxygen atom, and (b) the alkyl, alkenyl, alkynyl, cycloalkyl, aryl, arylalkyl or bicyclic hydrocarbon group is optionally substituted with at least one, (e.g., one to three) halogen or a —$C_1$-$C_4$-alkyl that is optionally branched, —$C_2$-$C_3$-alkynyl, —$C_5$-$C_7$-aryl, —$NR_5R_6$, —C≡N, or —$COR_7$;

$R_4$ is hydrogen, —$C_1$-$C_6$-alkyl, —$C_2$-$C_6$-alkenyl, —$C_2$-$C_6$-alkynyl, —$SO_2NR_5R_6$, —$SO_2R_7$, —$COR_7$, —$COOR_7$ or —$CONR_5R_6$, wherein (a) one or more of the carbon atoms in the alkyl, alkenyl, or alkynyl group is each independently optionally replaced with a nitrogen, sulfur or oxygen atom, and (b) the alkyl, alkenyl or alkynyl group is optionally substituted with a halogen or a —$C_1$-$C_3$-alkyl;

$R_5$ and $R_6$ are each independently hydrogen, —$C_1$-$C_6$-alkyl, —$C_2$-$C_6$-alkenyl, —$C_2$-$C_6$-alkynyl, —$COR_7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, an oxygen or a —$C_1$-$C_3$-alkyl;

$R_7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with at least one halogen, a —$C_1$-$C_3$-alkyl, —$C_5$-$C_7$-aryl, or —$NR_5R_6$, —$OR_5$;

$R_8$ is —$C_1$-$C_6$-alkyl, —$C_2$-$C_6$-alkenyl, or —$C_2$-$C_6$-alkynyl, wherein (a) one or more of the carbon atoms in the alkyl, alkenyl or alkynyl, group is each independently optionally replaced with a nitrogen, sulfur or oxygen atom, and (b) the alkyl, alkenyl or alkynyl group is optionally substituted with a halogen or a —$C_1$-$C_3$-alkyl;

$R_9$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_{10}$-arylalkyl or —$C_7$-$C_{12}$-bicyclic hydrocarbon wherein at least one cyclic group is aromatic, wherein (a) one or more of the carbon atoms in the alkyl, alkenyl, alkynyl, aryl, arylalkyl or bicyclic hydrocarbon group is each independently optionally replaced with a nitrogen, sulfur or oxygen atom, and (b) the alkyl, alkenyl, alkynyl, aryl, arylalkyl or bicyclic hydrocarbon group is optionally substituted with at least one halogen, a —$C_1$-$C_4$- alkyl that is optionally branched, a —$C_5$-$C_7$-aryl, B—$C_5$-$C_7$-aryl, $NR_5R_6$, or —$COR_7$, and wherein one to three carbon atoms are each independently optionally replaced with an oxygen or nitrogen atom;

$R_{12}$ is —$CH_2$— or —$CH_2CH_2$—;

B is a bond, —O—, —$NR_7$— or —S—.

In some embodiments of the compound of Formula (I), $R_1$ is a halogen, for example, chlorine, bromine or fluorine.

In other embodiments of the compound of Formula (I), $R_1$ is a —$C_1$-$C_6$-alkyl, for example, —$CH_3$.

In still other embodiments of the compound of Formula (I), $R_1$ is hydrogen.

In other embodiments of the compound of Formula (I), $R_1$ is —$NO_2$.

In other embodiments of the compound of Formula (I), $R_1$ is —$NR_5R_6$, for example, —$NH_2$ or —$N(CH_3)_2$.

In other embodiments, in the compound of Formula (I), $R_1$ is a —$C_5$-$C_7$-cycloalkyl, —$C_5$-$C_7$-heterocycloalkyl, or —$C_5$-$C_7$-heteroaryl, for example,

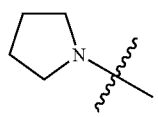 or 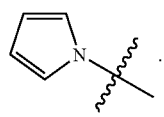.

In addition, compounds according to Formula (I) include those wherein $R_2$ is a —$C_5$-$C_7$-aryl, which is optionally substituted with one to three hydroxyl, halogen, —$C_1$-$C_6$-alkyl, —$C_2$-$C_6$-alkynyl, —$C_5$-$C_7$-aryl, —$C_5$-$C_{10}$-arylalkyl, —$C_5$-$C_{10}$-arylalkenyl, —$C_5$-$C_{10}$-arylalkynyl, —$NO_2$, —$C_5$-$C_7$-cycloalkyl, —$C_1$-$C_3$-alkyl-$C_5$-$C_7$-cycloalkyl, $BR_9$, —$COR_7$, —$C_1$-$C_3$-alkyl-$COR_7$, —$CH_2NR_5R_6$, or —$NR_5R_6$, and wherein one to three carbon atoms of the aryl or the substituent are each independently optionally replaced with a nitrogen, sulfur or oxygen atom, for example, and the substituent is optionally branched and optionally substituted with one to three halogen atoms or —$C_1$-$C_3$-alkyl groups. Examples of such $R_2$ include:

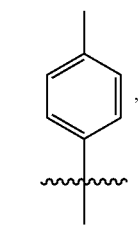, 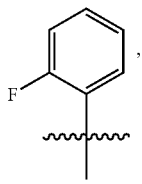,

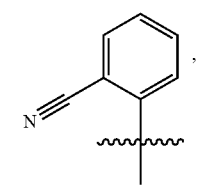, 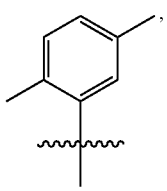,

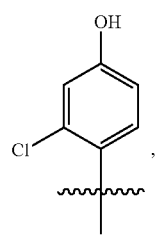, 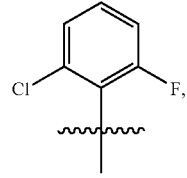,

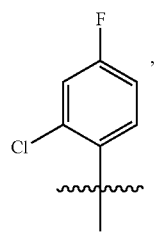, 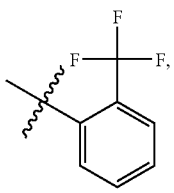,

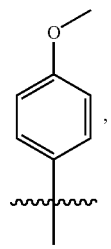, 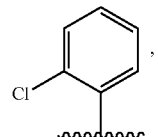, 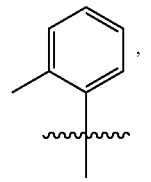, 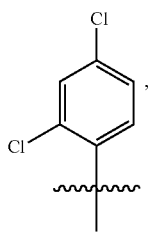, 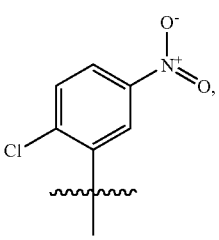,

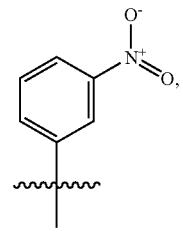, 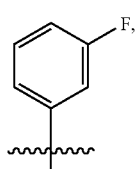,

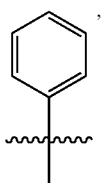, 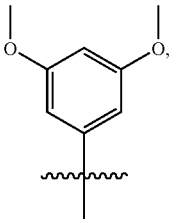,

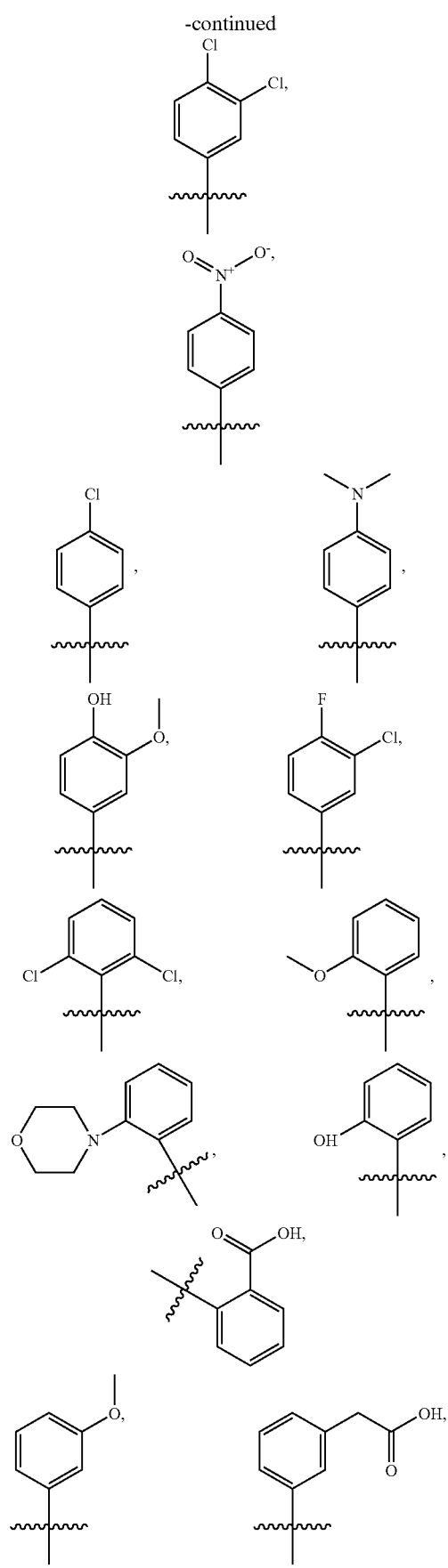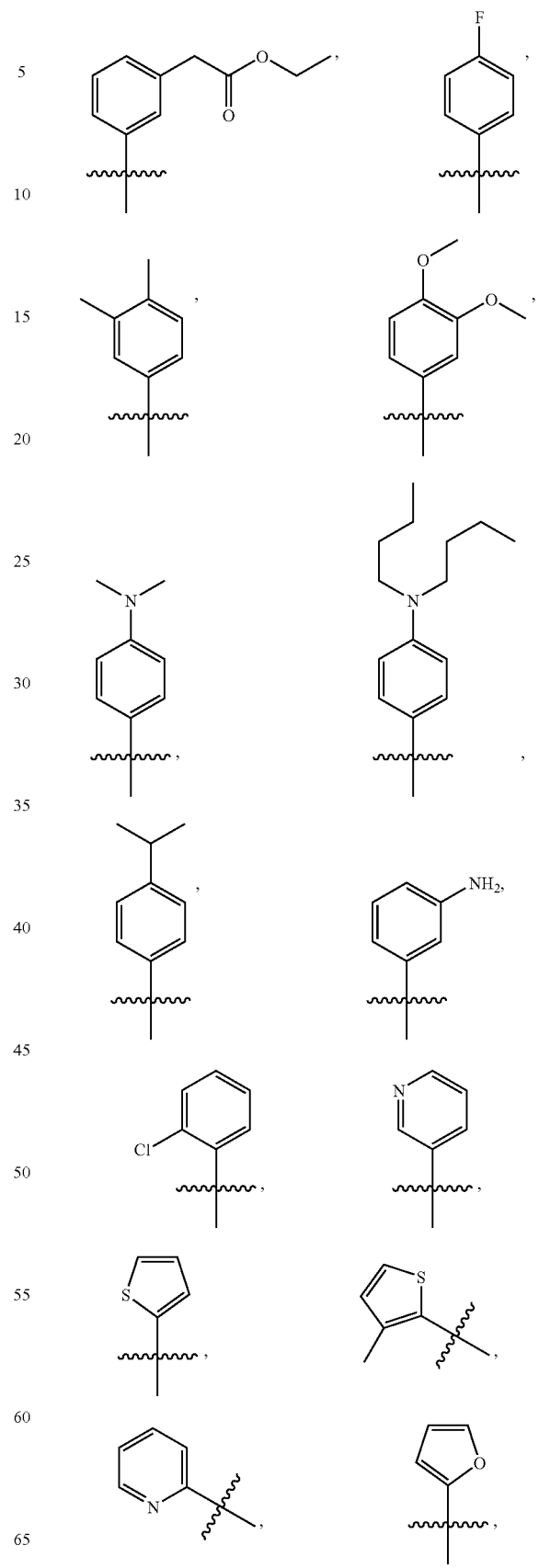

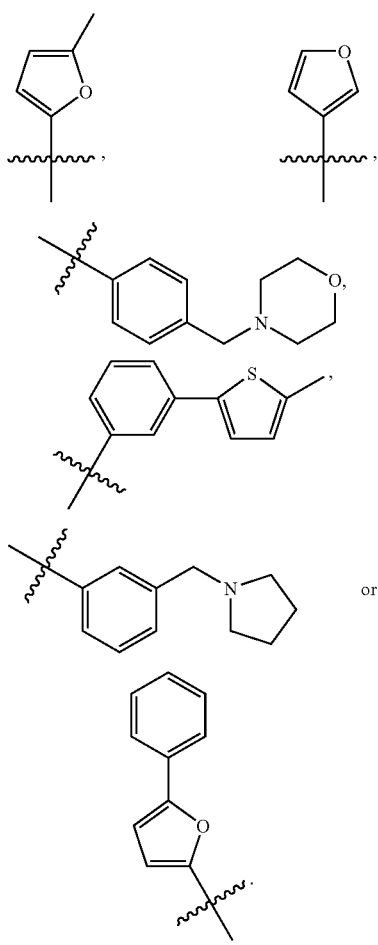

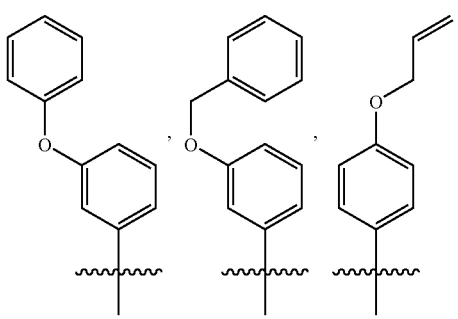

In other embodiments, R$_2$ is a —C$_5$-C$_7$-aryl, wherein one to three of the carbon atoms is each independently optionally replaced with a nitrogen, sulfur or oxygen atom, and the aryl group is optionally substituted with one or more —C$_5$-C$_7$-aryl, —C$_5$-C$_{10}$-arylalkyl, —C$_5$-C$_{10}$-arylalkenyl, —C$_5$-C$_{10}$-arylalkynyl, which optionally (1) has one to three of the carbon atoms each independently optionally replaced with a nitrogen, sulfur or oxygen atom, and (2) is substituted with a halogen, —C$_1$-C$_3$-alkyl that optionally has one to three of the carbon atoms optionally independently replaced with a nitrogen, sulfur or oxygen atom, for example:

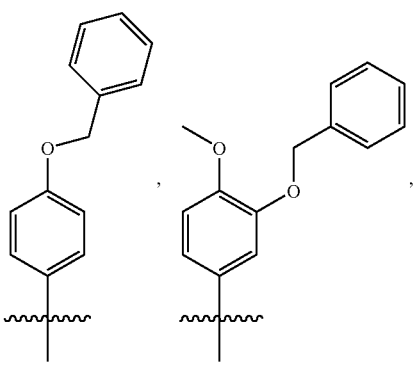

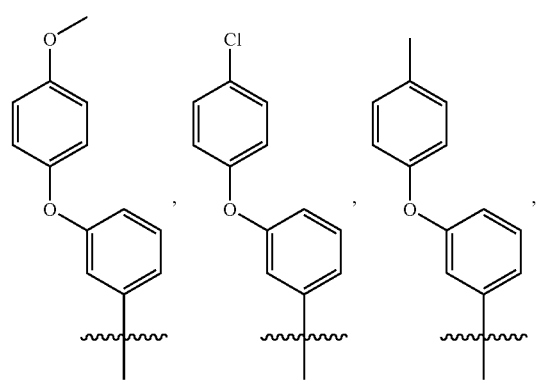

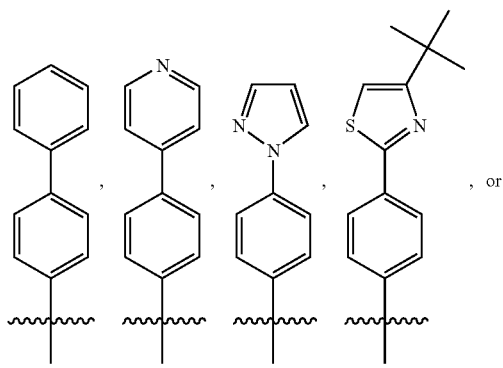

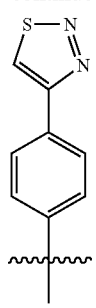

Also included are compounds of Formula (I), wherein $R_2$ is a —$C_7$-$C_{12}$-bicyclic or a $C_9$-$C_{15}$-tricyclic hydrocarbon wherein at least one cyclic group is aromatic, one to three carbon atoms are each independently, optionally replaced with a nitrogen, sulfur or oxygen atom, and the hydrocarbon group is optionally substituted with one or more oxygen atoms, halogen atoms, or one to three —$C_1$-$C_6$-alkyl groups having one to three carbon atoms optionally replaced with an oxygen, for example:

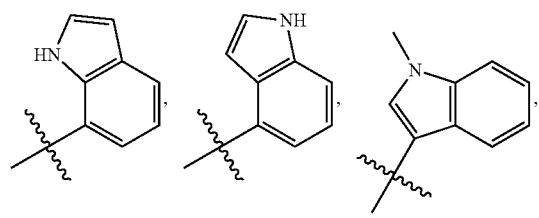

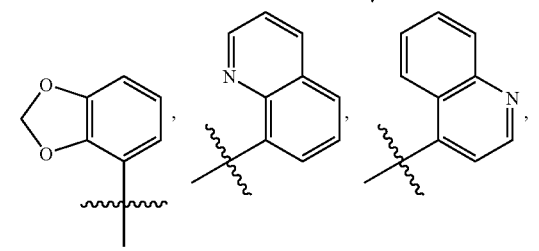

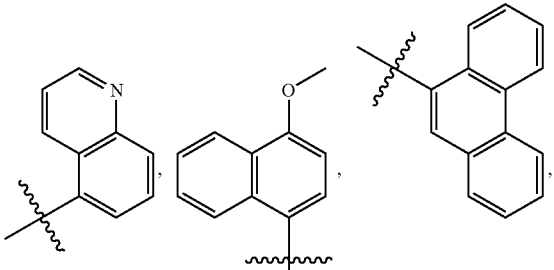

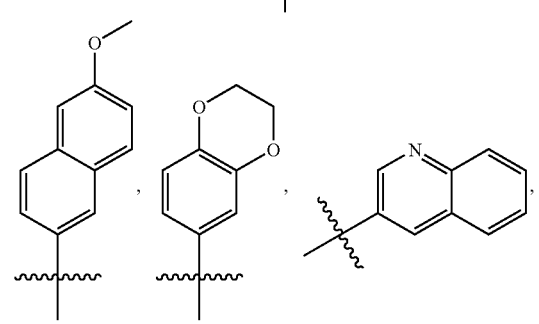

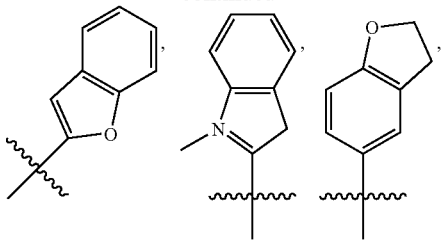

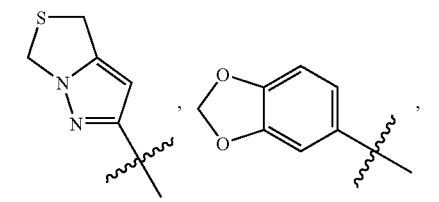

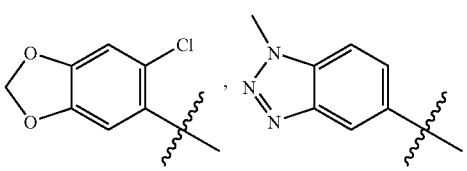

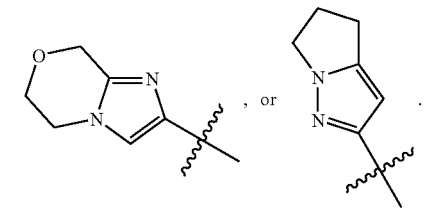

In addition, compounds of Formula (I) are those wherein $R_2$ is a —$C_2$-$C_6$-alkenyl, for example:

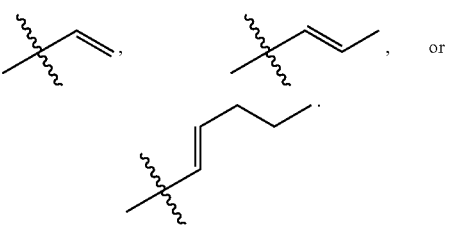

In other embodiments, $R_2$ is a —$C_5$-$C_{10}$-arylalkyl or —$C_5$-$C_{10}$-arylalkenyl, which is optionally substituted with a —$C_1$-$C_6$-alkyl, and wherein one to three carbon atoms of the alkyl is optionally replaced with an oxygen, for example:

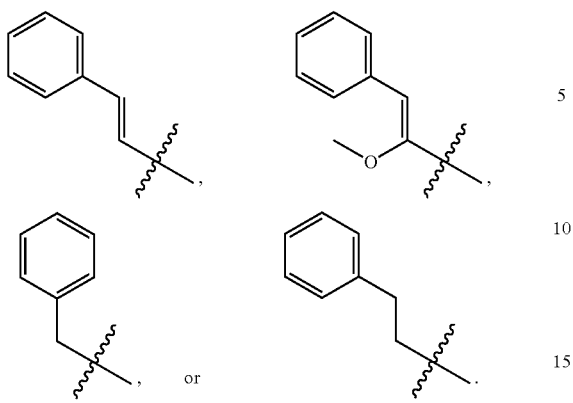

Further compounds of Formula (I) include those wherein $R_2$ is a —$C_5$-$C_7$-aryl, which is optionally substituted with —$CH_2NR_5R_6$, —$NR_5R_6$ or —$NR_5SO_2R_6$, wherein one to three of the carbon atoms is each independently optionally replaced with a nitrogen or oxygen atom, for example:

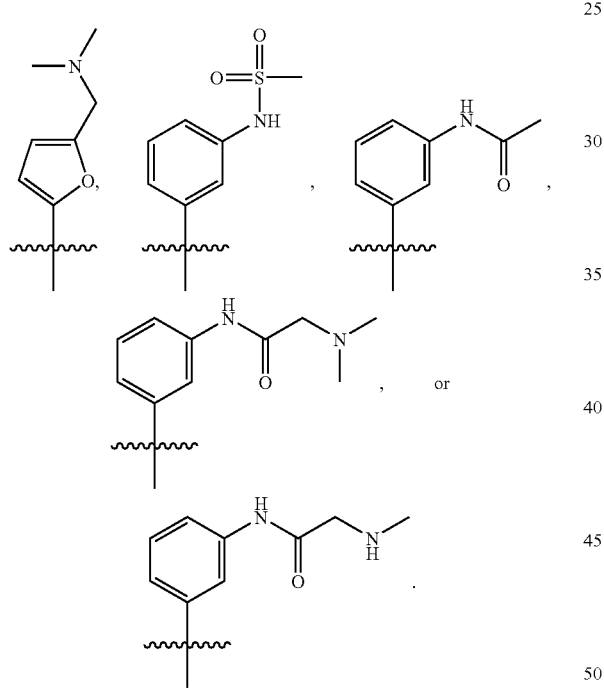

Particular embodiments of the compounds of Formula (I) include those wherein $R_1$ and $R_2$ are, in combination, as specified in the above identified embodiments.

Additionally, compounds of Formula (I) are those wherein $R_3$ is —$COR_8$—B—$R_9$ or —$R_8$—B—$R_9$, wherein $R_8$ is a —$C_1$-$C_3$-alkyl, $R_9$ is a —$C_5$-$C_7$-aryl or $C_7$-$C_{12}$-bicyclic hydrocarbon wherein at least one cyclic group is aromatic, wherein the aryl or bicyclic hydrocarbon is optionally substituted with one to three halogen atoms, —$C_1$-$C_4$-alkyl groups, —$C_5$-$C_7$-cycloalkyl groups, —$C_5$-$C_7$-aryl groups, —B—$C_5$-$C_7$-aryl groups, —$NR_5R_6$ groups, or —$COR_7$ groups and wherein one to three carbon atoms in the substituents are each independently optionally replaced with an oxygen or nitrogen atom, and B is a bond or —O—, for example:

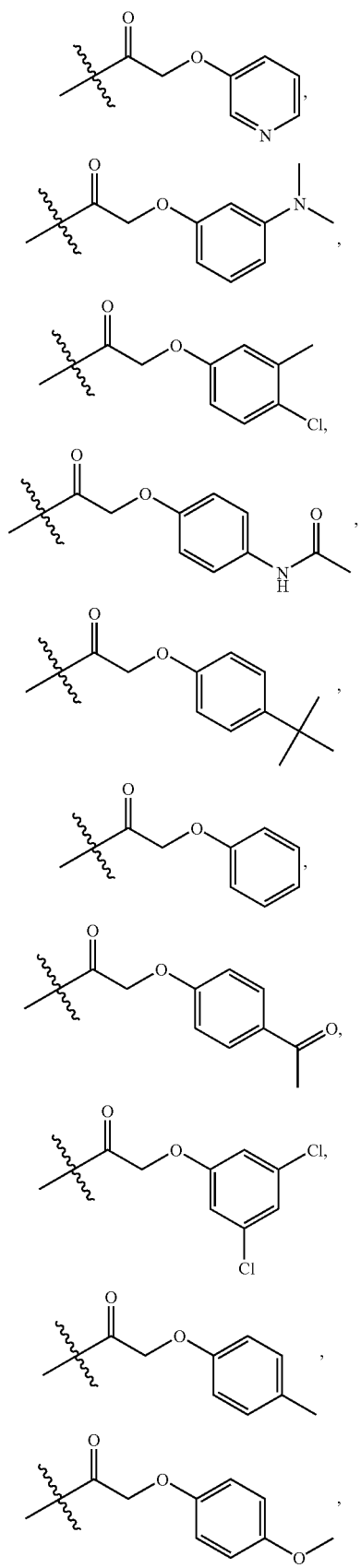

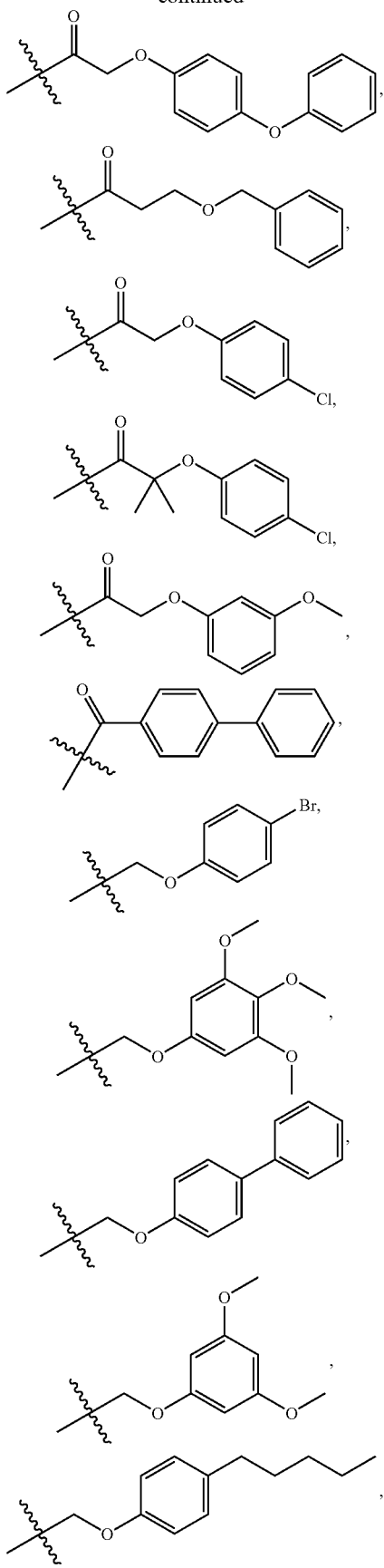

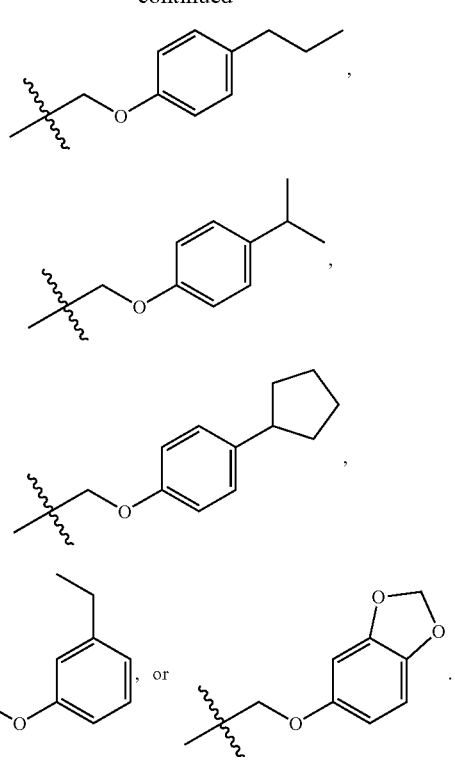

In other embodiments, $R_3$ is $-COR_8-B-R_9$, $-R_8-C_5$-$C_7$-cycloalkyl, or $-R_8-B-R_9$, wherein $R_8$ is a $-C_1$-$C_3$-alkyl, $R_7$ is a $-C_1$-$C_3$-alkyl or hydrogen; $R_9$ is a $-C_5$-$C_7$-aryl, $-R_{12}-C_5$-$C_7$-cycloalkyl, or $-R_{12}-C_7$-$C_{12}$-bicyclic hydrocarbon wherein at least one cyclic group is aromatic and $R_{12}$ is $-CH_2-$, wherein (a) one or more of the carbon atoms are each independently optionally replaced with a nitrogen or oxygen atom, and (b) the cycloalkyl, aryl or bicyclic hydrocarbon group is optionally substituted with one to three halogen, $-C_1$-$C_4$-alkyl groups, $-C_2$-$C_3$-alkynyl groups, $-C_5$-$C_7$-aryl groups, $-NR_5R_6$, $-C\equiv N$ or $-COR_7$, or any combination thereof; and B is $-NR_7-$, for example:

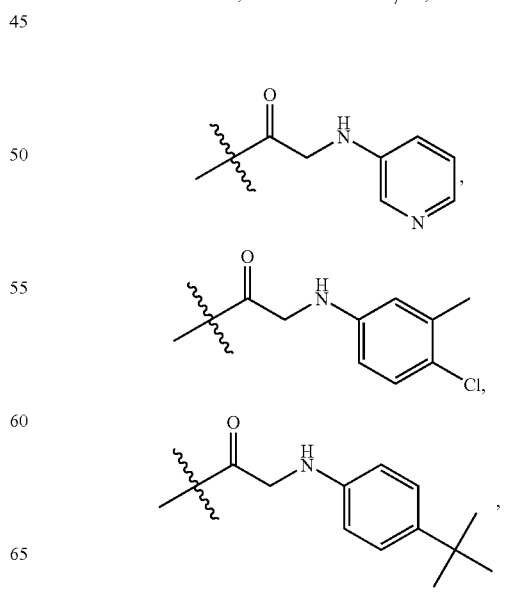

-continued

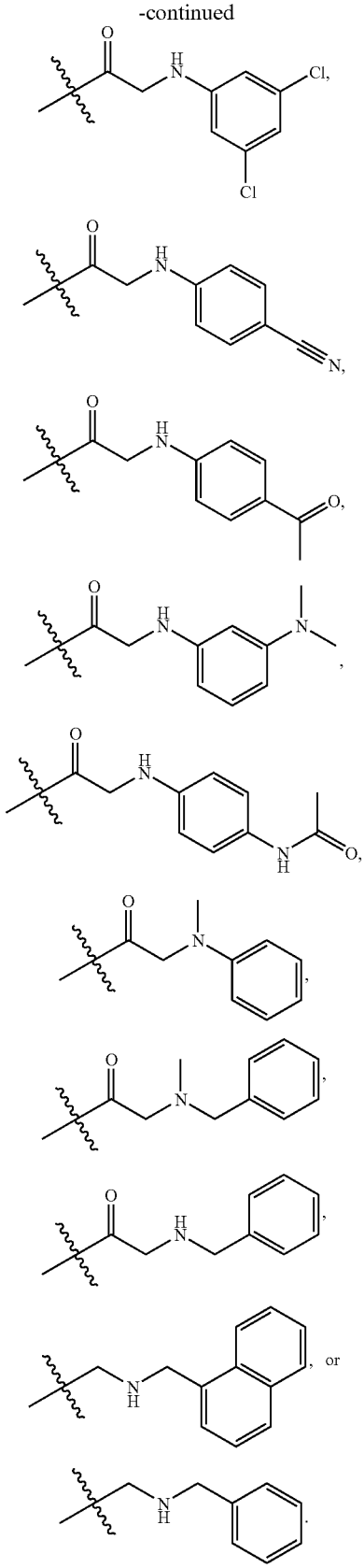

Other compounds include those wherein $R_3$ is —$R_8$—$C_5$-$C_7$-cycloalkyl or —$R_8$—B—$R_9$, wherein $R_8$ is a —$C_1$-$C_3$-alkyl, B is —$NR_7$—, $R_7$ is a —$C_1$-$C_3$-alkyl or hydrogen, $R_9$ is a —$C_5$-$C_7$-aryl or a —$R_{12}$—$C_7$-$C_{12}$-bicyclic hydrocarbon wherein at least one cyclic group is aromatic and $R_{12}$ is —$CH_2$—, wherein (a) one or more of the carbon atoms are each independently optionally replaced with a nitrogen or oxygen atom, and (b) the cycloalkyl, aryl or bicyclic hydrocarbon group is optionally substituted with a —$C_1$-$C_3$-alkyl or a —$C_5$-$C_7$-aryl, for example:

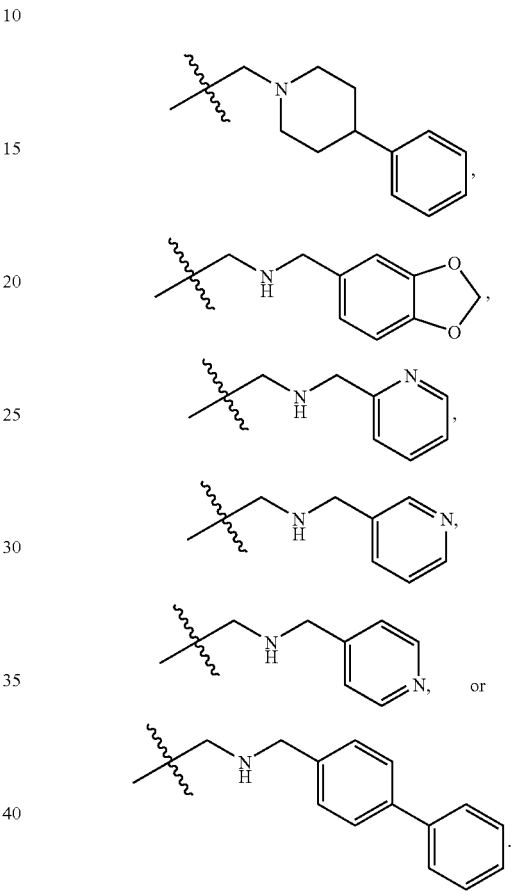

Alternatively, compounds of Formula (I) include those wherein $R_3$ is —$COR_7$, wherein $R_7$ is a —$C_1$-$C_6$-alkyl, —$C_5$-$C_7$-aryl or —$C_5$-$C_{10}$-arylalkyl, for example:

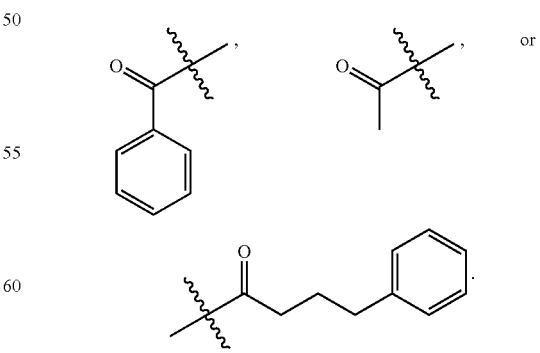

Also included are compounds of Formula (I) wherein $R_3$ is a —$C_5$-$C_{10}$-arylalkyl, and a carbon atom is optionally replaced with an oxygen atom, for example:

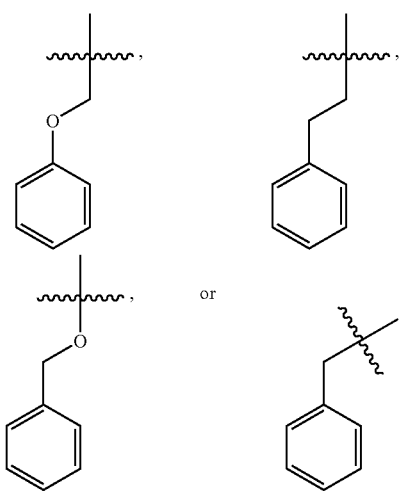

Compounds according to Formula (I) also include those wherein $R_3$ is a —$C_1$-$C_6$-alkyl optionally substituted with a halogen, for example:

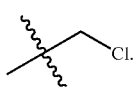

Particular embodiments of the compounds of Formula (I) include those wherein $R_1$, $R_2$ and $R_3$ are, in combination, as specified in the above identified embodiments.

Additionally, compounds according to Formula (I) include those wherein $R_4$ is —$C_1$-alkyl.

Additionally, compounds according to Formula (I) include those wherein $R_4$ is hydrogen.

Alternatively, compounds according to Formula (I) also include those wherein $R_4$ is —$SO_2R_7$.

Particular embodiments of the compounds of Formula (I) include those wherein $R_1$, $R_2$, $R_3$ and $R_4$ are, in combination, as specified in the above identified embodiments.

The 8-hydroxyquinoline Compounds of the invention may contain one or more asymmetric centers, and can thus give rise to optical isomers and diastereomers. While depicted without respect to stereochemistry in the compounds or pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is provided, it can in some embodiments be provided substantially free of its corresponding opposite enantiomer.

In addition, the compounds and pharmaceutically acceptable salts of compounds of the present invention may exist as tautomers. Such tautomers can be transient or isolatable as a stable product. These tautomers are within the scope of the present invention.

The following are examples of compounds of Formula (I):
N-[(5-chloro-8-hydroxyquinolin-7-yl)(4-methoxyphenyl)methyl]-2-(pyridin-3-yloxy)acetamide
N-[(5-chloro-8-hydroxyquinolin-7-yl)(4-methoxyphenyl)methyl]-2-[3-(dimethylamino)phenoxy]acetamide
N-[(5-chloro-8-hydroxyquinolin-7-yl)(4-methoxyphenyl)methyl]-2-(4-chloro-3-methylphenoxy)acetamide
2-[4-(acetylamino)phenoxy]-N-[(5-chloro-8-hydroxyquinolin-7-yl)(4-methoxyphenyl)methyl]acetamide
N-[(5-chloro-8-hydroxyquinolin-7-yl)(2-chlorophenyl)methyl]-2-[3-(dimethylamino)phenoxy]acetamide
N-[(5-chloro-8-hydroxyquinolin-7-yl)(2-chlorophenyl)methyl]-2-(4-chloro-3-methylphenoxy)acetamide
2-(4-tert-butylphenoxy)-N-[(5-chloro-8-hydroxyquinolin-7-yl)(2-chlorophenyl)methyl]acetamide
2-[4-(acetylamino)phenoxy]-N-[(5-chloro-8-hydroxyquinolin-7-yl)(2-chlorophenyl)methyl]acetamide
N-[(5-chloro-8-hydroxyquinolin-7-yl)(2-methylphenyl)methyl]-2-phenoxyacetamide
N-[(5-chloro-8-hydroxyquinolin-7-yl)(3-nitrophenyl)methyl]-2-(pyridin-3-yloxy)acetamide
2-(4-acetylphenoxy)-N-[(5-chloro-8-hydroxyquinolin-7-yl)(3-nitrophenyl)methyl]acetamide
N-[(5-chloro-8-hydroxyquinolin-7-yl)(3-nitrophenyl)methyl]-2-(4-chloro-3-methylphenoxy)acetamide
N-[(5-chloro-8-hydroxyquinolin-7-yl)(3-nitrophenyl)methyl]-2-(3,5-dichlorophenoxy)acetamide
N-[(5-chloro-8-hydroxyquinolin-7-yl)(3-fluorophenyl)methyl]-2-(pyridin-3-yloxy)acetamide
N-[(5-chloro-8-hydroxyquinolin-7-yl)(3-fluorophenyl)methyl]-2-[3-(dimethylamino)phenoxy]acetamide
2-(4-tert-butylphenoxy)-N-[(5-chloro-8-hydroxyquinolin-7-yl)(3-fluorophenyl)methyl]acetamide
2-[4-(acetylamino)phenoxy]-N-[(5-chloro-8-hydroxyquinolin-7-yl)(3-fluorophenyl)methyl]acetamide
N1-[(5-chloro-8-hydroxyquinolin-7-yl)(2-chlorophenyl)methyl]-N2-pyridin-3-ylglycinamide
N1-[(5-chloro-8-hydroxyquinolin-7-yl)(2-chlorophenyl)methyl]-N2-(4-chloro-3-methylphenyl)glycinamide
N2-(4-tert-butylphenyl)-N1-[(5-chloro-8-hydroxyquinolin-7-yl)(2-chlorophenyl)methyl]glycinamide
N1-[(5-chloro-8-hydroxyquinolin-7-yl)(2-chlorophenyl)methyl]-N2-(3,5-dichlorophenyl)glycinamide
N1-[(5-chloro-8-hydroxyquinolin-7-yl)(4-methylphenyl)methyl]-N2-pyridin-3-ylglycinamide
N1-[(5-chloro-8-hydroxyquinolin-7-yl)(4-methylphenyl)methyl]-N2-(4-cyanophenyl)glycinamide
N2-(4-acetylphenyl)-N-1-[(5-chloro-8-hydroxyquinolin-7-yl)(4-methylphenyl)methyl]glycinamide
N1-[(5-chloro-8-hydroxyquinolin-7-yl)(4-methylphenyl)methyl]-N2-[3-(dimethylamino)phenyl]glycinamide
N1-[(5-chloro-8-hydroxyquinolin-7-yl)(4-methylphenyl)methyl]-N2-(4-chloro-3-methylphenyl)glycinamide
N2-(4-tert-butylphenyl)-N-1-[(5-chloro-8-hydroxyquinolin-7-yl)(4-methylphenyl)methyl]glycinamide
N1-[(5-chloro-8-hydroxyquinolin-7-yl)(3-nitrophenyl)methyl]-N2-pyridin-3-ylglycinamide
N2-(4-acetylphenyl)-N-1-[(5-chloro-8-hydroxyquinolin-7-yl)(3-nitrophenyl)methyl]glycinamide
N1-[(5-chloro-8-hydroxyquinolin-7-yl)(3-nitrophenyl)methyl]-N2-(4-chloro-3-methylphenyl)glycinamide
N2-[4-(acetylamino)phenyl]-N-1-[(5-chloro-8-hydroxyquinolin-7-yl)(3-nitrophenyl)methyl]glycinamide
N1-[(5-chloro-8-hydroxyquinolin-7-yl)(3-fluorophenyl)methyl]-N2-pyridin-3-ylglycinamide
N1-[(5-chloro-8-hydroxyquinolin-7-yl)(3-fluorophenyl)methyl]-N2-(4-chloro-3-methylphenyl)glycinamide
N-[(5-chloro-8-hydroxyquinolin-7-yl)(2-fluorophenyl)methyl]-2-phenoxyacetamide
N-[(5-chloro-8-hydroxyquinolin-7-yl)(2-cyanophenyl)methyl]-2-phenoxyacetamide
N-[(5-chloro-8-hydroxyquinolin-7-yl)(2,4-dimethylphenyl)methyl]-2-phenoxyacetamide N-[(5-chloro-8-hydroxyquinolin-7-yl)(2,5-dimethylphenyl)methyl]-2-phenoxyacetamide
N-[(5-chloro-8-hydroxyquinolin-7-yl)(2-nitrophenyl)methyl]-2-phenoxyacetamide
N-[(2-chloro-4-hydroxyphenyl)(5-chloro-8-hydroxyquinolin-7-yl)methyl]-2-phenoxyacetamide
N-[(2-chloro-6-fluorophenyl)(5-chloro-8-hydroxyquinolin-7-yl)methyl]-2-phenoxyacetamide
N-[(2-chloro-4-fluorophenyl)(5-chloro-8-hydroxyquinolin-7-yl)methyl]-2-phenoxyacetamide
N-{(5-chloro-8-hydroxyquinolin-7-yl)[2-(trifluoromethyl)phenyl]methyl}-2-phenoxyacetamide
N-[(5-chloro-8-hydroxyquinolin-7-yl)(2,4-dichlorophenyl)methyl]-2-phenoxyacetamide
N-[(5-chloro-8-hydroxyquinolin-7-yl)(2-chloro-5-nitrophenyl)methyl]-2-phenoxyacetamide
N-[(2-chlorophenyl)(8-hydroxy-5-methylquinolin-7-yl)methyl]-2-phenoxyacetamide
N-[(8-hydroxy-5-methylquinolin-7-yl)(3-nitrophenyl)methyl]-2-phenoxyacetamide
N-[(8-hydroxy-5-methylquinolin-7-yl)(2-methylphenyl)methyl]-2-phenoxyacetamide
N-[(5-bromo-8-hydroxyquinolin-7-yl)(2-chlorophenyl)methyl]-2-phenoxyacetamide
N-[(5-bromo-8-hydroxyquinolin-7-yl)(3-nitrophenyl)methyl]-2-phenoxyacetamide
N-[(5-bromo-8-hydroxyquinolin-7-yl)(2-methylphenyl)methyl]-2-phenoxyacetamide
N-[(5-chloro-8-hydroxyquinolin-7-yl)(2-chlorophenyl)methyl]-N2-methyl-N-2-phenylglycinamide
N2-benzyl-N1-[(5-chloro-8-hydroxyquinolin-7-yl)(2-chlorophenyl)methyl]-N-2-methylglycinamide
N2-benzyl-N1-[(5-chloro-8-hydroxyquinolin-7-yl)(2-chlorophenyl)methyl]glycinamide
N1-[(5-chloro-8-hydroxyquinolin-7-yl)(3-fluorophenyl)methyl]-N2-methyl-N-2-phenylglycinamide
N2-benzyl-N1-[(5-chloro-8-hydroxyquinolin-7-yl)(3-fluorophenyl)methyl]-N-2-methylglycinamide
N2-benzyl-N1-[(5-chloro-8-hydroxyquinolin-7-yl)(3-fluorophenyl)methyl]glycinamide
2-(benzyloxy)-N-[(5-chloro-8-hydroxyquinolin-7-yl)(3-fluorophenyl)methyl]acetamide
N1-[(5-chloro-8-hydroxyquinolin-7-yl)(4-methylphenyl)methyl]-N2-methyl-N-2-phenylglycinamide
N2-benzyl-N1-[(5-chloro-8-hydroxyquinolin-7-yl)(4-methylphenyl)methyl]-N-2-methylglycinamide
N2-benzyl-N1-[(5-chloro-8-hydroxyquinolin-7-yl)(4-methylphenyl)methyl]glycinamide
2-(benzyloxy)-N-[(5-chloro-8-hydroxyquinolin-7-yl)(4-methylphenyl)methyl]acetamide
N1-[(5-chloro-8-hydroxyquinolin-7-yl)(3-nitrophenyl)methyl]-N2-methyl-N-2-phenylglycinamide
N2-benzyl-N1-[(5-chloro-8-hydroxyquinolin-7-yl)(3-nitrophenyl)methyl]-N-2-methylglycinamide
N2-benzyl-N1-[(5-chloro-8-hydroxyquinolin-7-yl)(3-nitrophenyl)methyl]glycinamide
N-[(8-hydroxyquinolin-7-yl)(phenyl)methyl]benzamide
N-[(8-hydroxyquinolin-7-yl)(phenyl)methyl]acetamide
N-[(5-chloro-8-hydroxyquinolin-7-yl)(phenyl)methyl]benzamide
N-[(5-chloro-8-hydroxyquinolin-7-yl)(phenyl)methyl]acetamide
N-[(5-chloro-8-hydroxyquinolin-7-yl)(pyridin-3-yl)methyl]-2-phenoxyacetamide
N-[(5-chloro-8-hydroxyquinolin-7-yl)(2-thienyl)methyl]-2-phenoxyacetamide
N-[(5-chloro-8-hydroxyquinolin-7-yl)(3,5-dimethoxyphenyl)methyl]-2-phenoxyacetamide
N-[(5-chloro-8-hydroxyquinolin-7-yl)(3,4-dichlorophenyl)methyl]-2-phenoxyacetamide
N-[(8-hydroxyquinolin-7-yl)(4-methoxyphenyl)methyl]-2-(4-methylphenoxy)acetamide
N-[(8-hydroxyquinolin-7-yl)(phenyl)methyl]-2-(4-methoxyphenoxy)acetamide
N-[(8-hydroxyquinolin-7-yl)(4-methoxyphenyl)methyl]-2-(4-phenoxyphenoxy)acetamide
N-[(8-hydroxyquinolin-7-yl)(phenyl)methyl]-2-(4-methylphenoxy)acetamide
N-[(8-hydroxyquinolin-7-yl)(4-methoxyphenyl)methyl]-2-(4-methoxyphenoxy)acetamide
N-[(8-hydroxyquinolin-7-yl)(phenyl)methyl]-2-(4-phenoxyphenoxy)acetamide
N-[(5-chloro-8-hydroxyquinolin-7-yl)(4-methoxyphenyl)methyl]-2-(4-methylphenoxy)acetamide
N-[(5-chloro-8-hydroxyquinolin-7-yl)(phenyl)methyl]-2-(4-methoxyphenoxy)acetamide
N-[(5-chloro-8-hydroxyquinolin-7-yl)(4-methoxyphenyl)methyl]-2-(4-phenoxyphenoxy)acetamide
N-[(5-chloro-8-hydroxyquinolin-7-yl)(phenyl)methyl]-2-(4-methylphenoxy)acetamide
N-[(8-hydroxyquinolin-7-yl)(4-nitrophenyl)methyl]-2-phenoxyacetamide
N-[(5-chloro-8-hydroxyquinolin-7-yl)(phenyl)methyl]-2-(4-phenoxyphenoxy)acetamide
N-[(8-hydroxyquinolin-7-yl)(phenyl)methyl]-2-phenoxyacetamide
N-[(8-hydroxyquinolin-7-yl)(4-methylphenyl)methyl]-2-phenoxyacetamide
N-[(8-hydroxyquinolin-7-yl)(4-methoxyphenyl)methyl]-2-phenoxyacetamide
N-[(2-chlorophenyl)(8-hydroxyquinolin-7-yl)methyl]-2-phenoxyacetamide
N-[(4-chlorophenyl)(8-hydroxyquinolin-7-yl)methyl]-2-phenoxyacetamide
N-[(5-chloro-8-hydroxyquinolin-7-yl)(phenyl)methyl]-2-phenoxyacetamide
N-[(5-chloro-8-hydroxyquinolin-7-yl)(4-methylphenyl)methyl]-2-phenoxyacetamide
N-[(5-chloro-8-hydroxyquinolin-7-yl)(2-chlorophenyl)methyl]-2-phenoxyacetamide
N-[(5-chloro-8-hydroxyquinolin-7-yl)(4-chlorophenyl)methyl]-2-phenoxyacetamide
N-[(5-chloro-8-hydroxyquinolin-7-yl)(3-nitrophenyl)methyl]-2-phenoxyacetamide
N-[(5-chloro-8-hydroxyquinolin-7-yl)(4-nitrophenyl)methyl]-2-phenoxyacetamide
N-[(3-fluorophenyl)(8-hydroxyquinolin-7-yl)methyl]-2-phenoxyacetamide
N-[[4-(dimethylamino)phenyl](8-hydroxyquinolin-7-yl)methyl]-2-phenoxyacetamide
N-[(5-chloro-8-hydroxyquinolin-7-yl)(4-hydroxy-3-methoxyphenyl)methyl]-2-phenoxyacetamide
N-[(5-chloro-8-hydroxyquinolin-7-yl)(phenyl)methyl]-2-(4-chlorophenoxy)acetamide
N-[(5-chloro-8-hydroxyquinolin-7-yl)(3-fluorophenyl)methyl]-2-phenoxyacetamide
N-[(3-chloro-4-fluorophenyl)(5-chloro-8-hydroxyquinolin-7-yl)methyl]-2-phenoxyacetamide
N-[(5-chloro-8-hydroxyquinolin-7-yl)(2,6-dichlorophenyl)methyl]-2-phenoxyacetamide
N-[(5-chloro-8-hydroxyquinolin-7-yl)(phenyl)methyl]-2-(pyridin-3-yloxy)acetamide N-[(5-chloro-8-hydroxyquinolin-7-yl)(4-methoxyphenyl)methyl]-2-(3-methoxyphenoxy)acetamide
2-(4-tert-butylphenoxy)-N-[(5-chloro-8-hydroxyquinolin-7-yl)(4-methoxyphenyl)methyl]acetamide
N-[(2-chlorophenyl)(8-hydroxy-5-nitroquinolin-7-yl)methyl]-2-phenoxyacetamide
N-[(8-hydroxy-5-nitroquinolin-7-yl)(2-methylphenyl)methyl]-2-phenoxyacetamide
N-[(8-hydroxy-5-nitroquinolin-7-yl)(phenyl)methyl]-2-phenoxyacetamide
N-[(5-fluoro-8-hydroxyquinolin-7-yl)(phenyl)methyl]-2-phenoxyacetamide
N-[(5-chloro-8-hydroxyquinolin-7-yl)(2-methylphenyl)methyl]-4-phenylbutanamide
N-[(5-chloro-8-hydroxyquinolin-7-yl)(2-chlorophenyl)methyl]-4-phenylbutanamide
N-[(5-chloro-8-hydroxyquinolin-7-yl)(4-methylphenyl)methyl]-4-phenylbutanamide
N-[(5-chloro-8-hydroxyquinolin-7-yl)(3-nitrophenyl)methyl]-4-phenylbutanamide
N-[(5-chloro-8-methoxyquinolin-7-yl)(phenyl)methyl]-2-phenoxyacetamide
N-[(5-chloro-8-methoxyquinolin-7-yl)(2-chlorophenyl)methyl]-2-phenoxyacetamide
N—[(S)-(5-chloro-8-hydroxyquinolin-7-yl)(2-chlorophenyl)methyl]-2-phenoxyacetamide
N—[(R)-(5-chloro-8-hydroxyquinolin-7-yl)(2-chlorophenyl)methyl]-2-phenoxyacetamide
N—[(R)-(5-chloro-8-hydroxyquinolin-7-yl)(phenyl)methyl]-2-phenoxyacetamide
N—[(S)-(5-chloro-8-hydroxyquinolin-7-yl)(phenyl)methyl]-2-phenoxyacetamide
N-[(5-chloro-8-hydroxyquinolin-7-yl)(2-methoxyphenyl)methyl]-2-phenoxyacetamide
N-[(5-chloro-8-hydroxyquinolin-7-yl)(2-morpholin-4-ylphenyl)methyl]-2-phenoxyacetamide
N-[(5-chloro-8-hydroxyquinolin-7-yl)(2-hydroxyphenyl)methyl]-2-phenoxyacetamide
2-{(5-chloro-8-hydroxyquinolin-7-yl)[(phenoxyacetyl)amino]methyl}benzoic acid
N-[(5-chloro-8-hydroxyquinolin-7-yl)(3-methoxyphenyl)methyl]-2-phenoxyacetamide
ethyl(3-{(5-chloro-8-hydroxyquinolin-7-yl)[(phenoxyacetyl)amino]methyl}phenyl)acetate
N-{(5-chloro-8-hydroxyquinolin-7-yl)[3-(4-methoxyphenoxy)phenyl]methyl}-2-phenoxyacetamide
N-{(5-chloro-8-hydroxyquinolin-7-yl)[3-(4-chlorophenoxy)phenyl]methyl}-2-phenoxyacetamide
N-{(5-chloro-8-hydroxyquinolin-7-yl)[3-(4-methylphenoxy)phenyl]methyl}-2-phenoxyacetamide
N-[(5-chloro-8-hydroxyquinolin-7-yl)(3-phenoxyphenyl)methyl]-2-phenoxyacetamide
N-[[3-(benzyloxy)phenyl](5-chloro-8-hydroxyquinolin-7-yl)methyl]-2-phenoxyacetamide
N-[(5-chloro-8-hydroxyquinolin-7-yl)(4-fluorophenyl)methyl]-2-phenoxyacetamide
N-{(5-chloro-8-hydroxyquinolin-7-yl)[4-(dimethylamino)phenyl]methyl}-2-phenoxyacetamide
N-{(5-chloro-8-hydroxyquinolin-7-yl)[4-(diethylamino)phenyl]methyl}-2-phenoxyacetamide
N-{(5-chloro-8-hydroxyquinolin-7-yl)[4-(dibutylamino)phenyl]methyl}-2-phenoxyacetamide
N-[(5-chloro-8-hydroxyquinolin-7-yl)(4-isopropylphenyl)methyl]-2-phenoxyacetamide
N-[[4-(allyloxy)phenyl](5-chloro-8-hydroxyquinolin-7-yl)methyl]-2-phenoxyacetamide
N-[(4-butoxyphenyl)(5-chloro-8-hydroxyquinolin-7-yl)methyl]-2-phenoxyacetamide
N-[(5-chloro-8-hydroxyquinolin-7-yl)(4-hex-1-yn-1-ylphenyl)methyl]-2-phenoxyacetamide
N-{(5-chloro-8-hydroxyquinolin-7-yl)[4-(phenylethynyl)phenyl]methyl}-2-phenoxyacetamide
N-[[4-(benzyloxy)phenyl](5-chloro-8-hydroxyquinolin-7-yl)methyl]-2-phenoxyacetamide
N-[biphenyl-4-yl(5-chloro-8-hydroxyquinolin-7-yl)methyl]-2-phenoxyacetamide
N-[(5-chloro-8-hydroxyquinolin-7-yl)(4-pyridin-4-ylphenyl)methyl]-2-phenoxyacetamide
N-{(5-chloro-8-hydroxyquinolin-7-yl)[4-(1H-pyrazol-1-yl)phenyl]methyl}-2-phenoxyacetamide
N-[[4-(4-tert-butyl-1,3-thiazol-2-yl)phenyl] (5-chloro-8-hydroxyquinolin-7-yl)methyl]-2-phenoxyacetamide
N-{(5-chloro-8-hydroxyquinolin-7-yl)[4-(1,2,3-thiadiazol-4-yl)phenyl]methyl}-2-phenoxyacetamide
N-[(5-chloro-8-hydroxyquinolin-7-yl)(3,4-dimethylphenyl)methyl]-2-phenoxyacetamide
N-[(5-chloro-8-hydroxyquinolin-7-yl)(3,4-dimethoxyphenyl)methyl]-2-phenoxyacetamide
N-[[3-(benzyloxy)-4-methoxyphenyl](5-chloro-8-hydroxyquinolin-7-yl)methyl]-2-phenoxyacetamide
N-[(5-chloro-8-hydroxyquinolin-7-yl)(2-furyl)methyl]-2-phenoxyacetamide
N-[(5-chloro-8-hydroxyquinolin-7-yl)(5-methyl-2-furyl)methyl]-2-phenoxyacetamide
N-[(5-chloro-8-hydroxyquinolin-7-yl)(3-furyl)methyl]-2-phenoxyacetamide
N-[(5-chloro-8-hydroxyquinolin-7-yl)(5-phenyl-2-furyl)methyl]-2-phenoxyacetamide
N-[(5-chloro-8-hydroxyquinolin-7-yl)(3-methyl-2-thienyl)methyl]-2-phenoxyacetamide
N-[(5-chloro-8-hydroxyquinolin-7-yl)(1H-indol-7-yl)methyl]-2-phenoxyacetamide
N-[(5-chloro-8-hydroxyquinolin-7-yl)(1H-indol-4-yl)methyl]-2-phenoxyacetamide
N-[(5-chloro-8-hydroxyquinolin-7-yl)(1-methyl-1H-indol-3-yl)methyl]-2-phenoxyacetamide
N-[1,3-benzodioxol-4-yl(5-chloro-8-hydroxyquinolin-7-yl)methyl]-2-phenoxyacetamide
N-[(5-chloro-8-hydroxyquinolin-7-yl)(quinolin-8-yl)methyl]-2-phenoxyacetamide
N-[(5-chloro-8-hydroxyquinolin-7-yl)(quinolin-4-yl)methyl]-2-phenoxyacetamide
N-[(5-chloro-8-hydroxyquinolin-7-yl)(quinolin-5-yl)methyl]-2-phenoxyacetamide
N-[(5-chloro-8-hydroxyquinolin-7-yl)(4-methoxy-1-naphthyl)methyl]-2-phenoxyacetamide
N-[(5-chloro-8-hydroxyquinolin-7-yl)(9-phenanthryl)methyl]-2-phenoxyacetamide
N-[(5-chloro-8-hydroxyquinolin-7-yl)(6-methoxy-2-naphthyl)methyl]-2-phenoxyacetamide
N-[(5-chloro-8-hydroxyquinolin-7-yl)(2,3-dihydro-1,4-benzodioxin-6-yl)methyl]-2-phenoxyacetamide
N-[(5-chloro-8-hydroxyquinolin-7-yl)(quinolin-3-yl)methyl]-2-phenoxyacetamide
N-[1-benzofuran-2-yl(5-chloro-8-hydroxyquinolin-7-yl)methyl]-2-phenoxyacetamide
N-[(5-chloro-8-hydroxyquinolin-7-yl)(1-methyl-1H-indol-2-yl)methyl]-2-phenoxyacetamide
N-[(5-chloro-8-hydroxyquinolin-7-yl)(2,3-dihydro-1-benzofuran-5-yl)methyl]-2-phenoxyacetamide
N-[(5-chloro-8-hydroxyquinolin-7-yl)(2,2-dimethyl-3,4-dihydro-2H-chromen-6-yl)methyl]-2-phenoxyacetamide N-[(5-chloro-8-hydroxyquinolin-7-yl)(4-oxo-4H-chromen-3-yl)methyl]-2-phenoxyacetamide
N-[(5-chloro-8-hydroxyquinolin-7-yl)(6-methyl-4-oxo-4H-chromen-3-yl)methyl]-2-phenoxyacetamide
N-[(5-chloro-8-hydroxyquinolin-7-yl)(4H-pyrazolo[1,5-c][1,3]thiazol-2-yl)methyl]-2-phenoxyacetamide
N-[1,3-benzodioxol-5-yl(5-chloro-8-hydroxyquinolin-7-yl)methyl]-2-phenoxyacetamide
N-[(6-chloro-1,3-benzodioxol-5-yl)(5-chloro-8-hydroxyquinolin-7-yl)methyl]-2-phenoxyacetamide
N-[(5-chloro-8-hydroxyquinolin-7-yl)(1-methyl-1H-1,2,3-benzotriazol-5-yl)methyl]-2-phenoxyacetamide
N-[(5-chloro-8-hydroxyquinolin-7-yl)(5,6-dihydro-8H-imidazo[2,1-c][1,4]oxazin-2-yl)methyl]-2-phenoxyacetamide
N-[(5-chloro-8-hydroxyquinolin-7-yl)(5,6-dihydro-4H-pyrrolo[1,2-b]pyrazol-2-yl)methyl]-2-phenoxyacetamide
N-[(5-chloro-8-hydroxyquinolin-7-yl)(phenyl)methyl]-3-phenylpropanamide
benzyl[(5-chloro-8-hydroxyquinolin-7-yl)(phenyl)methyl]carbamate
benzyl[(5-chloro-8-hydroxyquinolin-7-yl)(2-chlorophenyl)methyl]carbamate
benzyl[(5-chloro-8-hydroxyquinolin-7-yl)(pyridin-2-yl)methyl]carbamate
benzyl[(5-chloro-8-hydroxyquinolin-7-yl)(2-furyl)methyl]carbamate
benzyl[1,3-benzodioxol-5-yl(5-chloro-8-hydroxyquinolin-7-yl)methyl]carbamate
N-[1-(5-chloro-8-hydroxyquinolin-7-yl)prop-2-en-1-yl]-2-phenoxyacetamide
N-[(2E)-1-(5-chloro-8-hydroxyquinolin-7-yl)but-2-en-1-yl]-2-phenoxyacetamide
N-[(2E)-1-(5-chloro-8-hydroxyquinolin-7-yl)hex-2-en-1-yl]-2-phenoxyacetamide
N-[(5-chloro-8-hydroxyquinolin-7-yl)(cyclohex-1-en-1-yl)methyl]-2-phenoxyacetamide
N-[(2E)-1-(5-chloro-8-hydroxyquinolin-7-yl)-3-phenylprop-2-en-1-yl]-2-phenoxyacetamide
N-[(2Z)-1-(5-chloro-8-hydroxyquinolin-7-yl)-2-methoxy-3-phenylprop-2-en-1-yl]-2-phenoxyacetamide
benzyl[1-(5-chloro-8-hydroxyquinolin-7-yl)-2-phenylethyl]carbamate
N-[1-(5-chloro-8-hydroxyquinolin-7-yl)-3-phenylpropyl]-2-phenoxyacetamide
N-[(5-chloro-8-hydroxyquinolin-7-yl)(phenyl)methyl]-2-phenylacetamide
N-[(5-chloro-8-hydroxyquinolin-7-yl)(2-chlorophenyl)methyl]-2-phenylacetamide
N-[(5-chloro-8-hydroxyquinolin-7-yl)(4-fluorophenyl)methyl]-2-phenylacetamide
N-[[3-(benzyloxy)-4-methoxyphenyl](5-chloro-8-hydroxyquinolin-7-yl)methyl]-2-phenylacetamide
N-[(2E)-1-(5-chloro-8-hydroxyquinolin-7-yl)-3-phenylprop-2-en-1-yl]-2-phenylacetamide
N-[(5-chloro-8-hydroxyquinolin-7-yl)(3-methyl-2-thienyl)methyl]-2-phenyl acetamide
N-[(5-bromo-8-hydroxyquinolin-7-yl)(phenyl)methyl]-2-phenoxyacetamide
N-[(5-bromo-8-hydroxyquinolin-7-yl)(phenyl)methyl]-2-chloroacetamide
N-[(4-chloro-1-hydroxy-2-naphthyl)(phenyl)methyl]-2-phenoxyacetamide
N-[(3-aminophenyl)(5-chloro-8-hydroxyquinolin-7-yl)methyl]-2-phenoxyacetamide
5-chloro-7-{{3-[(methylsulfonyl)amino]phenyl}[(phenoxyacetyl)amino]methyl}quinolin-8-yl methanesulfonate
N-[[3-(acetylamino)phenyl](5-chloro-8-hydroxyquinolin-7-yl)methyl]-2-phenoxyacetamide
2-chloro-N-(3-{(5-chloro-8-hydroxyquinolin-7-yl)[(phenoxyacetyl)amino]methyl}phenyl)acetamide
N-(3-{(5-chloro-8-hydroxyquinolin-7-yl)[(phenoxyacetyl)amino]methyl}phenyl)-N2,N2-dimethylglycinamide
N-(3-{(5-chloro-8-hydroxyquinolin-7-yl)[(phenoxyacetyl)amino]methyl}phenyl)-N-2-methylglycinamide
(3-{(5-chloro-8-hydroxyquinolin-7-yl)[(phenoxyacetyl)amino]methyl}phenyl)acetic acid
2-(4-bromophenoxy)-N-[(5-chloro-8-hydroxyquinolin-7-yl)(phenyl)methyl]acetamide
N-[(5-chloro-8-hydroxyquinolin-7-yl)(phenyl)methyl]-2-(3,4,5-trimethoxyphenoxy)acetamide
2-(biphenyl-4-yloxy)-N-[(5-chloro-8-hydroxyquinolin-7-yl)(phenyl)methyl]acetamide
N-[(5-chloro-8-hydroxyquinolin-7-yl)(phenyl)methyl]-2-(3,5-dimethoxyphenoxy)acetamide
N-[(5-chloro-8-hydroxyquinolin-7-yl)(2-chlorophenyl)methyl]-2-(4-pentylphenoxy)acetamide
N-[(5-chloro-8-hydroxyquinolin-7-yl)(2-chlorophenyl)methyl]-2-(4-propylphenoxy)acetamide
N-[(5-chloro-8-hydroxyquinolin-7-yl)(2-chlorophenyl)methyl]-2-(4-isopropylphenoxy)acetamide
N-[(5-chloro-8-hydroxyquinolin-7-yl)(2-chlorophenyl)methyl]-2-(4-cyclopentylphenoxy)acetamide
N-[(5-chloro-8-hydroxyquinolin-7-yl)(2-chlorophenyl)methyl]-2-(3-ethylphenoxy)acetamide
N-[(5-chloro-8-hydroxyquinolin-7-yl)(2-chlorophenyl)methyl]-2-(3,5-dimethoxyphenoxy)acetamide
2-(biphenyl-4-yloxy)-N-[(5-chloro-8-hydroxyquinolin-7-yl)(2-chlorophenyl)methyl]acetamide
2-(4-bromophenoxy)-N-[(5-chloro-8-hydroxyquinolin-7-yl)(2-chlorophenyl)methyl]acetamide
2-(1,3-benzodioxol-5-yloxy)-N-[(5-chloro-8-hydroxyquinolin-7-yl)(2-chlorophenyl)methyl]acetamide
N-[(5-bromo-8-hydroxyquinolin-7-yl)(phenyl)methyl]-N2-(1-naphthylmethyl)glycinamide
N2-benzyl-N-[(5-chloro-8-hydroxyquinolin-7-yl)(phenyl)methyl]glycinamide
N-[(5-chloro-8-hydroxyquinolin-7-yl)(phenyl)methyl]-N2-(1-naphthylmethyl)glycinamide
N-[(5-chloro-8-hydroxyquinolin-7-yl)(phenyl)methyl]-2-(4-phenylpiperidin-1-yl)acetamide
N2-(1,3-benzodioxol-5-ylmethyl)-N-[(5-chloro-8-hydroxyquinolin-7-yl)(phenyl)methyl]glycinamide
N-[(5-chloro-8-hydroxyquinolin-7-yl)(phenyl)methyl]-N2-(pyridin-2-ylmethyl)glycinamide
N-[(5-chloro-8-hydroxyquinolin-7-yl)(phenyl)methyl]-N2-(pyridin-3-ylmethyl)glycinamide
N-[(5-chloro-8-hydroxyquinolin-7-yl)(phenyl)methyl]-N2-(pyridin-4-ylmethyl)glycinamide
N2-(biphenyl-4-ylmethyl)-N-[(5-chloro-8-hydroxyquinolin-7-yl)(phenyl)methyl]glycinamide
N-[(5-chloro-8-hydroxyquinolin-7-yl)(2-chlorophenyl)methyl]-N2-(1-naphthylmethyl)glycinamide
N2-(1,3-benzodioxol-5-ylmethyl)-N-[(5-chloro-8-hydroxyquinolin-7-yl)(2-chlorophenyl)methyl]glycinamide
N-[(5-amino-8-hydroxyquinolin-7-yl)(phenyl)methyl]-2-phenoxyacetamide
N-[[5-(dimethylamino)-8-hydroxyquinolin-7-yl](phenyl)methyl]-2-phenoxyacetamide
N-[[8-hydroxy-5-(1H-pyrrol-1-yl)quinolin-7-yl](phenyl)methyl]-2-phenoxyacetamide
N-[(8-hydroxy-5-pyrrolidin-1-ylquinolin-7-yl)(phenyl)methyl]-2-phenoxyacetamide
N-[2-(8-Hydroxyquinolin-7-yl)-1-phenylethyl]-2-phenoxyacetamide
N-[1-(1,3-Benzodioxol-5-yl)-2-(5-chloro-8-hydroxyquinolin-7-yl)ethyl]-2-phenoxyacetamide
2-[8-(Benzyloxy)-5-chloroquinolin-7-yl]-1-[4-(morpholin-4-ylmethyl)phenyl]ethanamine 2-[8-(Benzyloxy)-5-chloroquinolin-7-yl]-1-[3-(5-methyl-2-thienyl)phenyl]ethanamine
N-{2-[8-(Benzyloxy)-5-chloroquinolin-7-yl]-1-[4-(morpholin-4-ylmethyl)phenyl]ethyl}biphenyl-4-carboxamide
N-{2-[8-(Benzyloxy)-5-chloroquinolin-7-yl]-1-[3-(pyrrolidin-1-ylmethyl)phenyl]ethyl}biphenyl-4-carboxamide
N-{2-(5-Chloro-8-hydroxyquinolin-7-yl)-1-[4-(morpholin-4-ylmethyl)phenyl]ethyl}biphenyl-4-carboxamide
N-{2-(5-Chloro-8-hydroxyquinolin-7-yl)-1-[3-(pyrrolidin-1-ylmethyl)phenyl]ethyl}biphenyl-4-carboxamide
N-{2-(5-Chloro-8-hydroxyquinolin-7-yl)-1-[3-(5-methyl-2-thienyl)phenyl]ethyl}biphenyl-4-carboxamide
N-{2-(5-Chloro-8-hydroxyquinolin-7-yl)-1-[3-(pyrrolidin-1-ylmethyl)phenyl]ethyl}-2-phenoxyacetamide
N-{2-(5-Chloro-8-hydroxyquinolin-7-yl)-1-[3-(pyrrolidin-1-ylmethyl)phenyl]ethyl}-2-(4-chlorophenoxy)-2-methylpropanamide
N-{2-(5-Chloro-8-hydroxyquinolin-7-yl)-1-[3-(5-methyl-2-thienyl)phenyl]ethyl}-2-phenoxyacetamide
2-(Benzyloxy)-N-{2-(5-chloro-8-hydroxyquinolin-7-yl)-1-[3-(5-methyl-2-thienyl)phenyl]ethyl}acetamide
N-{2-(5-Chloro-8-hydroxyquinolin-7-yl)-1-[3-(5-methyl-2-thienyl)phenyl]ethyl}-2-(4-chlorophenoxy)-2-methylpropanamide
2-(4-tert-Butylphenoxy)-N-{2-(5-chloro-8-hydroxyquinolin-7-yl)-1-[3-(5-methyl-2-thienyl)phenyl]ethyl}acetamide
2-[8-(Benzyloxy)-5-chloroquinolin-7-yl]-1-{5-[(dimethylamino)methyl]-2-furyl}ethanamine
N-(2-[8-(Benzyloxy)-5-chloroquinolin-7-yl]-1-{5-[(dimethylamino)methyl]-2-furyl}ethyl)-2-phenoxyacetamide
N-[2-(5-Chloro-8-hydroxyquinolin-7-yl)-1-{5-[(dimethylamino)methyl]-2-furyl}ethyl]-2-phenoxyacetamide
N-[2-(8-Benzyloxy-5-chloro-quinolin-7-yl)-1-(5-dimethylaminomethyl-furan-2-yl)-ethyl]-isobutyramide
N-[2-(5-Chloro-8-hydroxyquinolin-7-yl)-1-{5-[(dimethylamino)methyl]-2-furyl}ethyl]-2-methylpropanamide
2-{[(phenoxyacetyl)amino](phenyl)methyl}quinolin-8-yl phenoxyacetate
N-[(8-hydroxyquinolin-2-yl)(phenyl)methyl]-2-phenoxyacetamide
2-[amino(phenyl)methyl]quinolin-8-ol
and pharmaceutically acceptable salts thereof.

4.3 Methods of Making 8-Hydroxyquinoline Compounds

The following methods may yield a mixture of stereoisomers or isolated stereoisomers. Any stereoisomers produced as mixtures can obviously be isolated if so desired. Both mixtures of any stereoisomers and any isolated stereoisomers are thus encompassed within the scope of this invention.

First General Synthetic Scheme for Preparation of 8-Hydroxyquinoline Compounds

Compounds of Formula (I) in which X is —N—, Y is —COR$_4$, R$_{13}$ is hydrogen, and p=0 may be prepared by the following synthetic scheme:

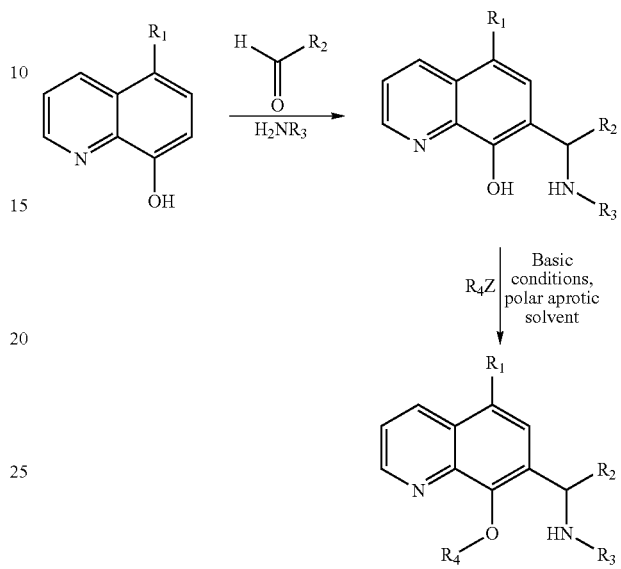

wherein Z is chlorine, bromine, or iodine and R$_1$, R$_2$, R$_3$, and R$_4$ are as defined above.

In certain embodiments, the first step may be run at a temperature between 100-200° C., alternatively between 120-180° C., and preferably between 140-160° C.

Additionally, in certain embodiments, the second step may be run at a temperature between 0-100° C., alternatively between 25-75° C., and preferably between 40-60° C.

In certain embodiments, weak bases such as DIEA or K$_2$CO$_3$ are used to create the basic conditions during the second step.

In some embodiments, the polar aprotic solvent may be DMF, DMSO, NMP, MeCN, or THF.

In one embodiment in the First General Synthetic Scheme, R$_3$ is —COR$_7$, and R$_7$ is as defined above.

Second General Synthetic Scheme for the Preparation of 8-Hydroxyquinoline Compounds Alternatively, compounds of Formula (I) in which X is —N—, Y is —COR$_4$, R$_{13}$ is hydrogen, and p=0 may be prepared by this second synthetic scheme:

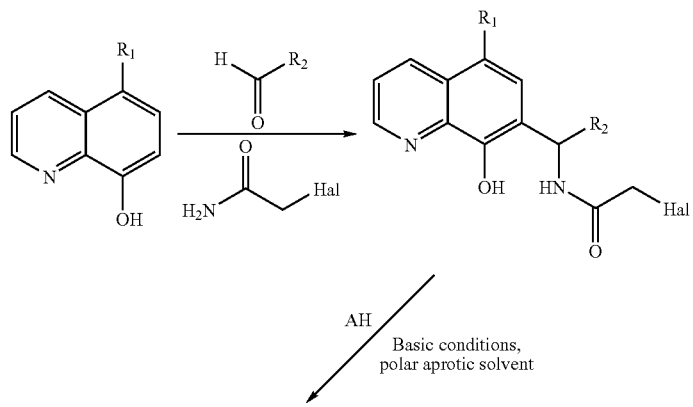

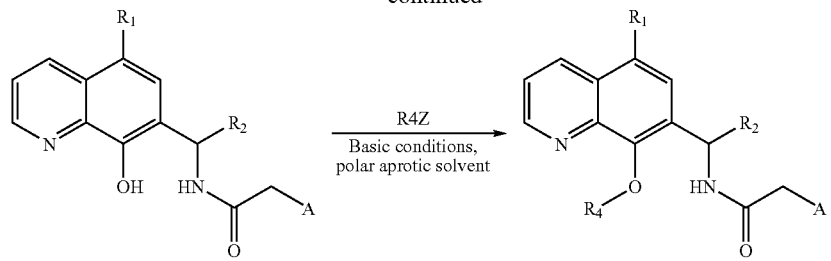

wherein Hal is halogen,
Z is chlorine, bromine, or iodine,
A is —$OR_7$, —$NR_5R_6$ or —$OR_8$—B—$R_9$,
$R_5$, $R_6$, $R_7$ and $R_9$ are each independently —$C_5$-$C_7$-aryl or —$C_5$-$C_{10}$-arylalkyl, as defined above, and $R_1$, $R_2$, $R_4$ and $R_8$ are as defined above.

In certain embodiments, the first step may be run at a temperature between 100-200° C., alternatively between 120-180° C., and preferably between 140-160° C.

When the second step is run with a strong base in a polar aprotic solvent, the temperature may be between −15° C. and 20° C., preferably between −5° C. and 10° C.

In some embodiments, strong bases such as NaH, KH, or t-BuOK are used to create the basic conditions.

In some embodiments, AH is

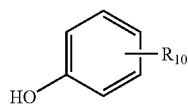

and the compound produced is of the formula:

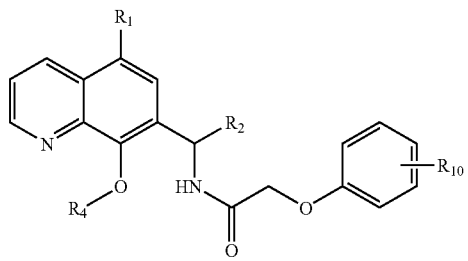

wherein $R_{10}$ is a hydrogen, halogen or —$C_1$-$C_3$-alkyl, and $R_1$, $R_2$, and $R_4$ are as previously defined.

When the second step is run with a weak base in a polar aprotic solvent, the temperature may be between 10° C. and 30° C., preferably between 15° C. and 25° C.

In some embodiments, weak bases such as DIEA or $K_2CO_3$ are used to create the basic conditions.

In some embodiments, AH is

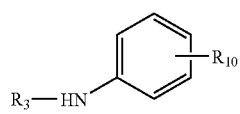

and the compound produced is of the formula:

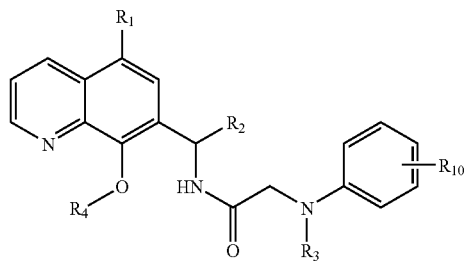

wherein $R_{10}$ is a hydrogen, halogen or —$C_1$-$C_3$-alkyl, and $R_1$, $R_2$, $R_3$, and $R_4$ are as previously defined.

In some embodiments using the Second General Synthetic Scheme, the polar aprotic solvent may be DMF, DMSO, NMP, MeCN, or THF.

In certain embodiments, the third step may be run at a temperature between 0-100° C., alternatively between 25-75° C., and preferably between 40-60° C.

In one embodiment, Scheme 1 is used to make the 8-Hydroxyquinoline Compounds.

Scheme 1

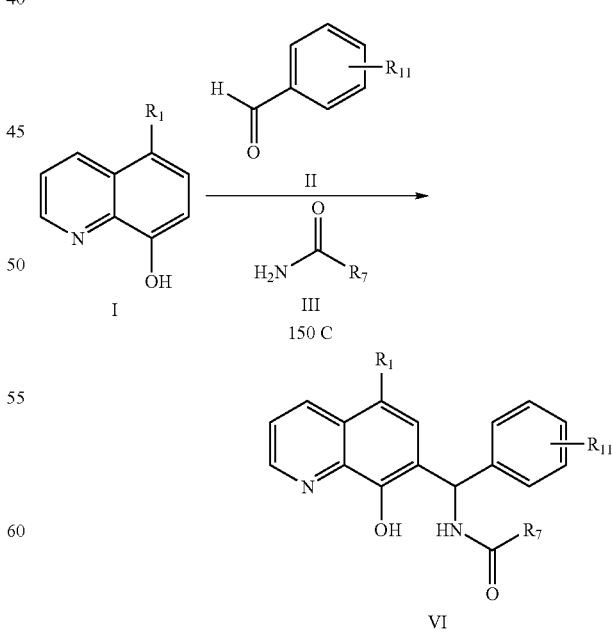

wherein $R_1$ and $R_7$ are as previously defined, and $R_{11}$ may be a hydrogen, halogen or a $C_1$-$C_3$ alkyl.

8-Hydroxyquinoline target molecules IV may be prepared according to Scheme 1 by reacting 8-Hydroxyquinolines I with aryl or heteroaryl aldehydes II and acetamides III at 150° C. similar to procedures found in Mohrle, H et. al. *Chem. Ber.* 1974, 107, 2675, Pirrone, F. *Gazz. Chim Ital.* 1936, 66, 518, and Pirrone, F. *Gazz. Chim Ital.* 1937, 67, 529 (all three references are fully incorporated herein by reference). 8-Hydroxyquinolines I can be purchased commercially or prepared synthetically via standard organic chemistry protocols. (Two examples include Shen, Liang et. al. *Tetrahedron Letters* 2004, 45, 3961, and Bradshaw, Jerald S. et. al. *Supramolecular Chemistry* 2001, 13, 499. Both are fully incorporated herein by reference.) Aryl or heteroaryl aldehydes II can be purchased commercially or prepared synthetically via standard organic chemistry protocols. Acetamides III can be purchased commercially or prepared synthetically via standard organic chemistry protocols.

In another embodiment, Scheme 2 is used to make the 8-Hydroxyquinoline Compounds.

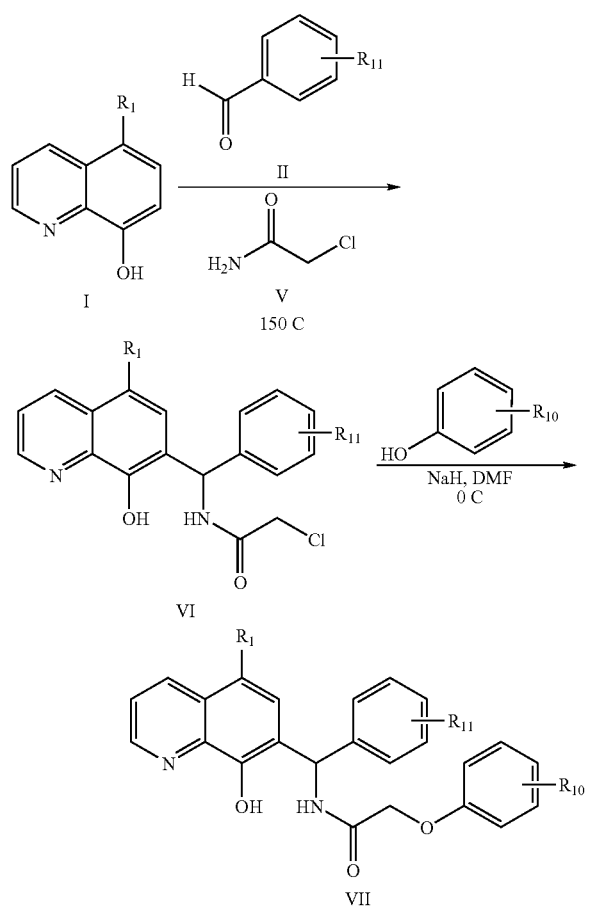

wherein $R_1$, $R_3$, $R_4$, $R_{10}$ and $R_{11}$ are as previously defined.

8-Hydroxyquinoline target molecules VII may be prepared according to Scheme 2 by reacting 8-Hydroxyquinolines I with aryl or heteroaryl aldehydes II and chloro acetamide V at 150° C. similar to procedures found in Mohrle, H et. al. *Chem. Ber.* 1974, 107, 2675, Pirrone, F. *Gazz. Chim Ital.* 1936, 66, 518, and Pirrone, F. *Gazz. Chim Ital.* 1937, 67, 529. Displacement of the chloride from resulting compound VI with commercially purchased or readily available phenols with a strong base such as NaH, KH or t-BuOK in a polar aprotic solvent such as DMF, DMSO, NMP, MeCN or THF affords VII.

In yet another embodiment, Scheme 3 is used to make the 8-Hydroxyquinoline Compounds.

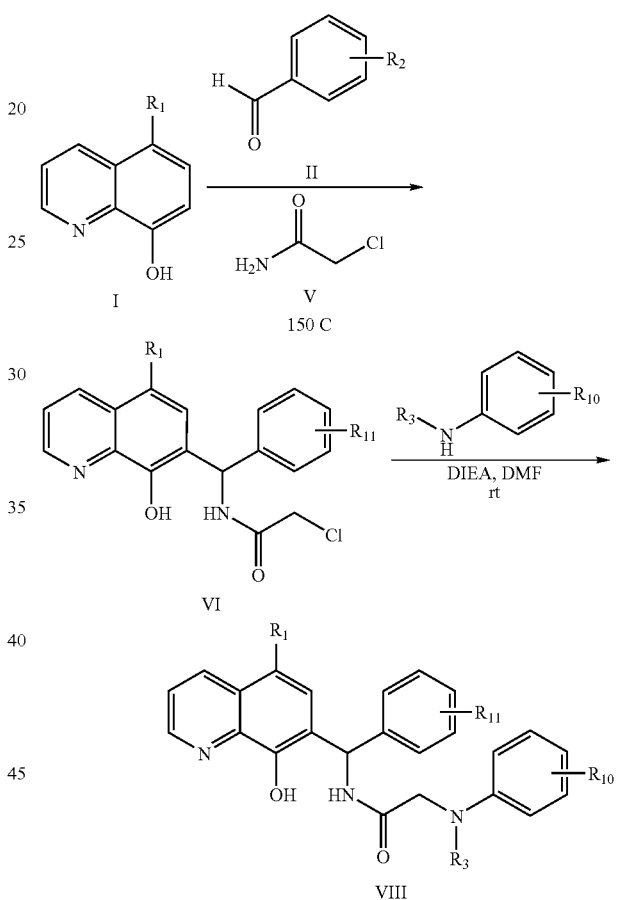

wherein $R_1$, $R_{10}$ and $R_{11}$ are as previously defined.

8-Hydroxyquinoline target molecules VIII may be prepared according to Scheme 3 by reacting 8-hydroxyquinolines I with aryl or heteroaryl aldehydes II and chloro acetamide V at 150° C. similar to procedures found in Mohrle, H et. al. *Chem. Ber.* 1974, 107, 2675, Pirrone, F. *Gazz. Chim Ital.* 1936, 66, 518, and Pirrone, F. *Gazz. Chim Ital.* 1937, 67, 529. Displacement of the chloride from resulting compound VI with commercially purchased or readily available anilines, heteroaryl derivatives of anilines, aryl amines, heteroaryl amines, or benzyl amines with a weak base such as DIEA or K2CO3 in a polar aprotic solvent such as DMF, DMSO, NMP, MeCN or THF affords VIII.

Scheme 4

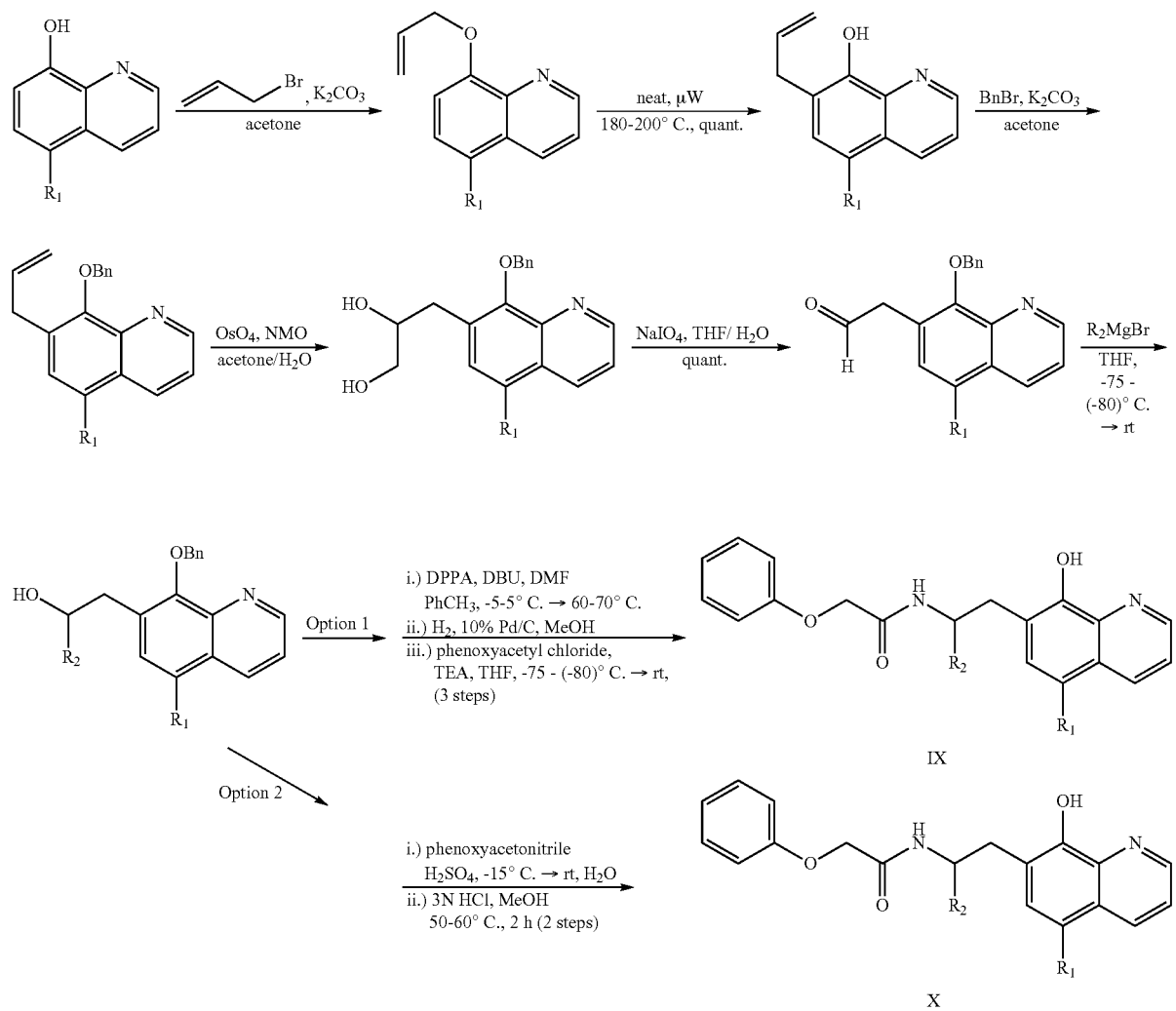

wherein
$R_1$ is hydrogen or halogen provided that Option 1 is used when $R_1$ is halogen;
$R_2$ is —$C_5$-$C_7$-aryl, —$C_5$-$C_{10}$-arylalkyl, —$C_5$-$C_{10}$-arylalkenyl, —$C_7$-$C_{12}$-bicyclic hydrocarbon wherein at least one cyclic group is aromatic, or $C_9$-$C_{15}$-tricyclic hydrocarbon wherein at least one cyclic group is aromatic.

8-Hydroxyquinoline target molecules IX and X may be prepared according to Scheme 4 by O-allylating 8-Hydroxyquinolines unsubstituted or substituted at the 5-position using allyl halide and an appropriate base such as potassium carbonate in acetone followed by Claisen rearrangement of the neat material or as a solution in a high-boiling solvent conducted by conventional heating or in a microwave reactor. The products are then O-benzyl protected with benzyl bromide and an appropriate base such as potassium carbonate in acetone followed by dihydroxylation of the double bond using a suitable oxidant such as the osmium tetroxide/4-methylmorpholine N-oxide system in water/acetone. The diols then undergo oxidative cleavage using sodium metaperiodate in water and a polar aprotic solvent miscible with water such as tetrahydrofuran to give the aldehydes that are stable at room temperature. Addition of aryl Grignard reagents to the aldehydes at low temperature in dry tetrahydrofuran or ether provides the alcohols. The alcohols are either converted to the azides with diphenyl phosphoryl azide and an appropriate base such as 1,8-diazabicyclo[5.4.0]undec-7-ene at elevated temperatures, hydrogenated under standard conditions using and appropriate metal catalyst such as 10% palladium on carbon and N-acylated with an acid chloride such as phenoxyacetyl chloride and an appropriate base such as triethylamine in tetrahydrofuran (Option 1 to give compounds IX) or subjected to a Ritter reaction with a nitrile such as phenoxyacetonitrile and strong acid such as sulfuric acid followed by deprotection with 3N HCl in a polar protic solvent such as methanol (Option 2 to give compounds X).

Scheme 5

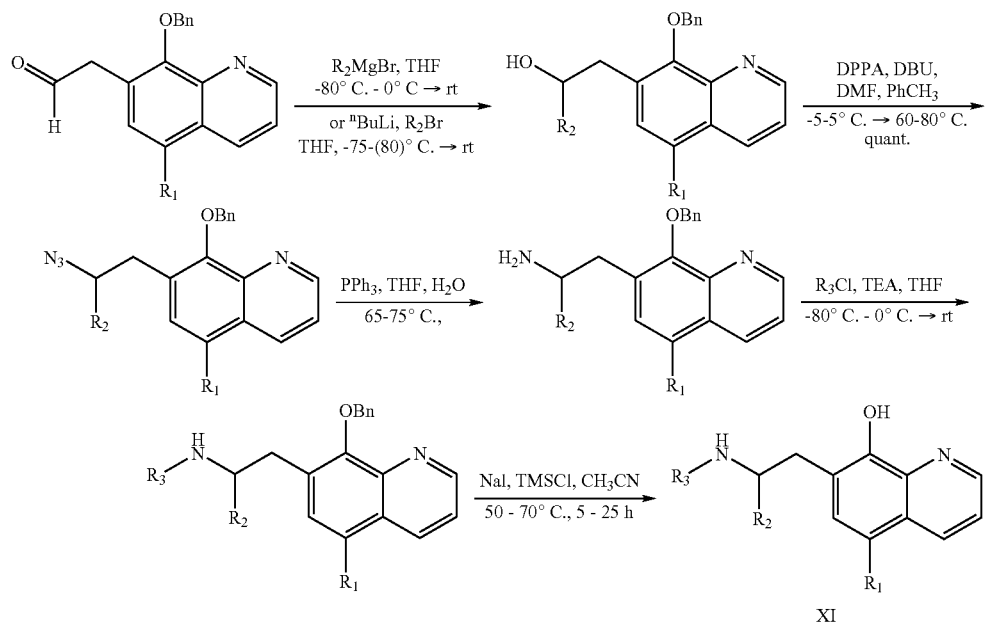

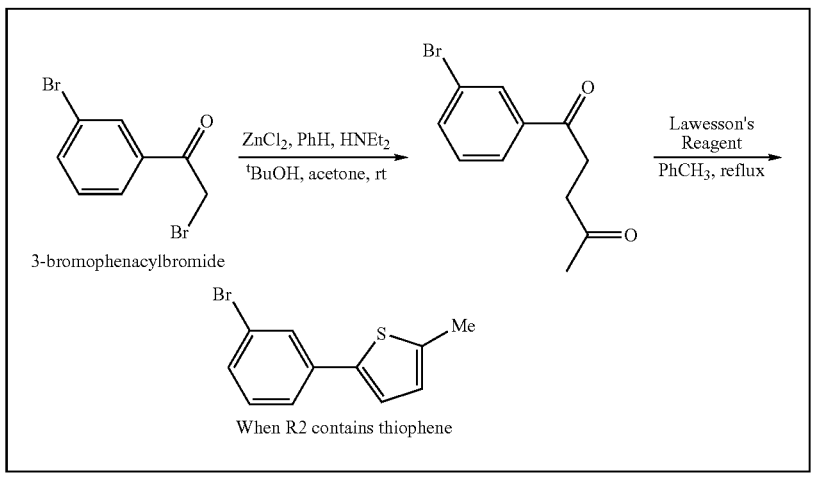

When R2 contains thiophene wherein
R$_1$ is halogen;
R$_2$ is —C$_5$-C$_7$-aryl that is optionally substituted with at least one —C$_1$-C$_6$-alkyl, —C$_2$-C$_6$-alkenyl, —C$_2$-C$_6$-alkynyl, —C$_5$-C$_7$-cycloalkyl, —C$_1$-C$_3$-alkyl-C$_5$-C$_7$-cycloalkyl, —C$_5$-C$_7$-aryl, —C$_5$-C$_{10}$-arylalkyl, —C$_5$-C$_{10}$-arylalkenyl, —C$_5$-C$_{10}$-arylalkynyl, wherein (1) at least one of the carbon atoms in the alkyl, alkenyl, alkynyl, cycloalkyl, aryl, arylalkyl, arylalkenyl or arylalkynyl group is optionally replaced with one to three nitrogen, sulfur or oxygen atoms, and (2) the alkyl, alkenyl, alkynyl, cycloalkyl, aryl arylalkyl, arylalkenyl or arylalkynyl group is optionally substituted with a halogen, a —C$_1$-C$_3$-alkyl or a —C$_5$-C$_7$-aryl, or is optionally branched;
R$_3$ is —COR$_7$ or —COR$_8$—B—R$_9$
R$_7$ is —C$_1$-C$_6$-alkyl, —C$_2$-C$_6$-alkenyl, —C$_2$-C$_6$-alkynyl, —C$_5$-C$_7$-aryl, or —C$_5$-C$_{10}$-arylalkyl, wherein (a) at least one of the carbon atoms in the alkyl, alkenyl, alkynyl, aryl or arylalkyl group is optionally replaced with one to three nitrogen, sulfur or oxygen atoms, and (b) the alkyl, alkenyl, alkynyl, aryl or arylalkyl is optionally substituted with at least one —C$_1$-C$_3$-alkyl or —C$_5$-C$_7$-aryl or is optionally branched;
and R$_8$, R$_9$, and B are as defined above.

In Scheme 5, the benzyl protected aldehydes whose synthesis is described in Scheme 4 are treated with either aryl Grignard reagents at low temperature in dry tetrahydrofuran or ether or aryl halides that have undergone lithium-halogen exchange at low temperature in dry tetrahydrofuran or ether to provide the alcohols which are then converted to azides using diphenyl phosphoryl azide and an appropriate base such as 1,8-diazabicyclo[5.4.0]undec-7-ene at elevated temperatures. The azides are subjected to a Staudinger reduction using triphenylphosphine in aqueous tetrahydrofuran followed by N-acylation with an acid chloride and an appropriate base such as triethylamine in tetrahydrofuran. The final O-benzyl deprotection is conducted with in situ generated iodotrimethylsilane using sodium iodide and chlorotrimethylsilane in acetonitrile at elevated temperature to give the final products XI. When R$_2$ contains thiophene, the aryl bromide was synthesized from 3-bromophenacylbromide by condensation with acetone in the presence of zinc chloride using the procedure found in Nevar, N. et al. Synthesis, 2000, 1259. The resulting 1,4-diketone is then cyclized in the presence of Lawesson's reagent at high temperature to give the required thiophene.

4.4 Therapeutic/Prophylactic Administration

Due to their activity, the 8-Hydroxyquinoline Compounds are advantageously useful in veterinary and human medicine. As described above, the 8-Hydroxyquinoline Compounds are useful for treating or preventing a Condition in a mammal in need thereof.

When administered to a mammal, the 8-Hydroxyquinoline Compounds can be administered as a component of a composition that comprises a physiologically acceptable carrier or vehicle. The present compositions, which comprise an 8-Hydroxyquinoline Compound, can be administered orally. The 8-Hydroxyquinoline Compounds can also be administered by any other convenient route, for example, by infusion or bolus injection, by absorption through epithelial or mucocutaneous linings (e.g., oral, rectal, or intestinal mucosa), by intratracheal administration, or by inhalation, and can be administered together with another biologically active agent. Administration can be systemic or local. Various known delivery systems, including encapsulation in liposomes, microparticles, microcapsules, and capsules, can be used.

Methods of administration include, but are not limited to, intradermal, intratracheal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration results in the release of the 8-Hydroxyquinoline Compounds into the bloodstream. The mode of administration can be left to the discretion of the practitioner.

In one embodiment, the 8-Hydroxyquinoline Compounds are administered orally.

In another embodiment, the 8-Hydroxyquinoline Compounds are administered intravenously.

In another embodiment, the 8-Hydroxyquinoline Compounds are administered topically.

In still another embodiment, the 8-Hydroxyquinoline Compounds are administered via inhalation.

In other embodiments, it can be desirable to administer the 8-Hydroxyquinoline Compounds locally. This can be achieved, for example, and not by way of limitation, by local infusion during surgery, topical application, e.g., in conjunction with a wound dressing after surgery, by injection, by means of a catheter, by intubation, by means of a suppository or enema, or by means of an implant, said implant being of a porous, non-porous, or gelatinous material, including membranes, such as silastic membranes, or fibers.

In certain embodiments, it can be desirable to introduce the 8-Hydroxyquinoline Compounds into the central nervous system, circulatory system or gastrointestinal tract by any suitable route, including intraventricular, intrathecal injection, paraspinal injection, epidural injection, enema, and by injection adjacent to a peripheral nerve. Intraventricular injection can be facilitated by an intraventricular catheter, for example, attached to a reservoir, such as an Ommaya reservoir.

Pulmonary administration can also be employed, e.g., by use of an inhaler of nebulizer, by intubation, and formulation with an aerosolizing agent, or via perfusion in a fluorocarbon or synthetic pulmonary surfactant. In certain embodiments, the 8-Hydroxyquinoline Compounds can be formulated as a suppository, with traditional binders and excipients such as triglycerides.

In another embodiment the 8-Hydroxyquinoline Compounds can be delivered in a vesicle, in particular a liposome (see Langer, *Science* 249:1527-1533 (1990) and Lopez-Berestein et al., *Liposomes in the Therapy of Infectious Disease and Cancer*, 317-327 and 353-365 (1989)).

In yet another embodiment the 8-Hydroxyquinoline Compounds can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the 8-Hydroxyquinoline Compounds, e.g., the spinal column, brain, colon, skin, heart, lung, trachea or gastrointestinal tract, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to a mammal. Water can be a particularly useful excipient when the 8-Hydroxyquinoline Compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, tablets, pills, pellets, capsules, capsules containing liquids, powders, sustained-release formulations, suppositories, emulsions, aerosols, sprays or any other form suitable for use. In one embodiment the composition is in the form of a capsule. Other examples of suitable physiologically acceptable excipients are described in *Remington's Pharmaceutical Sciences* (21st ed. 2005), incorporated herein by reference.

In one embodiment the 8-Hydroxyquinoline Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active platform driving an 8-Hydroxyquinoline Compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the 8-Hydroxyquinoline Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. The compositions' components can be supplied either separately or mixed together in unit dosage form, for example, as a dry lyophilized powder or water-free concentrate in a hermetically sealed container such as an ampule or sachette indicating the quantity of 8-Hydroxyquinoline Compound. Where the 8-Hydroxyquinoline Compounds are to be administered by infusion, they can be dispensed, for example, with an infusion bottle containing sterile pharmaceutical grade water or saline. Where the 8-Hydroxyquinoline Compounds are administered by injection, an ampule of sterile water for injection or saline can be provided so that the ingredients can be mixed prior to administration.

The 8-Hydroxyquinoline Compounds can be administered by controlled-release or sustained-release means or by delivery devices that are well known to those skilled in the art. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of an 8-Hydroxyquinoline Compound to treat or prevent the Condition in a minimal amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the 8-Hydroxyquinoline Compound, and can thus reduce the occurrence of adverse side effects.

Controlled- or sustained-release compositions can initially release an amount of an 8-Hydroxyquinoline Compound that promptly produces the desired therapeutic or prophylactic effect, and gradually and continually release other amounts of the 8-Hydroxyquinoline Compound to maintain this level of therapeutic or prophylactic effect over an extended period of time. To maintain a constant level of the 8-Hydroxyquinoline Compound in the body, the 8-Hydroxyquinoline Compound can be released from the dosage form at a rate that will replace the amount of 8-Hydroxyquinoline Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions.

The amount of the 8-Hydroxyquinoline Compound that is effective for treating or preventing a Condition can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of a health-care practitioner. Suitable effective dosage amounts, however, range from about 10 micrograms to about 5 grams about every 4 h, although they are typically about 500 mg or less per every 4 hours. Examples of effective dosages include about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one 8-Hydroxyquinoline Compound is administered, the effective dosage amounts correspond to the total amount administered.

The amount of an 8-Hydroxyquinoline Compound that is effective for treating or preventing a Condition typically ranges from about 0.01 mg/kg to about 100 mg/kg of body weight per day, in one embodiment, from about 0.1 mg/kg to about 50 mg/kg body weight per day, and in another embodiment, from about 1 mg/kg to about 20 mg/kg of body weight per day.

When an 8-Hydroxyquinoline Compound is a component of a solution that is useful for maintaining the viability of an organ ex vivo, the concentration of the 8-Hydroxyquinoline Compound in the solution that is effective for maintaining the viability of the organ is between about 1 nM to about 1 mM.

The 8-Hydroxyquinoline Compounds can be assayed in vitro or in vivo for the desired therapeutic or prophylactic activity prior to use in humans. Animal model systems can be used to demonstrate safety and efficacy.

The present methods for treating or preventing a Condition can further comprise administering another therapeutic agent to the mammal being administered an 8-Hydroxyquinoline Compound. In one embodiment the other therapeutic agent is administered in an effective dose.

Effective doses of the other therapeutic agents are well known to those skilled in the art. However, it is well within the skilled artisan's purview to determine the other therapeutic agent's optimal effective dose range. In one embodiment of the invention, where, another therapeutic agent is administered to a mammal, the effective dose of the 8-Hydroxyquinoline Compound is less than its effective dose would be where the other therapeutic agent is not administered. In this case, without being bound by theory, it is believed that the 8-Hydroxyquinoline Compounds and the other therapeutic agent act synergistically.

In one embodiment the other therapeutic agent is an anti-inflammatory agent. Examples of useful anti-inflammatory agents include, but are not limited to, adrenocorticosteroids, such as cortisol, cortisone, fluorocortisone, prednisone, prednisolone, 6α-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In a further embodiment the other therapeutic agent is an anti-cardiovascular-disease agent. Examples of useful anti-cardiovascular-disease agents include, but are not limited to, carnitine; thiamine; lidocaine; amiodarone; procainamide; mexiletine; bretylium tosylate; propranolol; sotalol; and muscarinic receptor antagonists, such as atropine, scopolamine, homatropine, tropicamide, pirenzepine, ipratropium, tiotropium, and tolterodine.

An 8-Hydroxyquinoline Compound and the other therapeutic agent can act additively or, in one embodiment, synergistically. In one embodiment, an 8-Hydroxyquinoline Compound is administered concurrently with another therapeutic agent. In another embodiment, the present compositions can further comprise another therapeutic agent. In a further embodiment, a composition comprising an effective dose of an 8-Hydroxyquinoline Compound and an effective dose of another therapeutic agent can be administered. Alternatively, a composition comprising an effective dose of an 8-Hydroxyquinoline Compound and a different composition comprising an effective dose of another therapeutic agent can be concurrently administered. In another embodiment, an effective dose of an 8-Hydroxyquinoline Compound is administered prior or subsequent to administration of an effective dose of another therapeutic agent. In this embodiment, the 8-Hydroxyquinoline Compound is administered while the other therapeutic agent exerts its therapeutic effect, or the other therapeutic agent is administered while the 8-Hydroxyquinoline Compound exerts its preventative or therapeutic effect for treating or preventing a Condition.

A composition of the invention can be prepared using a method comprising admixing an 8-Hydroxyquinoline Compound and a physiologically acceptable carrier or excipient. Admixing can be accomplished using methods well known for admixing a compound (or salt) and a physiologically acceptable carrier or excipient.

4.5 Therapeutic or Prophylactic Uses of the 8-Hydroxyquinoline Compounds

In one embodiment, the 8-Hydroxyquinoline Compounds of the present invention and compositions thereof are useful as metalloproteinase modulators.

In another embodiment, the 8-Hydroxyquinoline Compounds of the present invention and compositions thereof are useful for treating a condition.

In one embodiment, the invention provides a method for treating a metalloproteinase-related disorder, comprising administering to a mammal in need thereof an effective dose of an 8-Hydroxyquinoline Compound or a composition thereof.

The 8-Hydroxyquinoline Compounds and compositions thereof are useful for treating or preventing the following disorders: an arthritic disorder, osteoarthritis, malignant neoplasm, rheumatoid arthritis, asthma, chronic obstructive pulmonary disease, atherosclerosis, age-related macular degeneration, myocardial infarction, a corneal ulceration, an ocular surface disease, hepatitis, an aortic aneurysm, tendonitis, a central nervous system disorder, abnormal wound healing, angiogenesis, restenosis, cirrhosis, multiple sclerosis, glomerulonephritis, graft versus host disease, diabetes, an inflammatory bowel disease, shock, invertebral disc degeneration, stroke, osteopenia, or a periodontal disease.

In one embodiment, the disorder is osteoarthritis.

In one embodiment, the present invention provides a method of treating a disorder in a mammal in need thereof, which comprises administering an effective dose of an 8-Hydroxyquinoline Compound or a pharmaceutically acceptable salt or hydrate thereof, wherein the disorder is an arthritic disorder, osteoarthritis, malignant neoplasm, rheumatoid arthritis, asthma, chronic obstructive pulmonary disease, atherosclerosis, age-related macular degeneration, myocardial infarction, a corneal ulceration, an ocular surface disease, hepatitis, an aortic aneurysm, tendonitis, a central nervous system disorder, abnormal wound healing, angiogenesis, restenosis, cirrhosis, multiple sclerosis, glomerulonephritis, graft versus host disease, diabetes, an inflammatory bowel disease, shock, invertebral disc degeneration, stroke, osteopenia, or a periodontal disease.

4.6 Kits

The invention encompasses kits that can simplify the administration of the 8-Hydroxyquinoline Compounds or compositions of the invention to a mammal.

A typical kit of the invention comprises a unit dosage of an 8-Hydroxyquinoline Compound. In one embodiment, the unit dosage form is in a container, which can be sterile, containing an effective dose of an 8-Hydroxyquinoline Compound and a physiologically acceptable vehicle. In another embodiment, the unit dosage form is in a container containing an effective dose of an 8-Hydroxyquinoline Compound as a lyophilate or pharmaceutically acceptable salt. In this instance, the kit can further comprise another container that contains a solution useful for the reconstitution of the lyophilate or dissolution of the salt. The kit can also comprise a label or printed instructions for use of the 8-Hydroxyquinoline Compounds.

In a further embodiment, the kit comprises a unit dosage form of a composition of the invention.

Kits of the invention can further comprise one or more devices that are useful for administering the unit dosage forms of the 8-Hydroxyquinoline Compounds or a composition of the invention. Examples of such devices include, but are not limited to, a syringe, a drip bag, a patch or an enema, which optionally contain the unit dosage forms.

The present invention is not to be limited in scope by the specific embodiments disclosed in the examples which are intended as illustrations of a few aspects of the invention and any embodiments that are functionally equivalent are within the scope of this invention.

5. EXAMPLES

Examples 1-121

Examples 1-121 are prepared by one of the following procedures as set forth below (Procedures A, B and C).

General Experimental for the Preparation of 8-Hydroxyquinolin-7-Yl (Procedure A)

To the desired acetamide (0.45 mmol, 0.9 eq) and desired 8-hydroxyquinoline (0.5 mmol, 1 eq) was added the desired aromatic/heteroaromatic aldehyde (1.0 mmol, 2 equiv.) The resulting suspension was stirred for 180 min at 180° C., 5 mL MeOH was added, and the reaction allowed to cool to room temperature upon which a solid often precipitated. The suspension was filtered and the solid recrystallized on purified via preparative HPLC. If no solid was formed the crude mixture was evaporated in a Speed-Vac.

If purification via preparative HPLC was necessary the following conditions were utilized. The Gilson crude material was dissolved in 1.5 ml DMSO: 0.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions were analyzed by LC/MS as described below. Combining pure fractions and evaporating the solvent in a Speed-Vac isolated the title compound.

General Experimental for the Preparation of 8-Hydroxyquinolin-7-Yl (Procedure B)

To the desired chloro acetamide (15.6 mmol, 0.9 eq) and desired 8-hydroxyquinoline (17.3 mmol, 1 eq) was added the desired aromatic/heteroaromatic aldehyde (87 mmol, 5 equiv.) The resulting suspension was stirred for 120 min at 150° C., poured onto 100 mL MeOH, and the reaction allowed to cool to room temperature upon which a solid precipitated. The suspension was filtered and the solid recrystallized with MeOH. In some cases product remained in the filtrate and was subject to recrystallization. The resulting chloro compound was then utilized in the following step.

To the desired phenol (0.14 mmol, 1 eq) in DMF (1 mL) cooled to 0° C. was added NaH (60% suspension, 0.28 mmol, 2 eq.). The resulting suspension was then stirred at 0° C. for 15 min upon which the desired chloro compound (0.14 mmol, 1 eq) in DMF (1 mL) was added. The suspension was allowed to stir for 12 hrs. The crude mixture was evaporated in a Speed-Vac and purified via preparative HPLC under the following conditions.

The Gilson crude material was dissolved in 1.5 ml DMSO: 0.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions were analyzed by LC/MS as described below. Combining pure fractions and evaporating the solvent in a Speed-Vac isolated the title compound and then 0 min at 150° C., poured onto 100 mL MeOH, and the reaction allowed to cool to room temperature upon which a solid precipitated. The suspension was filtered and the solid recrystallized with MeOH. If purification via preparative HPLC was necessary the following conditions were utilized. The Gilson crude material was dissolved in 1.5 ml DMSO: 0.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions were analyzed by LC/MS as described below. Combining pure fractions and evaporating the solvent in a Speed-Vac isolated the title compound.

General Experimental for the Preparation of 8-Hydroxyquinolin-7-Yl (Procedure C)

To the desired chloro acetamide (15.6 mmol, 0.9 eq) and desired 8-hydroxyquinoline (17.3 mmol, 1 eq) was added the desired aromatic/heteroaromatic aldehyde (87 mmol, 5 equiv.) The resulting suspension was stirred for 120 min at 150° C., poured onto 100 mL MeOH, and the reaction allowed to cool to room temperature upon which a solid precipitated. The suspension was filtered and the solid recrystallized with MeOH. In some cases product remained in the filtrate and was subject to recrystallization. The resulting chloro compound was then utilized in the following step.

To the desired aniline (0.18 mmol, 1.3 eq) and chloro compound (0.14 mmol, 1 eq) in DMF (1 mL) was added DIEA (0.18 mmol, 1.3 eq). The reaction mixture was headed to 90° C. and allowed to stir for 12 hrs. The crude mixture was evaporated in a Speed-Vac and purified via preparative HPLC under the following conditions.

The Gilson crude material was dissolved in 1.5 ml DMSO: 0.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions were analyzed by LC/MS as described below. Combining pure fractions and evaporating the solvent in a Speed-Vac isolated the title compound and then 0 min at 150° C., poured onto 100 mL MeOH, and the reaction allowed to cool to room temperature upon which a solid precipitated. The suspension was filtered and the solid recrystallized with MeOH. If purification via preparative HPLC was necessary the following conditions were utilized. The Gilson crude material was dissolved in 1.5 ml DMSO: 0.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions were analyzed by LC/MS as described below. Combining pure fractions and evaporating the solvent in a Speed-Vac isolated the title compound.

The following compounds were prepared according to the above procedures and analyzed under the following conditions:

| Example No. | Compound | LC/MS MW Observed[b] | Retention Time[a] | Procedure |
|---|---|---|---|---|
| 1 | N-[(5-chloro-8-hydroxyquinolin-7-yl)(4-methoxyphenyl)methyl]-2-(pyridin-3-yloxy)acetamide | 450 | 1.88 | B |
| 2 | N-[(5-chloro-8-hydroxyquinolin-7-yl)(4-methoxyphenyl)methyl]-2-[3-(dimethylamino)phenoxy]acetamide | 492 | 2.55 | B |

-continued

| | | | | |
|---|---|---|---|---|
| 3 | N-[(5-chloro-8-hydroxyquinolin-7-yl)(4-methoxyphenyl)methyl]-2-(4-chloro-3-methylphenoxy)acetamide | 497 | 2.63 | B |
| 4 | 2-[4-(acetylamino)phenoxy]-N-[(5-chloro-8-hydroxyquinolin-7-yl)(4-methoxyphenyl)methyl]acetamide | 506 | 2.22 | B |
| 5 | N-[(5-chloro-8-hydroxyquinolin-7-yl)(2-chlorophenyl)methyl]-2-[3-(dimethylamino)phenoxy]acetamide | 496 | 2.60 | B |
| 6 | N-[(5-chloro-8-hydroxyquinolin-7-yl)(2-chlorophenyl)methyl]-2-(4-chloro-3-methylphenoxy)acetamide | 501 | 2.68 | B |
| 7 | 2-(4-tert-butylphenoxy)-N-[(5-chloro-8-hydroxyquinolin-7-yl)(2-chlorophenyl)methyl]acetamide | 509 | 2.77 | B |
| 8 | 2-[4-(acetylamino)phenoxy]-N-[(5-chloro-8-hydroxyquinolin-7-yl)(2-chlorophenyl)methyl]acetamide | 510 | 2.29 | B |
| 9 | N-[(5-chloro-8-hydroxyquinolin-7-yl)(2-methylphenyl)methyl]-2-phenoxyacetamide | 433 | 2.54 | A |
| 10 | N-[(5-chloro-8-hydroxyquinolin-7-yl)(3-nitrophenyl)methyl]-2-(pyridin-3-yloxy)acetamide | 465 | 2.29 | B |
| 11 | 2-(4-acetylphenoxy)-N-[(5-chloro-8-hydroxyquinolin-7-yl)(3-nitrophenyl)methyl]acetamide | 506 | 2.39 | B |
| 12 | N-[(5-chloro-8-hydroxyquinolin-7-yl)(3-nitrophenyl)methyl]-2-(4-chloro-3-methylphenoxy)acetamide | 512 | 2.65 | B |
| 13 | N-[(5-chloro-8-hydroxyquinolin-7-yl)(3-nitrophenyl)methyl]-2-(3,5-dichlorophenoxy)acetamide | 532 | 2.70 | B |
| 14 | N-[(5-chloro-8-hydroxyquinolin-7-yl)(3-fluorophenyl)methyl]-2-(pyridin-3-yloxy)acetamide | 438 | 2.22 | B |
| 15 | N-[(5-chloro-8-hydroxyquinolin-7-yl)(3-fluorophenyl)methyl]-2-[3-(dimethylamino)phenoxy]acetamide | 480 | 2.60 | B |
| 16 | 2-(4-tert-butylphenoxy)-N-[(5-chloro-8-hydroxyquinolin-7-yl)(3-fluorophenyl)methyl]acetamide | 493 | 2.77 | B |
| 17 | 2-[4-(acetylamino)phenoxy]-N-[(5-chloro-8-hydroxyquinolin-7-yl)(3-fluorophenyl)methyl]acetamide | 494 | 2.28 | B |
| 18 | $N^1$-[(5-chloro-8-hydroxyquinolin-7-yl)(2-chlorophenyl)methyl]-$N^2$-pyridin-3-ylglycinamide | 453 | 2.38 | C |
| 19 | $N^1$-[(5-chloro-8-hydroxyquinolin-7-yl)(2-chlorophenyl)methyl]-$N^2$-(4-chloro-3-methylphenyl)glycinamide | 500 | 2.62 | C |
| 20 | $N^2$-(4-tert-butylphenyl)-$N^1$-[(5-chloro-8-hydroxyquinolin-7-yl)(2-chlorophenyl)methyl]glycinamide | 508 | 2.72 | C |
| 21 | $N^1$-[(5-chloro-8-hydroxyquinolin-7-yl)(2-chlorophenyl)methyl]-$N^2$-(3,5-dichlorophenyl)glycinamide | 520 | 2.65 | C |
| 22 | $N^1$-[(5-chloro-8-hydroxyquinolin-7-yl)(4-methylphenyl)methyl]-$N^2$-pyridin-3-ylglycinamide | 433 | 2.40 | C |
| 23 | $N^1$-[(5-chloro-8-hydroxyquinolin-7-yl)(4-methylphenyl)methyl]-$N^2$-(4-cyanophenyl)glycinamide | 457 | 2.39 | C |
| 24 | $N^2$-(4-acetylphenyl)-$N^1$-[(5-chloro-8-hydroxyquinolin-7-yl)(4-methylphenyl)methyl]glycinamide | 474 | 2.33 | C |
| 25 | $N^1$-[(5-chloro-8-hydroxyquinolin-7-yl)(4-methylphenyl)methyl]-$N^2$-[3-(dimethylamino)phenyl]glycinamide | 475 | 2.53 | C |
| 26 | $N^1$-[(5-chloro-8-hydroxyquinolin-7-yl)(4-methylphenyl)methyl]-$N^2$-(4-chloro-3-methylphenyl)glycinamide | 480 | 2.64 | C |
| 27 | $N^2$-(4-tert-butylphenyl)-$N^1$-[(5-chloro-8-hydroxyquinolin-7-yl)(4-methylphenyl)methyl]glycinamide | 488 | 2.75 | C |
| 28 | $N^1$-[(5-chloro-8-hydroxyquinolin-7-yl)(3-nitrophenyl)methyl]-$N^2$-pyridin-3-ylglycinamide | 464 | 2.30 | C |
| 29 | $N^2$-(4-acetylphenyl)-$N^1$-[(5-chloro-8-hydroxyquinolin-7-yl)(3-nitrophenyl)methyl]glycinamide | 505 | 2.25 | C |
| 30 | $N^1$-[(5-chloro-8-hydroxyquinolin-7-yl)(3-nitrophenyl)methyl]-$N^2$-(4-chloro-3-methylphenyl)glycinamide | 511 | 2.54 | C |
| 31 | $N^2$-[4-(acetylamino)phenyl]-$N^1$-[(5-chloro-8-hydroxyquinolin-7-yl)(3-nitrophenyl)methyl]glycinamide | | | C |
| 32 | $N^1$-[(5-chloro-8-hydroxyquinolin-7-yl)(3-fluorophenyl)methyl]-$N^2$-pyridin-3-ylglycinamide | 437 | 2.33 | C |
| 33 | $N^1$-[(5-chloro-8-hydroxyquinolin-7-yl)(3-fluorophenyl)methyl]-$N^2$-(4-chloro-3-methylphenyl)glycinamide | 484 | 2.58 | C |
| 34 | N-[(5-chloro-8-hydroxyquinolin-7-yl)(2-fluorophenyl)methyl]-2-phenoxyacetamide | 437 | 2.49 | A |
| 35 | N-[(5-chloro-8-hydroxyquinolin-7-yl)(2-cyanophenyl)methyl]-2-phenoxyacetamide | 444 | 2.38 | A |

-continued

| | | | | |
|---|---|---|---|---|
| 36 | N-[(5-chloro-8-hydroxyquinolin-7-yl)(2,4-dimethylphenyl)methyl]-2-phenoxyacetamide | 447 | 2.61 | A |
| 37 | N-[(5-chloro-8-hydroxyquinolin-7-yl)(2,5-dimethylphenyl)methyl]-2-phenoxyacetamide | 447 | 2.60 | A |
| 38 | N-[(5-chloro-8-hydroxyquinolin-7-yl)(2-nitrophenyl)methyl]-2-phenoxyacetamide | 464 | 2.41 | A |
| 39 | N-[(2-chloro-4-hydroxyphenyl)(5-chloro-8-hydroxyquinolin-7-yl)methyl]-2-phenoxyacetamide | 469 | 2.31 | A |
| 40 | N-[(2-chloro-6-fluorophenyl)(5-chloro-8-hydroxyquinolin-7-yl)methyl]-2-phenoxyacetamide | 471 | 2.57 | A |
| 41 | N-[(2-chloro-4-fluorophenyl)(5-chloro-8-hydroxyquinolin-7-yl)methyl]-2-phenoxyacetamide | 471 | 2.55 | A |
| 42 | N-{(5-chloro-8-hydroxyquinolin-7-yl)[2-(trifluoromethyl)phenyl]methyl}-2-phenoxyacetamide | 487 | 2.60 | A |
| 43 | N-[(5-chloro-8-hydroxyquinolin-7-yl)(2,4-dichlorophenyl)methyl]-2-phenoxyacetamide | 487 | 2.66 | A |
| 44 | N-[(5-chloro-8-hydroxyquinolin-7-yl)(2-chloro-5-nitrophenyl)methyl]-2-phenoxyacetamide | 498 | 2.51 | A |
| 45 | N-[(2-chlorophenyl)(8-hydroxy-5-methylquinolin-7-yl)methyl]-2-phenoxyacetamide | 433 | 2.39 | A |
| 46 | N-[(8-hydroxy-5-methylquinolin-7-yl)(3-nitrophenyl)methyl]-2-phenoxyacetamide | 444 | 2.38 | A |
| 47 | N-[(8-hydroxy-5-methylquinolin-7-yl)(2-methylphenyl)methyl]-2-phenoxyacetamide | 413 | 2.38 | A |
| 48 | N-[(5-bromo-8-hydroxyquinolin-7-yl)(2-chlorophenyl)methyl]-2-phenoxyacetamide | 497 | 2.51 | A |
| 49 | N-[(5-bromo-8-hydroxyquinolin-7-yl)(3-nitrophenyl)methyl]-2-phenoxyacetamide | 508 | 2.48 | A |
| 50 | N-[(5-bromo-8-hydroxyquinolin-7-yl)(2-methylphenyl)methyl]-2-phenoxyacetamide | 477 | 2.52 | A |
| 51 | $N^1$-[(5-chloro-8-hydroxyquinolin-7-yl)(2-chlorophenyl)methyl]-$N^2$-methyl-$N^2$-phenylglycinamide | 466 | 2.51 | C |
| 52 | $N^2$-benzyl-$N^1$-[(5-chloro-8-hydroxyquinolin-7-yl)(2-chlorophenyl)methyl]-$N^2$-methylglycinamide | 480 | 2.07 | C |
| 53 | $N^2$-benzyl-$N^1$-[(5-chloro-8-hydroxyquinolin-7-yl)(2-chlorophenyl)methyl]glycinamide | 466 | 2.03 | C |
| 54 | $N^1$-[(5-chloro-8-hydroxyquinolin-7-yl)(3-fluorophenyl)methyl]-$N^2$-methyl-$N^2$-phenylglycinamide | 450 | 2.49 | C |
| 55 | $N^2$-benzyl-$N^1$-[(5-chloro-8-hydroxyquinolin-7-yl)(3-fluorophenyl)methyl]-$N^2$-methylglycinamide | 464 | 2.05 | C |
| 56 | $N^2$-benzyl-$N^1$-[(5-chloro-8-hydroxyquinolin-7-yl)(3-fluorophenyl)methyl]glycinamide | 450 | 2.01 | C |
| 57 | 2-(benzyloxy)-N-[(5-chloro-8-hydroxyquinolin-7-yl)(3-fluorophenyl)methyl]acetamide | 451 | 2.50 | C |
| 58 | $N^1$-[(5-chloro-8-hydroxyquinolin-7-yl)(4-methylphenyl)methyl]-$N^2$-methyl-$N^2$-phenylglycinamide | 446 | 2.55 | C |
| 59 | $N^2$-benzyl-$N^1$-[(5-chloro-8-hydroxyquinolin-7-yl)(4-methylphenyl)methyl]-$N^2$-methylglycinamide | 460 | 2.09 | C |
| 60 | $N^2$-benzyl-$N^1$-[(5-chloro-8-hydroxyquinolin-7-yl)(4-methylphenyl)methyl]glycinamide | 446 | 2.05 | C |
| 61 | 2-(benzyloxy)-N-[(5-chloro-8-hydroxyquinolin-7-yl)(4-methylphenyl)methyl]acetamide | 447 | 2.56 | C |
| 62 | $N^1$-[(5-chloro-8-hydroxyquinolin-7-yl)(3-nitrophenyl)methyl]-$N^2$-methyl-$N^2$-phenylglycinamide | 477 | 2.45 | C |
| 63 | $N^2$-benzyl-$N^1$-[(5-chloro-8-hydroxyquinolin-7-yl)(3-nitrophenyl)methyl]-$N^2$-methylglycinamide | 491 | 2.03 | C |
| 64 | $N^2$-benzyl-$N^1$-[(5-chloro-8-hydroxyquinolin-7-yl)(3-nitrophenyl)methyl]glycinamide | 477 | 1.99 | C |
| 65 | N-[(8-hydroxyquinolin-7-yl)(phenyl)methyl]benzamide | | | A |
| 66 | N-[(8-hydroxyquinolin-7-yl)(phenyl)methyl]acetamide | | | A |
| 67 | N-[(5-chloro-8-hydroxyquinolin-7-yl)(phenyl)methyl]benzamide | | | A |
| 68 | N-[(5-chloro-8-hydroxyquinolin-7-yl)(phenyl)methyl]acetamide | | | A |
| 69 | N-[(5-chloro-8-hydroxyquinolin-7-yl)(pyridin-3-yl)methyl]-2-phenoxyacetamide | 420 | 2.34 | A |
| 70 | N-[(5-chloro-8-hydroxyquinolin-7-yl)(2-thienyl)methyl]-2-phenoxyacetamide | 425 | 2.49 | A |
| 71 | N-[(5-chloro-8-hydroxyquinolin-7-yl)(3,5-dimethoxyphenyl)methyl]-2-phenoxyacetamide | 479 | 2.49 | A |
| 72 | N-[(5-chloro-8-hydroxyquinolin-7-yl)(3,4-dichlorophenyl)methyl]-2-phenoxyacetamide | | | A |
| 73 | N-[(5-chloro-8-hydroxyquinolin-7-yl)(3,4-dichlorophenyl)methyl]-2-phenoxyacetamide | 429 | 2.41 | B |
| 74 | N-[(8-hydroxyquinolin-7-yl)(4-methoxyphenyl)methyl]-2-(4-methylphenoxy)acetamide | 415 | 2.32 | B |
| 75 | N-[(8-hydroxyquinolin-7-yl)(phenyl)methyl]-2-(4-methoxyphenoxy)acetamide | 507 | 2.58 | B |
| 76 | N-[(8-hydroxyquinolin-7-yl)(4-methoxyphenyl)methyl]-2-(4-phenoxyphenoxy)acetamide | 399 | 2.44 | B |

-continued

| | | | | |
|---|---|---|---|---|
| 77 | N-[(8-hydroxyquinolin-7-yl)(phenyl)methyl]-2-(4-methylphenoxy)acetamide | 445 | 2.30 | B |
| 78 | N-[(8-hydroxyquinolin-7-yl)(4-methoxyphenyl)methyl]-2-(4-methoxyphenoxy)acetamide | 477 | 2.60 | B |
| 79 | N-[(8-hydroxyquinolin-7-yl)(phenyl)methyl]-2-(4-phenoxyphenoxy)acetamide | 463 | 2.59 | B |
| 80 | N-[(5-chloro-8-hydroxyquinolin-7-yl)(4-methoxyphenyl)methyl]-2-(4-methylphenoxy)acetamide | 449 | 2.51 | B |
| 81 | N-[(5-chloro-8-hydroxyquinolin-7-yl)(phenyl)methyl]-2-(4-methoxyphenoxy)acetamide | 541 | 2.72 | B |
| 82 | N-[(5-chloro-8-hydroxyquinolin-7-yl)(4-methoxyphenyl)methyl]-2-(4-phenoxyphenoxy)acetamide | 433 | 2.61 | B |
| 83 | N-[(5-chloro-8-hydroxyquinolin-7-yl)(phenyl)methyl]-2-(4-methylphenoxy)acetamide | 479 | 2.49 | B |
| 84 | N-[(8-hydroxyquinolin-7-yl)(4-nitrophenyl)methyl]-2-phenoxyacetamide | 430 | 2.41 | A |
| 85 | N-[(5-chloro-8-hydoxyquinolin-7-yl)(phenyl)methyl]-2-(4-phenoxyphenoxy)acetamide | 511 | 2.73 | B |
| 86 | N-[(8-hydroxyquinolin-7-yl)(phenyl)methyl]-2-phenoxyacetamide | 385 | 2.34 | A |
| 87 | N-[(8-hydroxyquinolin-7-yl)(4-methylphenyl)methyl]-2-phenoxyacetamide | 399 | 2.43 | A |
| 88 | N-[(8-hydroxyquinolin-7-yl)(4-methoxyphenyl)methyl]-2-phenoxyacetamide | 415 | 2.32 | A |
| 89 | N-[(2-chlorophenyl)(8-hydroxyquinolin-7-yl)methyl]-2-phenoxyacetamide | 419 | 2.39 | A |
| 90 | N-[(4-chlorophenyl)(8-hydroxyquinolin-7-yl)methyl]-2-phenoxyacetamide | 419 | 2.48 | A |
| 91 | N-[(5-chloro-8-hydroxyquinolin-7-yl)(phenyl)methyl]-2-phenoxyacetamide | 419 | 2.53 | A |
| 92 | N-[(5-chloro-8-hydroxyquinolin-7-yl)(4-methylphenyl)methyl]-2-phenoxyacetamide | 433 | 2.61 | A |
| 93 | N-[(5-chloro-8-hydroxyquinolin-7-yl)(4-methylphenyl)methyl]-2-phenoxyacetamide | 449 | 2.51 | A |
| 94 | N-[(5-chloro-8-hydroxyquinolin-7-yl)(2-chlorophenyl)methyl]-2-phenoxyacetamide | 453 | 2.56 | A |
| 95 | N-[(5-chloro-8-hydroxyquinolin-7-yl)(4-chlorophenyl)methyl]-2-phenoxyacetamide | 453 | 2.65 | A |
| 96 | N-[(5-chloro-8-hydroxyquinolin-7-yl)(3-nitrophenyl)methyl]-2-phenoxyacetamide | 464 | 2.52 | A |
| 97 | N-[(5-chloro-8-hydroxyquinolin-7-yl)(4-nitrophenyl)methyl]-2-phenoxyacetamide | 464 | 2.52 | A |
| 98 | N-[(3-fluorophenyl)(8-hydroxyquinolin-7-yl)methyl]-2-phenoxyacetamide | 403 | 2.37 | A |
| 99 | N-[[4-(dimethylamino)phenyl](8-hydroxyquinolin-7-yl)methyl]-2-phenoxyacetamide | 428 | 2.03 | A |
| 100 | N-[(5-chloro-8-hydroxyquinolin-7-yl)(4-hydroxy-3-methoxyphenyl)methyl]-2-phenoxyacetamide | | | A |
| 101 | N-[(5-chloro-8-hydroxyquinolin-7-yl)(phenyl)methyl]-2-(4-chlorophenoxy)acetamide | 453 | 2.60 | B |
| 102 | N-[(5-chloro-8-hydroxyquinolin-7-yl)(3-fluorophenyl)methyl]-2-phenoxyacetamide | 437 | 2.54 | A |
| 103 | N-[(3-chloro-4-fluorophenyl)(5-chloro-8-hydroxyquinolin-7-yl)methyl]-2-phenoxyacetamide | 471 | 2.63 | A |
| 104 | N-[(5-chloro-8-hydroxyquinolin-7-yl)(2,6-dichlorophenyl)methyl]-2-phenoxyacetamide | 487 | 2.68 | A |
| 105 | N-[(5-chloro-8-hydroxyquinolin-7-yl)(phenyl)methyl]-2-(pyridin-3-yloxy)acetamide | 420 | 1.86 | B |
| 106 | N-[(5-chloro-8-hydroxyquinolin-7-yl)(4-methoxyphenyl)methyl]-2-(3-methoxyphenoxy)acetamide | 479 | 2.46 | B |
| 107 | 2-(4-tert-butylphenoxy)-N-[(5-chloro-8-hydroxyquinolin-7-yl)(4-methoxyphenyl)methyl]acetamide | 505 | 2.73 | B |
| 108 | N-[(2-chlorophenyl)(8-hydroxy-5-nitroquinolin-7-yl)methyl]-2-phenoxyacetamide | 464 | 2.33 | A |
| 109 | N-[(8-hydroxy-5-nitroquinolin-7-yl)(2-methylphenyl)methyl]-2-phenoxyacetamide | 444 | 2.33 | A |
| 110 | N-[(8-hydroxy-5-nitroquinolin-7-yl)(phenyl)methyl]-2-phenoxyacetamide | 430 | 2.31 | A |
| 111 | N-[(5-fluoro-8-hydroxyquinolin-7-yl)(phenyl)methyl]-2-phenoxyacetamide | 403 | 2.38 | A |
| 112 | N-[(5-chloro-8-hydroxyquinolin-7-yl)(2-methylphenyl)methyl]-4-phenylbutanamide | | | A |
| 113 | N-[(5-chloro-8-hydroxyquinolin-7-yl)(2-chlorophenyl)methyl]-4-phenylbutanamide | | | A |
| 114 | N-[(5-chloro-8-hydroxyquinolin-7-yl)(4-methylphenyl)methyl]-4-phenylbutanamide | | | A |
| 115 | N-[(5-chloro-8-hydroxyquinolin-7-yl)(3-nitrophenyl)methyl]-4-phenylbutanamide | | | A |

| | | | | |
|---|---|---|---|---|
| 116 | N-[(5-chloro-8-methoxyquinolin-7-yl)(phenyl)methyl]-2-phenoxyacetamide | 433 | 2.44 | A |
| 117 | N-[(5-chloro-8-methoxyquinolin-7-yl)(2-chlorophenyl)methyl]-2-phenoxyacetamide | 467 | 2.46 | A |
| 118 | N-[(S)-(5-chloro-8-hydroxyquinolin-7-yl)(2-chlorophenyl)methyl]-2-phenoxyacetamide | | | A |
| 119 | N-[(R)-(5-chloro-8-hydroxyquinolin-7-yl)(2-chlorophenyl)methyl]-2-phenoxyacetamide | | | A |
| 120 | N-[(R)-(5-chloro-8-hydroxyquinolin-7-yl)(phenyl)methyl]-2-phenoxyacetamide | | | A |
| 121 | N-[(S)-(5-chloro-8-hydroxyquinolin-7-yl)(phenyl)methyl]-2-phenoxyacetamide | | | A |

[a]HPLC Conditions: Instrument - Agilent 1100
Column: Thermo Aquasil C18, 50 × 2.1 mm, 5um
Mobile Phase    A: 0.1% Formic Acid in water
                        B: 0.1% Formic Acid in ACN
Flow Rate: 0.800 mL/min
Column Temperature: 40° C.
Injection Volume: 5 mL
UV: monitor 215, 230, 254, 280, and 300 nm
Purity is reported at 254 nm unless otherwise noted

| | Time (min) | % B |
|---|---|---|
| Gradient Table: | 0 | 5 |
| | 2.5 | 95 |
| | 4.0 | 95 |
| | 4.1 | 5 |
| | 5.5 | 5 |

[b]MS Conditions: Instrument: Agilent MSD; Ionization Mode: API-ES; Gas Temperature: 350° C.; Drying Gas: 11.0 L/min.; Nebulizer Pressure: 55psig; Polarity: 50% positive, 50% negative; VCap: 3000 V (positive), 2500 V (negative); Fragmentor: 80 (positive), 120 (negative); Mass Range: 100-1000 m/z; Threshold: 150; Step size: 0.15; Gain: 1; Peak width: 0.15 min.

Examples 122-201

General Experimental for the Preparation of Hydroxyquinoline Compounds

The hydroxyquinolines were prepared in a single step by means of a three component coupling reaction [an aromatic variant of the Mannich reaction]: A mixture of 5-chloro-8-hydroxyquinoline (1-1.1 equiv.), amide component (1 equiv.) and aldehyde component (2.5-4 equiv.) were heated neat at 145-150° C. for 3-6 hours. Typically, the hydroxyquinoline was isolated by multiple trituration with hexanes and isopropyl ether followed by recrystallization from ethanol furnishing product in 14-80% yield.

The subsequent 88 examples follow the above procedure:

| Example No. | Compound | MS (ESI) m/z |
|---|---|---|
| 122 | N-[(5-chloro-8-hydroxyquinolin-7-yl)(2-methoxyphenyl)methyl]-2-phenoxyacetamide | 449.2 |
| 123 | N-[(5-chloro-8-hydroxyquinolin-7-yl)(2-morpholin-4-ylphenyl)methyl]-2-phenoxyacetamide | 504.2 |
| 124 | N-[(5-chloro-8-hydroxyquinolin-7-yl)(2-hydroxyphenyl)methyl]-2-phenoxyacetamide | 435.2 |
| 125 | 2-{(5-chloro-8-hydroxyquinolin-7-yl)[(phenoxyacetyl)amino]methyl}benzoic acid | 461.3 |
| 126 | N-[(5-chloro-8-hydroxyquinolin-7-yl)(3-methoxyphenyl)methyl]-2-phenoxyacetamide | 449.2 |
| 127 | ethyl(3-{(5-chloro-8-hydroxyquinolin-7-yl)[(phenoxyacetyl)amino]methyl}phenyl)acetate | 505 |
| 128 | N-{(5-chloro-8-hydroxyquinolin-7-yl)[3-(4-methoxyphenoxy)phenyl]methyl}-2-phenoxyacetamide | 541.4 |
| 129 | N-{(5-chloro-8-hydroxyquinolin-7-yl)[3-(4-chlorophenoxy)phenyl]methyl}-2-phenoxyacetamide | 545.3 |
| 130 | N-{(5-chloro-8-hydroxyquinolin-7-yl)[3-(4-methylphenoxy)phenyl]methyl}-2-phenoxyacetamide | 525.3 |
| 131 | N-[(5-chloro-8-hydroxyquinolin-7-yl)(3-phenoxyphenyl)methyl]-2-phenoxyacetamide | 511.3 |
| 132 | N-[[3-(benzyloxy)phenyl](5-chloro-8-hydroxyquinolin-7-yl)methyl]-2-phenoxyacetamide | 525.4 |
| 133 | N-[(5-chloro-8-hydroxyquinolin-7-yl)(4-fluorophenyl)methyl]-2-phenoxyacetamide | 437.2 |
| 134 | N-{(5-chloro-8-hydroxyquinolin-7-yl)[4-(dimethylamino)phenyl]methyl}-2-phenoxyacetamide | 462.2 252.1 |
| 135 | N-{(5-chloro-8-hydroxyquinolin-7-yl)[4-(diethylamino)phenyl]methyl}-2-phenoxyacetamide | 490.4 |
| 136 | N-{(5-chloro-8-hydroxyquinolin-7-yl)[4-(dibutylamino)phenyl]methyl}-2-phenoxyacetamide | 546.3 273.6 |
| 137 | N-[(5-chloro-8-hydroxyquinolin-7-yl)(4-isopropylphenyl)methyl]-2-phenoxyacetamide | 461.2 |
| 138 | N-[[4-(allyloxy)phenyl](5-chloro-8-hydroxyquinolin-7-yl)methyl]-2-phenoxyacetamide | 475.2 |
| 139 | N-[(4-butoxyphenyl)(5-chloro-8-hydroxyquinolin-7-yl)methyl]-2-phenoxyacetamide | 491.3 |

-continued

| Example No. | Compound | MS (ESI) m/z |
|---|---|---|
| 140 | N-[(5-chloro-8-hydroxyquinolin-7-yl)(4-hex-1-yn-1-ylphenyl)methyl]-2-phenoxyacetamide | 499.4 977.8 180.1 |
| 141 | N-{(5-chloro-8-hydroxyquinolin-7-yl)[4-(phenylethynyl)phenyl]methyl}-2-phenoxyacetamide | 519.3 1037.6 |
| 142 | N-[[4-(benzyloxy)phenyl](5-chloro-8-hydroxyquinolin-7-yl)methyl]-2-phenoxyacetamide | 525.3 |
| 143 | N-[biphenyl-4-yl(5-chloro-8-hydroxyquinolin-7-yl)methyl]-2-phenoxyacetamide | 495.3 |
| 144 | N-[(5-chloro-8-hydroxyquinolin-7-yl)(4-pyridin-4-ylphenyl)methyl]-2-phenoxyacetamide | 496.3 269.2 |
| 145 | N-{(5-chloro-8-hydroxyquinolin-7-yl)[4-(1H-pyrazol-1-yl)phenyl]methyl}-2-phenoxyacetamide | 485.2 |
| 146 | N-[[4-(4-tert-butyl-1,3-thiazol-2-yl)phenyl](5-chloro-8-hydroxyquinolin-7-yl)methyl]-2-phenoxyacetamide | 558.3 279.7 1115.7 |
| 147 | N-{(5-chloro-8-hydroxyquinolin-7-yl)[4-(1,2,3-thiadiazol-4-yl)phenyl]methyl}-2-phenoxyacetamide | 503.3 |
| 148 | N-[(5-chloro-8-hydroxyquinolin-7-yl)(3,4-dimethylphenyl)methyl]-2-phenoxyacetamide | 447.2 |
| 149 | N-[(5-chloro-8-hydroxyquinolin-7-yl)(3,4-dimethoxyphenyl)methyl]-2-phenoxyacetamide | 479.1 |
| 150 | N-[[3-(benzyloxy)-4-methoxyphenyl](5-chloro-8-hydroxyquinolin-7-yl)methyl]-2-phenoxyacetamide | 555.3 |
| 151 | N-[(5-chloro-8-hydroxyquinolin-7-yl)(2-furyl)methyl]-2-phenoxyacetamide | 409.1 |
| 152 | N-[(5-chloro-8-hydroxyquinolin-7-yl)(5-methyl-2-furyl)methyl]-2-phenoxyacetamide | 423 |
| 153 | N-[(5-chloro-8-hydroxyquinolin-7-yl)(3-furyl)methyl]-2-phenoxyacetamide | 409 |
| 154 | N-[(5-chloro-8-hydroxyquinolin-7-yl)(5-phenyl-2-furyl)methyl]-2-phenoxyacetamide | 485.2 |
| 155 | N-[(5-chloro-8-hydroxyquinolin-7-yl)(3-methyl-2-thienyl)methyl]-2-phenoxyacetamide | 439.1 |
| 156 | N-[(5-chloro-8-hydroxyquinolin-7-yl)(1H-indol-7-yl)methyl]-2-phenoxyacetamide | 458.1 915.2 |
| 157 | N-[(5-chloro-8-hydroxyquinolin-7-yl)(1H-indol-4-yl)methyl]-2-phenoxyacetamide | 458.2 915.5 |
| 158 | N-[(5-chloro-8-hydroxyquinolin-7-yl)(1-methyl-1H-indol-3-yl)methyl]-2-phenoxyacetamide | 472.1 |
| 159 | N-[1,3-benzodioxol-4-yl(5-chloro-8-hydroxyquinolin-7-yl)methyl]-2-phenoxyacetamide | 463.3 |
| 160 | N-[(5-chloro-8-hydroxyquinolin-7-yl)(quinolin-8-yl)methyl]-2-phenoxyacetamide | 470.3 |
| 161 | N-[(5-chloro-8-hydroxyquinolin-7-yl)(quinolin-4-yl)methyl]-2-phenoxyacetamide | 470.1 |
| 162 | N-[(5-chloro-8-hydroxyquinolin-7-yl)(quinolin-5-yl)methyl]-2-phenoxyacetamide | 470.1 |
| 163 | N-[(5-chloro-8-hydroxyquinolin-7-yl)(4-methoxy-1-naphthyl)methyl]-2-phenoxyacetamide | 499.3 997.7 |
| 164 | N-[(5-chloro-8-hydroxyquinolin-7-yl)(9-phenanthryl)methyl]-2-phenoxyacetamide | 519.4 1037.7 |
| 165 | N-[(5-chloro-8-hydroxyquinolin-7-yl)(6-methoxy-2-naphthyl)methyl]-2-phenoxyacetamide | 499.3 997.7 |
| 166 | N-[(5-chloro-8-hydroxyquinolin-7-yl)(2,3-dihydro-1,4-benzodioxin-6-yl)methyl]-2-phenoxyacetamide | 477.3 |
| 167 | N-[(5-chloro-8-hydroxyquinolin-7-yl)(quinolin-3-yl)methyl]-2-phenoxyacetamide | 470.3 |
| 168 | N-[1-benzofuran-2-yl(5-chloro-8-hydroxyquinolin-7-yl)methyl]-2-phenoxyacetamide | 459.3 |
| 169 | N-[(5-chloro-8-hydroxyquinolin-7-yl)(1-methyl-1H-indol-2-yl)methyl]-2-phenoxyacetamide | 472.2 943.5 |
| 170 | N-[(5-chloro-8-hydroxyquinolin-7-yl)(2,3-dihydro-1-benzofuran-5-yl)methyl]-2-phenoxyacetamide | 461.2 |
| 171 | N-[(5-chloro-8-hydroxyquinolin-7-yl)(2,2-dimethyl-3,4-dihydro-2H-chromen-6-yl)methyl]-2-phenoxyacetamide | 503.3 1005.6 |
| 172 | N-[(5-chloro-8-hydroxyquinolin-7-yl)(4-oxo-4H-chromen-3-yl)methyl]-2-phenoxyacetamide | 487.2 |
| 173 | N-[(5-chloro-8-hydroxyquinolin-7-yl)(6-methyl-4-oxo-4H-chromen-3-yl)methyl]-2-phenoxyacetamide | 501.3 1001.7 |
| 174 | N-[(5-chloro-8-hydroxyquinolin-7-yl)(4H-pyrazolo[1,5-c][1,3]thiazol-2-yl)methyl]-2-phenoxyacetamide | 467.2 |
| 175 | N-[1,3-benzodioxol-5-yl(5-chloro-8-hydroxyquinolin-7-yl)methyl]-2-phenoxyacetamide | 463.1 |
| 176 | N-[(6-chloro-1,3-benzodioxol-5-yl)(5-chloro-8-hydroxyquinolin-7-yl)methyl]-2-phenoxyacetamide | 497.1 |
| 177 | N-[(5-chloro-8-hydroxyquinolin-7-yl)(1-methyl-1H-1,2,3-benzotriazol-5-yl)methyl]-2-phenoxyacetamide | 474.2 947.3 |
| 178 | N-[(5-chloro-8-hydroxyquinolin-7-yl)(5,6-dihydro-8H-imidazo[2,1-c][1,4]oxazin-2-yl)methyl]-2-phenoxyacetamide | 465.2 |

| Example No. | Compound | MS (ESI) m/z |
|---|---|---|
| 179 | N-[(5-chloro-8-hydroxyquinolin-7-yl)(5,6-dihydro-4H-pyrrolo[1,2-b]pyrazol-2-yl)methyl]-2-phenoxyacetamide | 449.2 |
| 180 | N-[(5-chloro-8-hydroxyquinolin-7-yl)(phenyl)methyl]-3-phenylpropanamide | 417.2 |
| 181 | benzyl [(5-chloro-8-hydroxyquinolin-7-yl)(phenyl)methyl]carbamate | 419 |
| 182 | benzyl [(5-chloro-8-hydroxyquinolin-7-yl)(2-chlorophenyl)methyl]carbamate | 453.1 |
| 183 | benzyl [(5-chloro-8-hydroxyquinolin-7-yl)(pyridin-2-yl)methyl]carbamate | 420.1 |
| 184 | benzyl [(5-chloro-8-hydroxyquinolin-7-yl)(2-furyl)methyl]carbamate | 409 |
| 185 | benzyl [1,3-benzodioxol-5-yl(5-chloro-8-hydroxyquinolin-7-yl)methyl]carbamate | 463.1 |
| 186 | N-[1-(5-chloro-8-hydroxyquinolin-7-yl)prop-2-en-1-yl]-2-phenoxyacetamide | 369.1 |
| 187 | N-[(2E)-1-(5-chloro-8-hydroxyquinolin-7-yl)but-2-en-1-yl]-2-phenoxyacetamide | 383.1 |
| 188 | N-[(2E)-1-(5-chloro-8-hydroxyquinolin-7-yl)hex-2-en-1-yl]-2-phenoxyacetamide | 411.2 |
| 189 | N-[(5-chloro-8-hydroxyquinolin-7-yl)(cyclohex-1-en-1-yl)methyl]-2-phenoxyacetamide | 423.2 |
| 190 | N-[(2E)-1-(5-chloro-8-hydroxyquinolin-7-yl)-3-phenylprop-2-en-1-yl]-2-phenoxyacetamide | 445.2 |
| 191 | N-[(2Z)-1-(5-chloro-8-hydroxyquinolin-7-yl)-2-methoxy-3-phenylprop-2-en-1-yl]-2-phenoxyacetamide | 475.2 |
| 192 | benzyl [1-(5-chloro-8-hydroxyquinolin-7-yl)-2-phenylethyl]carbamate | 433.2 |
| 193 | N-[1-(5-chloro-8-hydroxyquinolin-7-yl)-3-phenylpropyl]-2-phenoxyacetamide | 447.2 |
| 194 | N-[(5-chloro-8-hydroxyquinolin-7-yl)(phenyl)methyl]-2-phenylacetamide | 403.1 |
| 195 | N-[(5-chloro-8-hydroxyquinolin-7-yl)(2-chlorophenyl)methyl]-2-phenylacetamide | 437.1 |
| 196 | N-[(5-chloro-8-hydroxyquinolin-7-yl)(4-fluorophenyl)methyl]-2-phenylacetamide | 421.1 |
| 197 | N-[[3-(benzyloxy)-4-methoxyphenyl](5-chloro-8-hydroxyquinolin-7-yl)methyl]-2-phenylacetamide | 539.2 |
| 198 | N-[(2E)-1-(5-chloro-8-hydroxyquinolin-7-yl)-3-phenylprop-2-en-1-yl]-2-phenylacetamide | 429.2 |
| 199 | N-[(5-chloro-8-hydroxyquinolin-7-yl)(3-methyl-2-thienyl)methyl]-2-phenylacetamide | 423.2 |
| 200 | N-[(5-bromo-8-hydroxyquinolin-7-yl)(phenyl)methyl]-2-phenoxyacetamide | 463.2 |
| 201 | N-[(5-bromo-8-hydroxyquinolin-7-yl)(phenyl)methyl]-2-chloroacetamide | 405.1 |

Example 202

A mixture of N-[(3-nitrophenyl)(5-chloro-8-hydroxyquinolin-7-yl)methyl]-2-phenoxyacetamide (2 g, 4.31 mmol) and 10% Pd/C (250 mg, Lancaster) in THF was hydrogenated for 20 h at 40 psi. The catalyst was filtered off, and solvent was removed under vacuum. The residue was triturated with ether, filtered and the cake was washed with ether to give 1.1 g of N-[(3-aminophenyl)(5-chloro-8-hydroxyquinolin-7-yl)methyl]-2-phenoxyacetamide as an off-white solid.

N-[(3-aminophenyl)(5-chloro-8-hydroxyquinolin-7-yl)methyl]-2-phenoxyacetamide

MS (ESI) m/z 434.1;
MS (ESI) m/z 238.1.

Example 203

A mixture of N-[(3-aminophenyl)(5-chloro-8-hydroxyquinolin-7-yl)methyl]-2-phenoxyacetamide (120 mg, 0.28 mmol), methanesulfonylchloride (39.90 mg, 0.28 mmol in pyridine (7.5 ml) were stirred at room temperature for 18 h. To the reaction mixture was added water and solids were filtered and dried. The brown solid (100 mg) was purified by column chromatography (eluent: ethylacetate/DCM 1:3) to give 42 mg (29%) of 5-chloro-7-{{3-[(methylsulfonyl)amino]phenyl}[(phenoxyacetyl)amino]methyl}quinolin-8-yl methanesulfonate as a white solid.

5-chloro-7-{{3-[(methylsulfonyl)amino]phenyl}[(phenoxyacetyl)amino]methyl}quinolin-8-yl methanesulfonate MS (ESI) m/z 588.2;
MS (ESI) m/z 1177.4.

Example 204

To the suspension of N-[(3-aminophenyl)(5-chloro-8-hydroxyquinolin-7-yl)methyl]-2-phenoxyacetamide (150 mg, 0.35 mmol) in methylenechloride (4 ml) cooled to 0 C was added DIEA (50 mg, 0.38 mmol) followed by acetylchloride (32.4 mg, 0.42 mmol). Purification by flush chromatography (eluent 30% acetone/DCM) afforded 96 mg (57%) of N-[[3-(acetylamino)phenyl](5-chloro-8-hydroxyquinolin-7-yl)methyl]-2-phenoxyacetamide as a white solid.

N-[[3-(acetylamino)phenyl](5-chloro-8-hydroxyquinolin-7-yl)methyl]-2-phenoxyacetamide MS (ESI) m/z 476.2;
MS (ESI) m/z 951.4.

Example 205

To a suspension of N-[(3-aminophenyl)(5-chloro-8-hydroxyquinolin-7-yl)methyl]-2-phenoxyacetamide (800 mg, 1.84 mmol) in methylenechloride (30 ml) cooled to 0 C was added DIEA (300 mg, 2.32 mmol) followed by chloroacetyl chloride (300 mg, 2.65 mmol). Purification by flush chromatography (eluent 30% acetone/DCM) afforded 500 mg (53%) of 2-chloro-N-(3-{(5-chloro-8-hydroxyquinolin-7-yl)[(phenoxyacetyl)amino]methyl}phenyl)acetamide an off-white solid.

2-chloro-N-(3-{(5-chloro-8-hydroxyquinolin-7-yl)
[(phenoxyacetyl)amino]methyl}phenyl)acetamide MS (ESI) m/z 509.8.

Example 206

A solution of 2-chloro-N-(3-{(5-chloro-8-hydroxyquinolin-7-yl)[(phenoxyacetyl)amino]methyl}phenyl)acetamide (100 mg, 0.20 mmol) and dimethylamine (2M/THF, 10 eq.) was heated at 45 C for 18 h. The solvent was removed in vacuo, the residue was dissolved in methylene chloride and washed with water and brine. The organic layer was dried over sodium sulfate and concentrated in vacuo to afford 48 mg (46%) of N-(3-{(5-chloro-8-hydroxyquinolin-7-yl) [(phenoxyacetyl)amino]methyl}phenyl)-N2,N2-dimethylglycinamide as a beige solid.

N-(3-{(5-chloro-8-hydroxyquinolin-7-yl)[(phenoxyacetyl)amino]methyl}phenyl)-N2,N2-dimethylglycinamide MS (ESI) m/z 519.3;
MS (ESI) m/z 260.1;
HRMS: calcd for C28H27ClN4O4+H+, 519.17936; found (ESI-FTMS, [M+H]1+), 519.1812.

Example 207

A solution of 2-chloro-N-(3-{(5-chloro-8-hydroxyquinolin-7-yl) [(phenoxyacetyl)amino]methyl}phenyl)acetamide (100 mg, 0.20 mmol) and methylamine (33% in ethanol, 10 eq.) in THF was stirred at room temperature for 4 h. The solvent was removed in vacuo, the residue was dissolved in methylene chloride and washed with water and brine. The organic layer was dried over sodium sulfate and concentrated in vacuo to afford 47 mg (47%) of N-(3-{(5-chloro-8-hydroxyquinolin-7-yl)[(phenoxyacetyl)amino]methyl}phenyl)-N-2-methylglycinamide a beige solid.

N-(3-{(5-chloro-8-hydroxyquinolin-7-yl)[(phenoxyacetyl)amino]methyl}phenyl)-N-2-methylglycinamide MS (ESI) m/z 505.3;
HRMS: calcd for C27H25ClN4O4+H+, 505.16371; found (ESI-FTMS, [M+H]1+), 505.16483.

Examples 208-212

The solution of 100 mg of ethyl(3-{(5-chloro-8-hydroxyquinolin-7-yl) [(phenoxyacetyl)amino]methyl}phenyl)acetate in THF and Sodium hydroxide (aqueous, 5 eq.) were stirred at room temperature for 48 h. The reaction mixture was acidified to pH 3 with 2N aq. HCl, then concentrated. The residue was diluted with methylene chloride, washed with water, dried over sodium sulfate and concentrated. Solids were triturated with ether and filtered to give 40 mg (43%) of (3-{(5-chloro-8-hydroxyquinolin-7-yl)[(phenoxyacetyl) amino]methyl}phenyl)acetic acid as a white solid.

(3-{(5-chloro-8-hydroxyquinolin-7-yl)[(phenoxyacetyl)amino]methyl}phenyl)acetic acid MS (ESI) m/z 477.1;
2-chloro-N-[(5-chloro-8-hydroxyquinolin-7-yl)(phenyl) methyl]acetamide was reacted with a series of aromatic phenols in an acetonitrile/DMPU solution.

The subsequent four examples follow the above procedure:

| Example No. | Compound | MS (ESI) m/z |
|---|---|---|
| 209 | 2-(4-bromophenoxy)-N-[(5-chloro-8-hydroxyquinolin-7-yl)(phenyl)methyl]acetamide | 497.1 |
| 210 | N-[(5-chloro-8-hydroxyquinolin-7-yl)(phenyl)methyl]-2-(3,4,5-trimethoxyphenoxy)acetamide | 509.2 |
| 211 | 2-(biphenyl-4-yloxy)-N-[(5-chloro-8-hydroxyquinolin-7-yl)(phenyl)methyl]acetamide | 495.2 989.6 |
| 212 | N-[(5-chloro-8-hydroxyquinolin-7-yl)(phenyl)methyl]-2-(3,5-dimethoxyphenoxy)acetamide | 479.2 |

Examples 213-215

2-chloro-N-[(5-chloro-8-hydroxyquinolin-7-yl)(2-chlorophenyl)methyl]acetamide (0.632 mmol), was dissolved in acetone (4 mL) in a screw-cap 20 mL vial. The phenol (0.948 mmol) was added, followed by CsCO₃ (1.03 g, 3.16 mmol). The vial was sealed, heated to 50° C., and stirred for 3 h. The reaction was then filtered and the white solid was washed with acetone. The filtrate had the solvent removed leaving a brown solid. The solid was dissolved in DMSO, and purified with a Gilson HPLC. Yielding coupled product (15-33%).

The subsequent three examples follow the above procedure:

| Example No. | Compound | MS (ESI) m/z |
|---|---|---|
| 213 | N-[(5-chloro-8-hydroxyquinolin-7-yl)(2-chlorophenyl)methyl]-2-(4-pentylphenoxy)acetamide | 523 1045 |
| 214 | N-[(5-chloro-8-hydroxyquinolin-7-yl)(2-chlorophenyl)methyl]-2-(4-propylphenoxy)acetamide | 495.1 |
| 215 | N-[(5-chloro-8-hydroxyquinolin-7-yl)(2-chlorophenyl)methyl]-2-(4-isopropylphenoxy)acetamide | 495.4 989.7 |

Examples 216-221

2-chloro-N-[(5-chloro-8-hydroxyquinolin-7-yl)(phenyl) methyl]acetamide (0.632 mmol), was dissolved in acetone (4 mL) in a screw-cap 20 mL vial. The phenol (0.948 mmol) was added, followed by CsCO₃ (1.03 g, 3.16 mmol). The vial was sealed, heated to 50° C., and stirred for 3 h. The reaction was then filtered and the white solid removed was rinsed with acetone. The filtrate had the solvent removed leaving a brown solid. The solid was dissolved in DMSO, and purified on a Gilson HPLC. Yielding coupled product (15-33%).

The subsequent six examples follow the above procedure:

| Example No. | Compound | MS (ESI) m/z |
|---|---|---|
| 216 | N-[(5-chloro-8-hydroxyquinolin-7-yl)(2-chlorophenyl)methyl]-2-(4-cyclopentylphenoxy)acetamide | 521.2 1041.6 |
| 217 | N-[(5-chloro-8-hydroxyquinolin-7-yl)(2-chlorophenyl)methyl]-2-(3-ethylphenoxy)acetamide | 481.2 |

-continued

| Example No. | Compound | MS (ESI) m/z |
|---|---|---|
| 218 | N-[(5-chloro-8-hydroxyquinolin-7-yl)(2-chlorophenyl)methyl]-2-(3,5-dimethoxyphenoxy)acetamide | 513.3 |
| 219 | 2-(biphenyl-4-yloxy)-N-[(5-chloro-8-hydroxyquinolin-7-yl)(2-chlorophenyl)methyl]acetamide | 529.2 1057.6 |
| 220 | 2-(4-bromophenoxy)-N-[(5-chloro-8-hydroxyquinolin-7-yl)(2-chlorophenyl)methyl]acetamide | 531.1 |
| 221 | 2-(1,3-benzodioxol-5-yloxy)-N-[(5-chloro-8-hydroxyquinolin-7-yl)(2-chlorophenyl)methyl]acetamide | 497.1 |

Example 222

To N-[(5-bromo-8-hydroxyquinolin-7-yl)(phenyl)methyl]-2-chloroacetamide (0.632 mmol), was added $CH_3CN$ (1 mL) followed by DMPU (1 mL). 1-naphthalenemethylamine (1.55 mmol) was added and the reaction stirred at room temp. for 4 h. Acetonitrile was removed at reduced pressure, and the remaining material was dissolved in DMSO and purified with a Gilson HPLC. Yielding N-[(5-bromo-8-hydroxyquinolin-7-yl)(phenyl)methyl]-N2-(1-naphthylmethyl)glycinamide (62%).

N-[(5-bromo-8-hydroxyquinolin-7-yl)(phenyl)methyl]-N2-(1-naphthylmethyl)glycinamide HRMS: calcd for $C_{29}H_{24}BrN_3O_2$+H+, 526.11246; found (ESI-FTMS, [M+H]1+), 526.11283.

Examples 223-230

To 2-chloro-N-[(5-chloro-8-hydroxyquinolin-7-yl)(phenyl)methyl]acetamide (0.632 mmol), was added $CH_3CN$ (1 mL) followed by DMPU (1 mL). The amine (1.55 mmol) was added and the reaction stirred at room temp. for 4 h. Acetonitrile was removed at reduced pressure, and the remaining material was dissolved in DMSO and purified with a Gilson HPLC. Yielding coupled product (40-60%).

The subsequent eight examples follow the above procedure:

| Example No. | Compound | MS (ESI) m/z |
|---|---|---|
| 223 | N2-benzyl-N-[(5-chloro-8-hydroxyquinolin-7-yl)(phenyl)methyl]glycinamide | 432.2 |
| 224 | N-[(5-chloro-8-hydroxyquinolin-7-yl)(phenyl)methyl]-N2-(1-naphthylmethyl)glycinamide | 482.2 963.4 |
| 225 | N-[(5-chloro-8-hydroxyquinolin-7-yl)(phenyl)methyl]-2-(4-phenylpiperidin-1-yl)acetamide | 486.2 243.6 |
| 226 | $N^2$-(1,3-benzodioxol-5-ylmethyl)-N-[(5-chloro-8-hydroxyquinolin-7-yl)(phenyl)methyl]glycinamide | 476.2 951.4 |
| 227 | N-[(5-chloro-8-hydroxyquinolin-7-yl)(phenyl)methyl]-N2-(pyridin-2-ylmethyl)glycinamide | 433.2 217.1 |
| 228 | N-[(5-chloro-8-hydroxyquinolin-7-yl)(phenyl)methyl]-N2-(pyridin-3-ylmethyl)glycinamide | 433.2 237.6 217.1 |
| 229 | N[(5-chloro-8-hydroxyquinolin-7-yl)(phenyl)methyl]-N2-(pyridin-4-ylmethyl)glycinamide | 433.2 237.6 217.1 |
| 230 | $N^2$-(biphenyl-4-ylmethyl)-N-[(5-chloro-8-hydroxyquinolin-7-yl)(phenyl)methyl]glycinamide | 508.2 |

Examples 231 & 232

To 2-chloro-N-[(5-chloro-8-hydroxyquinolin-7-yl)(2-chlorophenyl)methyl]acetamide (0.632 mmol), was added $CH_3CN$ (1 mL) followed by DMPU (1 mL). The amine (1.55 mmol) was added and the reaction stirred at room temp. for 4 h. Acetonitrile was removed at reduced pressure, and the remaining material was dissolved in DMSO and purified with a Gilson HPLC. Yielding coupled product (40-60%).

The subsequent two examples follow the above procedure:

| Example No. | Compound | MS (ESI) m/z |
|---|---|---|
| 231 | N-[(5-chloro-8-hydroxyquinolin-7-yl)(2-chlorophenyl)methyl]-N2-(1-naphthylmethyl)glycinamide | 516.2 1031.3 |
| 232 | N2-(1,3-benzodioxol-5-ylmethyl)-N-[(5-chloro-8-hydroxyquinolin-7-yl)(2-chlorophenyl)methyl]glycinamide | 510.2 1019.3 |

Example 233

N-[(8-hydroxy-5-nitroquinolin-7-yl)(phenyl)methyl]-2-phenoxyacetamide (4.0 g, 9.31 mmol), 10% Pd/C (420 mg) in 70 ml THF were hydrogenated at 42 psi for 20 h. The reaction mixture was filtered through Celite 545, dried over sodium sulfate and concentrated to afford 2.3 g of N-[(5-amino-8-hydroxyquinolin-7-yl)(phenyl)methyl]-2-phenoxyacetamide as a brown foam.

N-[(5-amino-8-hydroxyquinolin-7-yl)(phenyl)methyl]-2-phenoxyacetamide

MS (ESI) m/z 400.3.

Example 234

N-[(5-amino-8-hydroxyquinolin-7-yl)(phenyl)methyl]-2-phenoxyacetamide (150 mg, 0.37 mmol), sodium cyanoborohydride 1M/THF (0.9 ml, 2.5 eq.) and 37% aq. Formaldehyde (0.2 ml) in 1.5 ml methanol were stirred at room temperature for 2 h. The reaction mixture was concentrated, the residue was diluted with water and pH brought to 3 with 1M aq. HCl. After stirring for 20 min the reaction mixture was neutralized with aq. Sodium bicarbonate and filtered. The solids were dissolved in ether, washed with water, dried over sodium sulfate, filtered and concentrated in vacuo to afford N-[[5-(dimethylamino)-8-hydroxyquinolin-7-yl](phenyl)methyl]-2-phenoxyacetamide as a yellow solid.

N-[[5-(dimethylamino)-8-hydroxyquinolin-7-yl](phenyl)methyl]-2-phenoxyacetamide

MS (ESI) m/z 428.3;
MS (ESI) m/z 486.4.

Example 235

N-[(5-amino-8-hydroxyquinolin-7-yl)(phenyl)methyl]-2-phenoxyacetamide (150 mg, 0.37 mmol), 2,5-dimethoxydihydrofuran (50 mg, 0.37 mmol) in acetic acid (1 ml) were heated at 65 C for 40 min. The reaction mixture was concentrated, dissolved in ethylacetate, washed with aq. Sodium bicarbonate and dried over sodium sulfate. The solvent was removed in vacuo to afford N-[[8-hydroxy-5-(1H-pyrrol-1-yl)quinolin-7-yl](phenyl)methyl]-2-phenoxyacetamide as a tan solid.

N-[[8-hydroxy-5-(1H-pyrrol-1-yl)quinolin-7-yl](phenyl)methyl]-2-phenoxyacetamide Example 236

N-[(5-amino-8-hydroxyquinolin-7-yl)(phenyl)methyl]-2-phenoxyacetamide (200 mg, 0.5 mmol), dibromobutane (0.1 ml), TEA (0.2 ml) in isopropanol were heated at reflux for 16 h. The reaction mixture was concentrated in vacuo, the residue dissolved in methylene chloride, washed with brine. The organic layer was dried over sodium sulfate and filtered. To the filtrate was added 1M HCl/ether, the solids filtered, washed with ether to give N-[(8-hydroxy-5-pyrrolidin-1-ylquinolin-7-yl)(phenyl)methyl]-2-phenoxyacetamide as a purple solid.

N-[(8-hydroxy-5-pyrrolidin-1-ylquinolin-7-yl)(phenyl)methyl]-2-phenoxyacetamide

MS (ESI) m/z 454.4;
MS (ESI) m/z 538.4;

Examples 237-278

Examples 237-278 were accomplished using commercially available dry solvents. The reactions were performed under an inert atmosphere of nitrogen unless otherwise noted. All reagents were purchased from either Aldrich (Milwaukee, Wis.), Sigma (St. Louis, Mo.), Acros (Pittsburgh, Pa.), or Alfa Aesar (Ward Hill, Mass.). Microwave reactions were conducted using a Biotage (Personal Chemistry) Emrys Optimizer microwave reactor. Preparative scale HPLC separations were conducted on the crude material dissolved in DMSO and filtered through a 0.45 μM GMF filter on a Gilson HPLC using a Phenomenex Gemini C18 column: 100×30 mm, micron particle size with solvent A=0.02% TFA in H2O and Solvent B=0.02% TFA in CH3CN gradient elution. Method I was utilized for the majority of products while Method II was utilized for the less polar products containing the biphenyl functionality.

HPLC Methods:

| Method I | | Method II | |
|---|---|---|---|
| Time (min) | % B | Time (min) | % B |
| 0-6 | 10 | 0-6 | 10 |
| 6-25 | 95 | 6-45 | 95 |
| 25-30 | 95 | 45-50 | 95 |

Purity of fractions in separations was determined by analytical HPLC using the following conditions:

[a]HPLC Conditions A: Used for all compounds excluding N-{2-(5-Chloro-8-hydroxyquinolin-7-yl)-1-[3-(5-methyl-2-thienyl)phenyl]ethyl}biphenyl-4-carboxamide
Instrument - Agilent 1100
Column: Prodigy ODS3, 0.46 × 15 cm, 3 μM particle size
Mobile Phase   A: 0.02% TFA in H2O
               B: 0.02% TFA in CH3CN
Flow Rate: 1.0 mL/min
Column Temp.: 40° C.
Injection Volume: 3.5 μL
UV: PDA, purity reported at 215 nM

| Time (min) | % B |
|---|---|
| Gradient Table:  0 | 10 |
| 20 | 95 |
| 25 | 95 |
| 30 | 10 |

[b]HPLC Conditions B: Used for N-{2-(5-Chloro-8-hydroxyquinolin-7-yl)-1-[3-(5-methyl-2-thienyl)phenyl]ethyl}biphenyl-4-carboxamide
Instrument: Agilent 1946B
Column: Prodigy ODS3, 0.46 × 15 cm, 3 μM particle size
Mobile Phase   A: 0.1% formic acid in H2O
               B: 0.1% NH4TFA in ethanol
Flow Rate: 1.0 mL/min
Column Temp.: 40° C.
Injection Volume: 1.0 μL
UV: PDA, purity reported at 215 nM

| Time (min) | % B |
|---|---|
| Gradient Table:  0 | 75 |
| 20 | 95 |

Analtech uniplate F254 precoated 250 μM glass backed plates were used for thin layer chromatography (TLC) analysis. For column chromatography, an ISCO Combi-Flash Companion system was used. Redi-Sep columns containing normal phase silica gel, 35-60 micron average, 230-400 mesh particle size were utilized with monitoring at 254 nM for collection of fractions. For 120 g columns, flow rate was set at 85 mL/min; for 40 g columns, flow rate was set at 40 mL/min. Each product was analyzed by TLC (single spot) and spectroscopic methods including HPLC and mass spectrometry.

Scheme A: Synthesis of N-[2-(8-Hydroxyquinolin-7-yl)-1-phenylethyl]-2-phenoxyacetamide

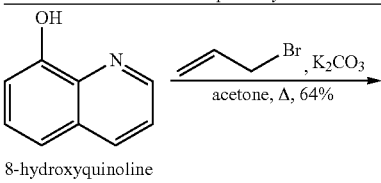

8-hydroxyquinoline

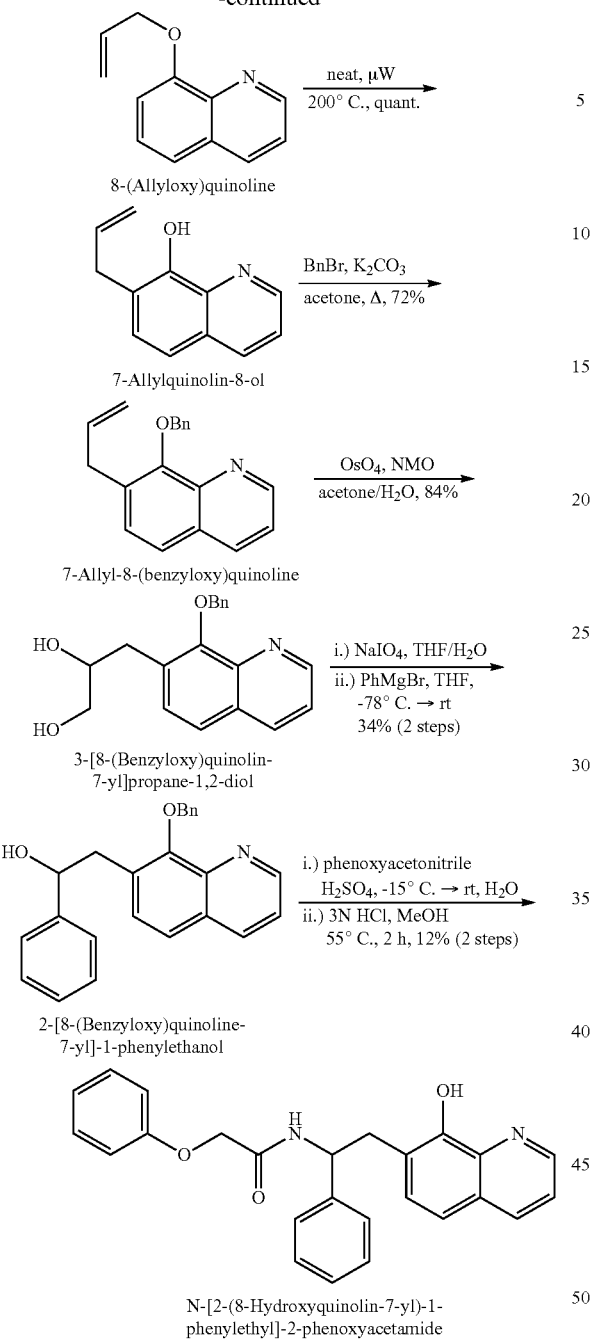
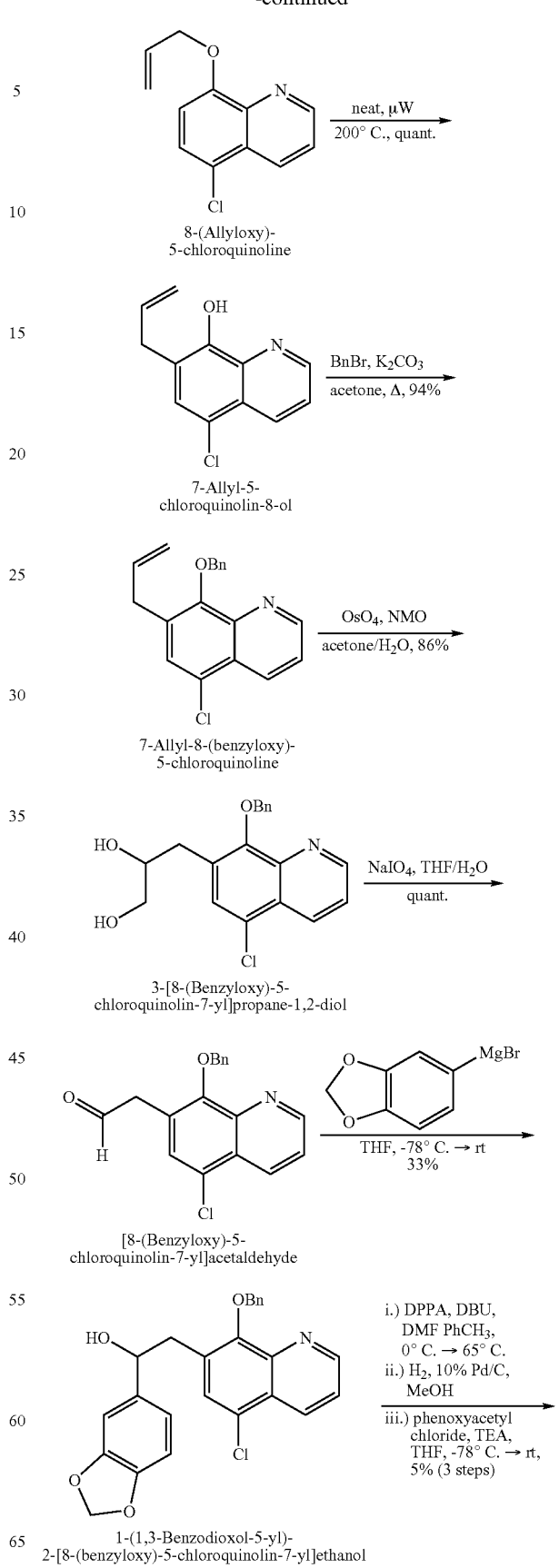
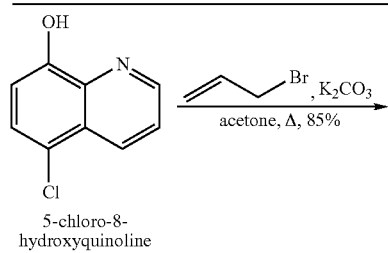

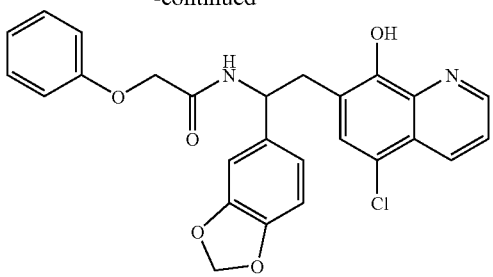

N-[1-(1,3-Benzodioxol-5-yl)-2-(5-chloro-8-hydroxyquinolin-7-yl)ethyl]-2-phenoxyacetamide General Procedure for Allylation of Hydroxyquinolines:

To a stirring solution of the appropriate hydroxyquinoline (55.68 mmol, 1 eq.) in acetone (300 mL) in a round bottom flask equipped with a reflux condenser was added potassium carbonate (904.42 mmol, 16.25 eq.) followed by allyl bromide (83.52 mmol, 1.5 eq.) and the resulting solution was stirred and heated to reflux for 20 h. The reaction mixture was then cooled to room temperature and diluted with 300 mL of diethyl ether. The resulting suspension was filtered and the filtrate concentrated to an orange oil that solidified under vacuum and was purified by either column chromatography or recrystallization.

Example 237

8-(Allyloxy)quinoline

Prepared from 8-hydroxyquinoline (68.90 mmol) according to the general procedure described above. Purified by column chromatography using 5% acetone/dichloromethane to give the product as an orange oil (43.79 mmol, 64%). MS (ESI) m/z 186.1; HRMS: calcd for C12H11NO+H+, 186.09134; found (ESI-FTMS, [M+H]1+), 186.09107.

Example 238

8-(Allyloxy)-5-chloroquinoline

Prepared from 5-chloro-8-hydroxyquinoline (278.40 mmol) according to the general procedure described above. Purified by recrystallization from hexanes to give the product as a light beige solid (235.81 mmol, 85%). MS (ESI) m/z 220.1; HRMS: calcd for C12H10ClNO+H+, 220.05237; found (ESI-FTMS, [M+H]1+), 220.05229.

General Procedure for Microwave Induced Claisen Rearrangement:

The appropriate allylated hydroxyquinoline (40.77 mmol, 1 eq.) was added neat to a microwave vial prior to the vial being sealed. In the cases where the substrate was a solid, the vial was heated with a heat gun until the solid melted and gave a homogenous liquid. The vial was then placed in the microwave and irradiated at 200° C. for 60 min. After cooling to room temperature, the vial was uncapped and the pure product was scraped out.

Example 239

7-Allylquinolin-8-ol

Prepared from 8-(allyloxy)quinoline (40.77 mmol) using the general procedure described above. Crude product was obtained as a brown solid (40.77 mmol, quant.) and required no further purification. MS (ESI) m/z 184.1; HRMS: calcd for C12H11NO+H+, 186.09134; found (ESI-FTMS, [M+H]1+), 186.09112.

Example 240

7-Allyl-5-chloroquinolin-8-ol

Prepared from 8-(allyloxy)-5-chloroquinoline (17.16 mmol) using the general procedure described above. Crude product was obtained as a light brown solid (17.16 mmol, quant.) and required no further purification. MS (ESI) m/z 220.1; HRMS: calcd for C12H10ClNO+H+, 220.05237; found (ESI, [M+H]+ Obs'd), 220.0523.

Example 241

7-Allyl-8-(benzyloxy)quinoline

To a stirring solution of 7-allylquinolin-8-ol (14.56 mmol, 1 eq.) in acetone (50 mL) in a round bottom flask equipped with a reflux condenser was added potassium carbonate (151.94 mmol, 10.44 eq.) followed by benzyl bromide (17.47 mmol, 1.2 eq.) and the resulting solution was stirred and heated to reflux for 20 h. Additional potassium carbonate (151.94 mmol, 10.44 eq.) was added followed by additional benzyl bromide (29.12 mmol, 2 eq.) and the resulting mixture was heated at reflux and stirred 2 h. The reaction mixture was then cooled to room temperature and diluted with 50 mL of diethyl ether. The resulting suspension was filtered and the filtrate concentrated to a yellow oil that was purified by column chromatography using 10% acetone/dichloromethane to give the product as a pale yellow oil (10.48 mmol, 72%). MS (ESI) m/z 276.2; HRMS: calcd for C19H17NO+H+, 276.13829; found (ESI-FTMS, [M+H]1+), 276.13828.

Example 242

7-Allyl-8-(benzyloxy)-5-chloroquinoline

To a stirring solution of 7-allyl-5-chloroquinolin-8-ol (17.16 mmol, 1 eq.) in acetone (60 mL) in a round bottom flask equipped with a reflux condenser was added potassium carbonate (179.08 mmol, 10.44 eq.) followed by benzyl bromide (18.02 mmol, 1.05 eq.) and the resulting solution was stirred and heated to reflux for 4 h. The reaction mixture was then cooled to room temperature and diluted with 60 mL of diethyl ether. The resulting suspension was filtered and the filtrate concentrated to a yellow oil that was purified by column chromatography using 30% ethyl acetate/hexanes to give the product as a light amber oil (16.08 mmol, 94%). MS (ESI) m/z 310.2; HRMS: calcd for C19H16ClNO+H+, 310.09932; found (ESI, [M+H]+ Obs'd), 310.0993.

General Procedure for Dihydroxylation of Allylated O-Benzyl-hydroxyquinolines:

To a stirring solution of the appropriate allylated O-benzyl-hydroxyquinoline (10.13 mmol, 1 eq.) in acetone (100 mL) and water (10 mL) in a round bottom flask was added 4-methylmorpholine-N-oxide (15.20 mmol, 1.5 eq.) followed by a 2.5 wt. % solution of osmium tetroxide in tert-butanol (0.10 mmol, 0.01 eq.) and the resulting solution was stirred for 20 h. A saturated aqueous solution of sodium metabisulfite (1.5 mL) was added and the solution was stirred 5 min and the acetone was removed by rotary evaporation. Purification was completed by either aqueous workup followed by column chromatography or by recrystallization.

Example 243

3-[8-(Benzyloxy)quinolin-7-yl]propane-1,2-diol

Prepared from 7-allyl-8-(benzyloxy)quinoline (10.13 mmol) according to the general procedure described above. To the residue obtained after acetone removal was added water (20 mL) and the resulting solution was extracted with dichloromethane (3×15 mL). The organic fractions were dried (MgSO4), filtered and concentrated to the crude product that was purified by column chromatography using 5% methanol/dichloromethane to give the product as thick yellow syrup (8.42 mmol, 84%). MS (ESI) m/z 310.3; HRMS: calcd for C19H19NO3+H+, 310.14377; found (ESI-FTMS, [M+H]1+), 310.14426.

Example 244

3-[8-(Benzyloxy)-5-chloroquinolin-7-yl]propane-1,2-diol

Prepared from 7-allyl-8-(benzyloxy)-5-chloroquinoline (72.53 mmol) according to the general procedure described above. To the residue obtained after acetone removal was added a 90/10 mixture of hexanes/ether (50 mL) resulting in precipitation of a solid and all solvent was then removed by rotary evaporation. The solid obtained was recrystallized from dichloromethane/hexanes containing trace ether and methanol (for initial dissolution of the solid crude product) to give the product as a white solid (62.59 mmol, 86%). MS (ESI) m/z 344.2; HRMS: calcd for C19H18ClNO3+H+, 344.10480; found (ESI, [M+H]+ Obs'd), 344.1048.

Example 245

[8-(Benzyloxy)-5-chloroquinolin-7-yl]acetaldehyde

To a stirring solution of 3-[8-(benzyloxy)-5-chloroquinolin-7-yl]propane-1,2-diol (2.95 mmol) in tetrahydrofuran (21 mL) and water (7 mL) in a round bottom flask was added sodium (meta)periodate (14.73 mmol, 5.0 eq.) all at once and the resulting solution was stirred for 5 min. The tetrahydrofuran was then removed by rotary evaporation at room temperature (elevated temperatures will result in decomposition of the product) and the resulting heterogeneous mixture was diluted with water (30 mL) and washed with diethyl ether (2×30 mL). The organic layers were combined, dried (MgSO4), filtered and concentrated (at room temperature) to give the product as a light brown solid (2.95 mmol, quant.) that was analytically pure and used directly in the ensuing step. (Caution: Compound decomposes rapidly at temperatures greater than 25° C., in the presence of silica gel, and potentially if brought to dryness in presence of periodate salts present in crude reaction mixture.) MS (ESI) m/z 312.1.

Example 246

2-[8-(Benzyloxy)quinolin-7-yl]-1-phenylethanol

To a stirring solution of 3-[8-(benzyloxy)quinolin-7-yl]propane-1,2-diol (8.08 mmol) in tetrahydrofuran (60 mL) and water (20 mL) in a round bottom flask was added sodium (meta)periodate (8.08 mmol, 1.0 eq.) all at once and the resulting solution was stirred for 30 min. The tetrahydrofuran was then removed by rotary evaporation at room temperature (elevated temperatures will result in decomposition of the product) and the resulting heterogeneous mixture was diluted with water (40 mL) and washed with diethyl ether (2×50 mL). The organic layers were combined, dried (MgSO4), filtered and concentrated (at room temperature) to give the product as a pale yellow oil that was analytically pure and used directly in the ensuing step. (Caution: Compound decomposes rapidly at temperatures greater than 25° C., in the presence of silica gel, and potentially if brought to dryness in presence of periodate salts present in crude reaction mixture.) To a stirring solution of the (8-benzyloxy-quinolin-7-yl)-acetaldehyde (8.08 mmol, 1.0 eq.) from the initial step in tetrahydrofuran (10 mL) at −78° C. was dropwise added a 1M solution of phenylmagnesium bromide in THF (8.08 mmol, 1.0 eq.). On completion of addition, the reaction mixture was allowed to stir at −78° C. for 1 h and was then warmed to room temperature and stirred 30 min. The reaction was then quenched by addition of saturated aqueous sodium bicarbonate solution (5 mL) and allowed to stir for 5 min. The resulting solution was diluted with water (50 mL) and extracted with ethyl acetate (3×50 mL). The organic layers were combined, dried (MgSO4), filtered and concentrated to give a thick yellow syrup that was purified by column chromatography using 20% ethyl acetate/hexanes to give the final product as a pale yellow solid (2.72, 34% for 2 steps). MS (ESI) m/z 356.3; HRMS: calcd for C24H21NO2+H+, 356.16451; found (ESI-FTMS, [M+H]1+), 356.16552.

Example 247

N-[2-(8-Hydroxyquinolin-7-yl)-1-phenylethyl]-2-phenoxyacetamide

To a stirring solution of the 2-[8-(benzyloxy)quinolin-7-yl]-1-phenylethanol (0.302 mmol) in phenoxyacetonitrile (9.05 mmol, 30 eq.) at −10° C. was dropwise added conc. sulfuric acid (1.51 mmol, 5.0 eq.). On completion of addition, the reaction mixture was allowed to warm to room temperature and was stirred 16 h. The reaction was then diluted with ice that was allowed to melt and was then stirred 2 h. The mixture was next brought to pH=7 by the addition of saturated aqueous sodium bicarbonate solution and then diluted with water (5 mL) and extracted with ethyl acetate (2×5 mL). The organic layers were combined, dried (MgSO4), filtered and concentrated to give sulfuric acid mono-{7-[2-(2-phenoxy-acetylamino)-2-phenyl-ethyl]-quinolin-8-yl}ester as a yellow oil that was purified by column chromatography using 20% methanol/dichloromethane. To a stirring suspension of the sulfuric acid mono-{7-[2-(2-phenoxy-acetylamino)-2-phenyl-ethyl]-quinolin-8-yl}ester (0.089 mmol, 1.0 eq.) from the initial step in methanol (9 mL) was added 3N HCl (18 mL) and the resulting suspension was heated to 55° C. and stirred 2 h. The reaction mixture was then cooled to room temperature and organic solvents were removed by rotary evaporation resulting in a precipitate that was filtered yielding the pure product as a yellow solid (0.059 mmol, 12% for 2 steps). HRMS: calcd for C25H22N2O3+H+, 399.17032; found (ESI-FTMS, [M+H]1+), 399.17059.

Example 248

1-(1,3-Benzodioxol-5-yl)-2-[8-(benzyloxy)-5-chloroquinolin-7-yl]ethanol

To a stirring solution of [8-(benzyloxy)-5-chloroquinolin-7-yl]acetaldehyde (0.380 mmol) in tetrahydrofuran (4 mL) at −78° C. was dropwise added a 1M solution of 3,4-(methylenedioxy)phenylmagnesium bromide in 1:1 toluene/tetrahydrofuran (0.380 mmol, 1.0 eq.) and stirring at −78° C. was continued for 10 min. The reaction mixture was then allowed to warm to room temperature and was stirred 1 h then quenched with saturated aqueous sodium bicarbonate solution (2 mL). After stirring 15 min the reaction mixture was extracted with ethyl acetate (3×5 mL) and the combined organic layers were dried (MgSO4), filtered and concentrated to give a brown oil that was purified by column chromatography using 30% ethyl acetate/hexanes to give the final product as a white foam (0.126 mmol, 33%). MS (ESI) m/z 434.2; HRMS: calcd for C25H20ClNO4+H+, 434.11536; found (ESI, [M+H]+ Obs'd), 434.1150.

Example 249

N-[1-(1,3-Benzodioxol-5-yl)-2-(5-chloro-8-hydroxyquinolin-7-yl)ethyl]-2-phenoxyacetamide To a stirring solution of 1-(1,3-benzodioxol-5-yl)-2-[8-(benzyloxy)-5-chloroquinolin-7-yl]ethanol (0.893 mmol) in toluene (4.5 mL) and dimethylformamide (0.9 mL) at 0° C. was added diphenyl phosphoryl azide (1.34 mmol, 1.5 eq.) followed by dropwise addition of 1,8-diazabicyclo[5.4.0]undec-7-ene (1.34 mmol, 1.5 eq.). The reaction mixture was then warmed to 65° C. and stirred 4 h then cooled to room temperature. The mixture was next diluted with saturated aqueous lithium bromide solution (5 mL) and extracted with ethyl acetate (3×5 mL). The combined organic layers were dried (MgSO4), filtered and concentrated to a light brown oil that was purified by column chromatography using 20% ethyl acetate/hexanes to give 7-(2-azido-2-benzo[1,3]dioxol-5-yl-ethyl)-8-benzyloxy-5-chloro-quinoline that was used directly in the next step. To a round bottom flask containing 7-(2-azido-2-benzo[1,3]dioxol-5-yl-ethyl)-8-benzyloxy-5-chloro-quinoline (0.530 mmol, 1.0 eq.) from the initial step was added 10% palladium on carbon (0.053 mmol, 0.1 eq.) followed by methanol (5 mL) and ethyl acetate (0.3 mL). The reaction vessel was flushed with hydrogen then capped with a hydrogen filled balloon and the mixture was stirred 20 h. The reaction mixture was then filtered through a pad of celite eluting with methanol then a small amount of dimethylformamide. The filtrate was then concentrated to a yellow foam that was treated with a small amount of ether that initially dissolved the foam and then resulted in a precipitate that was filtered. The filtrate was concentrated to a yellow foam and ether addition resulted in a second crop of precipitate that was filtered and combined with the first crop. The combined yellow solid was used directly in the ensuing step without further purification. To a round bottom flask containing the 7-(2-amino-2-benzo[1,3]dioxol-5-yl-ethyl)-5-chloro-quinolin-8-ol (0.297 mmol, 1.0 eq.) from the preceding step at −78° C. was added a solution of phenoxyacetyl chloride (0.609 mmol, 2.05 eq.) and triethylamine (0.609 mmol, 2.05 eq.) in tetrahydrofuran (3 mL) that was pre-mixed and stirred 5 min prior to addition. After warming to room temperature, the resulting solution was stirred 1 h and diluted with water (10 mL) and extracted with ethyl acetate (2×10 mL). The combined organic layers were dried (MgSO4), filtered and concentrated to a yellow foam that was purified by preparative scale HPLC to give the final product as a very light yellow solid (0.048 mmol, 5% for 3 steps). MS (ESI) m/z 477.3; HRMS: calcd for C26H21ClN2O5+H+, 477.12118; found (ESI, [M+H]+ Obs'd), 477.1215.

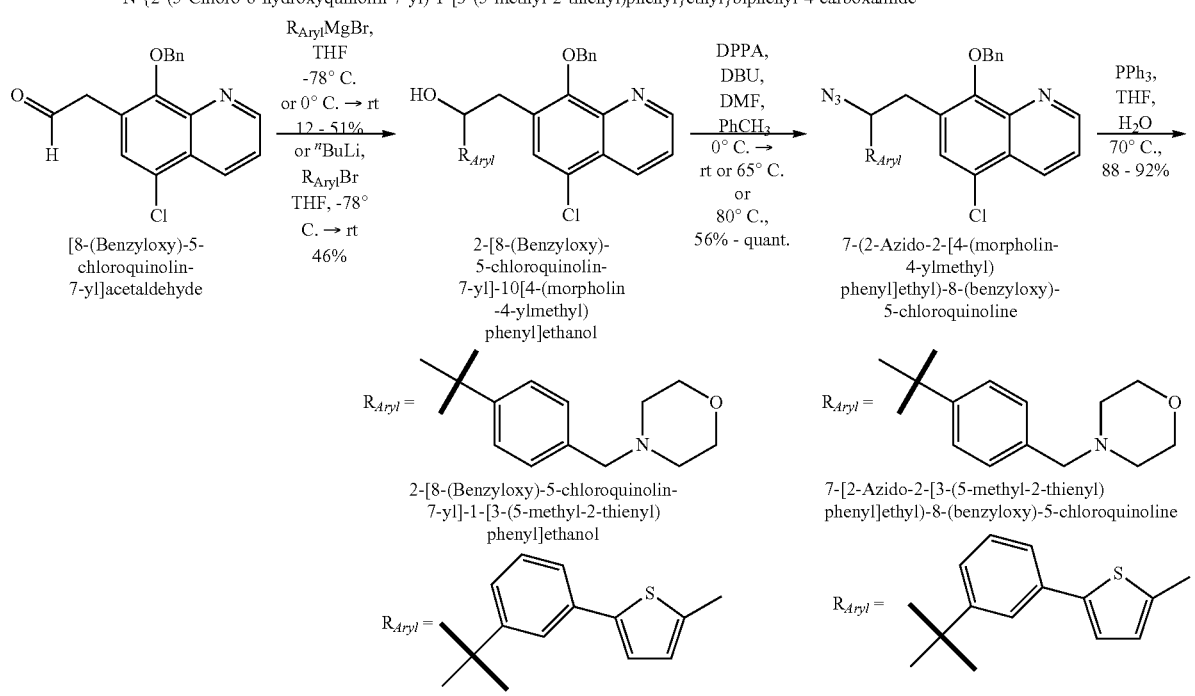

Scheme C: Synthesis of N-{2-(5-Chloro-8-hydroxyquinolin-7-yl)-1-[4-(morpholin-4-ylmethyl)phenyl]ethyl}biphenyl-4-carboxamide, N-{2-(5-Chloro-8-hydroxyquinolin-7-yl)-1-[3-(pyrrolidin-1-ylmethyl)phenyl]ethyl}-2-phenoxyacetamide, N-{2-(5-Chloro-8-hydroxyquinolin-7-yl)-1-[3-(pyrrolidin-1-ylmethyl)phenyl]ethyl}-2-(4-chlorophenoxy)-2-methylpropanamide, N-{2-(5-Chloro-8-hydroxyquinoline-7-yl)-1-[3-(pyrrolidin-1-ylmethyl)phenyl]ethyl}biphenyl-4-carboxamide, N-{2-(5-Chloro-8-hydroxyquinolin-7-yl)-1-[3-(5-methyl-2-thienyl)phenyl]ethyl}-2-phenoxyacetamide, 2-(Benzyloxy)-N-{2-(5-chloro-8-hydroxyquinolin-7-yl)-1-[3-(5-methyl-2-thienyl)phenyl]ethyl}acetamide, N-{2-(5-Chloro-8-hydroxyquinolin-7-yl)-1-[3-(5-methyl-2-thienyl)phenyl]ethyl}-2-(4-chlorophenoxy)-2-methylpropanamide, 2-(4-tert-Butylphenoxy)-N-{2-(5-chloro-8-hydroxyquinolin-7-yl)-1-[3-(5-methyl-2-thienyl)phenyl]ethyl}acetamide and N-{2-(5-Chloro-8-hydroxyquinolin-7-yl)-1-[3-(5-methyl-2-thienyl)phenyl]ethyl}biphenyl-4-carboxamide -continued
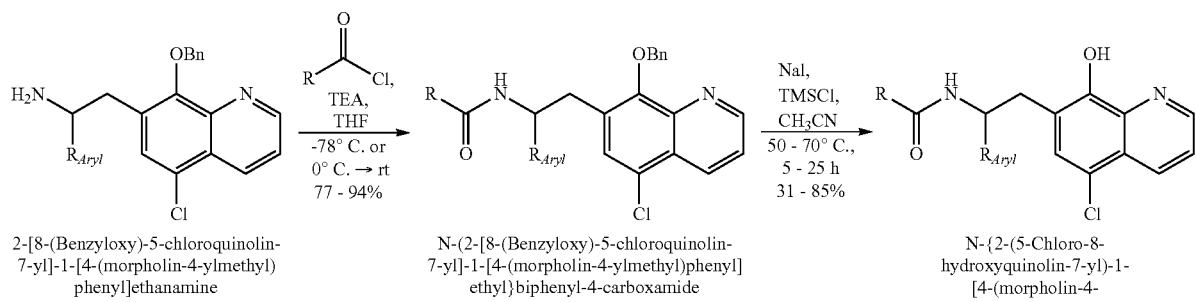
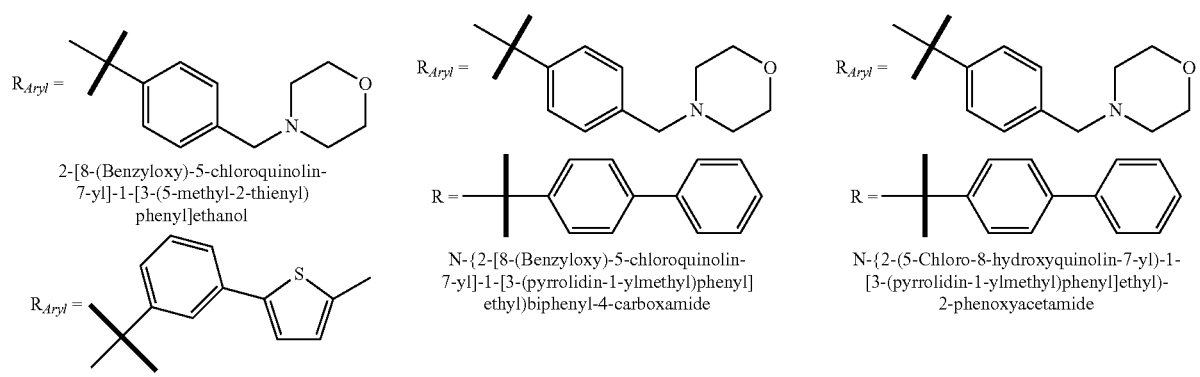
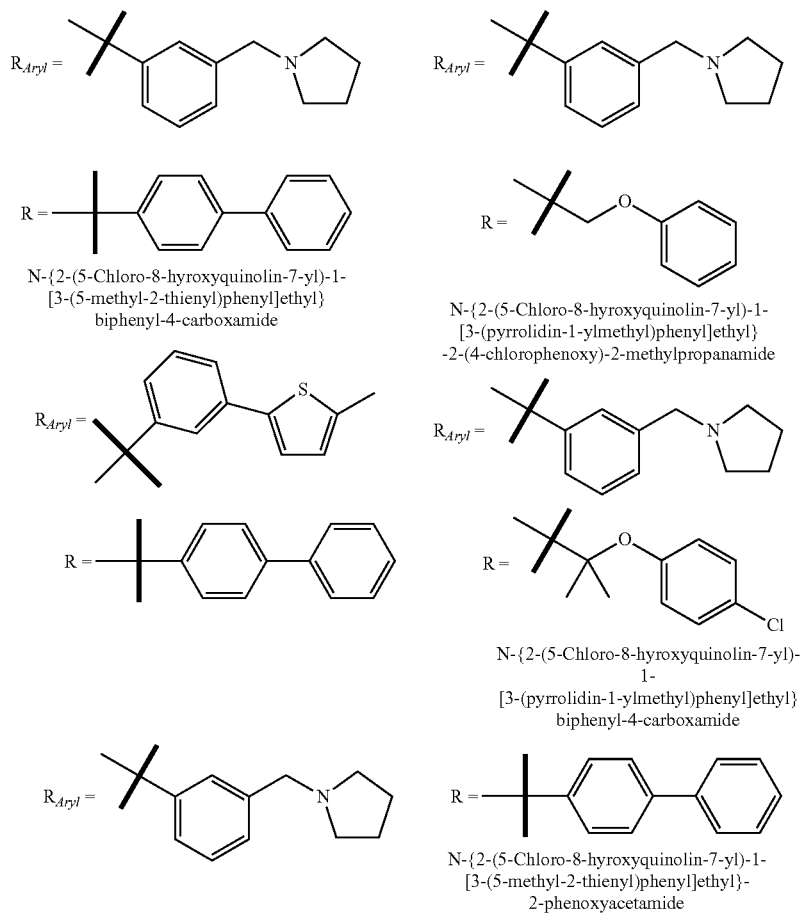

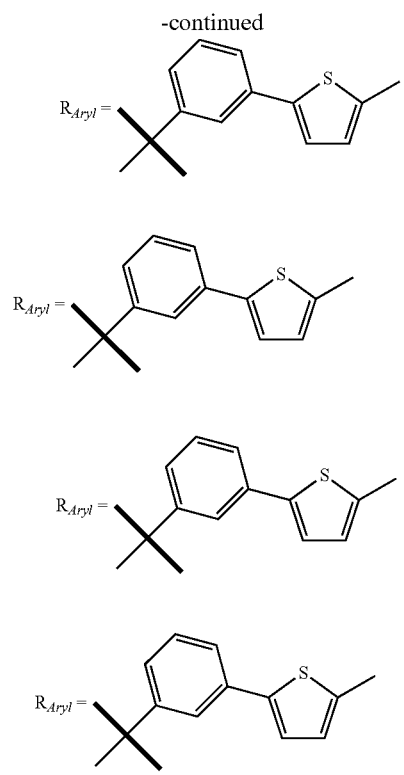
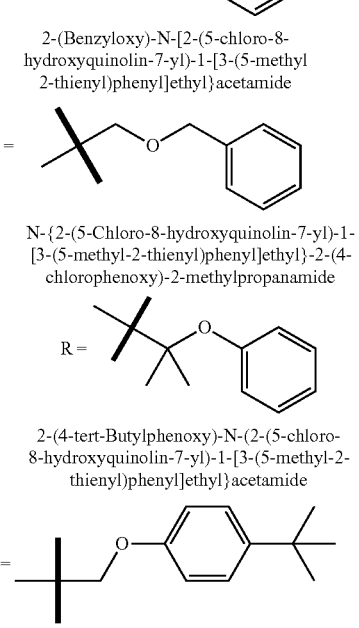

2-(Benzyloxy)-N-[2-(5-chloro-8-hydroxyquinolin-7-yl)-1-[3-(5-methyl 2-thienyl)phenyl]ethyl}acetamide N-{2-(5-Chloro-8-hydroxyquinolin-7-yl)-1-[3-(5-methyl-2-thienyl)phenyl]ethyl}-2-(4-chlorophenoxy)-2-methylpropanamide 2-(4-tert-Butylphenoxy)-N-(2-(5-chloro-8-hydroxyquinolin-7-yl)-1-[3-(5-methyl-2-thienyl)phenyl]ethyl}acetamide

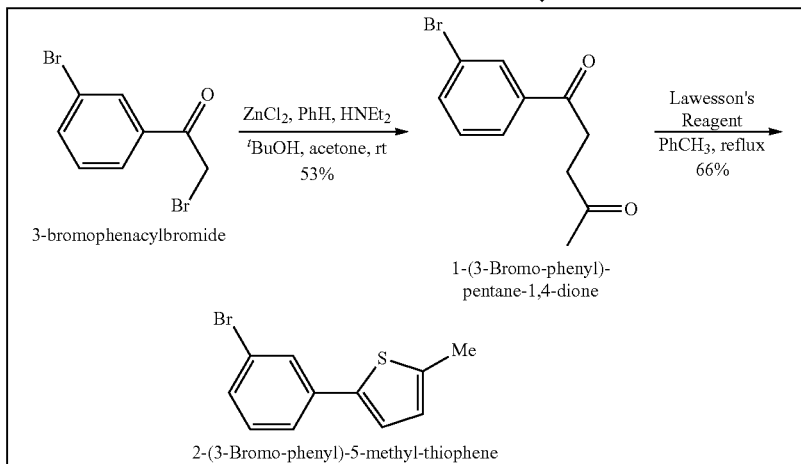

Example 250

2-[8-(Benzyloxy)-5-chloroquinolin-7-yl]-1-[4-(morpholin-4-ylmethyl)phenyl]ethanol To a stirring solution of [8-(benzyloxy)-5-chloroquinolin-7-yl]acetaldehyde (12.50 mmol) in tetrahydrofuran (100 mL) at 0° C. was dropwise added a 0.25M solution of [4-(4-morpholinylmethyl)phenyl]magnesium bromide in tetrahydrofuran (12.50 mmol, 1.0 eq.) and stirring at 0° C. was continued for 30 min. The reaction mixture was then allowed to warm to room temperature and was stirred 20 min then quenched with saturated aqueous sodium bicarbonate solution (100 mL). After stirring 5 min the reaction mixture was extracted with ethyl acetate (3×75 mL) and the combined organic layers were dried (MgSO4), filtered and concentrated to give a thick brown syrup that was purified by column chromatography using 30% acetone/dichloromethane to give the final product as a white solid (1.50 mmol, 12%). MS (ESI) m/z 489.3; HRMS: calcd for C29H29ClN2O3+H+, 489.19395; found (ESI, [M+H]+ Obs'd), 489.1941.

Example 251

1-(3-Bromo-phenyl)-pentane-1,4-dione

A round bottom flask containing zinc chloride (71.95 mmol, 2.0 eq.) was heated under vacuum until the solid melted (~300° C.) and the molten solid was kept under vacuum for 5 min. The molten solid was then allowed to cool to room temperature resulting in solidification. The flask was then filled with nitrogen and benzene (36 mL) was added followed by diethylamine (53.97 mmol, 1.5 eq.) and tert-butanol (53.97 mmol, 1.5 eq.). This mixture was stirred until the solid zinc chloride dissolved and then 3-bromophenacylbromide (35.98 mmol, 1.0 eq.) was added followed by acetone (53.97 mmol, 1.5 eq.). The resulting solution was stirred 4 d and quenched by the addition of 0.1N HCl (100 mL) and diluted with brine solution (25 mL) and extracted with ethyl acetate (3×75 mL). The combined organic layers were dried (MgSO4), filtered and concentrated to give an orange oil that was purified by column chromatography using 5% acetone/dichloromethane to give the final product as an orange solid (18.93 mmol, 53%). HRMS: calcd for $C_{11}H_{11}BrO_2$+H+, 255.00152; found (ESI, [M+H]+ Obs'd), 255.0020.

Example 252

2-(3-Bromo-phenyl)-5-methyl-thiophene

To a stirring solution of 1-(3-bromo-phenyl)-pentane-1,4-dione (18.32 mmol) in toluene (90 mL) was added Lawesson's Reagent (19.24 mmol, 1.05 eq.) and the mixture was heated to reflux for 20 min. The reaction mixture was then cooled to room temperature and diluted with 1:1 hexanes/ether (90 mL) resulting in a precipitate. The mixture was filtered through a small pad of celite and the filtrate was concentrated to a light yellow solid that was purified by recrystallization from hexanes to give the final product as a white solid (12.17 mmol, 66%). MS (ESI) m/z 254.3.

Example 253

2-[8-(Benzyloxy)-5-chloroquinolin-7-yl]-1-[3-(5-methyl-2-thienyl)phenyl]ethanol

To a stirring solution of 2-(3-bromo-phenyl)-5-methyl-thiophene (0.395 mmol) in tetrahydrofuran (4 mL) at −78° C. was slowly added a 2M solution of n-butyllithium in cyclohexane (0.435 mmol, 1.1 eq.). The resulting solution was stirred 30 min at −78° C. and solid [8-(benzyloxy)-5-chloroquinolin-7-yl]acetaldehyde (0.395 mmol) was added. Stirring at −78° C. was continued for 10 min and the reaction was allowed to warm to room temperature and was stirred 1 h. The reaction mixture was then quenched with saturated aqueous ammonium chloride solution (10 mL) and extracted with ethyl acetate (3×10 mL). The combined organic layers were dried (MgSO4), filtered and concentrated to give a yellow oil that was purified by column chromatography using 20% ethyl acetate/hexanes to give the final product as a light yellow solid (0.18 mmol, 46%). MS (ESI) m/z 486.4.

General Procedure for Conversion of Alcohols to Azides:

To a stirring solution of the appropriate alcohol (0.347 mmol, 1.0 eq.) in toluene (1.8 mL) and dimethylformamide (0.35 mL) at 0° C. was added diphenyl phosphoryl azide (0.866 mmol, 2.5 eq.) followed by dropwise addition of 1,8-diazabicyclo[5.4.0]undec-7-ene (0.866 mmol, 2.5 eq.). The reaction mixture was then warmed to room temperature and stirred 16 h. The mixture was next diluted with saturated aqueous lithium bromide solution (5 mL) and extracted with ethyl acetate (3×5 mL). The combined organic layers were dried (MgSO4), filtered and concentrated to the crude product that was either taken on crude or purified by column chromatography.

Example 254

7-{2-Azido-2-[4-(morpholin-4-ylmethyl)phenyl]ethyl}-8-(benzyloxy)-5-chloroquinoline Prepared from 2-[8-(benzyloxy)-5-chloroquinolin-7-yl]-1-[4-(morpholin-4-ylmethyl)phenyl]ethanol (0.347 mmol) according to the general procedure described above. Crude product obtained was an amber syrup that was purified by column chromatography using 20% acetone/dichloromethane to give the final product as a clear oil (0.347 mmol, quant.). MS (ESI) m/z 514.3; HRMS: calcd for $C_{29}H_{28}ClN_5O_2$+H+, 514.20043; found (ESI, [M+H]+ Obs'd), 514.2006.

Example 255

7-{2-Azido-2-[3-(5-methyl-2-thienyl)phenyl]ethyl}-8-(benzyloxy)-5-chloroquinoline Prepared from 2-[8-(benzyloxy)-5-chloroquinolin-7-yl]-1-[3-(5-methyl-2-thienyl)phenyl]ethanol (4.151 mmol) according to the general procedure described above. After stirring the reaction 16 h at room temperature, dimethylformamide (10 mL) was added and the resulting solution was heated to 80° C. for 1.5 h after which time the reaction was cooled to room temperature and worked up as described above. Crude product obtained was an amber syrup that was purified by column chromatography using 20% ethyl acetate/hexanes to give the final product as a clear syrup (3.16 mmol, 76%). MS (ESI) m/z 511.4.

General Procedure for Staudinger Reduction of Azides:

To a stirring solution of the appropriate azide (0.970 mmol, 1.0 eq.) in tetrahydrofuran (3.13 mL) and water (1 mL) in a round bottom flask equipped with a reflux condenser was added triphenylphosphine (1.067 mmol, 1.1 eq.) (CAUTION: vigorous gas evolution, do not seal reaction vessel) and the resulting mixture was then warmed to 70° C. and stirred 3 h. The reaction mixture was then allowed to cool to room temperature, diluted with ethyl acetate (50 mL) and was washed with 1N HCl (3×25 mL). The aqueous layers were combined, backextracted with ethyl acetate (25 mL) and then adjusted to pH=12 by addition of 5N NaOH resulting in a precipitate. The aqueous solution was extracted with ethyl acetate (3×50 mL) and the organic layers were combined, dried (MgSO4), filtered and concentrated to the product that was either pure or taken on crude.

Example 256

2-[8-(Benzyloxy)-5-chloroquinolin-7-yl]-1-[4-(morpholin-4-ylmethyl)phenyl]ethanamine Prepared from 7-{2-azido-2-[4-(morpholin-4-ylmethyl)phenyl]ethyl}-8-(benzyloxy)-5-chloroquinoline (0.970 mmol) according to the general procedure described above. Pure product as a white solid was obtained from the acid/base extraction (0.890 mmol, 92%). MS (ESI) m/z 488.4; HRMS: calcd for $C_{29}H_{30}ClN_3O_2$+H+, 488.20993; found (ESI, [M+H]+ Obs'd), 488.2106.

Example 257

2-[8-(Benzyloxy)-5-chloroquinolin-7-yl]-1-[3-(5-methyl-2-thienyl)phenyl]ethanamine Prepared from 7-{2-azido-2-[3-(5-methyl-2-thienyl)phenyl]ethyl}-8-(benzyloxy)-5-chloroquinoline (3.001 mmol) according to the general procedure described above. Extraction of the product into the aqueous layer was performed using 2N HCl in place of 1N HCl. Pure product as a light tan solid was obtained from the acid/base extraction (2.65 mmol, 88%). MS (ESI) m/z 485.3; HRMS: calcd for C29H25ClN2OS+H+, 485.14489; found (ESI, [M+H]+ Obs'd), 485.1455.

General Procedure for N-acylations:

To a round bottom flask containing the appropriate amine (0.45 mmol, 1.0 eq.) at −78° C. was added a solution of 4-biphenylcarbonyl chloride (0.50 mmol, 1.1 eq.) and triethylamine (0.50 mmol, 1.1 eq.) in tetrahydrofuran (5 mL) that was pre-mixed and stirred 5 min prior to addition. After warming to room temperature, the resulting solution was stirred 15 min and quenched with saturated aqueous sodium bicarbonate solution (5 mL). The tetrahydrofuran was removed by rotary evaporation and the resulting aqueous solution was extracted with dichloromethane (2×5 mL). The combined organic layers were dried (MgSO4), filtered and concentrated to the crude product that was purified by column chromatography or recrystallization.

Example 258

N-{2-[8-(Benzyloxy)-5-chloroquinolin-7-yl]-1-[4-(morpholin-4-ylmethyl)phenyl]ethyl}biphenyl-4-carboxamide Prepared from 2-[8-(benzyloxy)-5-chloroquinolin-7-yl]-1-[4-(morpholin-4-ylmethyl)phenyl]ethanamine (0.45 mmol) according to the general procedure described above. Crude product obtained was a white solid which was purified by column chromatography using 10% methanol/dichloromethane followed by recrystallization from dichloromethane/hexanes to give the product as a white solid (0.344 mmol, 77%). MS (ESI) m/z 668.4; HRMS: calcd for C42H38ClN3O3+H+, 668.26745; found (ESI, [M+H]+ Obs'd), 668.2675.

Example 259

N-{2-[8-(Benzyloxy)-5-chloroquinolin-7-yl]-1-[3-(pyrrolidin-1-ylmethyl)phenyl]ethyl}biphenyl-4-carboxamide To a stirring solution of [8-(benzyloxy)-5-chloroquinolin-7-yl]acetaldehyde (10.54 mmol) in tetrahydrofuran (75 mL) at −78° C. was slowly added a 0.25M solution of [3-(1-pyrrolidinylmethyl)phenyl]magnesium bromide in tetrahydrofuran (12.50 mmol, 1.2 eq.) and stirring at −78° C. was continued for 20 min. The reaction mixture was then quenched with saturated aqueous ammonium chloride solution (10 mL) and allowed to warm to room temperature. The mixture was then diluted with saturated aqueous ammonium chloride solution (65 mL) and extracted with ethyl acetate (2×75 mL). The combined organic layers were dried (MgSO4), filtered and concentrated to give 2-(8-benzyloxy-5-chloro-quinolin-7-yl)-1-(3-pyrrolidin-1-ylmethyl-phenyl)-ethanol as a yellow oil that was purified by column chromatography using 70/29/1 dichloromethane/acetone/diisopropylethylamine. The 2-(8-benzyloxy-5-chloro-quinolin-7-yl)-1-(3-pyrrolidin-1-ylmethyl-phenyl)-ethanol was subjected to the general conditions described above for conversion of alcohols to azides to give 7-[2-Azido-2-(3-pyrrolidin-1-ylmethyl-phenyl)-ethyl]-8-benzyloxy-5-chloro-quinoline. 7-[2-Azido-2-(3-pyrrolidin-1-ylmethyl-phenyl)-ethyl]-8-benzyloxy-5-chloro-quinoline (5.34 mmol) was subjected to the general conditions described above for Staudinger reduction of azides to give 2-(8-Benzyloxy-5-chloro-quinolin-7-yl)-1-(3-pyrrolidin-1-ylmethyl-phenyl)-ethylamine an amber oil and was used directly in the ensuing step. 2-(8-Benzyloxy-5-chloro-quinolin-7-yl)-1-(3-pyrrolidin-1-ylmethyl-phenyl)-ethylamine (0.675 mmol) was subjected to the general conditions described above for N-acylation with 4-biphenylcarbonyl chloride to give an off-white solid which was purified by twice recrystallizing from dichloromethane/hexanes to give the title compound as a white solid (0.311 mmol, 18% for 4 steps). MS (ESI) m/z 652.5; HRMS: calcd for C42H38ClN3O2+H+, 652.27253; found (ESI, [M+H]+ Obs'd), 652.2730.

Example 260

N-{2-(5-Chloro-8-hydroxyquinolin-7-yl)-1-[4-(morpholin-4-ylmethyl)phenyl]ethyl}biphenyl-4-carboxamide To a stirring suspension of N-{2-[8-(benzyloxy)-5-chloroquinolin-7-yl]-1-[4-(morpholin-4-ylmethyl)phenyl]ethyl}biphenyl-4-carboxamide (0.315 mmol) in acetonitrile (5 mL) was added sodium iodide (1.57 mmol, 5.0 eq.) followed by chlorotrimethylsilane (1.57 mmol, 5.0 eq.) and the resulting solution was heated to 50° C., capped and stirred 1 h. Additional acetonitrile (5 mL) was added and the reaction was stirred at 50° C. for an additional 4 h. The reaction mixture was then cooled to room temperature and concentrated by rotary evaporation to a brown solid which was purified by preparative scale HPLC to give the trifluoroacetate salt of the final product as a light brown solid (0.175 mmol, 56%). MS (ESI) m/z 578.4; HRMS: calcd for C35H32ClN3O3+H+, 578.22050; found (ESI, [M+H]+ Obs'd), 578.2210.

Example 261

N-{2-(5-Chloro-8-hydroxyquinolin-7-yl)-1-[3-(pyrrolidin-1-ylmethyl)phenyl]ethyl}biphenyl-4-carboxamide To a stirring suspension of N-{2-[8-(benzyloxy)-5-chloroquinolin-7-yl]-1-[3-(pyrrolidin-1-ylmethyl)phenyl]ethyl}biphenyl-4-carboxamide (0.303 mmol) in acetonitrile (7.5 mL) was added sodium iodide (1.513 mmol, 5.0 eq.) followed by chlorotrimethylsilane (1.513 mmol, 5.0 eq.) and the resulting solution was heated to 50° C., capped and stirred 5 h. The reaction mixture was then cooled to room temperature and additional sodium iodide (1.513 mmol, 5.0 eq.) and chlorotrimethylsilane (1.513 mmol, 5.0 eq.) were added followed by reheating to 50° C. for 16 h. The reaction mixture was then cooled to room temperature and concentrated by rotary evaporation to a brown solid to which was added pH=7.4 phosphate buffer (10 mL). This mixture was extracted with a solution of 19:1 chloroform/methanol and the combined organic layers were dried (MgSO4), filtered and concentrated to a brown solid which was purified by preparative scale HPLC followed by concentration to a solid which was washed with water (2×3 mL) followed by hexanes (4×3 mL) to give the trifluoroacetate salt of the final product as a light tan solid (0.101 mmol, 33%). MS (ESI) m/z 562.5; HRMS: calcd for C35H32ClN3O2+H+, 562.22558; found (ESI, [M+H]+ Obs'd), 562.2259.

Alternate General Procedure for N-Acylations:

To a round bottom flask containing the appropriate amine (0.701 mmol, 1.0 eq.) at 0° C. was added a solution of the acid chloride (0.771 mmol, 1.1 eq.) and triethylamine (0.771 mmol, 1.1 eq.) in tetrahydrofuran (7 mL) that was pre-mixed and stirred 5 min prior to addition. After warming to room temperature, the resulting solution was stirred 15 min and quenched with saturated aqueous sodium bicarbonate solution (7 mL). The tetrahydrofuran was removed by rotary evaporation and the resulting aqueous solution was extracted with dichloromethane (2×7 mL). The combined organic layers were dried (MgSO4), filtered and concentrated to the crude product that was either recrystallized or used crude in the ensuing reaction.

Example 262

N-{2-(5-Chloro-8-hydroxyquinolin-7-yl)-1-[3-(5-methyl-2-thienyl)phenyl]ethyl}biphenyl-4-carboxamide 2-[8-(benzyloxy)-5-chloroquinolin-7-yl]-1-[3-(5-methyl-2-thienyl)phenyl]ethanamine (0.412 mmol) and 4-biphenylcarbonyl chloride (0.453 mmol, 1.1 eq.) were subjected to the conditions described above (Alternate General Procedure for N-Acylations). Crude N-{2-(8-benzyloxy-5-chloro-quinolin-7-yl)-1-[3-(5-methyl-thiophen-2-yl)-phenyl]-ethyl}-2-(biphenyl-4-yloxy)-acetamide obtained was a tan solid that was used directly in the ensuing reaction. To a stirring suspension of N-{2-(8-benzyloxy-5-chloro-quinolin-7-yl)-1-[3-(5-methyl-thiophen-2-yl)-phenyl]-ethyl}-2-(biphenyl-4-yloxy)-acetamide (0.226 mmol) in acetonitrile (3.5 mL) and 1,2-dichloroethane (7 mL) was added sodium iodide (2.258 mmol, 10.0 eq.) followed by chlorotrimethylsilane (2.258 mmol, 10.0 eq.) and the resulting solution was heated to 70° C., capped and stirred 2 h. The reaction mixture was then cooled to room temperature and concentrated by rotary evaporation to remove the vast majority of the solvent. Water (5 mL) was added and the resulting suspension was stirred 1 h and concentrated by rotary evaporation to a brown solid. Water (5 mL) was added and the resulting mixture was sonicated for 5 min then filtered with the solid being washed with additional water. The solid was returned to a round bottom flask and toluene (5 mL) was added followed by removal of the solvent by rotary evaporation. The solid was then dissolved in a warm solution of 19:1 chloroform/methanol (10 mL) and this solution was washed with a 10% aqueous solution of sodium thiosulfate. The organic layer was dried (MgSO4), filtered and concentrated to a light green solid that was recrystallized from dichloromethane to give the title compound as an off-white solid (0.191 mmol, 37% for 2 steps). HRMS: calcd for C35H27ClN2O2S+H+, 575.15545; found (ESI, [M+H]+ Obs'd), 575.1555.

General Procedure for TMSI-Mediated O-Benzyl Deprotection:

To a round bottom flask containing the appropriate O-benzyl protected hydroxyquinoline (0.285 mmol, 1.0 eq.) was added sodium iodide (1.423 mmol, 5.0 eq.) followed by acetonitrile (4.5 mL) and finally chlorotrimethylsilane (1.423 mmol, 5.0 eq.). After warming to 70° C., the solution was capped and stirred 16 h then cooled to room temperature and quenched by the addition of pH=7.4 phosphate buffer (0.5 mL) and stirred 5 min. The acetonitrile was then removed by rotary evaporation and the resulting solution was diluted with pH=7.4 phosphate buffer (10 mL) and brine (2 mL) and extracted with a solution of 19:1 chloroform/methanol (3×8 mL). The organic layer was dried (MgSO4), filtered and concentrated to a dark brown solid. To this solid was added toluene (10 mL) and methanol (~5 drops) and the organic solvents were removed by rotary evaporation repeating this process 3 times affording the crude product that was purified by either preparative scale HPLC or column chromatography.

Example 263

N-{2-(5-Chloro-8-hydroxyquinolin-7-yl)-1-[3-(pyrrolidin-1-ylmethyl)phenyl]ethyl}-2-phenoxyacetamide To a stirring solution of [8-(benzyloxy)-5-chloroquinolin-7-yl]acetaldehyde (10.54 mmol) in tetrahydrofuran (75 mL) at −78° C. was slowly added a 0.25M solution of [3-(1-pyrrolidinylmethyl)phenyl]magnesium bromide in tetrahydrofuran (12.50 mmol, 1.2 eq.) and stirring at −78° C. was continued for 20 min. The reaction mixture was then quenched with saturated aqueous ammonium chloride solution (10 mL) and allowed to warm to room temperature. The mixture was then diluted with saturated aqueous ammonium chloride solution (65 mL) and extracted with ethyl acetate (2×75 mL). The combined organic layers were dried (MgSO4), filtered and concentrated to give a yellow oil that was purified by column chromatography using 70/29/1 dichloromethane/acetone/diisopropylethylamine to give 2-(8-benzyloxy-5-chloro-quinolin-7-yl)-1-(3-pyrrolidin-1-ylmethyl-phenyl)-ethanol as a white solid which was used directly in the next step. 2-(8-benzyloxy-5-chloro-quinolin-7-yl)-1-(3-pyrrolidin-1-ylmethyl-phenyl)-ethanol (5.34 mmol) was subjected to the general conditions described above for conversion of alcohols to azides to give 7-[2-azido-2-(3-pyrrolidin-1-ylmethyl-phenyl)-ethyl]-8-benzyloxy-5-chloro-quinoline as an amber oil that was used directly in the ensuing step. 7-[2-azido-2-(3-pyrrolidin-1-ylmethyl-phenyl)-ethyl]-8-benzyloxy-5-chloro-quinoline (5.34 mmol) was subjected to the general conditions described above for Staudinger reduction of azides to give 2-(8-benzyloxy-5-chloro-quinolin-7-yl)-1-(3-pyrrolidin-1-ylmethyl-phenyl)-ethylamine as an amber oil that was used directly in the ensuing step. 2-(8-benzyloxy-5-chloro-quinolin-7-yl)-1-(3-pyrrolidin-1-ylmethyl-phenyl)-ethylamine (0.701 mmol) and phenoxyacetyl chloride (0.771 mmol, 1.1 eq.) were subjected to the general procedure described above (Alternate General Procedure for N-Acylations) to give the crude product obtained as an off-white solid that was purified by recrystallization from dichloromethane/ether to give N-[2-(8-benzyloxy-5-chloro-quinolin-7-yl)-1-(3-pyrrolidin-1-ylmethyl-phenyl)-ethyl]-2-phenoxy-acetamide as a light tan solid. N-[2-(8-benzyloxy-5-chloro-quinolin-7-yl)-1-(3-pyrrolidin-1-ylmethyl-phenyl)-ethyl]-2-phenoxy-acetamide was subjected to the general procedure described above for TMSI-mediated O-benzyl deprotection. After stirring 16 h at 70° C., 1,2-dichloroethane (2 mL) was added and the reaction was stirred 5 h at 70° C. after which time the reaction was quenched and worked up as described above. Crude product obtained was a brown oil that was purified by preparative scale HPLC to give the trifluoroacetate salt of the title compound as a yellow solid (0.109 mmol, 9% for 5 steps). MS (ESI) m/z 516.2052; HRMS: calcd for C30H30ClN3O3+H+, 516.20485; found (ESI, [M+H]+ Obs'd), 516.2052.

Example 264

N-{2-(5-Chloro-8-hydroxyquinolin-7-yl)-1-[3-(pyrrolidin-1-ylmethyl)phenyl]ethyl}-2-(4-chlorophenoxy)-2-methylpropanamide To a stirring solution of [8-(benzyloxy)-5-chloroquinolin-7-yl]acetaldehyde (10.54 mmol) in tetrahydrofuran (75 mL) at −78° C. was slowly added a 0.25M solution of [3-(1-pyrrolidinylmethyl)phenyl]magnesium bromide in tetrahydrofuran (12.50 mmol, 1.2 eq.) and stirring at −78° C. was continued for 20 min. The reaction mixture was then quenched with saturated aqueous ammonium chloride solution (10 mL) and allowed to warm to room temperature. The mixture was then diluted with saturated aqueous ammonium chloride solution (65 mL) and extracted with ethyl acetate (2×75 mL). The combined organic layers were dried (MgSO4), filtered and concentrated to give a yellow oil that was purified by column chromatography using 70/29/1 dichloromethane/acetone/diisopropylethylamine to give 2-(8-benzyloxy-5-chloro-quinolin-7-yl)-1-(3-pyrrolidin-1-ylmethyl-phenyl)-ethanol as a white solid which was used directly in the ensuing step. 2-(8-benzyloxy-5-chloro-quinolin-7-yl)-1-(3-pyrrolidin-1-ylmethyl-phenyl)-ethanol (5.34 mmol) was subjected to the general conditions described above for conversion of alcohols to azides to give 7-[2-azido-2-(3-pyrrolidin-1-ylmethyl-phenyl)-ethyl]-8-benzyloxy-5-chloro-quinoline as an amber oil that was used directly in the ensuing step. 7-[2-azido-2-(3-pyrrolidin-1-ylmethyl-phenyl)-ethyl]-8-benzyloxy-5-chloro-quinoline (5.34 mmol) was subjected to the general conditions described above for Staudinger reduction of azides to give 2-(8-benzyloxy-5-chloro-quinolin-7-yl)-1-(3-pyrrolidin-1-ylmethyl-phenyl)-ethylamine as an amber oil that was used directly in the ensuing step. 2-(8-benzyloxy-5-chloro-quinolin-7-yl)-1-(3-pyrrolidin-1-ylmethyl-phenyl)-ethylamine (0.701 mmol) and 2-(4-chlorophenoxy)-2-methylpropanoyl chloride (0.771 mmol, 1.1 eq.) were subjected to the general conditions described above (Alternate General Procedure for N-Acylations) to give N-[2-(8-benzyloxy-5-chloro-quinolin-7-yl)-1-(3-pyrrolidin-1-ylmethyl-phenyl)-ethyl]-2-(4-chloro-phenoxy)-2-methyl-propionamide as a tan solid that was purified by recrystallization from dichloromethane/ether. N-[2-(8-Benzyloxy-5-chloro-quinolin-7-yl)-1-(3-pyrrolidin-1-ylmethyl-phenyl)-ethyl]-2-(4-chloro-phenoxy)-2-methyl-propionamide (0.237 mmol) was subjected to the general procedure described above for TMSI-mediated O-benzyl deprotection. After stirring 16 h at 70° C., 1,2-dichloroethane (2 mL) was added and the reaction was stirred 5 h at 70° C. after which time the reaction was quenched and worked up as described above. Crude product obtained was a brown solid that was purified by preparative scale HPLC to give the trifluoroacetate salt of the title compound as a yellow solid (0.074 mmol, 6% for 5 steps). MS (ESI) m/z 578.1971; HRMS: calcd for C32H33Cl2N3O3+H+, 578.19717; found (ESI, [M+H]+ Obs'd), 578.1971.

Example 265

N-{2-(5-Chloro-8-hydroxyquinolin-7-yl)-1-[3-(5-methyl-2-thienyl)phenyl]ethyl}-2-phenoxyacetamide N-{2-(8-Benzyloxy-5-chloro-quinolin-7-yl)-1-[3-(5-methyl-thiophen-2-yl)-phenyl]-ethyl}-2-phenoxy-acetamide was prepared from 2-[8-(benzyloxy)-5-chloroquinolin-7-yl]-1-[3-(5-methyl-2-thienyl)phenyl]ethanamine (0.404 mmol) and phenoxyacetyl chloride (0.445 mmol, 1.1 eq.) according to the general procedure described above (Alternate General Procedure for N-Acylations). Ethyl acetate was used in place of dichloromethane in the workup procedure. Crude product obtained was a white foam that was subjected to the conditions described above for TMSI-mediated O-benzyl deprotection. After stirring 16 h at 70° C., 1,2-dichloroethane (5.6 mL) was added and the reaction was stirred 3 h at 70° C. after which time the reaction was quenched and worked up as described above. Crude product obtained was a brown oil that was purified by column chromatography using 10% acetone/dichloromethane followed by concentration and washing the solid with diethyl ether (3×5 mL) to give the title compound as a tan solid (0.171 mmol, 42% for 2 steps). MS (ESI) m/z 529.4.

Example 266

2-(Benzyloxy)-N-{2-(5-chloro-8-hydroxyquinolin-7-yl)-1-[3-(5-methyl-2-thienyl)phenyl]ethyl}acetamide 2-Benzyloxy-N-{2-(8-benzyloxy-5-chloro-quinolin-7-yl)-1-[3-(5-methyl-thiophen-2-yl)-phenyl]-ethyl}-acetamide was prepared from 2-[8-(benzyloxy)-5-chloroquinolin-7-yl]-1-[3-(5-methyl-2-thienyl)phenyl]ethanamine (0.411 mmol) and benzyloxyacetyl chloride (0.452 mmol, 1.1 eq.) according to the general procedure described above (Alternate General Procedure for N-Acylations). After stirring 15 min at room temperature, additional benzyloxyacetyl chloride (0.206 mmol, 0.5 eq.) and triethylamine (0.206 mmol, 0.5 eq.) was added. Stirring was continued for 2 min at room temperature and the reaction was worked up as described in the general procedure. Ethyl acetate was used in place of dichloromethane in the workup procedure. Crude product obtained was a white foam that was subjected to the conditions described above for TMSI-mediated O-benzyl deprotection. Crude product obtained was a brown solid that was purified by column chromatography using 10% acetone/dichloromethane to give the title compound as a tan solid (0.118 mmol, 29% for 2 steps). MS (ESI) m/z 543.4.

Example 267

N-{2-(5-Chloro-8-hydroxyquinolin-7-yl)-1-[3-(5-methyl-2-thienyl)phenyl]ethyl}-2-(4-chlorophenoxy)-2-methylpropan amide N-{2-(8-Benzyloxy-5-chloro-quinolin-7-yl)-1-[3-(5-methyl-thiophen-2-yl)-phenyl]-ethyl}-2-(4-chloro-phenoxy)-2-methyl-propionamide was prepared from 2-[8-(benzyloxy)-5-chloroquinolin-7-yl]-1-[3-(5-methyl-2-thienyl)phenyl]ethanamine (0.409 mmol) and 2-(4-chlorophenoxy)-2-methylpropanoyl chloride (0.450 mmol, 1.1 eq.) according to the general procedure described above (Alternate General Procedure for N-Acylations). Ethyl acetate was used in place of dichloromethane in the workup procedure. Crude product obtained was a tan solid that was subjected to the conditions described above for TMSI-mediated O-benzyl deprotection. Crude product from the deprotection was a brown solid that was purified by column chromatography using 5% methanol/dichloromethane to give the title compound as a white solid (0.270 mmol, 66% for 2 steps). MS (ESI) m/z 591.4.

Example 268

2-(4-tert-Butylphenoxy)-N-{2-(5-chloro-8-hydroxyquinolin-7-yl)-1-[3-(5-methyl-2-thienyl)phenyl]ethyl}acetamide N-{2-(8-Benzyloxy-5-chloro-quinolin-7-yl)-1-[3-(5-methyl-thiophen-2-yl)-phenyl]-ethyl}-2-(4-tert-butyl-phenoxy)-acetamide was prepared from 2-[8-(benzyloxy)-5-chloroquinolin-7-yl]-1-[3-(5-methyl-2-thienyl)phenyl]ethanamine (0.414 mmol) and 4-tert-butyl-phenoxyacetyl chloride (0.455 mmol, 1.1 eq.) according to the general procedure described above (Alternate General Procedure for N-Acylations). Ethyl acetate was used in place of dichloromethane in the workup procedure. Crude product obtained was a white solid that was subjected to the conditions described above for TMSI-mediated O-benzyl deprotection Crude product obtained was a brown solid that was purified by column chromatography using 5% methanol/dichloromethane to give the title compound as a white solid (0.262 mmol, 64% for 2 steps). MS (ESI) m/z 585.4.

Scheme D: Synthesis of N-[2-(5-Chloro-8-hydroxyquinolin-7-yl-1-{5-[(dimethylamino)methyl]-2-furyl}ethyl]-2-phenoxyacetamide and N-[2-(5-Chloro-8-hydroxyquinolin-7-yl)-1-{5-{(dimethylamino)methyl]-2-furyl}ethyl]-2-methylpropanamide

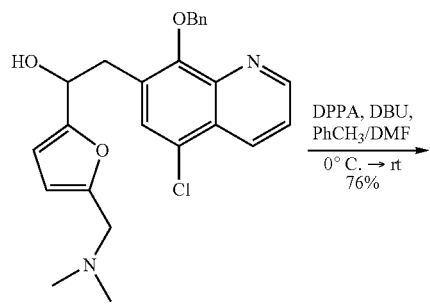

2-[8-(benzyloxy)-5-chloroquinolin-7-yl]-1-(5-{[(dimethylamino)methyl]-2-furyl}ethanol

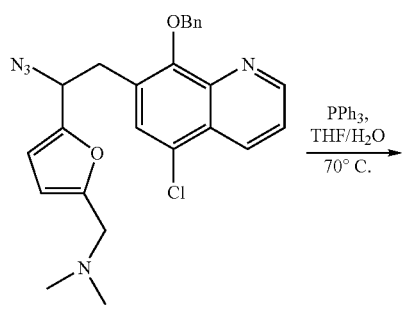

1-(5-{1-Azido-2-[8-(benzyloxy)-5-chloroquinolin-7-yl]ethyl}-2-furyl)-N,N-dimethylmethanamine

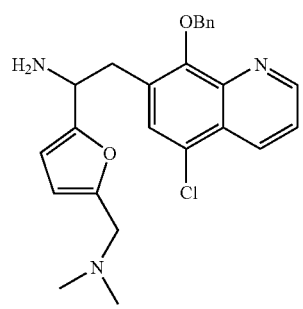

2-[8-(Benzyloxy)-5-chloroquinolin-7-yl]-1-(5-{[(dimethylamino)methyl]-2-furyl}ethanamine

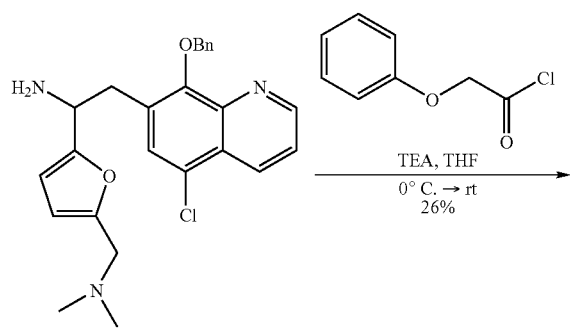

2-[8-(Benzyloxy)-5-chloroquinolin-7-yl]-1-(5-{[(dimethylamino)methyl]-2-furyl}ethanamine

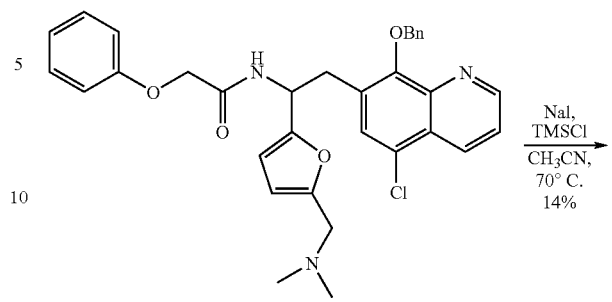

N-(2-[8-(Benzyloxy)-5-chloroquinolin-7-yl]-1-{5-[(dimethylamino)methyl]-2-furyl}ethyl-2-phenoxyacetamide

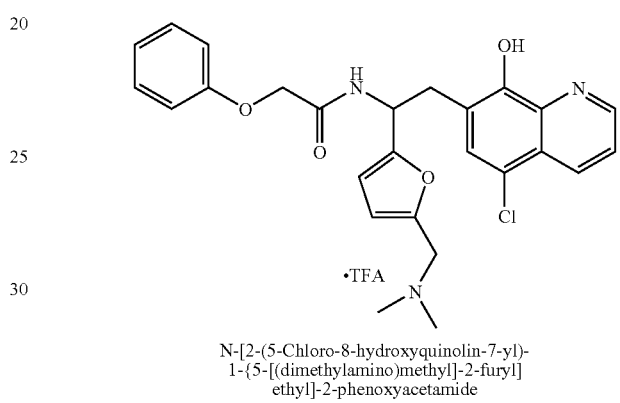

N-[2-(5-Chloro-8-hydroxyquinolin-7-yl)-1-{5-[(dimethylamino)methyl]-2-furyl]ethyl]-2-phenoxyacetamide

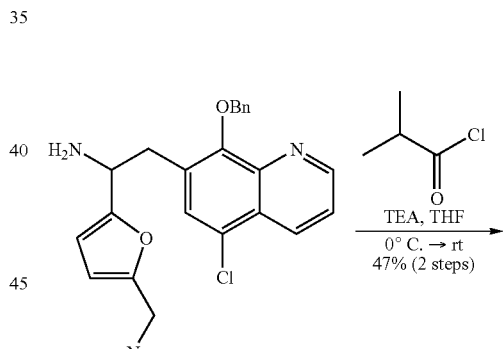

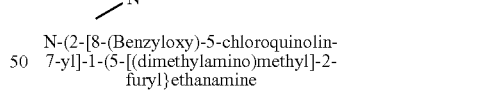

N-(2-[8-(Benzyloxy)-5-chloroquinolin-7-yl]-1-{5-[(dimethylamino)methyl]-2-furyl}ethanamine

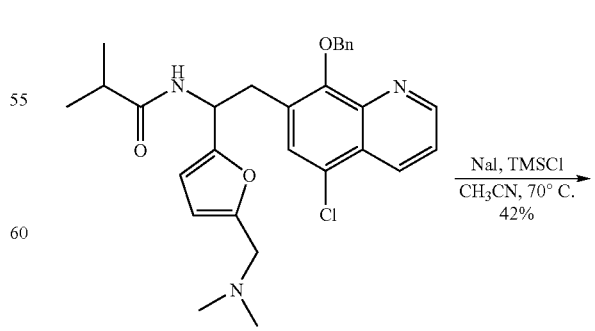

N-[2-(8-Benzyloxy-5-chloro-quinolin-7-yl)-1-(5-dimethylaminomethyl-furan-2-yl)-ethyl]-isobutyramide

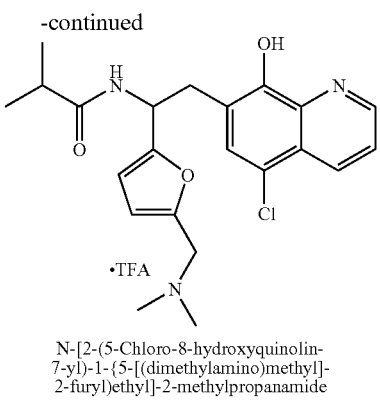

N-[2-(5-Chloro-8-hydroxyquinolin-7-yl)-1-{5-[(dimethylamino)methyl]-2-furyl)ethyl]-2-methylpropanamide Example 269

1-(5-{1-Azido-2-[8-(benzyloxy)-5-chloroquinolin-7-yl]ethyl}-2-furyl)-N,N-dimethylmethanamine To a stirring solution of 2-[8-(benzyloxy)-5-chloroquinolin-7-yl]-1-{5-[(dimethylamino)methyl]-2-furyl}ethanol (2.18 mmol) in toluene (13.5 mL) and dimethylformamide (2.7 mL) at 0° C. was added diphenyl phosphoryl azide (5.46 mmol, 2.5 eq.) followed by dropwise addition of 1,8-diazabicyclo[5.4.0]undec-7-ene (5.46 mmol, 2.5 eq.). The reaction mixture was stirred 5 min at 0° C. then warmed to room temperature and stirred 16 h. The mixture was next diluted with saturated aqueous lithium bromide solution (25 mL) and extracted with ethyl acetate (3×15 mL). The combined organic layers were dried (MgSO4), filtered and concentrated to a dark brown syrup that was purified by column chromatography using 30% acetone/dichloromethane to give the product as a brown syrup (1.65 mmol, 76%). MS (ESI) m/z 462.4; HRMS: calcd for C25H24ClN5O2+H+, 462.16913; found (ESI, [M+H]+ Obs'd), 462.1693.

Example 270

2-[8-(Benzyloxy)-5-chloroquinolin-7-yl]-1-{5-[(dimethylamino)methyl]-2-furyl}ethanamine To a stirring solution of 1-(5-{1-azido-2-[8-(benzyloxy)-5-chloroquinolin-7-yl]ethyl}-2-furyl)-N,N-dimethylmethanamine (0.1.451 mmol) in tetrahydrofuran (5 mL) and water (1.5 mL) in a round bottom flask equipped with a reflux condenser was added triphenylphosphine (1.596 mmol, 1.1 eq.) (CAUTION: vigorous gas evolution, do not seal reaction vessel) and the resulting mixture was then warmed to 70° C. and stirred 2 h. The reaction mixture was then allowed to cool to room temperature, diluted with ethyl acetate (50 mL) and was washed with 1N HCl (3×25 mL). The aqueous layers were combined, backextracted with ethyl acetate (25 mL) and then adjusted to pH=12 by addition of 5N NaOH resulting in a precipitate. The aqueous solution was extracted with ethyl acetate (3×50 mL) and the organic layers were combined, dried (MgSO4), filtered and concentrated a yellow oil that was used directly in the ensuing step. MS (ESI) m/z 436.4; HRMS: calcd for C25H26ClN3O2+H+, 436.17863; found (ESI, [M+H]+ Obs'd), 436.1788.

Example 271

N-(2-[8-(Benzyloxy)-5-chloroquinolin-7-yl]-1-{5-[(dimethylamino)methyl]-2-furyl}ethyl)-2-phenoxy-acetamide To a stirring solution of 2-[8-(benzyloxy)-5-chloroquinolin-7-yl]-1-{5-[(dimethylamino)methyl]-2-furyl}ethanamine (0.431 mmol) and triethylamine (0.474 mmol, 1.1 eq.) in tetrahydrofuran (4 mL) at 0° C. was added phenoxyacetyl chloride (0.474 mmol, 1.1 eq.) and the resulting solution was stirred 5 min at 0° C. then warmed to room temperature and stirred 15 min. The reaction was quenched with saturated aqueous sodium bicarbonate solution (15 mL) and the resulting aqueous solution was extracted with ethyl acetate (3×10 mL). The combined organic layers were dried (MgSO4), filtered and concentrated to a white foam that was purified by column chromatography using 10% methanol/dichloromethane to give the final product as a clear oil (0.113 mmol, 26%). MS (ESI) m/z 570.3; HRMS: calcd for C33H32ClN3O4+H+, 570.21541; found (ESI, [M+H]+ Obs'd), 570.2155.

Example 272

N-[2-(5-Chloro-8-hydroxyquinolin-7-yl)-1-{5-[(dimethylamino)methyl]-2-furyl}ethyl]-2-phenoxyacetamide To a stirring solution of N-(2-[8-(benzyloxy)-5-chloroquinolin-7-yl]-1-{5-[(dimethylamino)methyl]-2-furyl}ethyl)-2-phenoxyacetamide (0.113 mmol) in acetonitrile (3 mL) was added sodium iodide (0.565 mmol, 5.0 eq.) followed by chlorotrimethylsilane (0.565 mmol, 5.0 eq.). After warming to 70° C., the solution was capped and stirred 1.5 h then cooled to room temperature and quenched by the addition of 10% sodium thiosulfate (0.25 mL) and the acetonitrile was removed by rotary evaporation. The resulting solution was diluted with 0.1N NaOH (10 mL) and extracted with dichloromethane (3×8 mL). The combined organic layers were dried (MgSO4), filtered and concentrated to a yellow solid that was purified by preparative scale HPLC to give the trifluoroacetate salt of the final product as a yellow solid (0.016 mmol, 14%). MS (ESI) m/z 480.2.

Example 273

N-[2-(8-Benzyloxy-5-chloro-quinolin-7-yl)-1-(5-dimethylaminomethyl-furan-2-yl)-ethyl]-isobutyramide To a round bottom flask containing 2-[8-(benzyloxy)-5-chloroquinolin-7-yl]-1-{5-[(dimethylamino)methyl]-2-furyl}ethanamine (0.710 mmol) at 0° C. was added a solution of isobutyryl chloride (0.852 mmol, 1.2 eq.) and triethylamine (0.852 mmol, 1.2 eq.) in tetrahydrofuran (5 mL) that was pre-mixed and stirred 5 min prior to addition. After warming to room temperature, the resulting solution was stirred 2 h and quenched with saturated aqueous sodium bicarbonate solution (1 mL) and stirred 5 min. The reaction was diluted with 0.1N NaOH (15 mL) and extracted with ethyl acetate (3×10 mL). The combined organic layers were dried (MgSO4), filtered and concentrated to a yellow syrup that was purified by column chromatography to afford the final product as a white solid (0.344 mmol, 47% for 2 steps). HRMS: calcd for C29H32ClN3O3+H+, 506.22049; found (ESI, [M+H]+ Obs'd), 506.2208.

Example 274

N-[2-(5-Chloro-8-hydroxyquinolin-7-yl)-1-{5-[(dimethylamino)methyl]-2-furyl}ethyl]-2-methylpropanamide To a stirring solution of N-[2-(8-benzyloxy-5-chloroquinolin-7-yl)-1-(5-dimethylaminomethyl-furan-2-yl)-ethyl]-isobutyramide (0.266 mmol) in acetonitrile (3 mL) and 1,2-dichloroethane (1 mL) was added sodium iodide (1.33 mmol, 5.0 eq.) followed by chlorotrimethylsilane (1.33 mmol, 5.0 eq.). After warming to 70° C., the solution was capped and stirred 4 h then cooled to room temperature and quenched by the addition of 10% sodium thiosulfate (2 mL). The resulting solution was diluted with pH=7.4 phosphate buffer (15 mL) and extracted with dichloromethane (3×10 mL). The combined organic layers were dried (MgSO4), filtered and concentrated to a brown oil that was purified by preparative scale HPLC to give the trifluoroacetate salt of the final product as a yellow solid (0.111 mmol, 42%). MS (ESI) m/z 416.3.

Examples 275-277

2-[amino(phenyl)methyl]quinolin-8-ol, N-[(8-hydroxyquinolin-2-yl)(phenyl)methyl]-2-phenoxyacetamide and 2-{[(phenoxyacetyl)amino] (phenyl)methyl}quinolin-8-yl phenoxyacetate were prepared as outlined in below.

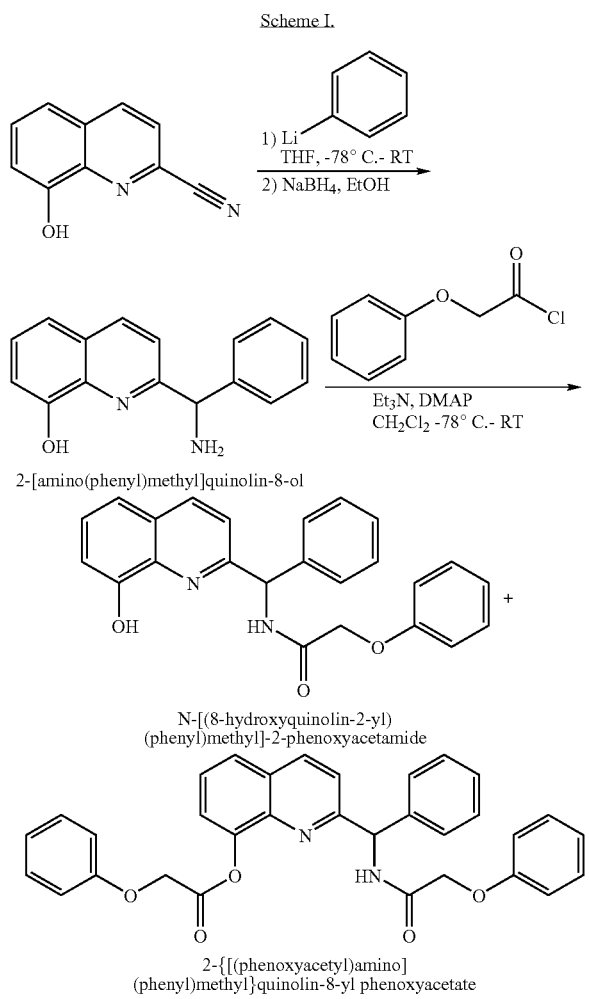

The experimentals are presented below:

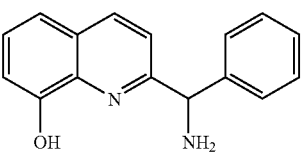

2-[amino(phenyl)methyl]quinolin-8-ol

To a solution of 8-hydroxyquinoline-2-carbonitrile (416 mg, 2.45 mmol) in THF (5 mL) at −78° C was added phenyllithium solution (1.8M in nBu2O) (2.72 mL, 4.9 mmol) dropwise. The flask was allowed to warm to room temperature over 2 h. After recooling to −78° C ethanol (7 mL) was added dropwise followed by sodium borohydride (110 mg, 2.9 mmol). Upon completion of the reduction 1 N HCl was added until hydrogen evolution ceased. The mixture was treated with saturated aqueous sodium bicarbonate and was then back extracted with chloroform. Combined organic layers were dried over sodium sulfate, filtered and reduced to dryness. Silica gel flash chromatography (dichloromethane, methanol) furnished 306 mg of an orange solid (50% yield).

2-[amino(phenyl)methyl]quinolin-8-ol

MS (ESI) m/z 251.2

To a solution of 2-[amino(phenyl)methyl]quinolin-8-ol in dichloromethane (10 mL) was added triethylamine (0.098 ml, 0.7 mmol) and 4-(dimethylamino)pyridine 5 mg. After cooling to −78° C phenoxyacetyl chloride (0.085 mL, 0.617 mmol) was added dropwise and the resulting solution was stirred for 12 h at room temperature. The reaction was partitioned between ether and water. The organic layer was dried over sodium sulfate, filtered and reduced to dryness. The resulting residue was subjected to silica gel flash chromatography (hexanes/ethyl acetate 30:1-2:1) and two products were eluted. Eluting first was 95 mg of a white solid (40% yield).

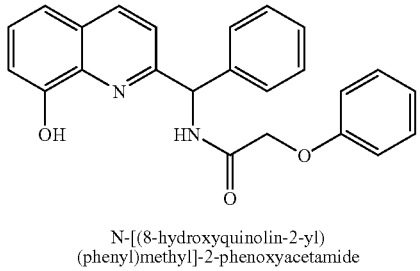

N-[(8-hydroxyquinolin-2-yl)(phenyl)methyl]-2-phenoxyacetamide

MS (ESI) m/z 385.2

Eluting second was 77 mg of a yellow solid (24% yield).

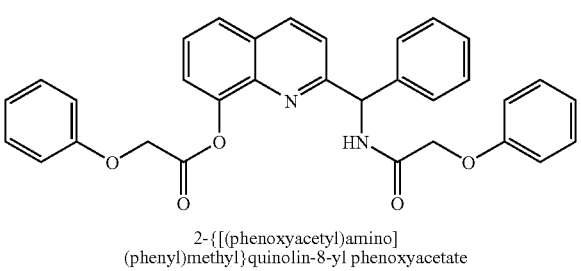

2-{[(phenoxyacetyl)amino](phenyl)methyl}quinolin-8-yl phenoxyacetate

MS (ESI) m/z 519.2

The Agg-1/Agg-2 FRET data for N-[(8-hydroxyquinolin-2-yl)(phenyl)methyl]-2-phenoxyacetamide and 2-{[(phenoxyacetyl)amino](phenyl)methyl}quinolin-8-yl phenoxyacetate is presented in Table 1.

TABLE 1

| | FRET IC$_{50}$ (μM) | |
|---|---|---|
| | Agg-1 | Agg-2 |
| 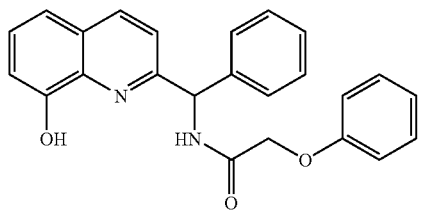 N-[(8-hydroxyquinolin-2-yl)(phenyl)methyl]-2-phenoxyacetamide | 15 | 32% @ 200 |
| 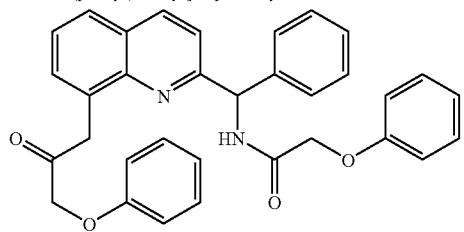 2-{[(phenoxyacetyl)amino](phenyl)meethyl}quinolin-8-yl phenoxyacetate | 4.0 | 52% @ 200 |

Example 278

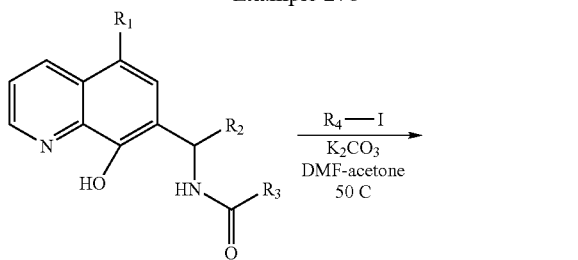

To a mixture of Ia (0.12 mmol) and potassium carbonate (0.13 mmol) in DMF:acetone (2 mL of 1:1 mixture) is added an alkyl iodide (0.13 mmol). The reaction is heated to 50 C and stirred for 18 h. The reaction mixture is concentrated and purification via preparative HPLC affords IIa. The scheme depicts synthesis of a compound of formula (I):

in which X is N, Y is —COR$_4$, R$_{13}$ is H and p is 0. Analogous reactions can be used to make compounds of formula (I) in which X is N, Y is —COR$_4$, R$_{13}$ is H and p is 1; in which X is —COR$_4$, Y is N, R$_1$ is H and p is 0; and in which X is —COR$_4$, Y is N, R$_1$ is H and p is 1; by substitution of the appropriate starting compound having a hydroxy group in place of the compound labeled "Ia" in the scheme.

Example 279

Aggrecanse 2 In vitro Enzyme Assay

A continuous assay was used in which the substrate was a synthetic peptide containing a fluorescent group (o-aminobenzyl, Abz), which was quenched by energy transfer to a 2,4-dinitrophenyl group (Dnp). The buffer used in this assay was 50 mM HEPES, pH 7.5, 100 mM NaCl, 5 mM CaCl$_2$, 0.1% CHAPS, 5% glycerol. The source of enzyme was purified recombinant human Aggrecanase-2 Agg2-Phe$_{628}$ (MW=41,737). This is a truncated form of full-length human aggrecanase-2 that was expressed in CHO cells and purified. The final concentration of Agg2-Phe$_{628}$ was 0.5 μg/ml. The substrate in the assay was synthesized by AnaSpec, Inc. and was >95% pure based on HPLC analysis. It is a synthetic peptide that is designed after a portion of brevican, one of the naturally occurring substrates of Aggrecanase-2, of the sequence Abz-TESESRGAIY-Dap(Dnp)-KK—NH$_2$ (mass=1740). The concentration of this substrate stock was spectrophotometrically determined using the extinction coefficient at 354 nm of 18,172 M$^{-1}$cm$^{-1}$. The V$_{max}$ and K$_m$ for this enzyme/substrate reaction were determined to be insensitive to DMSO up to at least 10% (v/v). The final concentration of substrate in the assay was 25 μM.

Test compounds (in duplicate) were serially diluted from 2 mM to 0.01 μM in 100% DMSO. The total reaction volume was 100 μl. The buffer and enzyme were added first followed by addition of 10× inhibitor from the dilution plate. Enzyme and buffer alone samples were included in order to obtain the maximal rate of substrate cleavage. The reaction was allowed to stand at 30° C. for 15 min. Then substrate was added, mixed and the reaction monitored for 40 min at 30° C. in kinetic mode using $\lambda_{ex}$: 340 nm and % $\lambda_{em}$: 420 (GeminiXS Molecular Devices).

Compound A, a hydroxamic acid with an Agg2 $IC_{50}$ of 36+/−4 nM, is of formula:

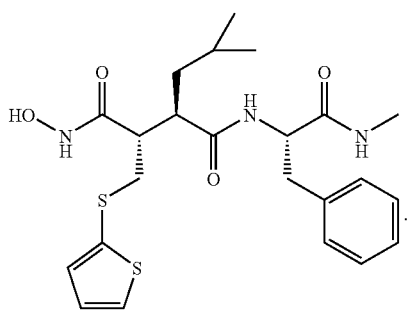

Compound A

Compound A was run on each plate (in duplicate) as a positive control for the assay at the following concentrations: 200 nM, 20 nM and 10 nM which correspond to 100, 60 and 40% inhibition of Agg2-$Phe_{628}$ activity respectively.

Example 280

Aggrecanse 2 Enzyme Fluorescence Polarization Assay a) Introduction

The fluorescence polarization assay is used to determine the dissociation constant of the enzyme:inhibitor complex (Ki) and the binding interaction mode (competitive, non-competitive or uncompetitive) of reversible inhibitors. The fluorescence polarization assay monitors the rotational motion of the fluorescent ligand. In the free state the fluorescent ligand has high rotational motion corresponding to a low polarization value and when fully bound to the protein, the fluorescent ligand has a lower rotational motion, corresponding to a higher polarization value. The rotational motion of the fluorescent ligand bound to the enzyme is compared to the rotational motion of the fluorescent ligand in the presence of increasing concentrations of inhibitors in order to assess the potency of small molecules.

b) Materials and Methods

The source of enzyme was purified recombinant human Aggrecanase-2, Agg2-$Phe_{628}$ (41737 Da). This is a truncated form of full-length human aggrecanase-2 that is purified. Aliquots of this enzyme are stored at −80° C. in 50 mM HEPES-NaOH (pH 7.4), 100 mM NaCl, 5 mM $CaCl_2$, 20% glycerol.

A fluorescent ligand was constructed from Compound B:

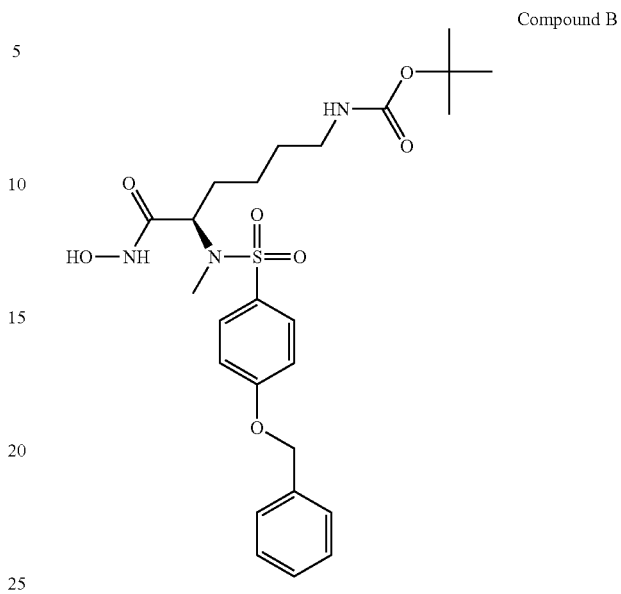

Compound B and Oregon Green 488 carboxylic acid, succinimidyl ester (Molecular Probes, Eugene, Oreg.). The fluorescent ligand, Compound C, has a mass of 815.8, is >95% pure based upon HPLC analysis and has the structure:

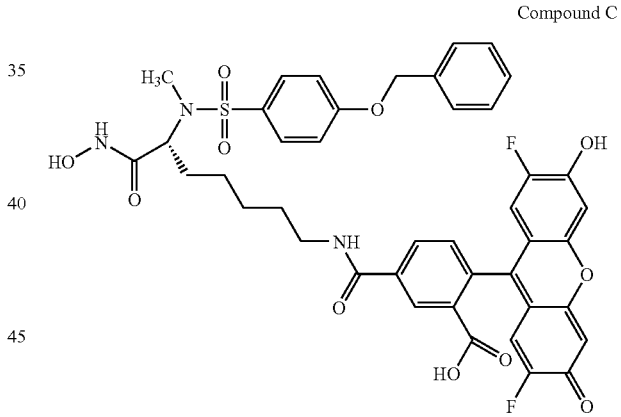

Compound C

Stock solutions of the fluorescent ligand are prepared in 100% DMSO and aliquots are stored at −80° C. The stock concentration was determined by a NMR ratio method, comparing the area under the control compound peak (TSP; trimethyl silyl proprionate sodium salt) to the area under a well-defined sample peak.

To determine the dissociation constant between Aggrecanase-2 and Compound C, saturation experiments were performed by adding various concentrations of aggrecanase to a constant concentration of Compound C (2 nM), in the assay buffer 50 mM HEPES-NaOH (pH 7.4), 100 mM NaCl, 5 mM $CaCl_2$, 0.005% Brij-35. Anisotropy values were calculated and converted to fraction bound values as described in the data analysis section below. The plot of the fraction of bound FP ligand against compound concentration were fit to a quadratic equation, assuming a single-site binding model, where $F_B$=Fraction of bound Fluorescent Ligand, Kd=Fluorescent Ligand Dissociation Constant, $E_0$=Total Enzyme Concentration and $L_0$=Total Ligand Concentration to determine the dissociation constant. The equilibrium dissociation constant was determined to be 60+/−2.9 nM.

$$F_B = \frac{(L_0 + K_d + E_0) - ((L_0 + K_d + E_0)^2 - (4 L_0 E_0))^{0.5}}{2 L_0}$$

The fluorescent polarization assay buffer contains 50 mM HEPES-NaOH (pH 7.4), 100 mM NaCl, 5 mM $CaCl_2$, 0.005% Brij-35. Each well of black polystyrene 384-well plate contains a 70 µl reaction consisting of assay buffer, Aggrecanase-2 (final concentration 165 nM; 2.75 times Kd), fluorescent ligand Compound C (final concentration 2 nM), and varied concentrations of inhibitor (prepared by serial dilution in DMSO in 96-well round-bottom polypropylene plates). For each compound a 12-point titration of sample and control (minus enzyme) is performed in duplicate. The reaction is mixed by pipetting up and down and allowed to reach equilibrium over 30 minutes, at room temperature. Final DMSO concentration is 10%-7.14% from the addition of the compound and 2.86% from the addition of Compound C.

Polarization values are determined using an Analyst AD fluorometer (LJL Biosystems Inc., Sunnyvale, Calif.) with a 485±20 nm excitation filter and a 530±25 nm emission filter. The instrument is set to use SmartRead detector counting with a sensitivity of 1 for 10 msec., with the attenuator in the out position.

c) Positive Control

A broad spectrum MMP inhibitor, Compound B, with an established $IC_{50}$ value of 37+/−2 nM and a Ki value of 39+/−0.7 nM for rAgg-2 was run in duplicate as a positive control for the assay.

d) Data Analysis

The anisotropy values were calculated from the parallel and perpendicular measurements using the equation: Anisotropy=$[I_{VV}-GI_{VH}]/[I_{VV}+2GI_{VH}]$, where $I_{VV}$=intensity of vertically excited and vertically emitted light, $I_{VH}$=intensity of vertically excited and horizontally emitted light, and G=G-factor=1.05. The total intensity values were calculated from the parallel and perpendicular measurements using the equation: Total Intensity=$[I_{VV}+2GI_{VH}]$, where $I_{VV}$=intensity of vertically excited and vertically emitted light, $I_{VH}$=intensity of vertically excited and horizontally emitted light, and G=G-factor=1.05.

Anisotropy values were converted to fraction of bound FP ligand using the equation: Fraction bound=$(r-r_{free})/(r-r_{free})+R(r_{bound}-r)$, where r=anisotropy, $r_{free}$=anisotropy of fluorescent ligand in the absence of enzyme, $r_{bound}$=anisotropy of fluorescent ligand in the presence of a saturating amount of enzyme, R=ratio of intensities of the free and bound fluorescent ligand=0.92. Plots of compound concentration against fraction bound are fit to the exact solution to the competitive inhibition equation to determine the Ki value, assuming a competitive single binding site, where $I_0$=Total Inhibitor Concentration, Ki=Inhibitor Dissociation Constant, Kd=Fluorescent Ligand Dissociation Constant, $f_B$=Fraction of bound Fluorescent Ligand, $E_0$=Total Enzyme Concentration and $L_0$=Total Ligand Concentration.

$$I_0 = \left(\frac{K_d F_b}{1 - F_b} + K_i\right)\left(\frac{E_0(1 - F_b)}{K_d F_b} - 1 - \frac{L_0(1 - F_b)}{K_d}\right)$$

Example 281

Aggrecanase 2 Cell Based Assay

Bovine carpal joints were obtained from young (1-2-week-old) animals, disinfected with 10% Wescodyne (Steris Corporation, St. Louis, Mo.) followed by 70% ethanol. Full-depth articular cartilage plugs were harvested using a cork borer and then sliced to generate individual articular cartilage discs about 6 mm wide and 1 mm thick. These cartilage discs (explants) were used for the explant assay.

Cartilage explants were cultured at 37° C. for 5 days in a humidified atmosphere of 5% $CO_2$ in air in cartilage explant culture medium. Explants were washed with media and 1 weighed explant per well were placed in a 96-well culture dish with 0.2 ml of medium and 6-8 replicates per treatment and cultured for 3 days in the presence or absence of recombinant human IL-1 (rhIL-1, 5 ng/ml, Sigma, St. Louis, Mo.) and presence or absence of test compounds. Media were replaced every day. The aggrecan content in the medium was measured each day by Dimethylmethelene Blue (DMMB) assay using chondroitin sulphate C as a standard. Measured aggrecan was expressed per weight of cartilage.

Assay Data

| Compound | Agg-2 FRET Median IC50 (nm) | Agg-2 FRET Median PCT INHIB (%) |
|---|---|---|
| N-[(5-chloro-8-hydroxyquinolin-7-yl)(phenyl)methyl]-2-phenoxyacetamide | 1218 | |
| N-[(5-chloro-8-hydroxyquinolin-7-yl)(2-chlorophenyl)methyl]-2-phenoxyacetamide | 350 | |
| N-[(5-chloro-8-hydroxyquinolin-7-yl)(3-nitrophenyl)methyl]-2-phenoxyacetamide | 488 | |
| N-[(5-chloro-8-hydroxyquinolin-7-yl)(4-nitrophenyl)methyl]-2-phenoxyacetamide | 953 | |
| N-[(2-chlorophenyl)(8-hydroxy-5-nitroquinolin-7-yl)methyl]-2-phenoxyacetamide | 938 | |
| N-[(8-hydroxy-5-nitroquinolin-7-yl)(phenyl)methyl]-2-phenoxyacetamide | 1351 | |
| N-[(5-chloro-8-hydroxyquinolin-7-yl)(2-fluorophenyl)methyl]-2-phenoxyacetamide | 1215 | |
| N-[(5-chloro-8-hydroxyquinolin-7-yl)(2-nitrophenyl)methyl]-2-phenoxyacetamide | 1207 | |
| N-[(S)-(5-chloro-8-hydroxyquinolin-7-yl)(2-chlorophenyl)methyl]-2-phenoxyacetamide | 1345 | |

| Compound | Agg-2 FRET Median IC50 (nm) | Agg-2 FRET Median PCT INHIB (%) |
| --- | --- | --- |
| N-[(R)-(5-chloro-8-hydroxyquinolin-7-yl)(2-chlorophenyl)methyl]-2-phenoxyacetamide | 1224 | |
| N-[(5-chloro-8-hydroxyquinolin-7-yl)(phenyl)methyl]-2-phenoxyacetamide | 2000 | |
| N-[(5-chloro-8-hydroxyquinolin-7-yl)(2-chlorophenyl)methyl]-2-phenoxyacetamide | 1550 | |
| N-[(5-chloro-8-hydroxyquinolin-7-yl)(2-furyl)methyl]-2-phenoxyacetamide | 2426 | |
| benzyl [(5-chloro-8-hydroxyquinolin-7-yl)(phenyl)methyl]carbamate | | 46 |
| benzyl [(5-chloro-8-hydroxyquinolin-7-yl)(2-chlorophenyl)methyl]carbamate | | 56 |
| benzyl [(5-chloro-8-hydroxyquinolin-7-yl)(2-furyl)methyl]carbamate | | 33 |
| benzyl [(5-chloro-8-hydroxyquinolin-7-yl)(pyridin-2-yl)mehyl]carbamate | | 50 |
| N-[(4-chloro-1-hydroxy-2-naphthyl(phenyl)methyl]-2-phenoxyacetamide | | 31 |
| N-[(5-chloro-8-hydroxyquinolin-7-yl)(5-methyl-2-furyl)methyl]-2-phenoxyacetamide | 2325 | |
| N-[(5-chloro-8-hydroxyquinolin-7-yl)(3-furyl)methyl]-2-phenoxyacetamide | 3459 | |
| N-[(5-chloro-8-hydroxyquinolin-7-yl)(5-phenyl-2-furyl)methyl]-2-phenoxyacetamide | | 54 |
| N-[(5-chloro-8-hydroxyquinolin-7-yl)(phenyl)methyl]-3-phenylpropanamide | | 23 |
| N-[1,3-benzodioxol-5-yl(5-chloro-8-hydroxyquinolin-7-yl)methyl]-2-phenoxyacetamide | 1565 | |
| N-[(5-chloro-8-hydroxyquinolin-7-yl)(3,4-dimethoxyphenyl)methyl]-2-phenoxyacetamide | 5189 | |
| benzyl [1,3-benzodioxol-5-yl(5-chloro-8-hydroxyquinolin-7-yl)methyl]carbamate | 1562 | |
| N-[(6-chloro-1,3-benzodioxol-5-yl)(5-chloro-8-hydroxyquinolin-7-yl)methyl]-2-phenoxyacetamide | 1367 | |
| N-[(5-chloro-8-hydroxyquinolin-7-yl)(3-nitrophenyl)methyl]-2-phenoxyacetamide | 1226 | |
| N-[(5-chloro-8-hydroxyquinolin-7-yl)(4-nitrophenyl)methyl]-2-phenoxyacetamide | 1222 | |
| N-[(5-chloro-8-hydroxyquinolin-7-yl)(3-methyl-2-thienyl)methyl]-2-phenoxyacetamide | 1367 | |
| N-[3-aminophenyl(5-chloro-8-hydroxyquinolin-7-yl)methyl]-2-phenoxyacetamide | 4588 | |
| N-[3-aminophenyl(5-chloro-8-hydroxyquinolin-7-yl)methyl]-2-phenoxyacetamide | 4361 | |
| N-[(5-chloro-8-hydroxyquinolin-7-yl)(1-methyl-1-H-1,2,3-benzotriazol-5-yl)methyl]-2-phenoxyacetamide | 1300 | |
| N-2--benzyl-N-[(5-chloro-8-hydroxyquinolin-7-yl)(phenyl)methyl]glycinamide | 3749 | |
| 5-chloro-7-[[3-[(methylsulfonyl)amino]phenyl][(phenoxyacetyl)amino]methyl]quinolin-8-yl methanesulfonate | | 20 |
| N-[[3-acetylamino)phenyl](5-chloro-8-hydroxyquinolin-7-yl)methyl]-2-phenoxyacetamide | 3759 | |
| N-[(5-chloro-8-hydroxyquinolin-7-yl)(phenyl)methyl]-N-2--(1-naphthylmethyl)glycinamide | 1564 | |
| N-[(5-chloro-8-hydroxyquinolin-7-yl)(phenyl)methyl]-2-(4-phenylpiperidin-1-yl)acetamide | | 57 |
| N-2--(1,3-benzodioxol-5-ylmethyl)-N-(5-chloro-8-hydroxyquinolin-7-yl)(phenyl)methyl]glycinamide | 2746 | |
| N-(5-chloro-8-hydroxyquinolin-7-yl)(phenyl)methyl]-N-2--(pyridin-3-ylmethyl)glycinamide | | 32 |
| N-[(5-chloro-8-hydroxyquinolin-7-yl)(phenyl)methyl]-N-2--(pyridin-4-ylmethyl)glycinamide | | 29 |
| N-[(2Z)-1-(5-chloro-8-hydroxyquinolin-7-yl)-2-methoxy-3-phenylprop-2-en-1-yl]-2-phenoxyacetamide | | 50 |
| N-[(5-chloro-8-hydroxyquinolin-7-yl)(4-isopropylphenyl)methyl]-2-phenoxyacetamide | | 45 |
| N-[(5-chloro-8-hydroxyquinolin-7-yl)(2-chlorophenyl)methyl]-2-(4-pentylphenoxy)acetamide | | 50 |
| N-[(5-chloro-8-hydroxyquinolin-7-yl)(2-chlorophenyl)methyl]-2-(4-propylphenoxy)acetamide | | 47 |
| N-[(5-chloro-8-hydroxyquinolin-7-yl)(1-methyl-1H-indol-2-yl)methyl]-2-phenoxyacetamide | | 57 |
| N-[(5-chloro-8-hydroxyquinolin-7-yl)(1-methyl-1H-indol-3-yl)methyl]-2-phenoxyacetamide | | 53 |

-continued

| Compound | Agg-2 FRET Median IC50 (nm) | Agg-2 FRET Median PCT INHIB (%) |
|---|---|---|
| N-[(5-chloro-8-hydroxyquinolin-7-yl)(quinolin-4-yl)methyl]-2-phenoxyacetamide | | 45 |
| N-[(5-chloro-8-hydroxyquinolin-7-yl)(quinolin-5-yl)methyl]-2-phenoxyacetamide | 3518 | |
| N-[(5-chloro-8-hydroxyquinolin-7-yl)(2-methoxyphenyl)methyl]-2-phenoxyacetamide | 2339 | |
| N-[(5-chloro-8-hydroxyquinolin-7-yl)(3-methoxyphenyl)methyl]-2-phenoxyacetamide | 1844 | |
| N-[(5-chloro-8-hydroxyquinolin-7-yl)(2-fluorophenyl)methyl]-2-phenoxyacetamide | 2201 | |
| N-[(5-chloro-8-hydroxyquinolin-7-yl)(2-hydroxyphenyl)methyl]-2-phenoxyacetamide | | 62 |
| N-[(5-chloro-8-hydroxyquinolin-7-yl)(4-oxo-4H-chromen-3-yl)methyl]-2-phenoxyacetamide | | 72 |
| N-[(5-chloro-8-hydroxyquinolin-7-yl)[3-(4-chlorophenoxy)phenyl]methyl]-2-phenoxyacetamide | | 52 |
| N-[(5-chloro-8-hydroxyquinolin-7-yl)(4-pyridin-4-yl)phenyl)methyl]-2-phenoxyacetamide | | 48 |
| N-[(5-chloro-8-hydroxyquinolin-7-yl)(4H-pyrazolo[1,5-c][1,3]thiazol-2-yl)-methyl]-2-phenoxyacetamide | | 40 |
| N-[(5-chloro-8-hydroxyquinolin-7-yl)(2-morpholin-4-ylphenyl)methyl]-2-phenoxyacetamide | | 43 |
| N-[(2E)-1-(5-chloro-8-hydroxyquinolin-7-yl)hex-2-en-1-yl]-2-phenoxyacetamide | | 47 |
| N-[(5-chloro-8-hydroxyquinolin-7-yl)(cyclohex-1-en-1-yl)methyl]-2-phenoxyacetamide | | 42 |
| N-[(5-chloro-8-hydroxyquinolin-7-yl)(1H-indol-7-yl)methyl]-2-phenoxyacetamide | | 69 |
| N-[(5-chloro-8-hydroxyquinolin-7-yl)(1H-indol-4-yl)methyl]-2-phenoxyacetamide | 2076 | |
| N-[(5-chloro-8-hydroxyquinolin-7-yl)[4-(phenylethynyl)phenyl]methyl]-2-phenoxyacetamide | | 50 |
| ethyl (3-[(5-chloro-8-hydroxyquinolin-7-yl)[(phenoxyacetyl)amino]methyl]phenyl)acetate | 1446 | |
| N-[(5-chloro-8-hydroxyquinolin-7-yl)(2-nitrophenyl)methyl]-2-phenoxyacetamide | | 58 |
| N-[(2E)-1-(5-chloro-8-hydroxyquinolin-7-yl)but-2-en-1-yl]-2-phenoxyacetamide | 2528 | |
| N-[1-(5-chloro-8-hydroxyquinolin-7-yl)prop-2-en-1-y1]-2-phenoxyacetmide | | 38 |
| (3-[(5-chloro-8-hydroxyquinolin-7-yl)[(phenoxyacetyl)amino]methyl]phenyl)acetic acid | 4480 | |
| N-[(5-chloro-8-hydroxyquinolin-7-yl)(9-phenanthryl)methyl]-2-phenoxyacetamide | | 51 |
| N-[(5-chloro-8-hydroxyquinolin-7-yl)(phenyl)methyl]-2-phenylacetamide | 2526 | |
| N-[(5-chloro-8-hydroxyquinolin-7-yl)(2-chlorophenyl)methyl]-2-phenylacetamide | 1542 | |
| N-[(5-chloro-8-hydroxyquinolin-7-yl)(4-fluorophenyl)methyl]-2-phenylacetamide | 2142 | |
| N-[[3-(benzyloxy)-4-methoxyphenyl](5-chloro-8-hydroxyquinolin-7-yl)methyl]-2-phenylacetamide | | 47 |
| N-[(2E)-1-(5-chloro-8-hydroxyquinolin-7-yl)-3-phenylprop-2-en-1-yl]-2-phenylacetamide | 50000 | |
| N-[(5-chloro-8-hydroxyquinolin-7-yl)(3-methyl-2-thienyl)methyl]-2-phenylacetamide | 2539 | |
| N-[(5-chloro-8-hydroxyquinolin-7-yl)[4-(1,2,3-thiadiazol-4-yl)phenyl]methyl]-2-phenoxyacetamide | 1072 | |
| N-[(R)-(5-chloro-8-hydroxyquinolin-7-yl)(2-chlorophenyl)methyl]-2-phenoxyacetamide | 970 | |
| N-[(S)-(5-chloro-8-hydroxyquinolin-7-yl)(2-chlorophenyl)methyl]-2-phenoxyacetamide | 876 | |
| N-[(5-bromo-8-hydroxyquinolin-7-yl)(phenyl)methyl]-2-phenoxyacetamide | 2479 | |
| N-[[8-hydroxy-5-(1H-pyrrol-1-yl)quinolin-7-yl](phenyl)methyl]-2-phenoxyacetamide | 1643 | |
| N-[[5-(dimethylamino)-8-hydroxyquinolin-7-yl](phenyl)methyl]-2-phenoxyacetamide | | 58 |
| N-[(5-amino-8-hydroxyquinolin-7-yl)(phenyl)methyl]-2-phenoxyacetamide | | 50 |
| N-[(8-hydroxy-5-pyrrolidin-1-ylquinolin-7-yl)(phenyl)methyl]-2-phenoxyacetamide | 10467 | |
| N-[(5-chloro-8-hydroxyquinolin-7-yl)(phenyl)methyl]-2-phenoxyacetmide | 780 | |
| N-[(5-chloro-8-hdroxyquinolin-7-yl)(4-nitrophenyl)methyl]-2-phenoxyacetamide | 457 | |

| Compound | Agg-2 FRET Median IC50 (nm) | Agg-2 FRET Median PCT INHIB (%) |
|---|---|---|
| N-[(5-chloro-8-hydroxyquinolin-7-yl)(2-furyl)methyl]-2-phenoxyacetamide | 3900 | |
| N-[(5-chloro-8-hydroxyquinolin-7-yl)(3,4-dimethoxyphenyl)methyl]-2-phenoxyacetamide | 1062 | |

| Compound | Agg-2 FRET Median IC50 (nM) | Agg-2 FRET Median PCT INHIB (%) |
|---|---|---|
| N-[(8-hydroxyquinolin-7-yl)(phenyl)methyl]-2-phenoxyacetamide | 2475 | |
| N-[(8-hydroxyquinolin-7-yl)(4-methylphenyl)methyl]-2-phenoxyacetamide | 3012 | |
| N-[(8-hydroxyquinolin-7-yl)(4-methoxyphenyl)methyl]-2-phenoxyacetamide | 4414 | |
| N-[(2-chlorophenyl)(8-hydroxyquinolin-7-yl)methyl]-2-phenoxyacetamide | 2496 | |
| N-[(4-chlorophenyl)(8-hydroxyquinolin-7-yl)methyl]-2-phenoxyacetamide | 3380 | |
| N-[(5-chloro-8-hydroxyquinolin-7-yl)(phenyl)methyl]-2-phenoxyacetamide | 1218 | |
| N-[(5-chloro-8-hydroxyquinolin-7-yl)(4-methylphenyl)methyl]-2-phenoxyacetamide | 759 | |
| N-[(5-chloro-8-hydroxyquinolin-7-yl)(4-methoxyphenyl)methyl]-2-phenoxyacetamide | 1117 | |
| N-[(5-chloro-8-hydroxyquinolin-7-yl)(2-chlorophenyl)methyl]-2-phenoxyacetamide | 350 | |
| N-[(5-chloro-8-hydroxyquinolin-7-yl)(4-chlorophenyl)methyl]-2-phenoxyacetamide | 829 | |
| N-[(5-chloro-8-hydroxyquinolin-7-yl)(3-nitrophenyl)methyl]-2-phenoxyacetamide | 488 | |
| N-[(5-chloro-8-hydroxyquinolin-7-yl)(4-nitrophenyl)methyl]-2-phenoxyacetamide | 953 | |
| N-[(8-hydroxyquinolin-7-yl)(4-methoxyphenyl)methyl]-2-(4-methylphenoxy)acetamide | 2830 | |
| N-[(8-hydroxyquinolin-7-yl)(phenyl)methyl]-2-(4-methoxyphenoxy)acetamide | 3342 | |
| N-[(8-hydroxyquinolin-7-yl)(methoxyphenyl)methyl]-2-(4-phenoxyphenoxy)acetamide | 3221 | |
| N-[(8-hydroxyquinolin-7-yl)(phenyl)methyl]-2-(4-methylphenoxy)acetamide | 2469 | |
| N-[(8-hydroxyquinolin-7-yl)(4-methoxyphenyl)methyl]-2-(4-methoxyphenoxy)acetamide | 4511 | |
| N-[(8-hydroxyquinolin-7-yl)(phenyl)methyl]-2-(4-phenoxyphenoxy)acetamide | 908 | |
| N-[(5-chloro-8-hydroxyquinolin-7-yl)(methoxyphenyl)methyl]-2-(4-methylphenoxy)acetamide | 774 | |
| N-[(5-chloro-8-hydroxyquinolin-7-yl)(phenyl)methyl]-2-(4-methoxyphenoxy)acetamide | 1379 | |
| N-[(5-chloro-8-hydroxyquinolin-7-yl)(4-methoxyphenyl)methyl]-2-(4-phenoxyphenoxy)acetamide | | 50 |
| N-[(5-chloro-8-hydroxyquinolin-7-yl)(phenyl)methyl]-2-(4-methylphenoxy)acetamide | 1898 | |
| N-[(5-chloro-8-hydroxyquinolin-7-yl)(4-methoxyphenyl)methyl]-2-(4-methoxyphenoxy)acetamide | 938 | |
| N-[(5-chloro-8-hydroxyquinolin-7-yl)(phenyl)methyl]-2-(4-phenoxyphenoxy)acetamide | | 50 |
| N-[(8-hydroxyquinolin-7-yl)(4-nitrophenyl)methyl]-2-phenoxyacetamide | 2395 | |
| N-[(5-chloro-8-hydroxyquinolin-7-yl)(pyridin-3-yl)ylmethyl]-2-phenoxyacetamide | 1920 | |
| N-[(5-chloro-8-hydroxyquinolin-7-yl)(2-thienyl)methyl]-2-phenoxyacetamide | 1220 | |
| N-[(5-chloro-8-hydroxyquinolin-7-yl)(3,5-dimethoxyphenyl)methyl]-2-phenoxyacetamide | 1093 | |
| N-[(5-chloro-8-hydroxyquinolin-7-yl)(3,4-dichlorophenyl)methyl]-2-phenoxyacetamide | 1360 | |
| N-[(3-fluorophenyl)(8-hydroxyquinolin-7-yl)methyl]-2-phenoxyacetamide | 2765 | |
| N-[[4-dimethylamino)phenyl](8-hydroxyquinolin-7-yl)methyl]-2-phenoxyacetamide | 5541 | |

| | | |
|---|---|---|
| N-[(5-chloro-8-hydroxyquinolin-7-yl)(4-hydroxy-3-methoxyphenyl)methyl]-2-phenoxyacetamide | 7302 | |
| N-[(5-chloro-8-hydroxyquinolin-7-yl)(3-fluorophenyl)methyl]-2-phenoxyacetamide | 624 | |
| N-[(3-chloro-4-fluorophenyl)(5-chloro-8-hydroxyquinolin-7-yl)methyl]-2-phenoxyacetamide | 1039 | |
| N-[(5-chloro-8-hydroxyquinolin-7-yl)(phenyl)methyl]-2-(4-chlorophenoxy)acetamide | 1020 | |
| N-[(5-chloro-8-hydroxyquinolin-7-yl)(4-methoxyphenyl)methyl]-2-(pyridin-3-yloxy)acetamide | 2980 | |
| N-[(5-chloro-8-hydroxyquinolin-7-yl)(4-methoxyphenyl)methyl]-2-(3-(dimethylamino)phenoxy]acetamide | 1673 | |
| N-[(5-chloro-8-hydroxyquinolin-7-yl)(4-methoxyphenyl)methyl]-2-(4-chloro-3-methylphenoxy)acetamide | | 57 |
| 2-[4-(acetylamino)phenoxy]-N-[(5-chloro-8-hydroxyquinolin-7-yl)(4-methoxyphenyl)methyl]acetamide | 3394 | |
| N-[(5-chloro-8-hydroxyquinolin-7-yl)(2-chlorophenyl)methyl]-2-[3-(dimethylamino)phenoxy]acetamide | 1725 | |
| N-[(5-chloro-8-hydroxyquinolin-7-yl)(2-chlorophenyl)methyl]-2-[4-chloro 3-methylphenoxy]acetamide | | 54 |
| 2-(4-tert-butylphenoxy)-N-[(5-chloro-8-hydroxyquinolin-7-yl)(2-chlorophenyl)methyl]acetamide | | 47 |
| 2-[4-(acetylamino)phenoxy]-N-[(5-chloro-8-hydroxyquinolin-7-yl)(2-chlorophenyl)methyl]acetamide | 2397 | |
| N-[(5-chloro-8-hydroxyquinolin-7-yl)(2-methylphenyl]-2-phenoxyacetamide | 1852 | |
| N-[(5-chloro-8-hydroxyquinolin-7-yl)(3-nitrophenyl)methyl]-2-(pyridin-3-yloxy)acetamide | 1658 | |
| 2-(4-acetylphenoxy)-N-[(5-chloro-8-hydroxyquinolin-7-yl)(3-nitrophenyl)methyl]acetamide | 2333 | |
| N-[(5-chloro-8-hydroxyquinolin-7-yl)(3-nitrophenyl)methyl]-2-(4-chloro-3-methylphenoxy)acetamide | | 53 |
| N-[(5-chloro-8-hydroxyquinolin-7-yl)(3-nitrophenyl)methyl]-2-(3,5-dichlorophenoxy)acetamide | | 51 |
| N-[(5-chloro-8-hydroxyquinolin-7-yl)(3-fluorophenyl)methyl]-2-(pyridin-3-yloxy)acetamide | | 58 |
| N-[(5-chloro-8-hydroxyquinolin-7-yl)(3-fluorophenyl)methyl]-2-[(3-(dimethylamino)phenoxy]acetamide | 1334 | |
| 2-(4-tert-butylphenoxy)-N-[(5-chloro-8-hydroxyquinolin-7-yl)(3-fluorophenyl)methyl]acetamide | | 43 |
| 2-[4-(acetylamino)phenoxy]-N-[(5-chloro-8-hydroxyquinolin-7-yl)(3-fluorophenyl)methyl]acetamide | 3372 | |
| N-[(2-chlorophenyl)(8-hydroxy-5-nitroquinolin-7-yl)methyl]-2-phenoxyacetamide | 938 | |
| N-[(8-hydroxy-5-nitroquinolin-7-yl)(2-methylphenyl)methyl]-2-phenoxyacetamide | 854 | |
| N-[(8-hydroxy-5-nitroquinolin-7-yl)(phenyl)methyl]-2-phenoxyacetamide | 1351 | |
| N-[(5-fluoro-8-hydroxyquinolin-7-yl)(phenyl)methyl]-2-phenoxyacetamide | 4840 | |
| N-1--[(5-chloro-8-hydroxyquinolin-7-yl)(2-chlorophenyl)methyl]-N-2--pyridin-3-ylglycinamide | 16861 | |
| N-1--[(5-chloro-8-hydroxyquinolin-7-yl)(2-chlorophenyl)methyl]-N-2--(4-chloro-3-methylphenyl)glycinamide | 1483 | |
| N-2--(4-tert-butylphenyl)-N-1--[(5-chloro-8-hydroxyquinolin-7-yl)(2-chlorophenyl)methyl]glycinamide | | 54 |
| N-1--[(5-chloro-8-hydroxyquinolin-7-yl)(4-methylphenyl)methyl]-N-2--pyridin-3-ylglycinamide | 9786 | |
| N-1--[(5-chloro-8-hydroxyquinolin-7-yl)(4-methylphenyl)methyl]-N-2--(4-cyanophenyl)glycinamide | 1011 | |
| N-2--(4-acetylphenyl)-N-1--[(5-chloro-8-hydroxyquinolin-7-yl)(4-methylphenyl)methyl]glycinamide | 1118 | |
| N-1--[(5-chloro-8-hydroxyquinolin-7-yl)(4-methylphenyl)methyl]-N-2--[3-(dimethylamino)phenyl]glycinamide | 1926 | |
| N-1--[(5-chloro-8-hydroxyquinolin-7-yl)(4-methylphenyl)methyl]-N-2--(4-chloro-3-methylphenyl)glycinamide | 1575 | |
| N-2--(4-tert-butylphenyl)-N-1--[(5-chloro-8-hydroxyquinolin-7-yl)(4-methylphenyl)methyl]glycinamide | | 57 |
| N-1--[(5-chloro-8-hydroxyquinolin-7-yl)(3-nitrophenyl)methyl]-N-2--pyridin-3-ylglycinamide | 1559 | |
| N-2--(4-acetylphenyl)-N-1--[(5-chloro-8-hydroxyquinolin-7-yl)(3-nitrophenyl)methyl]glycinamide | 1068 | |
| N-1--[(5-chloro-8-hydroxyquinolin-7-yl)(3-nitrophenyl)methyl]-N-2--(4-chloro-3-methylphenyl)glycinamide | 1194 | |

| | | |
|---|---|---|
| -continued | | |
| N-2--(4-acetylamino)-N-1--[(5-chloro-8-hydroxyquinolin-7-yl)(3-nitrophenyl)methyl]glycinamide | 2766 | |
| N-1--[(5-chloro-8-hydroxyquinolin-7-yl)(3-fluorophenyl)methyl]-N-2--pyridin-3-ylglycinamide | 15112 | |
| N-1--[(5-chloro-8-hydroxyquinolin-7-yl)(3-fluorophenyl)methyl]-N-2--(4-chloro-3-methylphenyl)gylcinamide | 1432 | |
| N-[(5-chloro-8-hydroxyquinolin-7-yl)(2-fluorophenyl)methyl]-2-phenoxyacetamide | 1215 | |
| N-[(5-chloro-8-hydroxyquinolin-7-yl)(2-cyanophenyl)methyl]-2-phenoxyacetamide | 2322 | |
| N-[(5-chloro-8-hydroxyquinolin-7-yl)(2,4-dimethylphenyl)methyl]-2-phenoxyacetamide | | 60 |
| N1-[(5-chloro-8-hydroxyquinolin-7-yl)(2,5-dimethylphenyl)methyl]-2-phenoxyacetamide | 1493 | |
| N-[(5-chloro-8-hydroxyquinolin-7-yl)(2-nitrophenyl)methyl]-2-phenoxyacetamide | 1207 | |
| N-[(2-chloro-4-hydroxyphenyl)(5-chloro-8-hydroxyquinolin-7-yl)methyl]-2-phenoxyacetamide | 1937 | |
| N-[(2-chloro-4-fluorophenyl)(5-chloro-8-hydroxyquinolin-7-yl)methyl]-2-phenoxyacetamide | 1086 | |
| N-[(5-chloro-8-hydroxyquinolin-7-yl)[2-(trifluoromethyl)phenyl]methyl)-2-phenoxyacetamide | 831 | |
| N-[(5-chloro-8-hydroxyquinolin-7-yl)(2,4-dichlorophenyl)methyl]-2-phenoxyacetamide | | 57 |
| N-[(5-chloro-8-hydroxyquinolin-7-yl)(2-chloro-5-nitrophenyl)methyl]-2-phenoxyacetamide | 523 | |
| N-[(5-chloro-8-hydroxyquinolin-7-yl)(2-methylphenyl)methyl]-4-phenylbutanamide | | 49 |
| N-[(5-chloro-8-hydroxyquinolin-7-yl)(2-chlorophenyl)methyl]-4-phenylbutanamide | | 48 |
| N-[(5-chloro-8-hydroxyquinolin-7-yl)(4-methylphenyl)methyl]-4-phenylbutanamide | | 41 |
| N-[(5-chloro-8-hydroxyquinolin-7-yl)(3-nitrophenyl)methyl]-4-phenylbutanamide | 1150 | |
| N-[(2-chlorophenyl)(8-hydroxy-5-methylquinolin-7-yl)methyl]-2-phenoxyacetamide | 2417 | |
| N-[(8-hydroxy-5-methylquinolin-7-yl(3-nitrophenyl)methyl]-2-phenoxyacetamide | 1322 | |
| N-[(8-hydroxy-5-methylquinolin-7-yl)(2-methylphenyl)methyl]-2-phenoxyacetamide | 3514 | |
| N-[(5-bromo-8-hydroxyquinolin-7-yl)(2-chlorophenyl)methyl]-2-phenoxyacetamide | 794 | |
| N-[(5-bromo-8-hydroxyquinolin-7-yl)(3-nitrophenyl)methyl]-2-phenoxyacetamide | 622 | |
| N-[(5-bromo-8-hydroxyquinolin-7-yl)(2-methylphenyl)methyl]-2-phenoxyacetamide | 1001 | |
| N-1--[(5-chloro-8-hydroxyquinolin-7-yl)(2-chlorophenyl)methyl]-N-2--methyl-N-2--phenylglycinamide | 996 | |
| N-2--benzyl-N-1--[(5-chloro-8-hydroxyquinolin-7-yl)(2-chlorophenyl)methyl]-N-2--methylglycinamide | 1308 | |
| N-2--benzyl-N-1--[(5-chloro-8-hydroxyquinolin-7-yl)(2-chlorophenyl)methyl]glycinamide | 1885 | |
| N-1--[(5-chloro-8-hydroxyquinolin-7-yl)(3-fluorophenyl)methyl]-N-2--methyl-N-2--phenylglycinamide | 1250 | |
| N-2--benzyl-N-1--[(5-chloro-8-hydroxyquinolin-7-yl)(3-fluorophenyl)methyl]-N-2--methylglycinamide | 1440 | |
| N-2--benzyl-N-1--[(5-chloro-8-hydroxyquinolin-7-yl)(3-fluorophenyl)methyl]glycinamide | 1701 | |
| 2-(benzyloxy)-N-[(5-chloro-8-hydroxyquinolin-7-yl)(3-fluorophenyl)methyl]acetamide | 828 | |
| N-1--[(5-chloro-8-hydroxyquinolin-7-yl)(4-methylphenyl)methyl]-N-2--methyl-N-2--phenylglycinamide | 776 | |
| N-2--benzyl-N-1--[(5-chloro-8-hydroxyquinolin-7-yl)(4-methylphenyl)methyl]-N-2--methylglycinamide | 1276 | |
| N-2--benzyl-N-1--[(5-chloro-8-hydroxyquinolin-7-yl)(4-methylphenyl)methyl]glycinamide | 1832 | |
| 2-(benzyloxy)-N-[(5-chloro-8-hydroxyquinolin-7-yl)(4-methylphenyl)methyl]acetamide | 695 | |
| N-1--[(5-chloro-8-hydroxyquinolin-7-yl)(3-nitrophenyl)methyl]-N-2--methyl-N-2--phenylglycinamide | 559 | |
| N-2--benzyl-N-1--[(5-chloro-8-hydroxyquinolin-7-yl)(3-nitrophenyl)methyl]-N-2--methylglycinamide | 819 | |
| N-2--benzyl-N-1--[(5-chloro-8-hydroxyquinolin-7-yl)(3-nitrophenyl)methyl]glycinamide | 765 | |
| N-[(5-chloro-8-methoxyquinolin-7-yl)(phenyl)methyl]-2-phenoxyacetamide | | 50 |
| N-[(5-chloro-8-methoxyquinolin-7-yl)(2-chlorophenyl)methyl]-2-phenoxyacetamide | | 32 |

-continued

| Compound | | |
|---|---|---|
| N-[(S)-(5-chloro-8-hydroxyquinolin-7-yl)(2-chlorophenyl)methyl]-2-phenoxyacetamide | 1345 | |
| N-[(R)-(5-chloro-8-hydroxyquinolin-7-yl)(2-chlorophenyl)methyl]-2-phenoxyacetamide | 1224 | |
| N-[(8-hydroxyquinolin-7-yl)(phenyl)methyl]benzamide | 4696 | |
| N-[(8-hydroxyquinolin-7-yl)(phenyl)methyl]acetamide | | 50 |
| N-[(5-chloro-8-hydroxyquinolin-7-yl)(phenyl)methyl]benzamide | 1312 | |
| N-[(5-chloro-8-hydroxyquinolin-7-yl)(phenyl)methyl]acetamide | 19718 | |
| N-[(5-chloro-8-hydroxyquinolin-7-yl)(phenyl)methyl]-2-phenoxyacetamide | 2000 | |
| N-[(5-chloro-8-hydroxyquinolin-7-yl)(2-chlorophenyl)methyl]-2-phenoxyacetamide | 1550 | |
| N-[(5-chloro-8-hydroxyquinolin-7-yl)(3-nitrophenyl)methyl]-2-phenoxyacetamide | 1226 | |
| N-[(5-chloro-8-hydroxyquinolin-7-yl)(4-nitrophenyl)methyl]-2-phenoxyacetamide | 1222 | |
| N-[(5-chloro-8-hydroxyquinolin-7-yl)(2-fluorophenyl)methyl]-2-phenoxyacetamide | 2201 | |
| N-[(5-chloro-8-hydroxyquinolin-7-yl)(2-nitrophenyl)methyl]-2-phenoxyacetamide | | 58 |
| N-[(R)-(5-chloro-8-hydroxyquinolin-7-yl)(2-chlorophenyl)methyl]-2-phenoxyacetamide | 970 | |
| N-[(S)-(5-chloro-8-hydroxyquinolin-7-yl)(2-chlorophenyl)methyl]-2-phenoxyacetamide | 876 | |
| N-[(8-hydroxyquinolin-7-yl)(phenyl)methyl]benzamide | 5470 | |
| N-[(5-chloro-8-hydroxyquinolin-7-yl)(phenyl)methyl]-2-phenoxyacetamide | 780 | |
| N-[(5-chloro-8-hydroxyquinolin-7-yl)(4-nitrophenyl)methyl]-2-phenoxyacetamide | 457 | |
| N-[(5-chloro-8-hydroxyquinolin-7-yl)(4-methoxyphenyl)methyl]-2-phenoxyacetamide | 1000 | |

| Compound | Agg1 IC50 (nM) | Agg2 IC50 (nM) |
|---|---|---|
| N-[(5-chloro-8-hydroxyquinolin-7-yl)(phenyl)methyl]-2-phenoxyacetamide | >22000 | 2000 |
| N-[(5-chloro-8-hydroxyquinolin-7-yl)(2-chlorophenyl)methyl]-2-phenoxyacetamide | >22000 | 1550 |
| N-[(5-chloro-8-hydroxyquinolin-7-yl)(2-methoxyphenyl)methyl]-2-Phenoxyacetamide | 48% @ 667000 | 2300 |
| N-[(5-chloro-8-hydroxyquinolin-7-yl)(2-fluorophenyl)methyl]-2-phenoxyacetamide | 46% @ 22200 | 2201 |
| N-[(5-chloro-8-hydroxyquinolin-7-yl)(2-morpholin-4-ylphenyl)methyl]-2-phenoxyacetamide | 59% @ 22000 | 43% @ 1200 |
| N-[(5-chloro-8-hydroxyquinolin-7-yl)(2-hydroxyphenyl)methyl]-2-phenoxyacetamide | 11000 +/− 3000 | 62% @ 2500 |
| N-[(5-chloro-8-hydroxyquinolin-7-yl)(2-nitrophenyl)methyl]-2-phenoxyacetamide | 48% @ 7400 | 58% @ 1200 |
| 2-[[(5-chloro-8-hydroxyquinolin-7-yl)[(phenoxyacetyl)amino]methyl]benzoic acid | | |
| N-[(5-chloro-8-hydroxyquinolin-7-yl)(3-methoxyphenyl)methyl]-2-phenoxyaceamide | 44% @ 22000 | 1800 |
| N-[(5-chloro-8-hydroxyquinolin-7-yl)(3-nitrophenyl)methyl]-2-phenoxyacetamide | 53% @ 22000 | 1226 |
| ethyl (3-[(5-chloro-8-hydroxyquinolin-7-yl)[(phenoxyacetyl)amino]methyl]phenyl)acetate | 41% @ 22000 | 50% @ 33000 |
| N-[(5-chloro-8-hydroxyquinolin-7-yl)[3-(4-methoxyphenoxy)phenyl]methyl)-2-phenoxyacetamide | 57% @ 7400 | 1100 |
| N-[(5-chloro-8-hydroxyquinolin-7-yl)[3-(4-chlorophenoxy)phenyl]methyl]-2-phenoxyacetamide | 51% @ 22000 | 52% @ 11000 |
| N-[(5-chloro-8-hydroxyquinolin-7-yl)[3-(4-methylphenoxy)phenyl]methyl]-2-phenoxyacetamide | 52% @ 22,000 | 58% @7400 |
| N-[(5-chloro-8-hydroxyquinolin-7-yl)(3-phenoxyphenyl)methyl]-2-Phenoxyacetamide | >67000 | 4100 |
| N-[[3-(benzyloxy)phenyl](5-chloro-8-hydroxyquinolin-7-yl)methyl]-2-phenoxyacetamide | 47% @ 22200 | 48% @ 3700 |
| N-[(5-chloro-8-hydroxyquinolin-7-yl)(4-fluorophenyl)methyl]-2-phenoxyacetamide | 48% @ 67000 | 1200 |
| N-[(5-chloro-8-hydroxyquinolin-7-yl)(4-nitrophenyl)methyl]-2-phenoxyacetamide | >20000 | 1223 |
| N-[(5-chloro-8-hydroxyquinolin-7-yl)[4-(dimethylamino)phenyl]methyl]-2-phenoxyacetamide | 54% @ 2500 | 1650 |
| N-[(5-chloro-8-hydroxyquinolin-7-yl)[4-(diethylamino)phenyl]methyl]-2-phenoxyacetamide | 22000-67000 | 2800 |
| N-[(5-chloro-8-hydroxyquinolin-7-yl)[4-(dibutylamino)phenyl]methyl]-2-phenoxyacetamide | 40% @ 66700 | 52% @ 33300 |

| | | |
|---|---|---|
| -continued | | |
| N-[(5-chloro-8-hydroxyquinolin-7-yl)(4-isopropylphenyl)methyl]-2-phenoxyacetamide | 47% @ 33000 | 45% @ 2500 |
| N-[[4-(allyloxy)phenyl](5-chloro-8-hydroxyquinolin-7-yl)methyl]-2-phenoxyacetamide | 52% @ 22000 | 20000 |
| N-[(4-butoxyphenyl)(5-chloro-8-hydroxyquinolin-7-yl)methyl]-2-phenoxyacetamide | 50% @ 67000 | 55% @ 2500 |
| N-[(5-chloro-8-hydroxyquinolin-7-yl)(4-hex-1-yn-1-ylphenyl)methyl]-2-phenoxyacetamide | 47% @ 50000 | 48% @ 33300 |
| N-[(5-chloro-8-hydroxyquinolin-7-yl)[4-(phenylethynyl)phenyl]methyl]-2-phenoxyacetamide | 48% @ 7400 | 58% @ 1200 |
| N-[[4-(benzyloxy)phenyl](5-chloro-8-hydroxyquinolin-7-yl)methyl]-2-phenoxyacetamide | >67000 | 4400 |
| N-[biphenyl-4-yl(5-chloro-8-hydroxyquinolin-7-yl)methyl]-2-phenoxyacetamide | >200,000 | 5400 |
| N-[(5-chloro-8-hydroxyquinolin-7-yl)(4-pyridin-4-ylphenyl)methyl]-2-phenoxyacetamide | 4700 +/− 500 | 48% @ 800 |
| N-[(5-chloro-8-hydroxyquinolin-7-yl)(4-1H-pyrazol-1-yl]phenyl]methyl]-2-phenoxyacetamide | 5800 | 1200 |
| N-[[4-(4-tert-butyl-1,3-thiazol-2-yl)phenyl](5-chloro-8hydroxyquinolin-7-yl)methyl]-2-phenoxyacetamide | 42% @ 66700 | 49% @ 11000 |
| N-[(5-chloro-8-hydroxyquinolin-7-yl)[4-(1,2,3-thiadiazol-4-yl)phenyl]methyl]-2-phenoxyacetamide | 4680 | 1072 |
| N-[(5-chloro-8-hydroxyquinolin-7-yl)(3,4-dimethylphenyl)methyl]-2-phenoxyacetamide | 66000-200000 | 1500 |
| N-[(5-chloro-8-hydroxyquinolin-7-yl)(3,4-dimethoxyphenyl)methyl]-2-phenoxyacetamide | >1500 | 5289 |
| N-[[3-(benzyloxy)-4-methoxyphenyl](5-chloro-8-hydroxyquinolin-7-yl)methyl]-2-phenoxyacetamide | 54% @7500 | 1040 |
| N-[(5-chloro-8-hydroxyquinolin-7-yl)(2-furyl)methyl]-2-phenoxyacetamide | 51% @ 67000 | 2426 |
| N-[(5-chloro-8-hydroxyquinolin-7-yl)(5-methyl-2-furyl)methyl]-2-phenoxyacetamide | >22000 | 2324 |
| N-[(5-chloro-8-hydroxyquinolin-7-yl)(3-furyl)methyl]-2-phenoxyacetamide | >22000 | 3459 |
| N-[(5-chloro-8-hydroxyquinolin-7-yl)(5-phenyl-2-furyl)methyl]-2-phenoxyacetamide | >22000 | >5000 |
| N-[(5-chloro-8-hydroxyquinolin-7-yl)(3-methyl-2-thienyl)methyl]-2-phenoxyacetamide | 33% @33000 | 1367 |
| N-[(5-chloro-8-hydroxyquinolin-7-yl)(1H-indol-7-yl)methyl]-2-phenoxyacetamide | 48% @ 7400 | 69% @ 1900 |
| N-[(5-chloro-8-hydroxyquinolin-7-yl)(1H-indol-4-yl)methyl]-2-phenoxyacetamide | 41% @ 800 | 2100 |
| N-[(5-chloro-8-hydroxyquinolin-7-yl)(1-methyl-1H-indol-3-yl)methyl]-2-phenoxyacetamide | 46% @ 11000 | 53% @ 2500 |
| N-[1,3-benzodioxol-4-yl(5-chloro-8-hydroxyquinolin-7-yl)methyl]-2-phenoxyacetamide | 54% @ 7400 | 1400 |
| N-[(5-chloro-8-hydroxyquinolin-7-yl)(quinolin-8-yl)methyl]-2-phenoxyacetamide | 55% @ 22000 | 2200 |
| N-[(5-chloro-8-hydroxyquinolin-7-yl)(quinolin-4-yl)methyl]-2-phenoxyacetamide | 34% @ 11000 | 45% @ 2800 |
| N-[(5-chloro-8-hydroxyquinolin-7-yl)(quinolin-5-yl)methyl]-2-phenoxyacetamide | 46% @ 22000 | 3500 |
| N-[(5-chloro-8-hydroxyquinolin-7-yl)(4-methoxy-1-naphthyl)methyl]-2-phenoxyacetamide | 62% @ 22000 | 800 |
| N-[(5-chloro-8-hydroxyquinolin-7-yl)(9-phenanthryl)methyl]-2-phenoxyacetamide | 54% @ 33000 | 51% @ 11000 |
| N-[(5-chloro-8-hydroxyquinolin-7-yl)(6-methoxy-2-naphthyl)methyl]-2-phenoxyacetarnide | 50% @ 22200 | 2300 |
| N-[(5-chloro-8-hydroxyquinolin-7-yl)(2,3-dihydro-1,4-benzodioxin-6-yl)methyl]-2-phenoxyacetamide | 51% @ 7400 | 850 |
| N-[(5-chloro-8-hydroxyquinolin-7-yl)(quinolin-3-yl)methyl]-2-phenoxyacetamide | 39% @ 16700 | 1300 |
| N-[1-benzofuran-2-yl)(5-chloro-8-hydroxyquinolin-7-yl)methyl]-2-phenoxyacetamide | 49% @ 66700 | 400-1200 |
| N-[(5-chloro-8-hydroxyquinolin-7-yl)(1-methyl-1H-indol-2-yl)methyl]-2-phenoxyacetamide | 48% @ 11000 | 57% @ 2500 |
| N-(5-chloro-8-hydroxyquinolin-7-yl)(2,3-dihydro-1-benzofuran-5-yl)methyl]-2-phenoxyacetamide | 43% @ 7400 | 2400 |
| N-[(5-chloro-8-hydroxyquinolin-7-yl)(2,2-dimethyl-3,4-dihydro-2H-chromen-6-yl)-2-phenoxyacetamide | 55% @ 66700 | 1400 |
| N-[(5-chloro-8-hydroxyquinolin-7-yl)(4-oxo-4H-chromen-3-yl)methyl]-2-phenoxyacetamide | ~11000 | 72% @ 2500 |
| N-[(5-chloro-8-hydroxyquinolin-7-yl)(6-methyl-4-oxo-4H-chromen-3-yl)methyl]-2-phenoxyacetamide | 43% 7400 | 1200 |
| N-[(5-chloro-8-hydroxyquinolin-7-yl)(4H-pyrazolo[1,5-c][1,3]thiazol-2-yl)-methyl]-2-phenoxyacetarnide | 42% @ 7000-22000 | 40% @ 1900 |
| N-[1,3-benzodioxol-5-yl(5-chloro-8-hydroxyquinolin-7-yl)methyl]-2-phenoxyacetamide | >22000 | 1565 |
| N-[(6-chloro-1,3-benzodioxol-5-yl)(5-chloro-8-hydroxyquinolin-7-yl)methyl]-2-phenoxyacetamide | >30,000 | 1367 |

-continued

| | | |
|---|---|---|
| N-[(5-chloro-8-hydroxyquinolin-7-yl)(1-methyl-1-H-1,2,3-benzotriazol-5-yl)methyl]-2-phenoxyacetamide | >20000 | 1300 |
| N-[(5-chloro-8-hydroxyquinolin-7-yl)(5,6-dihydro-8-H-imidazo[2,1-c][1,4]oxazin-2-yl)methyl]-2-phenoxyacetamide | >20000 | 6200 |
| N-[(5-chloro-8-hydroxyquinolin-7-yl)(5,6-dihydro-4-H-pyrrolo[1,2-b]pyrazol-2-yl)methyl]-2-phenoxyacetamide | >20000 | ~2500 |
| N-[(5-chloro-8-hydroxyquinolin-7-yl)(phenyl)methyl]-3-phenylpropanamide | qu | >5000 |
| benzyl [(5-chloro-8-hydroxyquinolin-7-yl)(phenyl)methyl]carbamate | >100,000 | >67,000 |
| benzyl [(5-chloro-8-hydroxyquinolin-7-yl)(2-chlorophenyl)methyl]carbamate | >67,000 | ~2500 |
| benzyl [(5-chloro-8-hydroxyquinolin-7-yl)(pyridin-2-yl)mehyl]carbamate | >67,000 | ~2500 |
| benzyl [(5-chloro-8-hydroxyquinolin-7-yl)(2-furyl)methyl]carbamate | >20,000 | >20,000 |
| benzyl [1,3-benzodioxol-5-yl(5-chloro-8-hydroxyquinolin-7-yl)methyl]carbamate | >3000 | 1562 |
| N-[1-(5-chloro-8-hydroxyquinolin-7-yl)prop-2-en-1-y1]-2-phenoxyacetmide | 50% @ 800 | 38% @ 3700 |
| N-[(2E)-1-(5-chloro-8-hydroxyquinolin-7-yl)but-2-en-1-yl]-2-phenoxyacetamide | 40% @ 800 | 2528 |
| N-[(2E)-1-(5-chloro-8-hydroxyquinolin-7-yl)hex-2-en-1-yl]-2-phenoxyacetamide | 30% @ 800 | 47% @ 2500 |
| N-[(5-chloro-8-hydroxyquinolin-7-yl)(cyclohex-1-en-1-yl)methyl]-2-phenoxyacetamide | 1000-8000 | 42% @ 1900 |
| N-[(2E)-1-(5-chloro-8-hydroxyquinolin-7-yl)-3-phenylprop-2-en-1-yl]-2-phenoxyacetamide | 50% @ 7500 | 1600 |
| N-[(2Z)-1-(5-chloro-8-hydroxyquinolin-7-yl)-2-methoxy-3-phenylprop-2-en-1-yl]-2-phenoxyacetamide | 47% @ 11000 | 50% @ 2500 |
| benzyl [1-(5-chloro-8-hydroxyquinolin-7-yl)-2-phenylethyl]carbamate | >67000 | >28,000 |
| N-[1-(5-chloro-8-hydroxyquinolin-7-yl)-3-phenylpropyl]-2-phenoxyacetamide | 56% @ 22000 | 1700 |
| N-[(5-chloro-8-hydroxyquinolin-7-yl)(phenyl)methyl]-2-phenylacetamide | 20% @ 1200 | 2526 |
| N-[(5-chloro-8-hydroxyquinolin-7-yl)(2-chlorophenyl)methyl]-2-phenylacetamide | 29% @ 1200 | 1542 |
| N-[(5-chloro-8-hydroxyquinolin-7-yl)(4-fluorophenyl)methyl]-2-phenylacetamide | 33% @ 3700 | 2142 |
| N-[[3-(benzyloxy)-4-methoxyphenyl](5-chloro-8-hydroxyquinolin-7-yl)methyl]-2-phenylacetamide | 36% @ 1200 | 47% @ 1200 |
| N-[(2E)-1-(5-chloro-8-hydroxyquinolin-7-yl)-3-phenylprop-2-en-1-yl]-2-phenylacetamide | 45% @ 20000 | 50000 |
| N-[(5-chloro-8-hydroxyquinolin-7-yl)(3-methyl-2-thienyl)methyl]-2-phenylacetamide | 52% @ 20000 | 2539 |
| N-[(8-hydroxy-5-nitroquinolin-7-yl)(phenyl)methyl]-2-phenoxyacetamide | 19300 | 50% @ 1200 |
| N-[(2-chlorophenyl)(8-hydroxy-5-nitroquinolin-7-yl)methyl]-2-phenoxyacetamide | 11400 | 50% @ 2500 |
| N-[(5-bromo-8-hydroxyquinolin-7-yl)(phenyl)methyl]-2-phenoxyacetamide | 64% @ 22200 | 2479 |
| N-[(5-bromo-8-hydroxyquinolin-7-yl)(phenyl)methyl]-2-chloroacetamide | 22000-67000 | 5400 |
| N-[(4-chloro-1-hydroxy-2-naphthyl(phenyl)methyl]-2-phenoxyacetamide | >22,000 | >67,000 |
| N-[3-aminophenyl(5-chloro-8-hydroxyquinolin-7-yl)methyl]-2-phenoxyacetamide | >2000 | 4588 |
| 5-chloro-7-[[3-[(methylsulfonyl)amino]phenyl][(phenoxyacetyl)amino]methyl]quinolin-8-yl methanesulfonate | >20000 | >30000 |
| N-[[3-acetylamino)phenyl](5-chloro-8-hydroxyquinolin-7-yl)methyl]-2-phenoxyacetamide | >20000 | 3759 |
| 2-chloro-N-(3-[(5-chloro-8-hydroxyquinolin-7-yl)[(phenoxyacetyl)amino]methyl]phenyl)acetamide | ~20000 | 1470 |
| N-(3-[(5-chloro-8-hydroxyquinolin-7-yl)[(phenoxyacetyl)amino]methyl]phenyl)-N-2-,N-2--dimethylglycinamide | 22000-67000 | 2900 |
| N-(3-[(5-chloro-8-hydroxyquinolin-7-yl)[(phenoxyacetyl)amino]methyl]phenyl)-N-2--methylglycinamide | 22000-67000 | 3500 |
| (3-[(5-chloro-8-hydroxyquinolin-7-yl)[(phenoxyacetyl)amino]methyl]phenyl)acetic acid | 37% @ 2500 | 4480 |
| 2-(4-bromophenoxy)-N-[(5-chloro-8-hydroxyquinolin-7-yl)(phenyl)methyl]acetamide | 44% @ 2500 | 18000 |
| N-[(5-chloro-8-hydroxyquinolin-7-yl)(phenyl)methyl]-2-(3,4,5-trimethoxyphenoxy)acetamide | 54% @ 7500 | 1800 |
| 2-(biphenyl-4-yloxy)-N-[(5-chloro-8-hydroxyquinolin-7-yl)(phenyl)methyl]acetamide | 7400-20000 | 2000 |

| -continued | | |
|---|---|---|
| N-[(5-chloro-8-hydroxyquinolin-7-yl)(phenyl)methyl]-2-(3,5-dimethoxyphenoxy)acetamide | 66-200 | 50% inh ~600-1800 |
| N-[(5-chloro-8-hydroxyquinolin-7-yl)(2-chlorophenyl)methyl]-2-(4-pentylphenoxy)acetamide | 44% @ 33000 | 50% @ 22000 nM |
| N-[(5-chloro-8-hydroxyquinolin-7-yl)(2-chlorophenyl)methyl]-2-(4-propylphenoxy)acetamide | 44% @ 1100 | 47% @ 2500 |
| N-[(5-chloro-8-hydroxyquinolin-7-yl)(2-chlorophenyl)methyl]-2-(4-isopropylphenoxy)acetamide | 56% @ 50000 | 1400 |
| N-[(5-chloro-8-hydroxyquinolin-7-yl)(2-chlorophenyl)methyl]-2-(4-cyclopentylphenoxy)acetamide | >20,000 | 2400 |
| N-[(5-chloro-8-hydroxyquinolin-7-yl)(2-chlorophenyl)methyl]-2-(3-ethylphenoxy)acetamide | 48% @ 10000 | 1280 |
| N-[(5-chloro-8-hydroxyquinolin-7-yl)(2-chlorophenyl)methyl]-2-(3,5-dimethoxyphenoxy)acetamide | ~22000 | 1000 |
| 2-(biphenyl-4-yloxy)-N-[(5-chloro-8-hydroxyquinolin-7-yl)(2-chlorophenyl)methyl]acetamide | 66000-200000 | 3300 |
| 2-(4-bromophenoxy)-N-[(5-chloro-8-hydroxyquinolin-7-yl)(2-chlorophenyl)methyl]acetamide | 22000-67000 | 2400 |
| 2-(1,3-benzodioxol-5-yloxy)-N-[(5-chloro-8-hydroxyquinolin-7-yl)(2-chlorophenyl)methyl]acetamide | 7400-20000 | 1000 |
| N-[(5-bromo-8-hydroxyquinolin-7-yl)(phenyl)methyl]-N-2--(1-naphthylmethyl)glycinamide | 7400-20000 | 1200-3700 |
| N-2-benzyl-N-[(5-chloro-8-hydroxyquinolin-7-yl)(phenyl)methyl]glycinamide | >20000 | 3749 |
| N-[(5-chloro-8-hydroxyquinolin-7-yl)(phenyl)methyl]-N-2--(1-naphthylmethyl)glycinamide | 17500 +/− 6600 | 1564 |
| N-[(5-chloro-8-hydroxyquinolin-7-yl)(phenyl)methyl]-2-(4-phenylpiperidin-1-yl)acetamide | ~11000 | ~3700 |
| N-2--(1,3-benzodioxol-5-ylmethyl)-N-(5-chloro-8-hydroxyquinolin-7-yl)(phenyl)methyl]glycinamide | >11000 | 2746 |
| N-(5-chloro-8-hydroxyquinolin-7-yl)(phenyl)methyl]-N-2--(pyridin-2-ylmethyl)glycinamide | >50000 | 3870 |
| N-(5-chloro-8-hydroxyquinolin-7-yl)(phenyl)methyl]-N-2--(pyridin-3-ylmethyl)glycinamide | >67000 | >11000 |
| N-(5-chloro-8-hydroxyquinolin-7-yl)(phenyl)methyl]-N-2--(pyridin-4-ylmethyl)glycinamide | >67000 | >11000 |
| N-2--(biphenyl-4-ylmethyl)-N-[(5-chloro-8-hydroxyquinolin-7-yl)(phenyl)methyl]glycinamide | >20000 | 1290 |
| N-[(5-chloro-8-hydroxyquinolin-7-yl)(2-chlorophenyl)methyl]-N--2(1-naphthylmethyl)glycinamide | ~20000 | 1370 |
| N-2--(1,3-benzodioxol-5-ylmethyl)-N-[(5-chloro-8-hydroxyquinolin-7-yl)(2chlorophenyl)methyl]glycinamide | 13700 +/− 2300 | 1800 |
| N-[(5-amino-8-hydroxyquinolin-7-yl)(phenyl)methyl]-2-phenoxyacetamide | 57% @ 22200 | 50% @ 22200 |
| N-[[5-(dimethylamino)-8-hydroxyquinolin-7-yl](phenyl)methyl]-2-phenoxyacetamide | ~25000 | 33300-100000 |
| N-[[8-hydroxy-5-(1H-pyrrol-1-yl)quinolin-7-yl](phenyl)methyl]-2-phenoxyacetamide | 54% @ 200000 | 1643 |
| N-[(8-hydroxy-5-pyrrolidin-1-ylquinolin-7-yl)(phenyl)methyl]-2-phenoxyacetamide | 49% @ 22200 | 10467 |
| N-[(R)-(5-chloro-8-hydroxyquinolin-7-yl)(2-chlorophenyl)methyl]-2-phenoxyacetamide | 49% @ 22200 | 970 |
| N-[(S)-(5-chloro-8-hydroxyquinolin-7-yl)(2-chlorophenyl)methyl]-2-phenoxyacetamide | 54% @ 22200 | 876 |

| Compound | Agg-1 IC50 (μM) or % Inhibition | Agg-2 IC50 (μM) or % Inhibition |
|---|---|---|
| 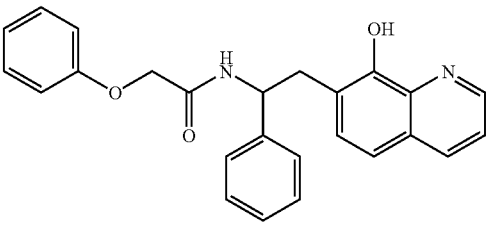<br>N-[2-(8-Hydroxyquinolin-7-yl)-1-phenylethyl]-2-phenoxyacetamide | 2.1 +/− 0.3 | 59% @ 100 uM |

-continued

| Compound | Agg-1 IC50 (μM) or % Inhibition | Agg-2 IC50 (μM) or % Inhibition |
| --- | --- | --- |
| N-[1-(1,3-Benzodioxol-5-yl)-2-(5-chloro-8-hydroxyquinolin-7-yl)ethyl]-2-phenoxyacetamide | 67% @ 22 μM | 9.6 +/− 3.7 |
| N-{2-(5-Chloro-8-hydroxyquinolin-7-yl)-1-[4-(morpholin-4-ylmethyl)phenyl]ethyl}biphenyl-4-carboxamide | 59% @ 22 μM | 50% @ 22 μM |
| N-{2-(5-Chloro-8-hydroxyquinolin-7-yl)-1-[3-(pyrrolidin-1-ylmethyl)phenyl]ethyl}biphenyl-4-carboxammide | 5.9 +/− 1.3 | 3.4 +/− 0.4 |

-continued

| Compound | Agg-1 IC50 (μM) or % Inhibition | Agg-2 IC50 (μM) or % Inhibition |
|---|---|---|
| 2-(Benzyloxy)-N-{2-(5-chloro-8-hydroxyquinolin-7-yl)-1-[3-(5-methyl-2-thienyl)phenyl]ethyl}acetamide | 48% @ 66.7 μM | 56% @ 22 μM |
| N-{2-(5-Chloro-8-hydroxyquinolin-7-yl)-1-[3-(5-methyl-2-thienyl)phenyl]ethyl}-2-(4-chlorophenoxy)-2-methylpropanamide | 47% @ 66.7 μM | 51% @ 22 μM |
| N-{2-(5-Chloro-8-hydroxyquinolin-7-yl)-1-[3-(5-methyl-2-thienyl)phenyl]ethyl}-2-phenoxyacetamide | 42% @ 66.7 μM | 58% @ 22 μM |

| Compound | Agg-1 IC50 (μM) or % Inhibition | Agg-2 IC50 (μM) or % Inhibition |
|---|---|---|
| 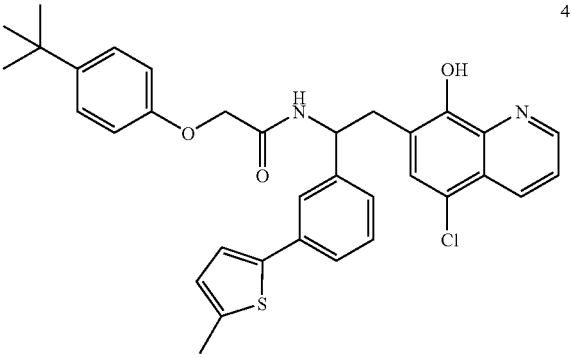<br>2-(4-tert-Butylphenoxy)-N-{2-(5-chloro-8-hydroxyquinolin-7-yl)-1-[3-(5-methyl-2-thienyl)phenyl]ethyl}acetamide | 46% @ 22 μM | 56% @ 200 μM |
| 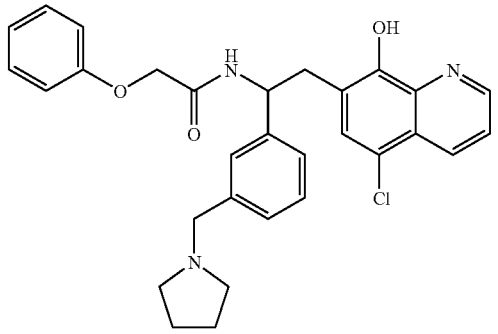<br>N-{2-(5-Chloro-8-hydroxyquinolin-7-yl)-1-[3-(pyrrolidin-1-ylmethyl)phenyl]ethyl}-2-phenoxyacetamide | 56% @ 200 μM | 20.0 +/− 3.4 |
| 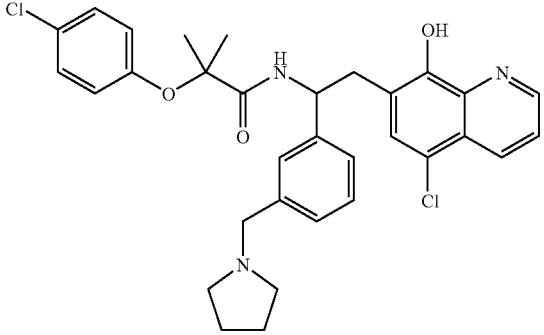<br>N-{2-(5-Chloro-8-hydroxyquinolin-7-yl)-1-[3-(pyrrolidin-1-ylmethyl)phenyl]ethyl}-2-(4-chlorophenoxy)-2-methylpropanamide | 50% @ 66.7 μM | 49% @ 22 μM |

| Compound | Agg-1 IC50 (μM) or % Inhibition | Agg-2 IC50 (μM) or % Inhibition |
|---|---|---|
| 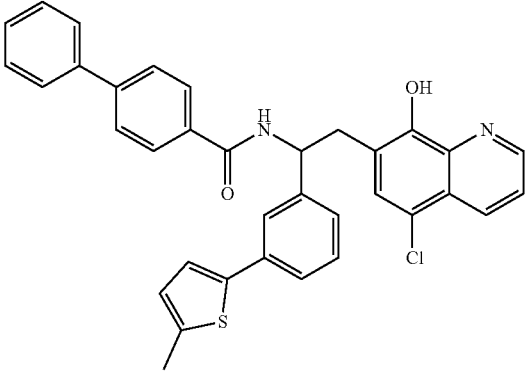<br>N-{2-(5-Chloro-8-hydroxyquinolin-7-yl)-1-[3-(5-methyl-2-thienyl)phenyl]ethyl}biphenyl-4-carboxamide | 54% @ 200 μM | 50% @ 50 μM |
| 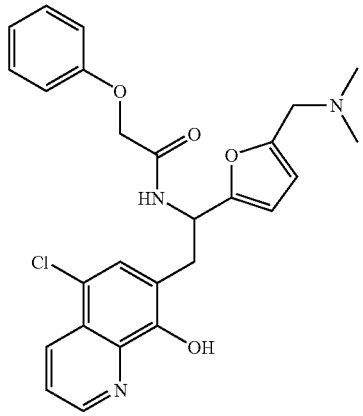<br>N-[2-(5-Chloro-8-hydroxyquinolin-7-yl)-1-{5-[(dimethylamino)methyl]-2-furyl}ethyl]-2-phenoxyacetamide | 16.8 +/− 2.8 | 68% @ 200 μM |
| 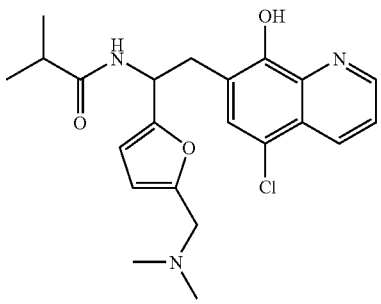<br>N-[2-(5-Chloro-8-hydroxyquinolin-7-yl)-1-{5-[(dimethylamino)methyl]-2-furyl}ethyl]-2-methylpropanamide | 56% @ 200 μM | 49% @ 200 μM |

When ranges are used herein for physical properties, such as molecular weight, or chemical properties, such as chemical formulae, all combination and subcombinations of ranges of specific embodiments therein are intended to be included.

The disclosure of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of the Formula (I):

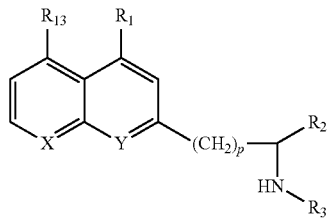

or a pharmaceutically acceptable salt thereof, wherein
X is —N— and Y is —$COR_1$;
p is 0 or 1;
$R_1$ is each independently hydrogen, halogen, —$C_1$-$C_6$-alkyl, —$NO_2$, $NH_2$, —$NR_5R_6$, -(1H-pyrrol-1-yl), -(pyrrolidin-1-yl);
$R_{13}$ is hydrogen;
$R_2$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_{10}$-arylalkyl, —$C_5$-$C_{10}$-arylalkenyl, —$C_7$-$C_{12}$-bicyclic hydrocarbon wherein at, least one, cyclic group is aromatic, $C_9$-$C_{15}$-tricyclic hydrocarbon wherein at least one cyclic group is aromatic or —$COR_7$, wherein (a) one or more of the carbon atoms in the alkyl, alkenyl, alkynyl, aryl, arylalkyl, arylalkenyl, bicyclic hydrocarbon or tricyclic hydrocarbon group is each independently optionally replaced with a nitrogen, sulfur or oxygen atom, and (b) the alkyl, alkenyl, alkynyl, aryl or arylalkyl, arylalkenyl, bicyclic hydrocarbon or tricyclic hydrocarbon group is optionally substituted with one or more hydroxyl, halogen, oxygen, —$C_1$-$C_6$-alkyl, —$C_5$-$C_7$-cycloalkyl, —$C_1$-$C_3$-alkyl-$C_5$-$C_7$-cycloalkyl, —$C_5$-$C_7$-aryl, —$C_5$-$C_{10}$-arylalkyl, —$C_5$-$C_{10}$-arylalkenyl, —$C_5$-$C_{10}$-arylalkynyl, —$NO_2$, —$CH_2NR_5R_6$, —$NR_5R_6$, —$NR_5SO_2R_5$, —$SO_2NR_5R_6$, —$SO_2R_7$, —$COR_7$, —$C_1$-$C_3$-alkyl-$COR_7$, —$COOR_7$ or —$CONR_5R_6$, wherein (1) one or more of the carbon atoms in the alkyl, alkenyl, alkynyl, cycloalkyl, aryl, arylalkyl, arylalkenyl or arylalkynyl group is each independently optionally replaced with a nitrogen, sulfur or oxygen atom, and (2) the alkyl, alkenyl, alkynyl, cycloalkyl, aryl arylalkyl, arylalkenyl or arylalkynyl group is optionally substituted with a halogen, a —$C_1$-$C_3$-alkyl;
$R_3$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_7$-cycloalkyl, —$R_8$—$C_5$-$C_7$-cycloalkyl, —$C_5$-$C_{10}$-arylalkyl, —$C_7$-$C_{12}$-bicyclic hydrocarbon or —$R_{12}$—$C_7$-$C_{12}$-bicyclic hydrocarbon wherein at least one cyclic group is aromatic, —$SO_2NR_5R_6$, —$COR_7$, —$COOR_7$, —$CONR_5R_6$, —$COR_8$—B—$R_9$, or —$R_3$—B—$R_9$, wherein (a) one or more of the carbon atoms in the alkyl, alkenyl, alkynyl, cycloalkyl, aryl, arylalkyl or bicyclic hydrocarbon group is each independently optionally replaced with a nitrogen, sulfur or oxygen atom, and (b) the alkyl, alkenyl, alkynyl, cycloalkyl, aryl, arylalkyl or bicyclic hydrocarbon group is optionally substituted with one to three substituents independently selected from halogen, —$C_2$-$C_3$-alkynyl, —$C_5$-$C_7$-aryl, —$NR_5R_6$, —C≡N, and —$COR_7$;
$R_4$ is hydrogen, —$C_1$-$C_6$-alkyl, —$C_2$-$C_6$-alkenyl, —$C_2$-$C_6$-alkynyl, —$SO_2NR_5R_6$, —$SO_2R_7$, —$COR_7$, —$COOR_7$ or —$CONR_5R_6$, wherein (a) one or more of the carbon atoms in the alkyl, alkenyl, or alkynyl group is each independently optionally replaced with a nitrogen, sulfur or oxygen atom, and (b) the alkyl, alkenyl or alkynyl group is optionally substituted with a halogen or a —$C_1$-$C_3$-alkyl;
$R_5$ and $R_6$ are each independently hydrogen, —$C_1$-$C_6$-alkyl, —$C_2$-$C_6$-alkenyl, —$C_2$-$C_6$-alkynyl, —$COR_7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, an oxygen;
$R_7$ is hydrogen, —$C_1$-$C_6$-alkyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with one to three substituents independently selected from halogen, —$C_1$-$C_3$-alkyl, —$C_5$-$C_7$-aryl, and —$NR_5R_6$;
$R_8$ is —$C_1$-$C_6$-alkyl, —$C_2$-$C_6$-alkenyl, or —$C_2$-$C_6$-alkynyl, wherein (a) one or more of the carbon atoms in the alkyl, alkenyl or alkynyl, group is each independently optionally replaced with a nitrogen, sulfur or oxygen atom, and (b) the alkyl, alkenyl or alkynyl group is optionally substituted with a halogen or a —$C_1$-$C_3$-alkyl;
$R_9$ is hydrogen, —$C_1$-$C_6$-alkyl, —$C_2$-$C_6$-alkenyl, —$C_2$-$C_6$-alkynyl, —$C_5$-$C_7$-aryl, —$C_5$-$C_{10}$-arylalkyl or —$C_7$-$C_{12}$-bicyclic hydrocarbon wherein at least one cyclic group is aromatic, wherein (a) one or more of the carbon atoms in the alkyl, alkenyl, alkynyl, aryl, arylalkyl or bicyclic hydrocarbon group is each independently optionally replaced with a nitrogen, sulfur or oxygen atom, and (b) the alkyl, alkenyl, alkynyl, aryl, arylalkyl or bicyclic hydrocarbon group is optionally substituted with one to three substituents independently selected from halogen, —$C_1$-$C_4$-alkyl branched, a —$C_5$-$C_7$-aryl, B—$C_5$-$C_7$-aryl, —$NR_5R_6$, and —$COR_7$, and wherein one to three carbon atoms are each independently optionally replaced with an oxygen or nitrogen atom;
$R_{12}$ is —$CH_2$— or —$CH_2CH_2$—;
B is a bond, —O—, —$NR_7$— or —S—.

2. The compound according to claim 1 of Formula (I), wherein $R_1$ is chlorine, bromine or fluorine.

3. The compound according to claim 1 of Formula (I), wherein $R_1$ is —$CH_3$.

4. The compound according to claim 1 of Formula (I), wherein $R_1$ is hydrogen.

5. The compound according to claim 1 of Formula (I), wherein $R_1$ is —$NO_2$.

6. The compound according to claim 1 of Formula (I), wherein $R_1$ is —$NR_5R_6$.

7. The compound according to claim 6 of Formula (I), wherein $R_1$ is —$NH_2$ or —$N(CH_3)_2$.

8. The compound according to claim 1 of Formula (I), wherein $R_1$ is

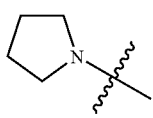 or 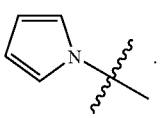

9. The compound according to claim 1 of Formula (I), wherein $R_2$ is —$C_5$-$C_7$-aryl.

10. The compound according to claim 9 of Formula (I), wherein $R_2$ is a —$C_5$-$C_7$-aryl, which is optionally substituted with one to three substituents independently selected from hydroxyl, halogen, —$C_1$-$C_6$-alkyl, —$C_2$-$C_6$-alkynyl, —$C_5$-$C_7$-aryl, —$C_5$-$C_{10}$-arylalkyl, —$C_5$-$C_{10}$-arylalkenyl, —$C_5$-$C_{10}$-arylalkynyl, —$NO_2$, —$C_5$-$C_7$-cycloalkyl, —$C_1$-$C_3$-alkyl-$C_5$-$C_7$-cycloalkyl, —$BR_9$, —$COR_7$, —$C_1$-$C_3$-alkyl-$COR_7$, —$CH_2NR_5R_6$, and —$NR_5R_6$, and wherein one to three carbon atoms of the aryl or the substituent are each independently optionally replaced with a nitrogen, sulfur or oxygen atom, and the substituent is optionally substituted with one to three halogen atoms or —$C_1$-$C_3$-alkyl groups that optionally have one to three of the carbon atoms each independently replaced with a nitrogen, sulfur or oxygen atom.

11. The compound according to claim 10 of Formula (I), wherein $R_2$ is

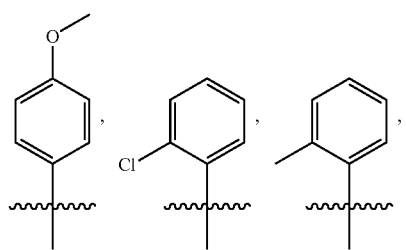

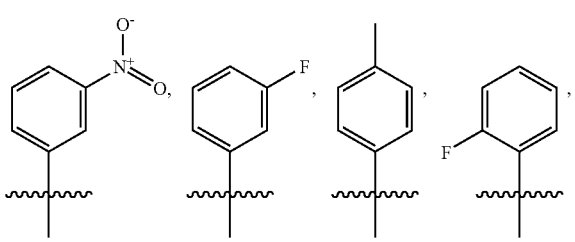

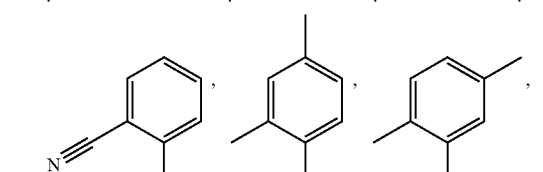

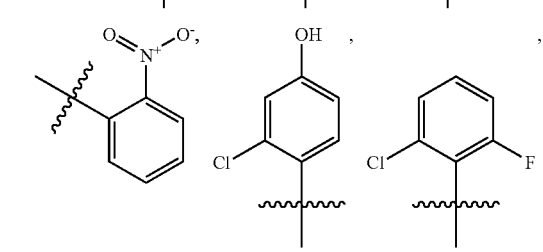

-continued

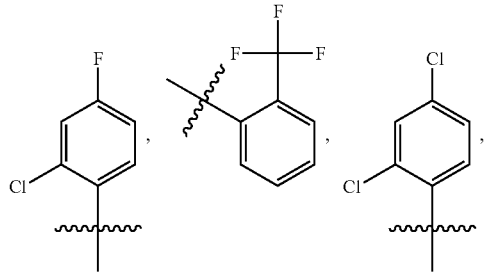

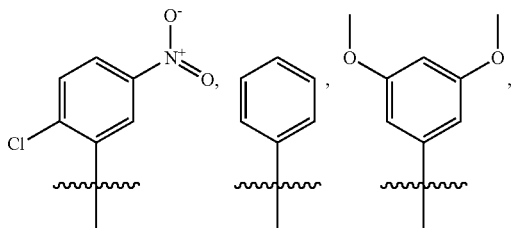

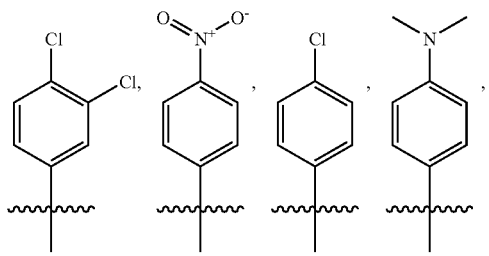

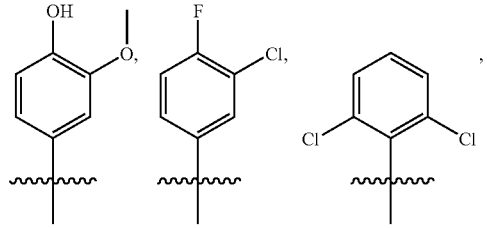

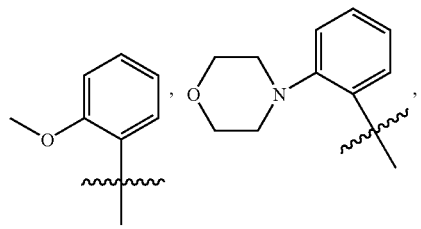

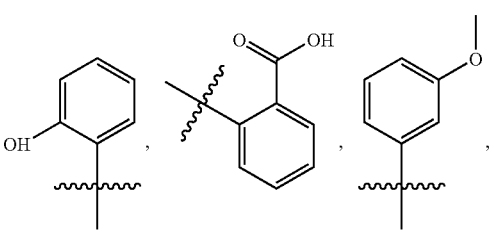

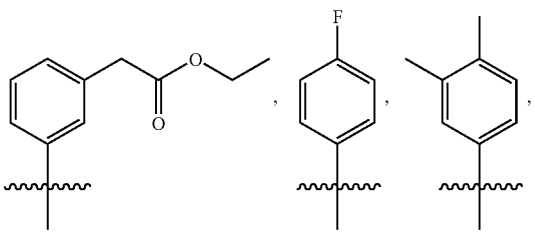

-continued
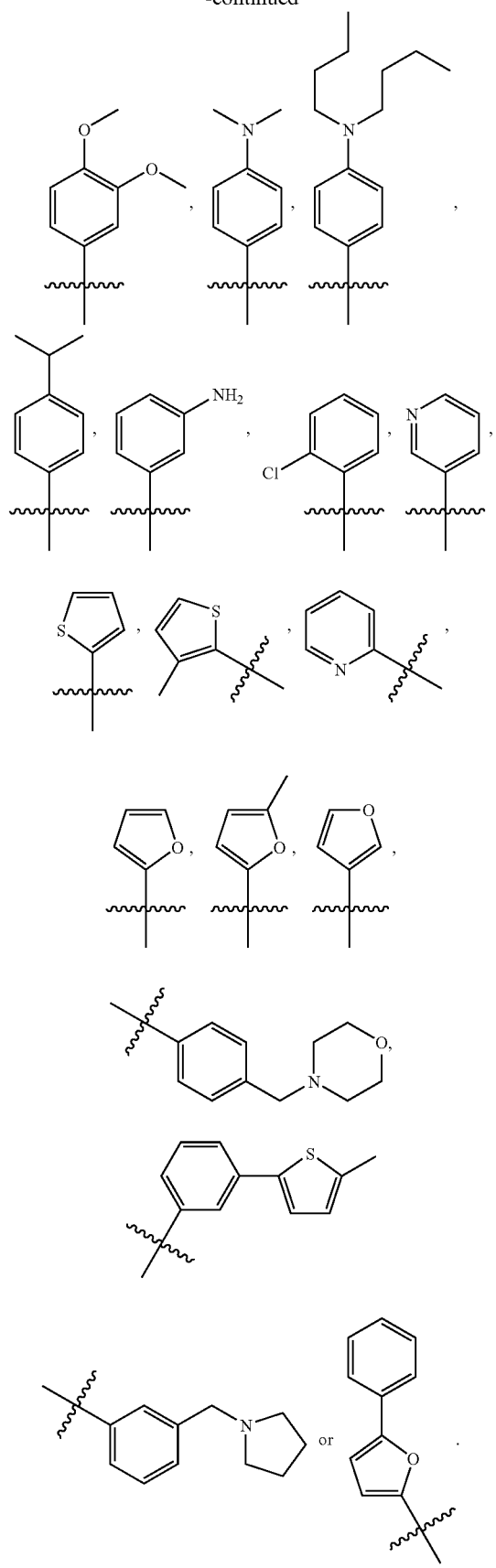
12. The compound according to claim 10 of Formula (I), wherein $R_2$ is:
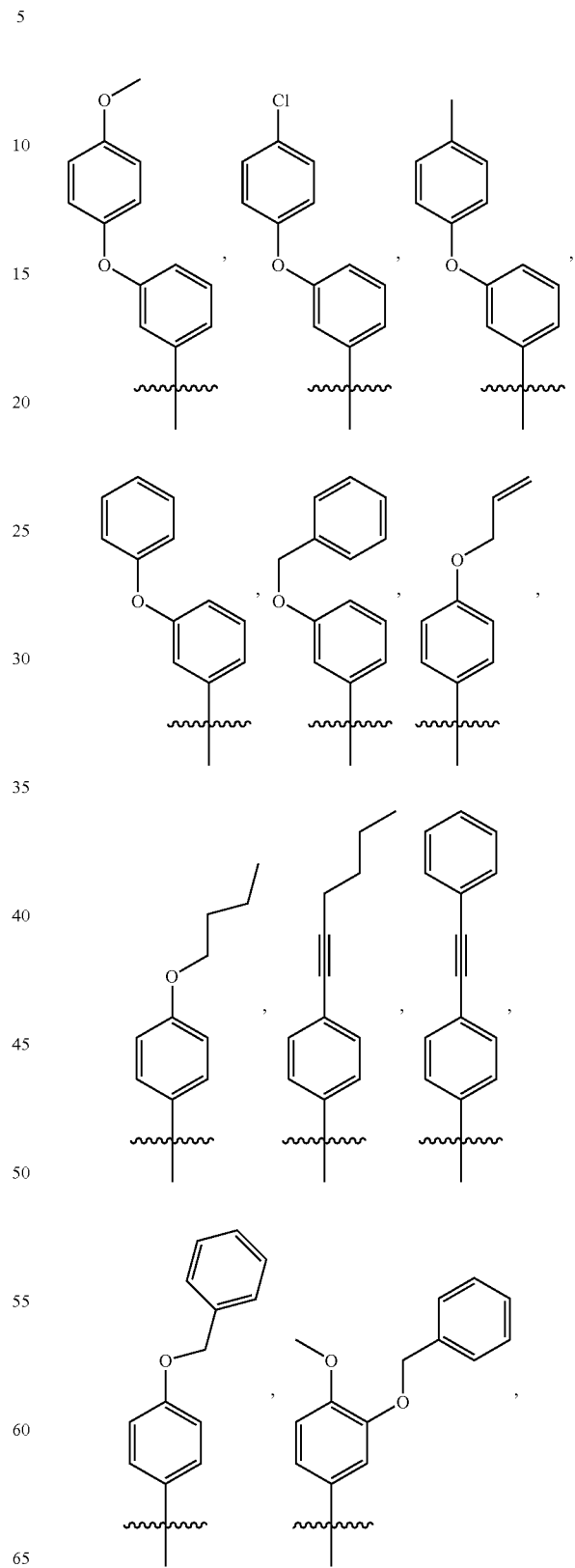

-continued

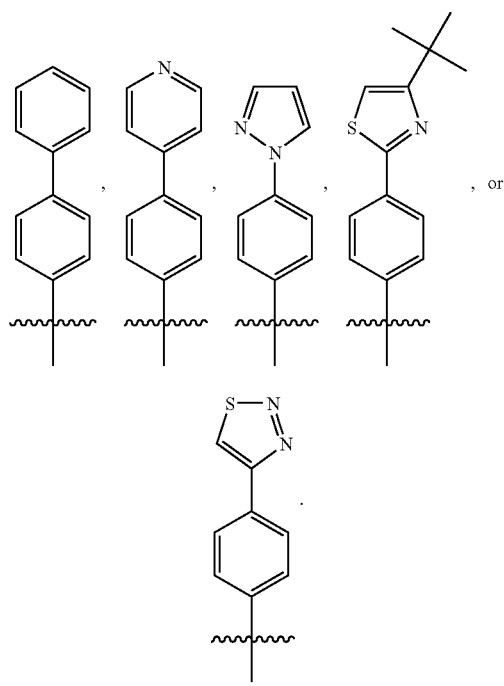

13. The compound according to claim 1 of Formula (I), wherein R₂, is a —C₇-C₁₂-bicyclic or a —C₉-C₁₅-tricyclic hydrocarbon.

14. The compound according to claim 13 of Formula (I), wherein R₂ is a —C₇-C₁₂-bicyclic or a C₉-C₁₅-tricyclic hydrocarbon wherein at least one cyclic group is aromatic, one to three carbon atoms are each independently optionally replaced with a nitrogen, sulfur or oxygen atom, and the hydrocarbon group is optionally substituted with an oxygen, halogen, or one to three —C₁-C₆-alkyl groups having one to three carbon atoms each independently optionally replaced with an oxygen atom.

15. The compound according to claim 14 of Formula (I), wherein R₂ is:

-continued

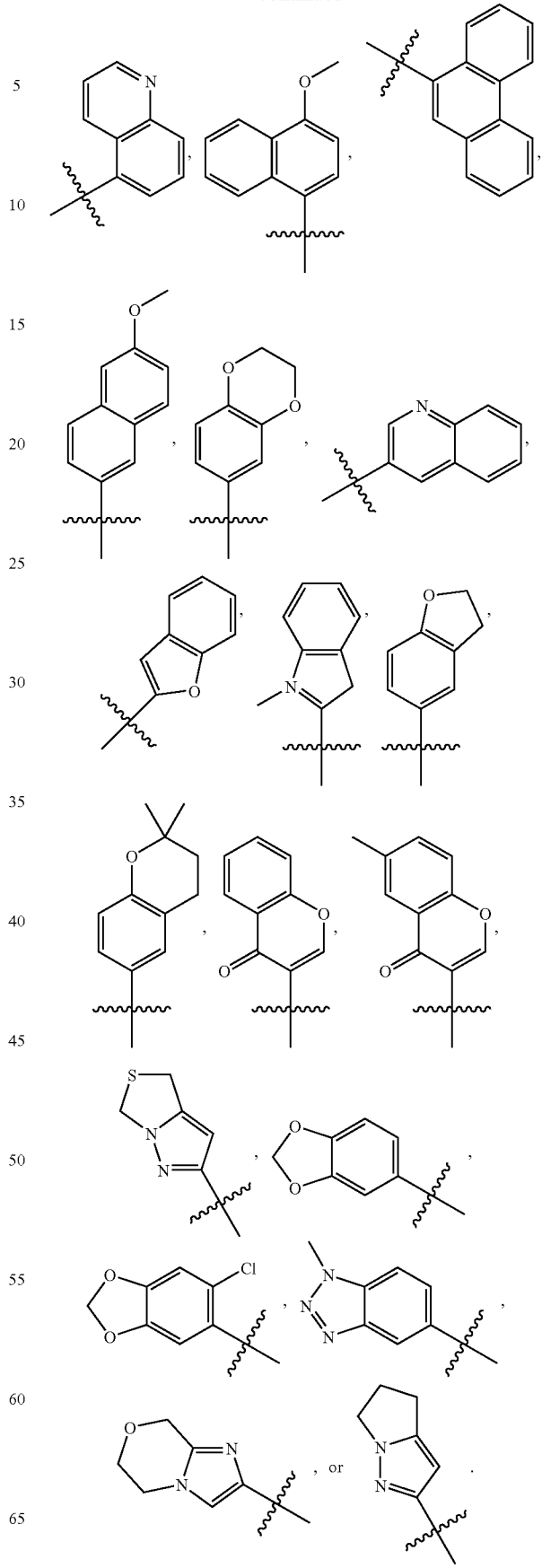

16. The compound according to claim 1 of Formula (I), wherein $R_2$ is —$C_2$-$C_6$-alkenyl.

17. The compound according to claim 16 of Formula (I), wherein $R_2$ is:

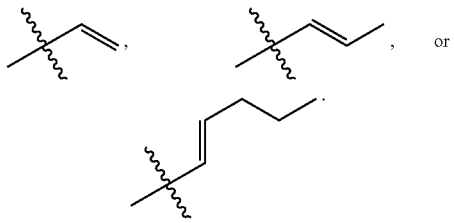

18. The compound according to claim 1 of Formula (I), wherein $R_2$ is —$C_5$-$C_{10}$-arylalkyl or —$C_5$-$C_{10}$-arylalkenyl.

19. The compound according to claim 18, wherein $R_2$ is a —$C_5$-$C_{10}$-arylalkyl or —$C_5$-$C_{10}$-arylalkenyl, which is optionally substituted with a —$C_1$-$C_6$-alkyl, and wherein one to three carbon atoms of the alkyl are each independently optionally replaced with an oxygen atom.

20. The compound according to claim 19 of Formula (I), wherein $R_2$ is:

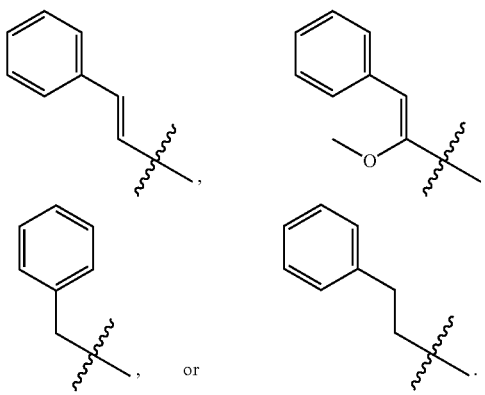

21. The compound according to claim 1 of Formula (I), wherein $R_2$ is a —$C_5$-$C_7$-aryl.

22. The compound according to claim 21 of Formula (I), wherein $R_2$ is a —$C_5$-$C_7$-aryl which is optionally substituted with —$CH_2NR_5R_6$, —$NR_5R_6$ or —$NR_5SO_2R_6$, and wherein one to three of the carbon atoms are each independently optionally replaced with a nitrogen or oxygen atom.

23. The compound according to claim 22 of Formula (I), wherein $R_2$ is:

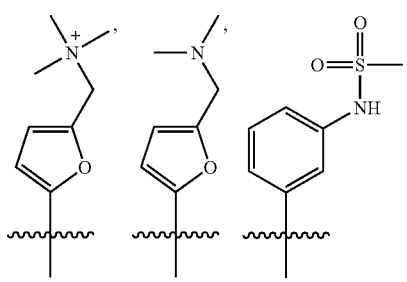

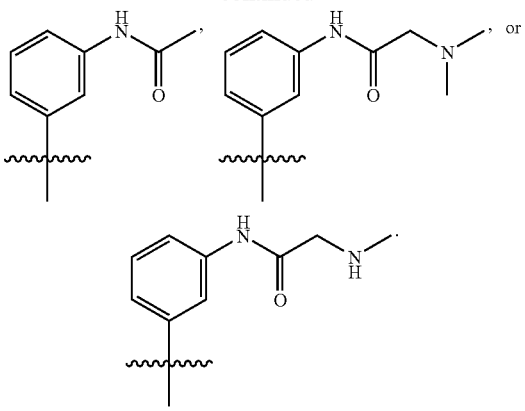

24. The compound according to claim 1 of Formula (I), wherein $R_3$ is —$COR_8$—B—$R_9$ or —$R_8$—B—$R_9$.

25. The compound according to claim 24 of Formula (I), wherein $R_3$ is —$COR_8$—B—$R_9$ or —$R_8$—B—$R_9$, wherein $R_8$ is a —$C_1$-$C_3$-alkyl, $R_9$ is a —$C_5$-$C_7$-aryl or $C_7$-$C_{17}$-bicyclic hydrocarbon wherein at least one cyclic group is aromatic, wherein the aryl or bicyclic hydrocarbon is each independently optionally substituted with one to three halogen atoms, —$C_1$-$C_4$-alkyl groups, —$C_5$-$C_7$-cycloalkyl groups, —$C_5$-$C_7$-aryl groups, —B—$C_5$-$C_7$-aryl groups, —$NR_5R_6$ groups, or —$COR_7$ groups and one to three carbon atoms are each independently optionally replaced with an oxygen or nitrogen atom, and B is —O—.

26. The compound according to claim 25 of Formula (I), wherein $R_3$ is:

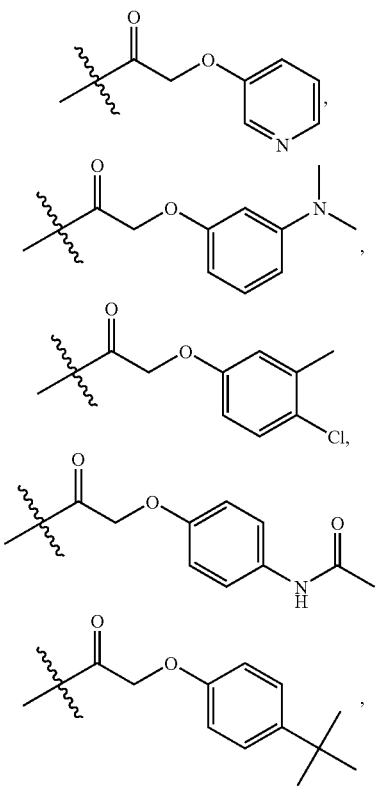

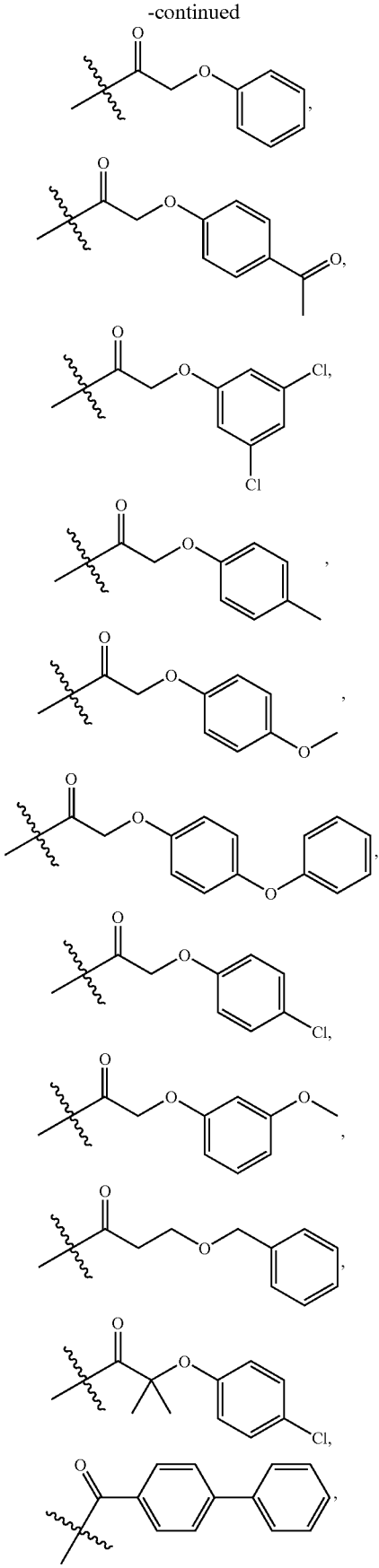
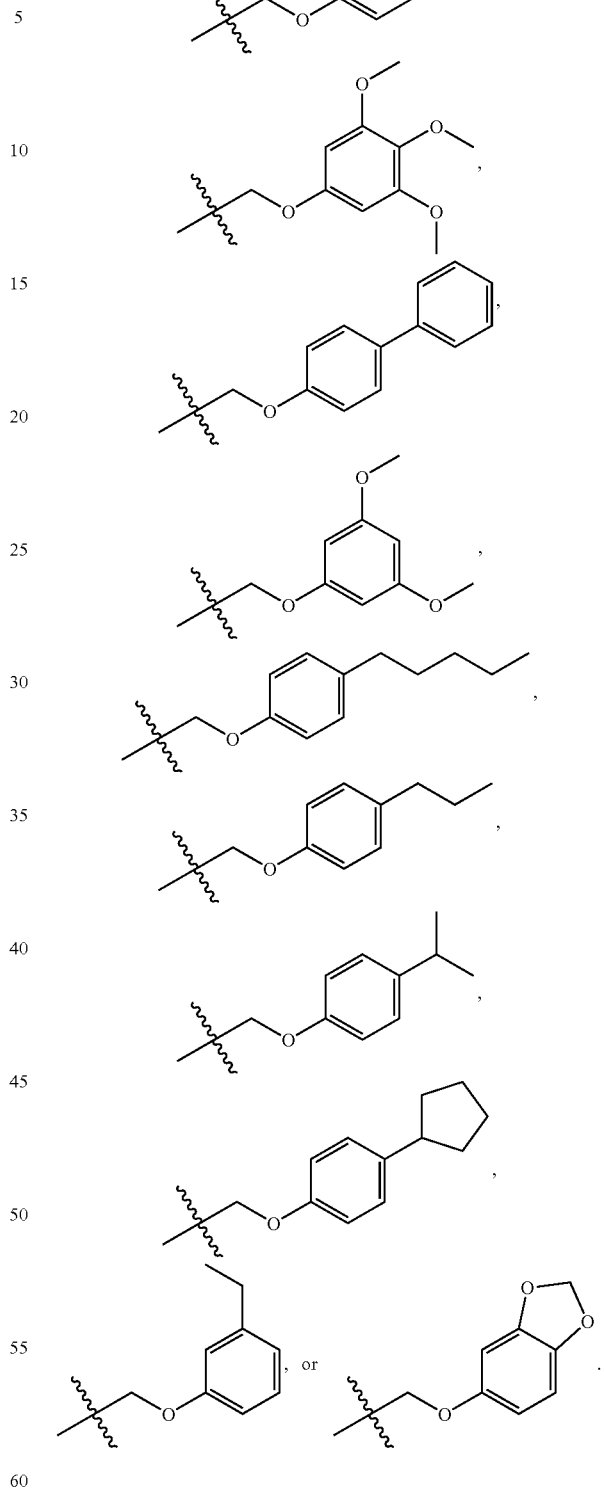
27. The compound according to claim 1 of Formula (I), wherein $R_3$ is —$COR_8$—B—$R_9$, —$R_8$—$C_5$-$C_7$-cycloalkyl, or —$R_8$—B—$R_9$.
28. The compound according to claim 27 of Formula (I), wherein $R_3$ is —$COR_8$—B—$R_9$, —$R_8$—$C_5$-$C_7$-cycloalkyl or —$R_8$—B—$R_9$, wherein $R_8$ is a —$C_1$-$C_3$-alkyl, $R_7$ is a —$C_1$-$C_3$-alkyl or hydrogen, $R_9$ is a —$C_5$-$C_7$-aryl, —$R_{12}$—$C_5$-$C_7$- cycloalkyl, or —R$_{12}$—C$_7$-C$_{12}$-bicyclic hydrocarbon wherein at least one cyclic group is aromatic and R$_{12}$ is —CH$_2$—, wherein (a) one or more of the carbon atoms are each independently optionally replaced with a nitrogen or oxygen atom, and (b) the cycloalkyl, aryl or bicyclic hydrocarbon group is optionally substituted with one to three halogen, —C$_1$-C$_4$-alkyl groups, —C$_2$-C$_3$-alkynyl groups, —C$_5$-C$_7$-aryl groups, —NR$_5$R$_6$, or —COR$_7$; and B is —NR$_7$—.

29. The compound according to claim 28 of Formula (I), wherein R$_3$ is:

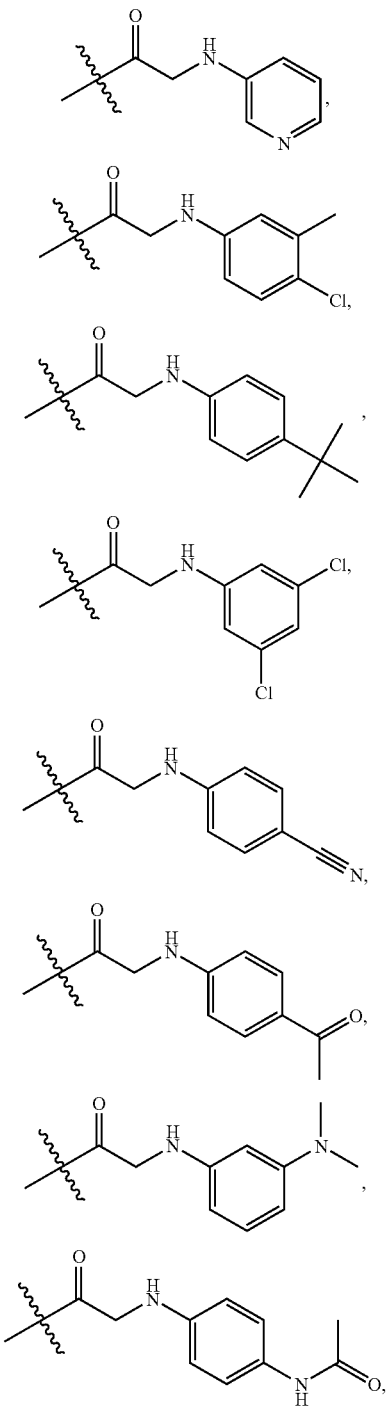

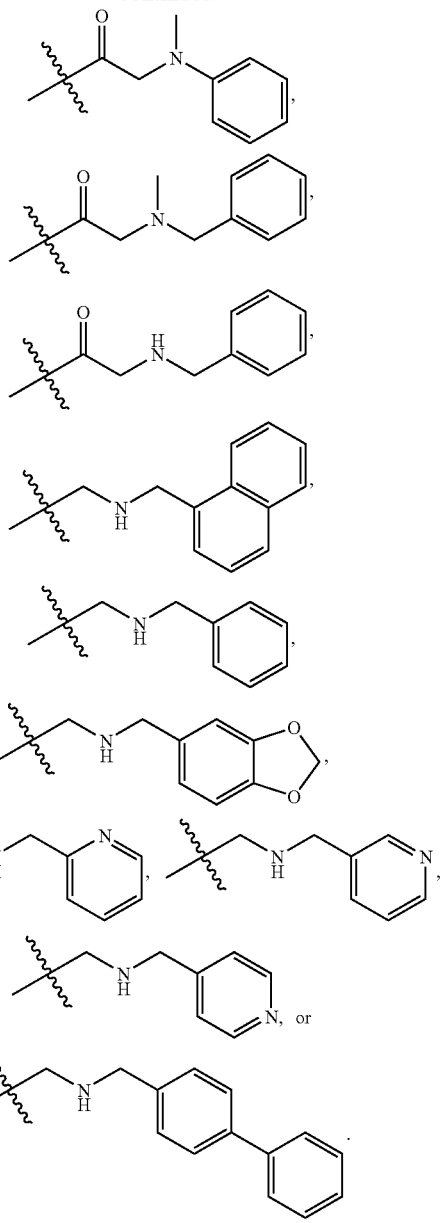

30. The compound according to claim 1 of Formula (I), wherein R$_3$ is —COR$_7$.

31. The compound according to claim 30 of Formula (I), wherein R$_3$ is —COR$_7$, and R$_7$ is a —C$_1$-C$_6$-alkyl, —C$_5$-C$_7$-aryl or —C$_5$-C$_{10}$-arylalkyl.

32. The compound according to claim 31 of Formula (I), wherein R$_3$ is:

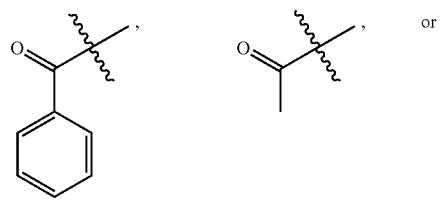

-continued

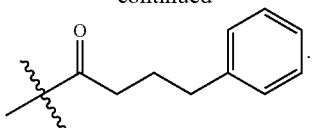

33. The compound according to claim 1 of Formula (I), wherein $R_3$ is —$C_5$-$C_{10}$-arylalkyl with a carbon atom optionally replaced with an oxygen atom.

34. The compound according to claim 33 of Formula (I), wherein $R_3$ is:

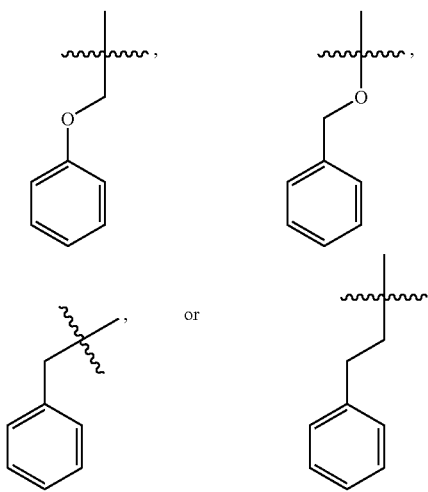

35. The compound according to claim 1 of Formula (I), wherein $R_3$ is —$C_1$-$C_6$-alkyl.

36. The compound according to claim 35 of Formula (I), wherein $R_3$ is —$C_1$-$C_6$-alkyl optionally substituted with a halogen.

37. The compound according to claim 36 of Formula (I), wherein $R_3$ is

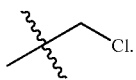

38. The compound according to claim 1 of Formula (I), wherein $R_4$ is hydrogen.

39. The compound according to claim 1 of Formula (I), wherein $R_4$ is methyl.

40. The compound according to claim 1 of Formula (I), wherein $R_4$ is —$SO_2R_7$.

41. A compound or pharmaceutically acceptable salt thereof wherein the compound is:
- N-[(5-chloro-8-hydroxyquinolin-7-yl)(4-methoxyphenyl)methyl]-2-(pyridin-3-yloxy)acetamide
- N-[(5-chloro-8-hydroxyquinolin-7-yl)(4-methoxyphenyl)methyl]-2-[3-(dimethylamino)phenoxy]acetamide
- N-[(5-chloro-8-hydroxyquinolin-7-yl)(4-methoxyphenyl)methyl]-2-(4-chloro-3-methylphenoxy)acetamide
- 2-[4-(acetylamino)phenoxy]-N-[(5-chloro-8-hydroxyquinolin-7-yl)(4-methoxyphenyl)methyl]acetamide
- N-[(5-chloro-8-hydroxyquinolin-7-yl)(2-chlorophenyl)methyl]-2-[3-(dimethylamino)phenoxy]acetamide
- N-[(5-chloro-8-hydroxyquinolin-7-yl)(2-chlorophenyl)methyl]-2-(4-chloro-3-methylphenoxy)acetamide
- 2-(4-tert-butylphenoxy)-N-[(5-chloro-8-hydroxyquinolin-7-yl)(2-chlorophenyl)methyl]acetamide
- 2-[4-(acetylamino)phenoxy]-N-[(5-chloro-8-hydroxyquinolin-7-yl)(2-chlorophenyl)methyl]acetamide
- N-[(5-chloro-8-hydroxyquinolin-7-yl)(2-methylphenyl)methyl]-2-phenoxyacetamide
- N-[(5-chloro-8-hydroxyquinolin-7-yl)(3-nitrophenyl)methyl]-2-(pyridin-3-yloxy)acetamide
- 2-(4-acetylphenoxy)-N-[(5-chloro-8-hydroxyquinolin-7-yl)(3-nitrophenyl)methyl]acetamide
- N-[(5-chloro-8-hydroxyquinolin-7-yl)(3-nitrophenyl)methyl]-2-(4-chloro-3-methylphenoxy)acetamide
- N-[(5-chloro-8-hydroxyquinolin-7-yl)(3-nitrophenyl)methyl]-2-(3,5-dichlorophenoxy)acetamide
- N-[(5-chloro-8-hydroxyquinolin-7-yl)(3-fluorophenyl)methyl]-2-(pyridin-3-yloxy)acetamide
- N-[(5-chloro-8-hydroxyquinolin-7-yl)(3-fluorophenyl)methyl]-2-[3-(dimethylamino)phenoxy]acetamide
- 2-(4-tert-butylphenoxy)-N-[(5-chloro-8-hydroxyquinolin-7-yl)(3-fluorophenyl)methyl]acetamide
- 2-[4-(acetylamino)phenoxy]-N-[(5-chloro-8-hydroxyquinolin-7-yl)(3-fluorophenyl)methyl]acetamide
- N1-[(5-chloro-8-hydroxyquinolin-7-yl)(2-chlorophenyl)methyl]-N2-pyridin-3-ylglycinamide
- N1-[(5-chloro-8-hydroxyquinolin-7-yl)(2-chlorophenyl)methyl]-N2-(4-chloro-3-methylphenyl)glycinamide
- N2-(4-tert-butylphenyl)-N1-[(5-chloro-8-hydroxyquinolin-7-yl)(2-chlorophenyl)methyl]glycinamide
- N1-[(5-chloro-8-hydroxyquinolin-7-yl)(2-chlorophenyl)methyl]-N2-(3,5-dichlorophenyl)glycinamide
- N1-[(5-chloro-8-hydroxyquinolin-7-yl)(4-methylphenyl)methyl]-N2-pyridin-3-ylglycinamide
- N1-[(5-chloro-8-hydroxyquinolin-7-yl)(4-methylphenyl)methyl]-N2-(4-cyanophenyl)glycinamide
- N2-(4-acetylphenyl)-N-1-[(5-chloro-8-hydroxyquinolin-7-yl)(4-methylphenyl)methyl]glycinamide
- N1-[(5-chloro-8-hydroxyquinolin-7-yl)(4-methylphenyl)methyl]-N2-[3-(dimethylamino)phenyl]glycinamide
- N1-[(5-chloro-8-hydroxyquinolin-7-yl)(4-methylphenyl)methyl]-N2-(4-chloro-3-methylphenyl)glycinamide
- N2-(4-tert-butylphenyl)-N1-[(5-chloro-8-hydroxyquinolin-7-yl)(4-methylphenyl)methyl]glycinamide
- N1-[(5-chloro-8-hydroxyquinolin-7-yl)(3-nitrophenyl)methyl]-N2-pyridin-3-ylglycinamide
- N2-(4-acetylphenyl)-N-1-[(5-chloro-8-hydroxyquinolin-7-yl)(3-nitrophenyl)methyl]glycinamide
- N1-[(5-chloro-8-hydroxyquinolin-7-yl)(3-nitrophenyl)methyl]-N2-(4-chloro-3-methylphenyl)glycinamide
- N2-[4-(acetylamino)phenyl]-N1-[(5-chloro-8-hydroxyquinolin-7-yl)(3-nitrophenyl)methyl]glycinamide
- N1-[(5-chloro-8-hydroxyquinolin-7-yl)(3-fluorophenyl)methyl]-N2-pyridin-3-ylglycinamide
- N1-[(5-chloro-8-hydroxyquinolin-7-yl)(3-fluorophenyl)methyl]-N2-(4-chloro-3-methylphenyl)glycinamide
- N-[(5-chloro-8-hydroxyquinolin-7-yl)(2-fluorophenyl)methyl]-2-phenoxyacetamide
- N-[(5-chloro-8-hydroxyquinolin-7-yl)(2-cyanophenyl)methyl]-2-phenoxyacetamide
- N-[(5-chloro-8-hydroxyquinolin-7-yl)(2,4-dimethylphenyl)methyl]-2-phenoxyacetamide
- N-[(5-chloro-8-hydroxyquinolin-7-yl)(2,5-dimethylphenyl)methyl]-2-phenoxyacetamide
- N-[(5-chloro-8-hydroxyquinolin-7-yl)(2-nitrophenyl)methyl]-2-phenoxyacetamide
- N-([2-chloro-4-hydroxyphenyl)(5-chloro-8-hydroxyquinolin-7-yl)methyl]-2-phenoxyacetamide N-[(2-chloro-6-fluorophenyl)(5-chloro-8-hydroxyquinolin-7-yl)methyl]-2-phenoxyacetamide
N-[(2-chloro-4-fluorophenyl)(5-chloro-8-hydroxyquinolin-7-yl)methyl]-2-phenoxyacetamide
N-{(5-chloro-8-hydroxyquinolin-7-yl)[2-(trifluoromethyl)phenyl]methyl}-2-phenoxyacetamide
N-[(5-chloro-8-hydroxyquinolin-7-yl)(2,4-dichlorophenyl)methyl]-2-phenoxyacetamide
N-[(5-chloro-8-hydroxyquinolin-7-yl)(2-chloro-5-nitrophenyl)methyl]-2-phenoxyacetamide
N-[(2-chlorophenyl)(8-hydroxy-5-methylquinolin-7-yl)methyl]-2-phenoxyacetamide
N-[(8-hydroxy-5-methylquinolin-7-yl)(3-nitrophenyl)methyl]-2-phenoxyacetamide
N-[(8-hydroxy-5-methylquinolin-7-yl)(2-methylphenyl)methyl]-2-phenoxyacetamide
N-[(5-bromo-8-hydroxyquinolin-7-yl)(2-chlorophenyl)methyl]-2-phenoxyacetamide
N-[(5-bromo-8-hydroxyquinolin-7-yl)(3-nitrophenyl)methyl]-2-phenoxyacetamide
N-[(5-bromo-8-hydroxyquinolin-7-yl)(2-methylphenyl)methyl]-2-phenoxyacetamide
N1-[(5-chloro-8-hydroxyquinolin-7-yl)(2-chlorophenyl)methyl]-N2-methyl-N-2-phenylglycinamide
N2-benzyl-N1-[(5-chloro-8-hydroxyquinolin-7-yl)(2-chlorophenyl)methyl]-N2-methylglycinamide
N2-benzyl-N1-[(5-chloro-8-hydroxyquinolin-7-yl)(2-chlorophenyl)methyl]glycinamide
N1-[(5-chloro-8-hydroxyquinolin-7-yl)(3-fluorophenyl)methyl]-N2-methyl-N2-phenylglycinamide
N2-benzyl-N1-[(5-chloro-8-hydroxyquinolin-7-yl)(3-fluorophenyl)methyl]-N2-methylglycinamide
N2-benzyl-N1-[(5-chloro-8-hydroxyquinolin-7-yl)(3-fluorophenyl)methyl]glycinamide
2-(benzyloxy)-N-[(5-chloro-8-hydroxyquinolin-7-yl)(3-fluorophenyl)methyl]acetamide
N1-[(5-chloro-8-hydroxyquinolin-7-yl)(4-methylphenyl)methyl]-N2-methyl-N2-phenylglycinamide
N2-benzyl-N1-[(5-chloro-8-hydroxyquinolin-7-yl)(4-methylphenyl)methyl]-N2-methylglycinamide
N2-benzyl-N1-[(5-chloro-8-hydroxyquinolin-7-yl)(4-methylphenyl)methyl]glycinamide
2-(benzyloxy)-N-[(5-chloro-8-hydroxyquinolin-7-yl)(4-methylphenyl)methyl]acetamide
N1-[(5-chloro-8-hydroxyquinolin-7-yl)(3-nitrophenyl)methyl]-N2-methyl-N2-phenylglycinamide
N2-benzyl-N1-[(5-chloro-8-hydroxyquinolin-7-yl)(3-nitrophenyl)methyl]-N2-methylglycinamide
N2-benzyl-N1-[(5-chloro-8-hydroxyquinolin-7-yl)(3-nitrophenyl)methyl]glycinamide
N-[8-hydroxyquinolin-7-yl)(phenyl)methyl]benzamide
N-[(8-hydroxyquinolin-7-yl)(phenyl)methyl]acetamide
N-[(5-chloro-8-hydroxyquinolin-7-yl)(phenyl)methyl]benzamide
N-[(5-chloro-8-hydroxyquinolin-7-yl)(phenyl)methyl]acetamide
N-[(5-chloro-8-hydroxyquinolin-7-yl)(pyridin-3-yl)methyl]-2-phenoxyacetamide
N-[(5-chloro-8-hydroxyquinolin-7-yl)(2-thienyl)methyl]-2-phenoxyacetamide
N-[(5-chloro-8-hydroxyquinolin-7-yl)(3,5-dimethoxyphenyl)methyl]-2-phenoxyacetamide
N-[5-chloro-8-hydroxyquinolin-7-yl)(3,4-dichlorophenyl)methyl]-2-phenoxyacetamide
N-[(8-hydroxyquinolin-7-yl)(4-methoxyphenyl)methyl]-2-(4-methylphenoxy)acetamide
N-[8-hydroxyquinolin-7-yl)(phenyl)methyl]-2-(4-methoxyphenoxy)acetamide
N-[8-hydroxyquinolin-7-yl)(4-methoxyphenyl)methyl]-2-(4-phenoxyphenoxy)acetamide
N-[8-hydroxyquinolin-7-yl)(phenyl)methyl]-2-(4-methylphenoxy)acetamide
N-[8-hydroxyquinolin-7-yl)(4-methoxyphenyl)methyl]-2-(4-methoxyphenoxy)acetamide
N-[(8-hydroxyquinolin-7-yl)(phenyl)methyl]-2-(4-phenoxyphenoxy)acetamide
N-[5-chloro-8-hydroxyquinolin-7-yl)(4-methoxyphenyl)methyl]-2-(4-methylphenoxy)acetamide
N-[5-chloro-8-hydroxyquinolin-7-yl)(phenyl)methyl]-2-(4-methoxyphenoxy)acetamide
N-[(5-chloro-8-hydroxyquinolin-7-yl)(4-methoxyphenyl)methyl]-2-(4-phenoxyphenoxy)acetamide
N-[5-chloro-8-hydroxyquinolin-7-yl)(phenyl)methyl]-2-(4-methylphenoxy)acetamide
N-[8-hydroxyquinolin-7-yl)(4-nitrophenyl)methyl]-2-phenoxyacetamide
N-[5-chloro-8-hydroxyquinolin-7-yl)(phenyl)methyl]-2-(4-phenoxyphenoxy)acetamide
N-[(8-hydroxyquinolin-7-yl)(phenyl)methyl]-2-phenoxyacetamide
N-[8-hydroxyquinolin-7-yl)(4-methylphenyl)methyl]-2-phenoxyacetamide
N-[8-hydroxyquinolin-7-yl)(4-methoxyphenyl)methyl]-2-phenoxyacetamide
N-[2-chlorophenyl)(8-hydroxyquinolin-7-yl)methyl]-2-phenoxyacetamide
N-[4-chlorophenyl)(8-hydroxyquinolin-7-yl)methyl]-2-phenoxyacetamide
N-[5-chloro-8-hydroxyquinolin-7-yl)(phenyl)methyl]-2-phenoxyacetamide
N-[(5-chloro-8-hydroxyquinolin-7-yl)(4-methylphenyl)methyl]-2-phenoxyacetamide
N-[5-chloro-8-hydroxyquinolin-7-yl)(2-chlorophenyl)methyl]-2-phenoxyacetamide
N-[5-chloro-8-hydroxyquinolin-7-yl)(4-chlorophenyl)methyl]-2-phenoxyacetamide
N-[5-chloro-8-hydroxyquinolin-7-yl)(3-nitrophenyl)methyl]-2-phenoxyacetamide
N-[5-chloro-8-hydroxyquinolin-7-yl)(4-nitrophenyl)methyl]-2-phenoxyacetamide
N-[3-fluorophenyl)(8-hydroxyquinolin-7-yl)methyl]-2-phenoxyacetamide
N-[[4-(dimethylamino)phenyl](8-hydroxyquinolin-7-yl)methyl]-2-phenoxyacetamide
N-[5-chloro-8-hydroxyquinolin-7-yl)(4-hydroxy-3-methoxyphenyl)methyl]-2-phenoxyacetamide
N-[(5-chloro-8-hydroxyquinolin-7-yl)(phenyl)methyl]-2-(4-chlorophenoxy)acetamide
N-[5-chloro-8-hydroxyquinolin-7-yl)(3-fluorophenyl)methyl]-2-phenoxyacetamide
N-[3-chloro-4-fluorophenyl)(5-chloro-8-hydroxyquinolin-7-yl)methyl]-2-phenoxyacetamide
N-[(5-chloro-8-hydroxyquinolin-7-yl)(2,6-dichlorophenyl)methyl]-2-phenoxyacetamide
N-[5-chloro-8-hydroxyquinolin-7-yl)(phenyl)methyl]-2-(pyridin-3-yloxy)acetamide
N-[5-chloro-8-hydroxyquinolin-7-yl)(4-methoxyphenyl)methyl]-2-(3-methoxyphenoxy)acetamide
2-(4-tert-butylphenoxy)-N-[(5-chloro-8-hydroxyquinolin-7-yl)(4-methoxyphenyl)methyl]acetamide
N-[2-chlorophenyl)(8-hydroxy-5-nitroquinolin-7-yl)methyl]-2-phenoxyacetamide N-[(8-hydroxy-5-nitroquinolin-7-yl)(2-methylphenyl)methyl]-2-phenoxyacetamide
N-[(8-hydroxy-5-nitroquinolin-7-yl)(phenyl)methyl]-2-phenoxyacetamide
N-[(5-fluoro-8-hydroxyquinolin-7-yl)(phenyl)methyl]-2-phenoxyacetamide
N-[5-chloro-8-hydroxyquinolin-7-yl)(2-methylphenyl)methyl]-4-phenylbutanamide
N-[5-chloro-8-hydroxyquinolin-7-yl)(2-chlorophenyl)methyl]-4-phenylbutanamide
N-[5-chloro-8-hydroxyquinolin-7-yl)(4-methylphenyl)methyl]-4-phenylbutanamide
N-[5-chloro-8-hydroxyquinolin-7-yl)(3-nitrophenyl)methyl]-4-phenylbutanamide
N-[(5-chloro-8-methoxyquinolin-7-yl)(phenyl)methyl]-2-phenoxyacetamide
N-[(5-chloro-8-methoxyquinolin-7-yl)(2-chlorophenyl)methyl]-2-phenoxyacetamide
N—[(S)-(5-chloro-8-hydroxyquinolin-7-yl)(2-chlorophenyl)methyl]-2-phenoxyacetamide
N—[(R)-(5-chloro-8-hydroxyquinolin-7-yl)(2-chlorophenyl)methyl]-2-phenoxyacetamide
N—[(R)-(5-chloro-8-hydroxyquinolin-7-yl)(phenyl)methyl]-2-phenoxyacetamide
N—[(S)-(5-chloro-8-hydroxyquinolin-7-yl)(phenyl)methyl]-2-phenoxyacetamide
N-[(5-chloro-8-hydroxyquinolin-7-yl)(2-methoxyphenyl)methyl]-2-phenoxyacetamide
N-[(5-chloro-8-hydroxyquinolin-7-yl)(2-morpholin-4-ylphenyl)methyl]-2-phenoxyacetamide
N-[5-chloro-8-hydroxyquinolin-7-yl)(2-hydroxyphenyl)methyl]-2-phenoxyacetamide
2-{(5-chloro-8-hydroxyquinolin-7-yl)[(phenoxyacetyl)amino]methyl}benzoic acid
N-[(5-chloro-8-hydroxyquinolin-7-yl)(3-methoxyphenyl)methyl]-2-phenoxyacetamide
ethyl(3-{(5-chloro-8-hydroxyquinolin-7-yl)[(phenoxyacetyl)amino]methyl}phenyl)acetate
N-{(5-chloro-8-hydroxyquinolin-7-yl)[3-(4-methoxyphenoxy)phenyl]methyl}-2-phenoxyacetamide
N-{(5-chloro-8-hydroxyquinolin-7-yl)[3-(4-chlorophenoxy)phenyl]methyl}-2-phenoxyacetamide
N-{(5-chloro-8-hydroxyquinolin-7-A[3-(4-methylphenoxy)phenyl]methyl}-2-phenoxyacetamide
N-[5-chloro-8-hydroxyquinolin-7-yl)(3-phenoxyphenyl)methyl]-2-phenoxyacetamide
N-[[3-(benzyloxy)phenyl](5-chloro-8-hydroxyquinolin-7-yl)methyl]-2-phenoxyacetamide
N-[(5-chloro-8-hydroxyquinolin-7-yl)(4-fluorophenyl)methyl]-2-phenoxyacetamide
N-{(5-chloro-8-hydroxyquinolin-7-yl)[4-(dimethylamino)phenyl]methyl}-2-phenoxyacetamide
N-{(5-chloro-8-hydroxyquinolin-7-yl)[4-(diethylamino)phenyl]methyl}-2-phenoxyacetamide
N-{(5-chloro-8-hydroxyquinolin-7-yl)[4-(dibutylamino)phenyl]methyl}-2-phenoxyacetamide
N-[(5-chloro-8-hydroxyquinolin-7-yl)(4-isopropylphenyl)methyl]-2-phenoxyacetamide
N-[[4-(allyloxy)phenyl](5-chloro-8-hydroxyquinolin-7-yl)methyl]-2-phenoxyacetamide
N-[(4-butoxyphenyl)(5-chloro-8-hydroxyquinolin-7-yl)methyl]-2-phenoxyacetamide
N-[(5-chloro-8-hydroxyquinolin-7-yl)(4-hex-1-yn-1-ylphenyl)methyl]-2-phenoxyacetamide
N-{(5-chloro-8-hydroxyquinolin-7-yl)[4-(phenylethynyl)phenyl]methyl}-2-phenoxyacetamide
N-[[4-(benzyloxy)phenyl](5-chloro-8-hydroxyquinolin-7-yl)methyl]-2-phenoxyacetamide
N-[biphenyl-4-yl(5-chloro-8-hydroxyquinolin-7-yl)methyl]-2-phenoxyacetamide
N-[(5-chloro-8-hydroxyquinolin-7-yl)(4-pyridin-4-ylphenyl)methyl]-2-phenoxyacetamide
N-{(5-chloro-8-hydroxyquinolin-7-yl)[4-(1H-pyrazol-1-yl)phenyl]methyl}-2-phenoxyacetamide
N-[[4-(4-tert-butyl-1,3-thiazol-2-yl)phenyl](5-chloro-8-hydroxyquinolin-7-yl)methyl]-2-phenoxyacetamide
N-{(5-chloro-8-hydroxyquinolin-7-yl)[4-(1,2,3-thiadiazol-4-yl)phenyl]methyl}-2-phenoxyacetamide
N-[(5-chloro-8-hydroxyquinolin-7-yl)(3,4-dimethylphenyl)methyl]-2-phenoxyacetamide
N-[(5-chloro-8-hydroxyquinolin-7-yl)(3,4-dimethoxyphenyl)methyl]-2-phenoxyacetamide
N-[[3-(benzyloxy)-4-methoxyphenyl](5-chloro-8-hydroxyquinolin-7-yl)methyl]-2-phenoxyacetamide
N-[(5-chloro-8-hydroxyquinolin-7-yl)(2-furyl)methyl]-2-phenoxyacetamide
N-[(5-chloro-8-hydroxyquinolin-7-yl)(5-methyl-2-furyl)methyl]-2-phenoxyacetamide
N-[(5-chloro-8-hydroxyquinolin-7-yl)(3-furyl)methyl]-2-phenoxyacetamide
N-[(5-chloro-8-hydroxyquinolin-7-yl)(5-phenyl-2-furyl)methyl]-2-phenoxyacetamide
N-[(5-chloro-8-hydroxyquinolin-7-yl)(3-methyl-2-thienyl)methyl]-2-phenoxyacetamide
N-[(5-chloro-8-hydroxyquinolin-7-yl)(1H-indol-7-yl)methyl]-2-phenoxyacetamide
N-[(5-chloro-8-hydroxyquinolin-7-yl)(1H-indol-4-yl)methyl]-2-phenoxyacetamide
N-[(5-chloro-8-hydroxyquinolin-7-yl)(1-methyl-1H-indol-3-yl)methyl]-2-phenoxyacetamide
N-[1,3-benzodioxol-4-yl(5-chloro-8-hydroxyquinolin-7-yl)methyl]-2-phenoxyacetamide
N-[(5-chloro-8-hydroxyquinolin-7-yl)(quinolin-8-yl)methyl]-2-phenoxyacetamide
N-[(5-chloro-8-hydroxyquinolin-7-yl)(quinolin-4-yl)methyl]-2-phenoxyacetamide
N-[(5-chloro-8-hydroxyquinolin-7-yl)(quinolin-5-yl)methyl]-2-phenoxyacetamide
N-[(5-chloro-8-hydroxyquinolin-7-yl)(4-methoxy-1-naphthyl)methyl]-2-phenoxyacetamide
N-[(5-chloro-8-hydroxyquinolin-7-yl)(9-phenanthryl)methyl]-2-phenoxyacetamide
N-[(5-chloro-8-hydroxyquinolin-7-yl)(6-methoxy-2-naphthyl)methyl]-2-phenoxyacetamide
N-[(5-chloro-8-hydroxyquinolin-7-yl)(2,3-dihydro-1,4-benzodioxin-6-yl)methyl]-2-phenoxyacetamide
N-[(5-chloro-8-hydroxyquinolin-7-yl)(quinolin-3-yl)methyl]-2-phenoxyacetamide
N-[1-benzofuran-2-yl(5-chloro-8-hydroxyquinolin-7-yl)methyl]-2-phenoxyacetamide
N-[(5-chloro-8-hydroxyquinolin-7-yl)(1-methyl-1H-indol-2-yl)methyl]-2-phenoxyacetamide
N-[(5-chloro-8-hydroxyquinolin-7-yl)(2,3-dihydro-1-benzofuran-5-yl)methyl]-2-phenoxyacetamide
N-[(5-chloro-8-hydroxyquinolin-7-yl)(2,2-dimethyl-3,4-dihydro-2H-chromen-6-yl)methyl]-2-phenoxyacetamide
N-[(5-chloro-8-hydroxyquinolin-7-yl)(4-oxo-4H-chromen-3-yl)methyl]-2-phenoxyacetamide
N-[(5-chloro-8-hydroxyquinolin-7-yl)(6-methyl-4-oxo-4H-chromen-3-yl)methyl]-2-phenoxyacetamide
N-[(5-chloro-8-hydroxyquinolin-7-yl)(4H-pyrazolo[1,5-c][1,3]thiazol-2-yl)methyl]-2-phenoxyacetamide N-[1,3-benzodioxol-5-yl(5-chloro-8-hydroxyquinolin-7-yl)methyl]-2-phenoxyacetamide
N-[(6-chloro-1,3-benzodioxol-5-yl)(5-chloro-8-hydroxyquinolin-7-yl)methyl]-2-phenoxyacetamide
N-[(5-chloro-8-hydroxyquinolin-7-yl)(1-methyl-1H-1,2,3-benzotriazol-5-yl)methyl]-2-phenoxyacetamide
N-[(5-chloro-8-hydroxyquinolin-7-yl)(5,6-dihydro-8H-imidazo[2,1-c][1,4]oxazin-2-yl)methyl]-2-phenoxyacetamide
N-[(5-chloro-8-hydroxyquinolin-7-yl)(5,6-dihydro-4H-pyrrolo[1,2-b]pyrazol-2-yl)methyl]-2-phenoxyacetamide
N-[(5-chloro-8-hydroxyquinolin-7-yl)(phenyl)methyl]-3-phenylpropanamide
benzyl[(5-chloro-8-hydroxyquinolin-7-yl)(phenyl)methyl]carbamate
benzyl[(5-chloro-8-hydroxyquinolin-7-yl)(2-chlorophenyl)methyl]carbamate
benzyl[(5-chloro-8-hydroxyquinolin-7-yl)(pyridin-2-yl)methyl]carbamate
benzyl[(5-chloro-8-hydroxyquinolin-7-yl)(2-furyl)methyl]carbamate
benzyl[1,3-benzodioxol-5-yl(5-chloro-8-hydroxyquinolin-7-yl)methyl]carbamate
N-[1-(5-chloro-8-hydroxyquinolin-7-yl)prop-2-en-1-yl]-2-phenoxyacetamide
N-[(2E)-1-(5-chloro-8-hydroxyquinolin-7-yl)but-2-en-1-yl]-2-phenoxyacetamide
N-[(2E)-1-(5-chloro-8-hydroxyquinolin-7-yl)hex-2-en-1-yl]-2-phenoxyacetamide
N-[(5-chloro-8-hydroxyquinolin-7-yl)(cyclohex-1-en-1-yl)methyl]-2-phenoxyacetamide
N-[(2E)-1-(5-chloro-8-hydroxyquinolin-7-yl)-3-phenylprop-2-en-1-yl]-2-phenoxyacetamide
N-[(2Z)-1-(5-chloro-8-hydroxyquinolin-7-yl)-2-methoxy-3-phenylprop-2-en-1-yl]-2-phenoxyacetamide
benzyl[1-(5-chloro-8-hydroxyquinolin-7-yl)-2-phenylethyl]carbamate
N-[1-(5-chloro-8-hydroxyquinolin-7-yl)-3-phenylpropyl]-2-phenoxyacetamide
N-[(5-chloro-8-hydroxyquinolin-7-yl)(phenyl)methyl]-2-phenylacetamide
N-[(5-chloro-8-hydroxyquinolin-7-yl)(2-chlorophenyl)methyl]-2-phenylacetamide
N-[(5-chloro-8-hydroxyquinolin-7-yl)(4-fluorophenyl)methyl]-2-phenylacetamide
N-[[3-(benzyloxy)-4-methoxyphenyl](5-chloro-8-hydroxyquinolin-7-yl)methyl]-2-phenylacetamide
N-[(2E)-1-(5-chloro-8-hydroxyquinolin-7-yl)-3-phenylprop-2-en-1-yl]-2-phenylacetamide
N-[(5-chloro-8-hydroxyquinolin-7-yl)(3-methyl-2-thienyl)methyl]-2-phenylacetamide
N-[(5-bromo-8-hydroxyquinolin-7-yl)(phenyl)methyl]-2-phenoxyacetamide
N-[(5-bromo-8-hydroxyquinolin-7-yl)(phenyl)methyl]-2-chloroacetamide
N-[(3-aminophenyl)(5-chloro-8-hydroxyquinolin-7-yl)methyl]-2-phenoxyacetamide
5-chloro-7-{{3-[(methylsulfonyl)amino]phenyl}[(phenoxyacetyl)amino]methyl}quinolin-8-yl methanesulfonate
N-[[3-(acetylamino)phenyl](5-chloro-8-hydroxyquinolin-7-yl)methyl]-2-phenoxyacetamide
2-chloro-N-(3-{(5-chloro-8-hydroxyquinolin-7-yl)[(phenoxyacetyl)amino]methyl}phenyl)acetamide
N-(3-{(5-chloro-8-hydroxyquinolin-7-yl)[(phenoxyacetyl)amino]methyl}phenyl)-N2,N2-dimethylglycinamide
N-(3-{(5-chloro-8-hydroxyquinolin-7-yl)[(phenoxyacetyl)amino]methyl}phenyl)-N2-methylglycinamide
(3-{(5-chloro-8-hydroxyquinolin-7-yl)[(phenoxyacetyl)amino]methyl}phenyl)acetic acid
2-(4-bromophenoxy)-N-[(5-chloro-8-hydroxyquinolin-7-yl)(phenyl)methyl]acetamide
N-[5-chloro-8-hydroxyquinolin-7-yl)(phenyl)methyl]-2-(3,4,5-trimethoxyphenoxy)acetamide
2-(biphenyl-4-yloxy)-N-[(5-chloro-8-hydroxyquinolin-7-yl)(phenyl)methyl]acetamide
N-[5-chloro-8-hydroxyquinolin-7-yl)(phenyl)methyl]-2-(3,5-dimethoxyphenoxy)acetamide
N-[5-chloro-8-hydroxyquinolin-7-yl)(2-chlorophenyl)methyl]-2-(4-pentylphenoxy)acetamide
N-[(5-chloro-8-hydroxyquinolin-7-yl)(2-chlorophenyl)methyl]-2-(4-propylphenoxy)acetamide
N-[(5-chloro-8-hydroxyquinolin-7-yl)(2-chlorophenyl)methyl]-2-(4-isopropylphenoxy)acetamide
N-[5-chloro-8-hydroxyquinolin-7-yl)(2-chlorophenyl)methyl]-2-(4-cyclopentylphenoxy)acetamide
N-[5-chloro-8-hydroxyquinolin-7-yl)(2-chlorophenyl)methyl]-2-(3-ethylphenoxy)acetamide
N-[5-chloro-8-hydroxyquinolin-7-yl)(2-chlorophenyl)methyl]-2-(3,5-dimethoxyphenoxy)acetamide
2-(biphenyl-4-yloxy)-N-[(5-chloro-8-hydroxyquinolin-7-yl)(2-chlorophenyl)methyl]acetamide
2-(4-bromophenoxy)-N-[(5-chloro-8-hydroxyquinolin-7-yl)(2-chlorophenyl)methyl]acetamide
2-(1,3-benzodioxol-5-yloxy)-N-[(5-chloro-8-hydroxyquinolin-7-yl)(2-chlorophenyl)methyl]acetamide
N-[5-bromo-8-hydroxyquinolin-7-yl)(phenyl)methyl]-N2-(1-naphthylmethyl)glycinamide
N2-benzyl-N-[(5-chloro-8-hydroxyquinolin-7-yl)(phenyl)methyl]glycinamide
N-[(5-chloro-8-hydroxyquinolin-7-yl)(phenyl)methyl]-N2-(1-naphthylmethyl)glycinamide
N-[5-chloro-8-hydroxyquinolin-7-yl)(phenyl)methyl]-2-(4-phenylpiperidin-1-yl)acetamide
N2-(1,3-benzodioxol-5-ylmethyl)-N-[(5-chloro-8-hydroxyquinolin-7-yl)(phenyl)methyl]glycinamide
N-[(5-chloro-8-hydroxyquinolin-7-yl)(phenyl)methyl]-N2-(pyridin-2-ylmethyl)glycinamide
N-[(5-chloro-8-hydroxyquinolin-7-yl)(phenyl)methyl]-N2-(pyridin-3-ylmethyl)glycinamide
N-[(5-chloro-8-hydroxyquinolin-7-yl)(phenyl)methyl]-N2-(pyridin-4-ylmethyl)glycinamide
N2-(biphenyl-4-ylmethyl)-N-[(5-chloro-8-hydroxyquinolin-7-yl)(phenyl)methyl]glycinamide
N-[(5-chloro-8-hydroxyquinolin-7-yl)(2-chlorophenyl)methyl]-N2-(1-naphthylmethyl)glycinamide
N2-(1,3-benzodioxol-5-ylmethyl)-N-[(5-chloro-8-hydroxyquinolin-7-yl)(2-chlorophenyl)methyl]glycinamide
N-[(5-amino-8-hydroxyquinolin-7-yl)(phenyl)methyl]-2-phenoxyacetamide
N-[5-(dimethylamino)-8-hydroxyquinolin-7-yl)(phenyl)methyl]-2-phenoxyacetamide
N-[[8-hydroxy-5-(1H-pyrrol-1-yl)quinolin-7-yl](phenyl)methyl]-2-phenoxyacetamide
N-[(8-hydroxy-5-pyrrolidin-1-ylquinolin-7-yl)(phenyl)methyl]-2-phenoxyacetamide
N-[2-(8-Hydroxyquinolin-7-yl)-1-phenylethyl]-2-phenoxyacetamide
N-[1-(1,3-Benzodioxol-5-yl)-2-(5-chloro-8-hydroxyquinolin-7-yl)ethyl]-2-phenoxyacetamide
2-[8-(Benzyloxy)-5-chloroquinolin-7-yl]-1-[4-(morpholin-4-ylmethyl)phenyl]ethanamine
2-[8-(Benzyloxy)-5-chloroquinolin-7-yl]-1-[3-(5-methyl-2-thienyl)phenyl]ethanamine
N-{2-[8-(Benzyloxy)-5-chloroquinolin-7-yl]-1-[4-(morpholin-4-ylmethyl)phenyl]ethyl}biphenyl-4-carboxamide N-{2-[8-(Benzyloxy)-5-chloroquinolin-7-yl]-1-[3-(pyrrolidin-1-ylmethyl)phenyl]ethyl}biphenyl-4-carboxamide N-{2-(5-Chloro-8-hydroxyquinolin-7-yl)-1-[4-(morpholin-4-ylmethyl)phenyl]ethyl}biphenyl-4-carboxamide N-{2-(5-Chloro-8-hydroxyquinolin-7-yl)-1-[3-(pyrrolidin-1-ylmethyl)phenyl]ethyl}biphenyl-4-carboxamide N-{2-(5-Chloro-8-hydroxyquinolin-7-yl)-1-[3-(5-methyl-2-thienyl)phenyl]ethyl}biphenyl-4-carboxamide N-{2-(5-Chloro-8-hydroxyquinolin-7-yl)-1-[3-(pyrrolidin-1-ylmethyl)phenyl]ethyl}-2-phenoxyacetamide N-{2-(5-Chloro-8-hydroxyquinolin-7-yl)-1-[3-(pyrrolidin-1-ylmethyl)phenyl]ethyl}-2-(4-chlorophenoxy)-2-methylpropanamide N-{2-(5-Chloro-8-hydroxyquinolin-7-yl)-1-[3-(5-methyl-2-thienyl)phenyl]ethyl}-2-phenoxyacetamide 2-(Benzyloxy)-N-{2-(5-chloro-8-hydroxyquinolin-7-yl)-1-[3-(5-methyl-2-thienyl)phenyl]ethyl}acetamide N-{2-(5-Chloro-8-hydroxyquinolin-7-yl)-1-[3-(5-methyl-2-thienyl)phenyl]ethyl}-2-(4-chlorophenoxy)-2-methylpropanamide 2-(4-tert-Butylphenoxy)-N-{2-(5-chloro-8-hydroxyquinolin-7-yl)-1-[3-(5-methyl-2-thienyl)phenyl]ethyl}acetamide 2-[8-(Benzyloxy)-5-chloroquinolin-7-yl]-1-{5-[(dimethylamino)methyl]-2-furyl}ethanamine N-(2-[8-(Benzyloxy)-5-chloroquinolin-7-yl]-1-{5-[(dimethylamino)methyl]-2-furyl}ethyl)-2-phenoxyacetamide N-[2-(5-Chloro-8-hydroxyquinolin-7-yl)-1-{5-[(dimethylamino)methyl]-2-furyl}ethyl]-2-phenoxyacetamide N-[2-(8-Benzyloxy-5-chloro-quinolin-7-yl)-1-(5-dimethylaminomethyl-furan-2-yl)-ethyl]-isobutyramide N-[2-(5-Chloro-8-hydroxyquinolin-7-yl)-1-{5-[(dimethylamino)methyl]-2-furyl}ethyl]-2-methylpropanamide 2-{[(phenoxyacetyl)amino](phenyl)methyl}quinolin-8-yl phenoxyacetate N-[(8-hydroxyquinolin-2-yl)(phenyl)methyl]-2-phenoxyacetamide or 2-[amino(phenyl)methyl]quinolin-8-ol.

42. A pharmaceutical composition comprising at least one compound according to claim 1 and a pharmaceutically acceptable carrier therefor.

43. The method of making a compound according to claim 1 of Formula (I), wherein said method comprises:

treating a compound of Formula (II):

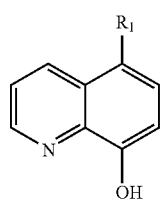

(II)

with a compound of Formula (III)

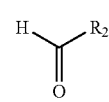

(III)

and H$_2$NR$_3$ followed by treatment with R$_4$Z under conditions effective to produce a compound of Formula (I)

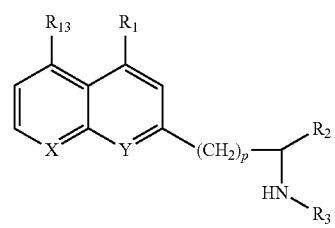

(I)

wherein Z is chlorine, bromine, or iodine, X is N, Y is COR$_4$, R$_{13}$ is hydrogen, p=0 and R$_1$, R$_2$, R$_3$, and R$_4$, are as defined in claim 1.

44. The method of making a compound according to claim 1, wherein said method comprises:

(a) treating a compound of Formula (II):

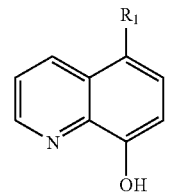

(II)

with an aldehyde of Formula (III)

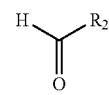

(III)

and at least one acetamide of Formula (IV)

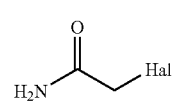

(IV)

wherein Hal is halogen, under conditions effective to produce a compound of Formula (V)

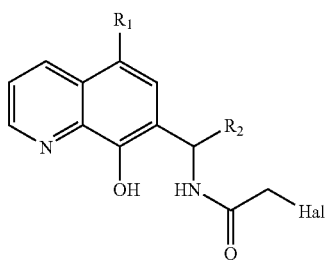

(b) first treating the compound of Formula (V) with a compound of formula AH under basic conditions, followed by treatment with $R_4Z$ to produce a compound of Formula (Ia)

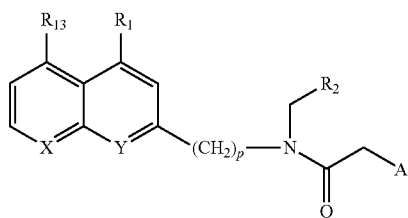

wherein A is $-OR_7$, $-NR_5R_6$ or $-OR_8-B-R_9$,
Z is chlorine, bromine, or iodine,
X is N, Y is $COR_4$, $R_{13}$ is hydrogen, p=0;
$R_1$, $R_2$, $R_3$, $R_4$ and $R_8$ are as defined in claim 1, and
$R_5$, $R_6$, $R_7$ and $R_9$ are each independently $-C_5-C_7$-aryl or $-C_5-C_{10}$-arylalkyl, as defined in claim 1.

45. A method of treating a disorder in a mammal in need thereof, which comprises administering an effective dose of at least one compound according to claim 1 or a pharmaceutically acceptable salt thereof, wherein the disorder is an arthritic disorder, osteoarthritis, rheumatoid arthritis, atherosclerosis, tendonitis, invertebral disc degeneration, or osteopenia.

46. The method of claim 45, wherein the disorder is osteoarthritis.

47. A method of treating a disorder in a mammal in need thereof, which comprises administering an effective dose of at least one compound according to claim 1 or a pharmaceutically acceptable salt thereof, wherein the disorder is malignant neoplasm, angiogenesis, or abnormal wound healing.

48. A method of treating a disorder in a mammal in need thereof, which comprises administering an effective dose of at least one compound according to claim 1 or a pharmaceutically acceptable salt thereof, wherein the disorder is asthma or chronic obstructive pulmonary disease.

49. A method of treating a disorder in a mammal in need thereof, which comprises administering an effective dose of at least one compound according to claim 1 or a pharmaceutically acceptable salt thereof, wherein the disorder is age-related macular degeneration, myocardial infarction, a corneal ulceration, or an ocular surface disease.

50. A method of treating a disorder in a mammal in need thereof, which comprises administering an effective dose of at least one compound according to claim 1 or a pharmaceutically acceptable salt thereof, wherein the disorder is a central nervous system disorder, stroke, or multiple sclerosis.

51. A method of treating a disorder in a mammal in need thereof, which comprises administering an effective dose of at least one compound according to claim 1 or a pharmaceutically acceptable salt thereof, wherein the disorder is hepatitis, an aortic aneurysm, restenosis, cirrhosis, glomerulonephritis, graft versus host disease, diabetes, an inflammatory bowel disease, shock, or a periodontal disease.

52. The compound of claim 1, wherein X is $-N-$, Y is $-COR_4$, $R_{13}$ is hydrogen, and p=0.

* * * * *